US006964769B2

(12) United States Patent
Sebbel et al.

(10) Patent No.: US 6,964,769 B2
(45) **Date of Patent: *Nov. 15, 2005**

(54) MOLECULAR ANTIGEN ARRAY

(75) Inventors: Peter Sebbel, Zürich (CH); Nicolas Dunant, Zürich (CH); Martin Bachmann, Winterthur (CH); Alain Tissot, Zürich (CH); Franziska Lechner, Zürich (CH); Wolfgang A. Renner, Zürich (CH); Frank Hennecke, Zürich (CH); Lars Nieba, Herisau (CH)

(73) Assignee: Cytos Biotechnology AG, Zurich-Schlieren (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/848,616

(22) Filed: May 4, 2001

(65) Prior Publication Data

US 2003/0054010 A1 Mar. 20, 2003

Related U.S. Application Data

(60) Provisional application No. 60/202,341, filed on May 5, 2000.

(51) Int. Cl.[7] .................... A61K 39/385; A61K 39/295; A61K 39/29; C07K 14/02; C07K 17/00

(52) U.S. Cl. ................................ 424/189.1; 424/193.1; 424/194.1; 424/196.11; 424/278.1; 424/281.1; 530/350; 530/402; 530/403; 530/404; 530/405; 530/408; 530/807

(58) Field of Search ................................ 530/350, 402, 530/403, 404, 405, 806, 807; 424/189.1, 193.1, 194.1, 196.11, 278.1, 281.1

(56) References Cited

U.S. PATENT DOCUMENTS

| | | | | |
|---|---|---|---|---|
| 4,722,840 A | | 2/1988 | Valenzuela et al. | 424/88 |
| 4,959,314 A | * | 9/1990 | Mark et al. | 435/69.1 |
| 5,071,651 A | | 12/1991 | Sabara et al. | 424/89 |
| 5,143,726 A | | 9/1992 | Thornton et al. | |
| 5,334,394 A | | 8/1994 | Kossovsky et al. | 424/494 |
| 5,374,426 A | | 12/1994 | Sabara et al. | 530/403 |
| 5,565,548 A | * | 10/1996 | Neurath et al. | 530/324 |
| 5,580,859 A | | 12/1996 | Felgner et al. | |
| 5,698,424 A | | 12/1997 | Mastico et al. | 435/172.3 |
| 5,739,026 A | | 4/1998 | Garoff et al. | 435/240.2 |
| 5,766,602 A | | 6/1998 | Xiong et al. | 424/218.1 |
| 5,770,380 A | | 6/1998 | Hamilton et al. | 435/7.1 |
| 5,789,245 A | | 8/1998 | Dubensky, Jr. et al. | 435/320.1 |
| 5,792,462 A | | 8/1998 | Johnston et al. | 424/199.1 |
| 5,814,482 A | | 9/1998 | Dubensky, Jr. et al. | 435/69.3 |
| 5,871,747 A | | 2/1999 | Gengoux-Sedlik et al. | 424/208.1 |
| 5,928,647 A | | 7/1999 | Rock | 424/196.11 |
| 5,935,821 A | | 8/1999 | Chatterjee et al. | |
| 6,004,763 A | | 12/1999 | Gengoux et al. | 435/7.24 |
| 6,054,312 A | | 4/2000 | Larocca et al. | 435/320.1 |
| 6,231,864 B1 | * | 5/2001 | Birkett | 424/189.1 |
| 2004/0059094 A1 | | 3/2004 | Bachmann et al. | |
| 2004/0076611 A1 | | 4/2004 | Bachmann et al. | |
| 2004/0076645 A1 | | 4/2004 | Bachmann et al. | |

FOREIGN PATENT DOCUMENTS

| | | | | |
|---|---|---|---|---|
| EP | 0 259 149 A2 | | 3/1988 | |
| EP | 0 283 505 B1 | | 9/1988 | |
| EP | 0 385 610 A1 | | 5/1990 | |
| EP | 0 425 082 A1 | | 5/1991 | |
| EP | 0 465 081 B1 | | 1/1992 | |
| EP | 0 578 293 A1 | | 1/1994 | |
| EP | 0 385 610 B1 | | 3/1994 | |
| WO | WO 92/11291 | | 7/1992 | |
| WO | WO 94/06472 A1 | | 3/1994 | |
| WO | WO 94/15585 A1 | | 7/1994 | |
| WO | WO 96/05293 A1 | | 2/1996 | |
| WO | WO 96/30523 A2 | | 10/1996 | |
| WO | WO 97/31948 A1 | | 9/1997 | |
| WO | WO 98/15631 A1 | | 4/1998 | |
| WO | 98/40100 | * | 9/1998 | A61K/39/39 |
| WO | WO 99/07839 A2 | | 2/1999 | |
| WO | WO 99/28478 | | 6/1999 | |
| WO | WO 99/40934 A1 | | 8/1999 | |
| WO | WO 99/50432 A1 | | 10/1999 | |
| WO | WO 99/57289 | | 11/1999 | |
| WO | WO 99/67293 A1 | | 12/1999 | |
| WO | WO 00/32227 A2 | | 6/2000 | |
| WO | WO 00/50461 | | 8/2000 | |

OTHER PUBLICATIONS

Pasek et al (Nature 282, 575–579, 1979).*

Zhou et al (Journal of Virology 66(9): 5393–5398, 1992).*

Abraham, J.M., et al., "An invertible element of DNA controls phase variation of type 1 fimbriae of *Escherichia coli*," *Proc Natl Acad Sci U S A*. Sep. 1985;82(17):5724–5727, National Academy Press (1985).

Abraham, S.N., et al., "Glycerol–induced unraveling of the tight helical conformation of *Escherichia coli* type 1 fimbriae," *J Bacteriol*. Aug. 1992;174(15):5145–5148, American Society for Microbiology (1992).

Amon, R., et al., "A mimotope peptide–based vaccine against *Schistosoma mansoni*: synthesis and characterization," *Immunology*. Dec. 2000;101(4):555–562, Blackwell Science, Ltd. (Dec. 2000).

(Continued)

*Primary Examiner*—Mary E. Mosher
(74) *Attorney, Agent, or Firm*—Sterne, Kessler, Goldstein & Fox P.L.L.C.

(57) ABSTRACT

The invention provides compositions and processes for the production of ordered and repetitive antigen or antigenic determinant arrays. The compositions of the invention are useful for the production of vaccines for the prevention of infectious diseases, the treatment of allergies and the treatment of cancers. Various embodiments of the invention provide for a core particle that is coated with any desired antigen in a highly ordered and repetitive fashion as the result of specific interactions.

24 Claims, 27 Drawing Sheets

OTHER PUBLICATIONS

Bachmann, M.F., et al., "TRANCE, a tumor necrosis factor family member critical for CD40 ligand–independent T helper cell activation," *J Exp Med*. Apr. 5, 1999;189(7):1025–1031, The Rockefeller University Press (1999).

Bass, S., and Yang, M., "Expressing cloned genes in *Escherichia coli*," *Protein Function*: A practical Approach, $2^{nd}$ ed., Creighton, T.E., ed., IRL Press, Oxford, Great Britain, pp. 29–55 (1997).

Blomfield, I.C., et al., "Type 1 fimbriation and fimE mutants of *Escherichia coli* K–12.," *J Bacteriol*. Sep. 1991;173(17):5298–5307, American Society for Microbiology (1991).

Blomfield, I.C., et al., "Integration host factor stimulates both FimB– and FimE–mediated site–specific DNA inversion that controls phase variation of type 1 fimbriae expression in *Escherichia coli*," *Mol Microbiol*. Feb. 1997;23(4):705–717, Blackwell Science, Ltd. (1997).

Boder, E.T., and Wittrup, K.D., "Yeast surface display for directed evolution of protein expression, affinity, and stability," *Methods Enzymol*. 2000;328:430–444, Academic Press (Oct. 2000).

Bonci, A., et al., "Relatedness and phylogeny within the family of periplasmic chaperones involved in the assembly of pili or capsule–like structures of gram–negative bacteria," *J Mol Evol*. Mar. 1997;44(3):299–309, Springer Verlag New York Inc. 1997.

Brinton, Jr., C.C., "the Structure, function, synthesis and genetic control of bacterial pili and a molecular model for DNA and RNA transport in gram negative bacteria," *Trans. N.Y. Acad. Sci*. 1965;27:1003–1054, New York Academy of Sciences (1965).

Brown, K.D., et al., "A family of small inducible proteins secreted by leukocytes are members of a new superfamily that includes leukocyte and fibroblast–derived inflammatory agents, growth factors, and indicators of various activation processes," *J Immunol*. Jan. 15, 1989;142(2):679–687, The American Association of Immunologists (1989).

Brown, P.M., et al., "A single–step purification of biologically active recombinant human interleukin–5 from a baculovirus expression system," *Protein Expr Purif*. Feb. 1995;6(1):63–71, Academic Press, Inc. (1995).

Burger, J.A., et al., "Blood–derived nurse–like cells protect chronic lymphocytic leukemia B cells from spontaneous apoptosis through stromal cell–derived factor–1," *Blood*. Oct. 2000;96(8):2655–63, The American Society of Hematology (Oct. 2000).

Burghoff, R.L., et al., "Utilization of the mouse large intestine to select an *Escherichia coli* F–18 DNA sequence that enhances colonizing ability and stimulates synthesis of type 1 fimbriae," *Infect Immun*. Apr. 1993;61(4):1293–1300, American Society for Microbiology (1993).

Daugherty, P.S. et al., "Development of an optimized expression system for the screening of antibody libraries displayed on the *Escherichia coli* surface," *Protein Eng*. Jul. 1999;12(7):613–621, Oxford University Press (Jul. 1999).

Eisenstein, B.I., et al., "Phase variation of type 1 fimbriae in *Escherichia coli* is under transcriptional control," *Science*, Oct. 16, 1981;214(4518):337–339, American Association for the Advancement of Science (1981).

Elisseeva, E.L., et al., "NMR studies of active N–terminal peptides of stromal cell–derived factor–1. Structural basis for receptor binding," *J Biol Chem*. Sep. 1, 2000;275(35):26799–26805, The American Society for Biochemistry and Molecular Biology Inc. (Sep. 2000).

Fehr, T., et al., "T cell–independent type I antibody response against B cell epitopes expressed repetitively on recombinant virus particles," *Proc Natl Acad Sci* U S A. Aug. 4, 1998;95(16):9477–9481, National Academy Press (1998).

Gally, D.L., et al., "Environmental regulation of the fim switch controlling type 1 fimbrial phase variation in *Escherichia coli* K–12: effects of temperature and media," *J Bacteriol*. Oct. 1993;175(19):6186–6193, American Society for Microbiology (1993).

Gally, D.L., et al., "Interaction of FimB and FimE with the fim switch that controls the phase variation of type 1 fimbriae in *Escherichia coli* K–12," *Mol Microbiol*. Aug. 1996;21(4):725–38, Blackwell Science Ltd: (1996).

Gherardi, E., et al., "A single–step procedure for cloning and selection of antibody–seceting hybridomas," *J Immunol Methods*. Jan. 24, 1990;126(1):61–68, Elsevier (1990).

Hanes, J., et al., "Picomolar affinity antibodies from a fully synthetic naive library selected and evolved by ribosome display," *Nat Biotechnol*, Dec. 2000;18(12):1287–1292, Nature Publishing Company (Dec. 2000).

Hanson, M.S., et al., "Purification of the *Escherichia coli* type 1 pillin and minor pilus proteins and partial characterization of the adhesin protein," *J Bacteriol*. Aug. 1968;170(8):3350–3358, American Society for Microbiology (1988).

Hanson, M.S., and Brinton, Jr., C.C., "Identification and characterization of *E. coli* type–1 pilus tip adhesion protein," *Nature*. Mar. 17, 1988;332(6161):265–8, Nature Publishing Group (1988).

Harrison, J.L., et al., "Screening of phage antibody libraries," *Methods Enzymol*. 1996;267:83–109, Macmillan Publisher Ltd. (1996).

Hirel, P.–H., et al., "Extent of N–terminal methionine excision from *Escherichia coli* proteins is governed by the side–chain length of the penultimate amino acid," *Proc Natl Acad Sci* U S A. Nov. 1989;86(21):8247–8251, National Academy Press (1989).

Holmgren, A., et al., "Conserved immunoglobulin–like features in a family of periplasmic pilus chaperones in bacteria," *EMBO J*. Apr. 1992;11(4):1617–1622, Oxford University Press (1992).

Holmgren, A., and Bränden, C.–I., "Crystal structure of chaperone protein PapD reveals an immunoglobulin fold," *Nature*. Nov. 16, 1989;342(6247):248–251, Nature Publishing Group (1989).

Hultgren, S.J., et al., "PapD and superfamily of periplasmic immunoglobulin–like pilus chaperones," *Adv Protein Chem*. 1992;44:99–123, Academic Press Inc. (1993).

Hultgren, S.J., et al., "Pilus and nonpilus bacterial adhesins: assembly and function in cell recognition," *Cell*. Jun. 4, 1993;73(5):887–901, Cell Press (1993).

Hultgren, S.J., et al., "Bacterial Adhesins and Their Assembly," *in Escherichia coli and Salmonella*, Neidhardt, F.C., et al., eds., ASM Press, Washington, D.C. pp. 2730–2756 (1996).

Hung, D.L., et al., "Molecular basis of two subfamilies of immunoglobulin–like chpaerones," *EMBO J*. Aug. 1, 1996;15(15):3792–3805, Oxford University Press (1996).

Ingley, E., et al., "Production and purification of recombinant human interleukin expression systems," *Eur J Biochem*. Mar. 28, 1991;196(3):623–629, Blackwell Science Ltd. (1991).

Jacob–Dubuisson, F., et al., "PapD chaperone function in pilus biogenesis depends on oxidant and chaperone–like activities of DsbA," *Proc Natl Acad Sci* U S A. Nov. 22, 1994;91(24):11552–11556, National Academy Press (1994).

Jacob–Dubuisson, F., et al., "Initiation of assembly and association of the structural elements of a bacterial pilus dependent on two specialized tip proteins," *EMBO J*. Mar. 1993;12(3):837–47, Oxford University Press (1993).

Jacob–Dubuisson, F., et al., "Chaperone–assisted self–assembly of pili independent of cellular energy," *J Biol Chem*. Apr. 29, 1994;269(17):12447–12455, The American Society for Biochemistry and Molecular Biology Inc. (1994).

Jones, C.H., et al., "FimC is a periplasmic PapD–like chaperone that directs assembly of type 1 pili in bacteria," *Proc Natl Acad Sci* U S A. Sep. 15, 1993;90(18):8397–8401, National Academy Press (1993).

Jones, C.H., et al., " FimH adhesin of type 1 pili is assembled into a fibrillar tip structure in the Enterobacteriaceae," *Proc Natl Acad Sci* U S A. Mar. 14, 1995;92(6):2081–2095, National Academy Press (1995).

Kim, H.–H., et al., "A cysteine–rich adipose tissue–specific secretory factor inhibits adipocyte differentiation," *J Biol Chem*. Apr. 6, 2001;276(14):11252–11256, The American Society for Biochemistry and Molecular Biology Inc. (Apr. 2001).

Klemm, P., et al., "The major subunit of *Escherichia coli* type 1 fimbriae is not require for D–mannose–specific adhesion," *Mol Microbiol*. Apr. 1990;4(4):553–559, Blackwell Scientific Publications (1990).

Klemm, P., et al., "The major subunit of *Escherichia coli* type 1 fimbriae is not require for D–mannose–specific adhesion," *Mol Microbiol*. Apr. 1990;4(4):553–559, Blackwell Scientific Publications (1990).

Klemm, P., "FimC, a chaperone–like periplasmic protein of *Escherichia coli* Involved in biogenesis of type 1 fimbriae," *Res Microbiol*. Nov.–Dec. 1992;143(9):831–838, Institute Pasteur/Elsevier (1992).

Klemm, P., and Krogfelt, K.A., " Type 1 Fimbriae of *Escherichia coli*," in *Fimbriae*, Klemm, P., ed., CRC Press, Inc., Boca Raton, EL., pp. 9–26 (1994).

Koschel, M., et al., "Extensive mutagenesis of the hepatitis B virus core gene and mapping of mutations that allow capsid formation," *J Virol*. Mar. 1999;73(3):2153–2160, American Society for Microbiology (Mar. 1999).

Krogfelt, K.A., et al., "Direct evidence that the FimH protein is the mannose–specific adhesin of *Escherichia coli* type 1 fimbriae," *Infect Immun*. Jun. 1990;58(6):1995–1998, American Society for Microbiology (1990).

Lowe, M.A., et al., "Immunoelectron microscopic analysis of elongation of type 1 fimbriae in *Escherichia coli," J Bacteriol*. Jan. 1987;169(1):157–163, American Society of Microbiology (1987).

Lu, D., et al., "Identification of the residues in the extracellular region of KDR Important for Interaction with vascular endothelial growth factor and neutralizing anti–KDR antibodies," *J Biol Chem*. May 12, 2000;275(19):14321–14330, The American Society for Biochemistry and Molecular Biology Inc (May 2000).

Luther, S.A., et al., "BLC expression in pancreatic islets causes B cell recruitment and lymphotoxin–dependent lymphoid neogenesis," *Immunity*. May 2000;12(5):471–481, Cell Press (May 2000).

Mackay, J.L., and Browning, J.L., "Turning off follicular dendritic cells," *Nature*. Sep. 3, 1998;395(6697):26–27, Macmillan Magazines Ltd. (1998).

Matthews, W., et al., "A receptor tyrosine kinase cDNA isolated from a population of enriched primitive hematopoietic cells and exhibiting close genetic linkage to c–kit," *Proc Natl Acad Sci* U S A. Oct. 15, 1991;88)20):9026–9030, National Academy Press (1991).

McClain, M.S., et al., "Roles of fimB and fimE in site–specific DNA inversion associated with phase variation of type 1 fimbriae in *Escherichia coli," J Bacteriol*. Sep. 1991;173(17):5308–5314, American Society for Microbiology (1991).

Mikulowska, A., et al., "Macrophage migration inhibitory factor is involved in the pathogenesis of collagen type II–induced arthritis in mice," *J Immunol*. Jun. 1, 1997;158(11):5514–5517, The American Association of Immunologists (1997).

Millauer, B., et al., "Glioblastoma growth inhibited in vivo by a dominant–negative Flk–1 mutant," *Nature*. Feb. 10, 1994;367(6463):576–579, Nature Publishing Group (1994).

Mitchell, D.L., et al., "Purification and characterisation of recombinant murine interleukin–5 glycoprotein, from a Baculovirus expression system," *Biochem Soc Trans*. Nov. 1993;21(4):332S, Portland Press (1993).

Naureckiene, S., and Uhlin., B.E., "In vitro analysis of mRNA processing by RNase E in the pap operon of *Escherichia coli," Mol Microbiol*. Jul. 1996;21(1):55–68, Blackwell Science Ltd. (1996).

Newman, J.V., et al., "Stimulation of *Escherichia coli* F–18Col– type –1 fimbriae synthesis by leuX," *FEMS Microbiol Lett*. Oct. 1, 1994;122(3):281–287, Elsevier (1994).

Nieland, J.D., et al., "Chimeric papillomavirus virus–like particles induce a murine self–antigen–specific protective and therapeutic antitumor immune response," *J Cell Biochem*. May 1, 1999;73(2):145–152, Wiley–Liss Inc. (May 1999).

Nilsson, P., et al., "Mutations affecting mRNA processing and fimbrial biogenesis in the *Escherichia coli* pap operon," *J Bacteriol*. Feb. 1996;178(3):683–690, American Society for Microbiology (1996).

Olszewska, W., et al., "Protection against measles virus–induced encephalitis by anti–mimotope antibodies: the role of antibody affinity," *Virology*, Jun. 20, 2000;272(1):98–105, Academic Press (Jun. 2000).

Orndorff, P.E., and Falkow, S., "Identification and characterization of a gene product that regulates type 1 piliation in *Escherichia coli," J Bacteriol*. Oct. 1984;160(1):61–66, American Society for Microbiology (1984).

Orndorff, P.E., and Falkow, S., "Nucleotide sequence of pilA, the gene encoding the structural component of type 1 pili in *Escherichia coli," J Bacteriol*. Apr. 1985;162(1):454–457, American Society for Microbiology (1985).

Pierson–Mullany, L.K. et al., "Characterization of polyclonal allergen–specific IgE responses by affinity distributions," *Mol Immunol*. Aug. 2000;37(10):613–620, Elsevier Science Ltd (Aug. 2000).

Ritter, A., et al., "The Pai–associated leuX specific tRNA5(Leu) affects type 1 fimbriation in pathogenic *Escherichia coli* by control of FimB recombinase expression," *Mol Microbiol.* Sep. 1997;25(5):871–882, Blackwell Science Ltd (1997).

Roesch, P.L., and Blomfield, I.C., "Leucine alters the interaction of the leucine–responsive regulatory protein (Lrp) with the fim switch to stimulate site–specific recombination in *Escherichia coli,*" *Mol Microbiol.* Feb. 1998;27(4):751–761, Blackwell Science Ltd (1998).

Russell, P.W., and Orndorff, P.E., "Lesions in two *Escherichia coli* type 1 pilus genes alter pilus number and length without affecting receptor binding," *Bacteriol.* Sep. 1992;174(18):5923–5935, American Society for Microbiology (1992).

Saulino, E.T., et al., "Ramifications of kinetic partitioning on usher–mediated pilus biogenesis," *EMBO J.* Apr. 15, 1998;17(8):2177–2185, Oxford University Press (1998).

Slepushkin, V.A., et al., "Protection of mice against influenza A virus challenge by vaccination with baculovirus–expressed M2 protein," *Vaccine.* 1995;13(15):1399–1402, Elsevier Science Ltd. (1995).

Slonim, L.N., et al., "Interactive surface in the PapD chaperone cleft is conserved in pilus chaperone superfamily and essential insubunit recognition and assembly," *EMBO J.* Dec. 1992;11(13):4747–4756, Oxford University Press (1992).

Smyth, C.J., et al., "Fimbrial adhesins: similarities and variations in structure and biogenesis," *FEMS Immunol Med Microbiol.* Dec. 1, 1996;16(2):127–139, Elsevier (1996).

Striker, R.T., et al., "Stable fiber–forming and nonfiber–forming chaperone–subunit complexes in pilus biogenesis," *J Biol Chem.* Apr. 22, 1994;269(16):12233–12239, The American Society for Biochemistry and Molecular Biology Inc. (1994).

Thanassi, D.G., et al., "The PapC usher forms an oligomeric channel: implications for pilus biogenesis across the outer membrane," *Proc Natl Acad Sci* U S A. Mar. 17, 1998;95(6):3146–3151, National Academy Press (1998).

Walse, B., et al., "Transferred nuclear Overhauser effect spectroscopy study of a peptide from the PapG pilus subunit bound by the *Escherichia coli* PapD chaperone," *FEBS Lett.* Jul. 21, 1997;412(1):115–120, Elsevier Science B.V. (1997).

Wynne, S.A., et al., "The crystal structure of the human hepatitis B virus capsid," *Mol Cell.* Jun. 1999;3(6):771–780, Cell Press (Jun. 1999).

Zuercher, A.W., et al., "Oral anti–IgE Immunization with epitope–displaying phage," *Eur J Immunol.* Jan. 2000;30(1):128–135, Wiley–Vch Verlag GmbH (Jan. 2000).

NCBI Entrez, GenBank Report, Accession No. P03153, from Seeger, C., et al. (Jan. 1990).

NCBI Entrez, GenBank Report, Accession No. X59397, from Jordan, C.T., et al. (Nov. 1991).

NCBI Entrez, GenBank Report, Accession No. 711678A, from Shipolini, R.A., et al. (Jul. 1992).

NCBI Entrez, GenBank Report, Accession No. M27603, from Orndorff, P.E., and Falkow, S. (Apr. 1993).

NCBI Entrez, GenBank Report, Accession No. M20706, from Nassal M. (Apr. 1993).

NCBI Entrez, GenBank Report, Accession No. AAA37490, from Rouvier E. (Jul. 1993).

NCBI Entrez, GenBank Report, Accession No. M90520, from Kew, M.C., et al. (Aug. 1993).

NCBI Entrez, GenBank Report, Accession No. X00981, from Klemm, P. (Sep. 1993).

NCBI Entrez, GenBank Report, Accession No. VCBPQB, from Maita, T., and Konigsberg, W. (Dec. 1993).

NCBI Entrez, GenBank Report, Accession No. AAA16663, from Koziovska, T.M., et al. (Mar. 1994).

NCBI Entrez, GenBank Report, Accession No. X02514, from Yanisch–Perron, C., et al. (May 1994).

NCBI Entrez, GenBank Report, Accession No. X85256, from Lai, M.E., et al. (Apr. 1995).

NCBI Entrez, GenBank Report, Accession No. X85259, from Lai, M.E., et al., (Apr. 1995).

NCBI Entrez, GenBank Report, Accession No. X85260, from Lai, M.E., et al. (Apr. 1995).

NCBI Entrez, GenBank Report, Accession No. X85272, from Lai, M.E., et al. (Apr. 1995).

NCBI Entrez, GenBank Report, Accession No. X85275, from Lai, M.E., et al. (Apr. 1995).

NCBI Entrez, GenBank Report, Accession No. X85284, from Lai, M.E., et al. (Apr. 1995).

NCBI Entrez, GenBank Report, Accession No. X85285, from Lai, M.E., et al. (Apr. 1995).

NCBI Entrez, GenBank Report, Accession No. X85286, from Lai, M.E., et al. (Apr. 1995).

NCBI Entrez, GenBank Report, Accession No. X85287, from Lai, M.E., et al. (Apr. 1995).

NCBI Entrez, GenBank Report, Accession No. X85291, from Lai, M.E., et al. (Apr. 1995).

NCBI Entrez, GenBank Report, Accession No. X85293, from Lai, M.E., et al. (Apr. 1995).

NCBI Entrez, GenBank Report, Accession No. X85295, from Lai, M.E., et al. (Apr. 1995).

NCBI Entrez, GenBank Report, Accession No. X85296, from Lai, M.E., et al. (Apr. 1995).

NCBI Entrez, GenBank Report, Accession No. X85297, from Lai, M.E., et al. (Apr. 1995).

NCBI Entrez, GenBank Report, Accession No. X85298, from Lai, M.E., et al. (Apr. 1995).

NCBI Entrez, GenBank Report, Accession No. X85299, from Lai, M.E., et al. (Apr. 1995).

NCBI Entrez, GenBank Report, Accession No. X85301, from Lai, M.E., et al. (Apr. 1995).

NCBI Entrez, GenBank Report, Accession No. X85302, from Lai, M.E., et al. (Apr. 1995).

NCBI Entrez, GenBank Report, Accession No. X85303, from Lai, M.E., et al. (Apr. 1995).

NCBI Entrez, GenBank Report, Accession No. X85305, from Lai, M.E., et al. (Apr. 1995).

NCBI Entrez, GenBank Report, Accession No. X85307, from Lai, M.E., et al. (Apr. 1995).

NCBI Entrez, GenBank Report, Accession No. X85311, from Lai, M.E., et al. (Apr. 1995).

NCBI Entrez, GenBank Report, Accession No. X85314, from Lai, M.E., et al. (Apr. 1995).

NCBI Entrez, GenBank Report, Accession No. X85315, from Lai, M.E., et al. (Apr. 1995).

NCBI Entrez, GenBank Report, Accession No. X85316, from Lai, M.E., et al. (Apr. 1995).

NCBI Entrez, GenBank Report, Accession No. X85317, from Lai, M.E., et al. (Apr. 1995).

NCBI Entrez, GenBank Report, Accession No. X895319, from Lai, M.E., et al. (Apr. 1995).

NCBI Entrez, GenBank Report, Accession No. X80925, from Karayiannis, P. (Dec. 1995).

NCBI Entrez, GenBank Report, Accession No. AAC50341, from Yao, Z., et al. (Jan. 1996).
NCBI Entrez, GenBank Report, Accession No. X72702, from Preisler–Adams, S., et al. (Feb. 1996).
NCBI Entrez, GenBank Report, Accession No. VCBPR7, from Weber, K., et al. (Apr. 1996).
NCBI Entrez, GenBank Report, Accession No. 1604193A, from Gomez, F., et al. (Oct. 1996).
NCBI Entrez, GenBank Report, Accession No. B56338, from Hoffman, D.R. (May 1997).
NCBI Entrez, GenBank Report, Accession No. U95551, from Rao, B.S., et al. (Jun. 1997).
NCBI Entrez, GenBank Report, Accession No. S14764, from Vandermeers, A., et al. (Oct. 1997).
NCBI Entrez, GenBank Report, Accession No. P03611, from Weber, K., et al. (Nov. 1997).
NCBI Entrez, GenBank Report, Accession No. AAC14699, from Beekwilder, M.J., et al. (Apr. 1998).
NCBI Entrez, GenBank Report, Accession No. AAC14704, from Beekwilder, M.J., et al. (Apr. 1998).
NCBI Entrez, GenBank Report, Accession No. AF043593, from Gunther, S., et al. (May 1998).
NCBI Entrez, GenBank Report, Accession No. 1POC, from Scott, D.L., et al. (Sep. 1998).
NCBI Entrez, GenBank Report, Accession No. CAA30374, from Inokuchi, Y., et al. (Feb. 1999).
NCBI Entrez, GenBank Report, Accession No. X02496, from Bichko, V., et al. (Apr. 1999).
NCBI Entrez, GenBank Report, Accession No. MFIV62, from Cox, N.J., et al. (Jul. 1999).
NCBI Entrez, GenBank Report, Accession No. VCBPFR, from Wittmann–Liebold, B., et al. (Jul. 1999).
NCBI Entrez, GenBank Report, Accession No. A59055, from Hoffman, D.R., and Schmidt, J.O. (Aug. 1999).
NCBI Entrez, GenBank Report, Accession No. B59055, from Hoffman, D.R., and Schmidt, J.O. (Aug. 1999).
NCBI Entrez, GenBank Report, Accession No. AF051814, from Boyd, E.F., and Hartl, D.L. (Sep. 1999).
NCBI Entrez, GenBank Report, Accession No. AF110999, from Chang, S.F., et al. (Oct. 1999).
NCBI Entrez, GenBank Report, Accession No. AB033559, from Okamoto, H., et al. (Oct. 1999).
NCBI Entrez, GenBank Report, Accession No. AB010289, from Koseki, T., et al. (Dec. 1999).
NCBI Entrez, GenBank Report, Accession No. AJ132364, from Graupner, S., et al. (Apr. 2000).
NCBI Entrez, GenBank Report, Accession No. AF237482, from Johnson, J.R., et al. (May 2000).
NCBI Entrez, GenBank Report, Accession No. M32138, from Tong, S.P., et al. (Jul. 2000).
NCBI Entrez, GenBank Report, Accession No. AF229646, from Skerker, J.M., and Shapiro, L. (Aug. 2000).
NCBI Entrez, GenBank Report, Accession No. M95589, from Shi, H., et al. (Jan. 2001).
NCBI Entrez, GenBank Report, Accession No. VCBPM2, from Min Jou, W., et al. (Jan. 2001).
NCBI Entrez, GenBank Report, Accession No. AF323080, from Steppan, C.M., et al. (Jan. 2001).
NCBI Entrez, GenBank Report, Accession No. AF323081, from Steppan, C.M., et al. (Jan. 2001).
NCBI Entrez, GenBank Report, Accession No. U14003, from Plunket, G., III, et al. (Jan. 2001).
NCBI Entrez, GenBank Report, Accession No. AF121239, from Hannoun, C., et al. (Feb. 2001).
NCBI Entrez, GenBank Report, Accession No. AF121240, from Hannoun, C., et al. (Feb. 2001).
NCBI Entrez, GenBank Report, Accession No. AF121242, from Hannoun, C., et al. (Feb. 2001).
NCBI Entrez, GenBank Report, Accession No. X59795, from Lai, M.E., et al. (Mar. 2001).
NCBI Entrez, GenBank Report, Accession No. X65257, from Lai, M.E., et al. (Mar. 2001).
NCBI Entrez, GenBank Report, Accession No. X65258, from Lai, M.E., et al. (Mar. 2001).
NCBI Entrez, GenBank Report, Accession No. AF151735, from Gerner, P., et al. (Apr. 2001).
NCBI Entrez, GenBank Report, Accession No. AJ000636, from Gousset, N., et al. (Nov. 2001).
NCBI Entrez, GenBank Report, Accession No. AAB59424, from Kenten, J.H., et al. (Feb. 2002).
NCBI Entrez, GenBank Report, Accession No. AAC06250, from Beekwilder, M.J., et al. (Mar. 2002).
NCBI Entrez, GenBank Report, Accession No. L09137, from Yanisch–Perron, C., et al. (May 2002).
NCBI Entrez, GenBank Report, Accession No. O09006, from Hromas, R., et al. (Jun. 2002).
NCBI Entrez, GenBank Report, Accession No. P40224, from Nagasawa, T., et al. (Jun. 2002).
NCBI Entrez, GenBank Report, Accession No. P34884, from Bernhagen, J., et al. (Jun. 2002).
NCBI Entrez, GenBank Report, Accession No. P06821, from Winter, G., et al. (Jun. 2002).
NCBI Entrez, GenBank Report, Accession No. P30904, from Sakai, M., et al. (Jun. 2002).
NCBI Entrez, GenBank Report, Accession No. NP_040754, from Inokuchi, Y., et al. (Jun. 2003).
NCBI Entrez, GenBank Report, Accession No. NP_061354, from Ishikawa, S., et al. (Sep. 2003).
NCBI Entrez, GenBank Report, Accession No. NP_031804, from Lenda, D.M., et al. (Sep. 2003).
NCBI Entrez, GenBank Report, Accession No. NP_006410, from Luther, S.A., et al. (Sep. 2003).
NCBI Entrez, GenBank Report, Accession No. NP_000748, from Yeo, G.Q., et al. (Sep. 2003).
NCBI Entrez, GenBank Report, Accession No. P03069, from Hinnebusch, A.G., et al. (Sep. 2003).
NCBI Entrez, GenBank Report, Accession No. O00585, from Hromas, R., et al. (Sep. 2003).
NCBI Entrez, GenBank Report, Accession No. P14174, from Weiser, W.Y., et al. (Sep. 2003).
NCBI Entrez, GenBank Report, Accession No. P48061, from Spotila, L.D., et al. (Sep. 2003).
NCBI Entrez, GenBank Report, Accession No. P80003, from Vandermeers, A., et al. (Sep. 2003).
Swiss–Prot/TrEMBL, TN11_Mouse, Primary Accession No. O35235, entered in Swiss–Prot in Oct. 2001.
Swiss–Prot/TrEMBL, TN11_Human, Primary Accession No. O14788, entered in Swiss–Prot in Oct. 2001.
Copy of co–pending U.S. Appl. No. 10/622,087, Inventors Bachmann et al., filed Jul. 18, 2003 (Not Published).
Copy of co–pending U.S. Appl. No. 10/733,582, inventors Renner et al., filed Dec. 12, 2003 (Not Published).
Jegerlehner, A., et al., "A molecular assembly system that renders antigens of choice highly repeptitive for induction of protective B cell responses," Vaccine 20:3104–3112, Elsevier Science, Ltd. (Aug. 2002).

NCBI Entrez, PubMed Abstract, PMID: 2205968, Diallo, A., et al., "Morbillivirus group: genome organization and proteins," Vet. Microbiol. 23:155–163 (1990).

Dialog File 351, Accession No. 1994–111516, Derwent WPI English language abstract for FR 2695563.

International Search Report for International Application No. PCT/IB02/00168 mailed on Nov. 4, 2002.

International Search Report for International Application No. PCt/IB02/00166 mailed on Oct. 29, 2002.

International Search Report for International Application No. PCT/IB02/00166, mailed Jan. 31, 2003.

Copy of Office Action mailed Jun. 6, 2001, for U.S. Appl. No. 09/449,631, Renner et al., filed Nov. 30, 1999.

Copy of Office Action mailed Feb. 27, 2002, for U.S. Appl. No. 09/449,631, Renner et al., filed Nov. 30, 1999.

Copy of Office Action mailed Nov. 14, 2002, for U.S. Appl. No. 09/449,631, Renner et al., filed Nov. 30, 1999.

Copy of Office Action mailed Mar. 1, 2004, for U.S. Appl. No. 10/050,902, Renner et al., filed Jan. 18, 2002.

Artelt, P. et al., "Vectors for efficient expression in mammalian fibroblastoid, myeloid and lymphoid cells via transfection or infection," *Gene 68*:213–219, Elsevier Science Publishers B.V. (1988).

Baba, T.W. et al., "Pathogenicity of Live, Attenuated SIV After Mucosal Infection of Neonatal Macaques," *Science 267*:1820–1825, American Association for the Advancement of Science (1995).

Bachmann, M.F. et al., "Dendritic cells process exogenous viral proteins and virus–like particles for class I presentation of $CD8^+$ cytotoxic T lymphocytes," *Eur. J. Immunol. 26*:2595–2600, VCH Verlagsgesellschaft mbH (1996).

Bachmann, M.F. and Zinkernagel R.M., "The influence of virus structure on antibody responses and virus serotype formation," *Immunol. Today 17*:553–558, Elseveir Science, Ltd. (1996).

Bachmann, M.F. and Zinkernagel, R.M., "Neutralizing Antiviral B Cell Responses," *Annu. Rev. Immunol. 15*:235–270, Annual Reviews, Inc. (1997).

Bard, F. et al., "Peripherally administered antibodies against amyloid β–peptide enter the central nervous system and reduce pathology in a mouse model of Alzheimer disease," *Nat. Med. 6*:916–919, Nature America, Inc. (Aug. 2000).

Boorsma, M. et al., "A temperature–regulated replicon–based DNA expression system," *Nat. Biotechnol. 18*:429–432, Nature America, Inc. (Apr. 2000).

Borisova, G. et al., "Hybrid Hepatitis B Virus Nucleocapsid Bearing an Immunodominant Region from Hepatitis B Virus Surface Antigen," *J. Virol. 67*:3696–3701, American Society for Microbiology/DC (1993).

Bullitt E. et al., "Development of pilus organelle subassemblies in vitro depends on chaperone uncapping of a beta zipper," *Proc. Natl. Acad. Sci USA 93*:12890–12895, National Academy Press (1996).

Bullitt, E. and Makowski, L., "Bacterial Adhesion Pili Are Heterologous Assemblies of Similar Subunits," *Biophys. J. 74*:623–632, Biophysical Society (1998).

Cesareni, G., "Peptide display on filamentous phage capsids," *FEBS Lett. 307*:66–70, Elsevier Science Publishers B.V. (1992).

Clark, H.F. et al., "Comparative Characterization of a C–Type Virus–Producing Cell Line (VSW) and a Virus–Free Cell Line (VH2) From *Vipera russelli*," *J. Natl. Cancer Inst. 51*:645–657, Oxford University Press (1973).

Cohen, C. and Parry, D.A.D., "α–Helical coiled coils—a widespread motif in proteins," *Trends Biochem. Sci. 11*:245–248, Elsevier Science Publishers B.V. (1986).

Connor, R.I. et al., "Immunological and Virological Analyses of Persons Infected by Human Immunodeficiency Virus Type 1 while Participating in Trials of Recombinant gp120 Subunit Vaccines," *J. Virol. 72*:1552–1576, American Society for Microbiology/DC (1998).

Crameri, R. and Suter M., "Display of biologically active proteins on the surface of filamentous phages: a cDNA cloning system for selection of functional gene products linked to the genetic information responsible for their production," *Gene 137*:69–75, Elsevier Science Publishers B.V. (1993).

Daniel, M.D. et al., "Protective Effects of a Live Attenuated SIV Vaccine with a Deletion in the nef Gene," *Science 258*:1938–1941, American Association for the Advancement of Science (1992).

Davis, N.L. et al., "In Vitro Synthesis of Infectious Venezuelan Equine Encephalitis Virus RNA from a cDNA Clone: Analysis of a Viable Deletion Mutant," *Virol. 171*:189–204, Academic Press, Inc. (1989).

de la Cruz, V.F. et al., "Immunogenicity and Epitope Mapping of Foreign Sequences via Genetically Engineered Filamentous Phage," *J. Biol. Chem. 263*:4318–4322, American Society for Biochemistry and Molecular Biology (1988).

Dodson, K.W. et al., "Outer–membrane PapC molecular usher discriminately recognizes periplasmic chaperone–pilus subunit complexes," *Proc. Natl. Acad. Sci. USA 90*:3670–3674, National Academy Press (1993).

Donnelly, J.J. et al., "DNA Vaccines," *Annu. Rev. Immunol. 15*:617–648, Annual Reviews, Inc. (1997).

Ebina, S. et al., "Chemical Modification of Bovine Pancreatic Trypsin Inhibitor for Single Site Coupling of Immunogenic Peptides for NMR Conformational Analysis," *J. Biol. Chem. 264*:7882–7888, American Society for Biochemistry and Molecular Biology, Inc. (1989).

Eshdat, Y. et al., "Dissociation and Reassembly of *Escherichia coli* Type 1 Pili," *J. Bacteriol. 148*:308–314, American Society for Microbiology/DC (1981).

Esposito, G. et al., "Conformational study of a short Pertussis toxin T cell epitope incorporated in a multiple antigen peptide template by CD and two–dimensional NMR. Analysis of the structural effects on the activity of synthetic immunogens," *Eur. J. Biochem. 217*:171–187, Blackwell Science, Ltd. (1993).

Fehr, T. et al., "Role of Repetitive Antigen Patterns for Induction of Antibodies Against Antibodies," *J. Exp. Med. 185*:1785–1792, Rockefeller University Press (1997).

Föster, E. et al., "Natural and recombinant enzymatically active or inactive bee venom phospholipase $A_2$ has the same potency to release histamine from basophils in patients with Hymenoptera allergy," *J. Allergy Clin. Immunol. 95*:1229–1235, Mosby (1995).

Frolov, I. et al., "Alphavirus–based expression vectors: Strategies and applications," *Proc. Natl. Acad. Sci. USA. 93*:11371–11377, National Academy Press (1996).

Fujiwara K. et al., "Novel Preparation Method of Immunogen for Hydrophobic Hapten, Enzyme Immunoassay for Daunomycin and Adriamycin," *J. Immunol. Methods* 45:195–203, Elsevier/North–Holland Biomedical Press (1981).

Gilbert, S.C. et al., "A protein particle vaccine containing multiple multiple malaria epitopes," *Nat. Biotechnocal. 15*:1280–1284, Nature America, Inc. (1997).

Greenstone, H.L. et al., "Chimeric papillomavirus virus–like particles elicit antitumor immunity against the E7 oncoprotein in an HPV16 tumor model," *Proc Natl. Acad. Sci. USA 95*:1800–1805, National Academy Press (1998).

Hahn, C.S. et al., "Infectious Sindbis virus transient expression vectors for studying antigen processing and presentation," *Proc. Natl. Acad. Sci. USA 89*:2679–2683, National Academy Press (1992).

Harding, C.V. and Song, R., "Phagocytic Processing of Exogenous Particulate Antigens by Macrophages for Presentation by Class I MHC Molecules," *J. Immunol. 153*:4925–4933, American Association of Immunologists (1994).

Haslam, D.B. et al., "The amino–terminal domain of the P–pilus adhesion determines receptor specificity," *Mol. Microbiol. 14*:399–409, Blackwell Scientific Publications (1994).

Hilleman, M.R., "Six decades of vaccine development–a personal history," *Nat. Med. 4*:507–514, Nature America, Inc. (1998).

Hui, E.K–W. et al., "Hepatitis B viral core proteins with an N–terminal extension can assemble into core–like particles but cannot be enveloped," *J. Gen. Virol. 80*:2647–2659, Society for General Microbiology (Oct. 1999).

Hultgren, S.J. et al., "The PapG adhesion of uropathogenic *Escherichia coli* contains separate regions of receptor binding and for the incorporation into the pilus," *Proc. Natl. Acad. Sci. USA 86*:4357–4361 (1989).

Hung, D.L. and Hultgren, S.J., "Pilus Biogenesis via the Chaperone/Usher Pathway: An Integration of Structure and Function," *J. Struct. Biol. 124*:201–220, Academic Press, Ltd. (1998).

Iannolo G. et al., "Modifying Filamentous Phage Capsid: Limits in the Size of the Major Capsid Protein," *J. Mol. Biol. 248*:835–844, Academic Press, Ltd. (1995).

Iannolo, G. et al., Construction, Exploitation and Evolution of a New Peptide Library Displayed at High Density by Fusion to the Major Coat Protein of Filamentous Phage, *Biol. Chem. 378*:517–521, Walter de Gruyter & Co. (1997).

Ikram, H. and Prince, A.M., "A method for coupling the hepatitis B surface antigen to aldehyde–fixed erythrocytes for use in passive hemmagglutination," *J. Virol. Methods 2*:269–275, Elsevier/North–Holland Biomedical Press (1981).

Jiang, X. et al., "Norwald Virus Genome Cloning and Characterization," *Science 250*:1580–1583, American Association for the Advancement of Science (1990).

Kilby, J.M. et al., "Potent suppression of HIV–1 replication in humans by T–20, a peptide inhibitor of gp41–mediated virus entry," *Nat. Med. 4*:1302–1307, Nature America, Inc. (1998).

Klemm, P. and Christiansen, G., "Three fim genes required for the regulation of length and mediation of adhesion of *Escherichia coli* type 1 fimbriae," *Mol. Gen. Genet. 208*:439–445, Springer–Verlag (1987).

Klemm, P. and Christiansen, G., "The fimD gene required for cell surface localization of *Escherichia coli* type 1 fimbriae," *Mol. Gen. Genet. 220*:334–338, Springer–Verlag (1990).

Kovacsovics–Bankowski, M. et al., "Efficient major histocompatibility, complex class I presentation of exogenous antigen upon phagocytosis by macrophages," *Proc. Natl. Acad. Sci. USA 90*:4942–4946, National Academy Press (1993).

Kratz, P.A. et al., "Native display of complete foreign protein domains on the surface of hepatitis B virus capsids," *Proc. Natl. Acad. Sci. USA 96*:1915–1920, *Proc. Natl. Acad. Sci. USA 96*:1915–1920 (Mar. 1999).

Kuehn, M.J. et al., "Structural Basis of Pilus Subunit Recognition by the PapD Chaperone," *Science 262*:1234–1241, American Association for the Advancement of Science (1993).

Landschulz, W.H. et al., "The Leucine Zipper: A Hypothetical Structure Common to a New Class of DNA Binding Proteins," *Science 240*:1759–1764, American Association for the Advancement of Science (1988).

Leake, C.J. et al., "Cytopathic Effect and Plaque Formation by Arboviruses in a Continuous Cell Line (XTC–2) from the Toad *Xenopus laevis," J. Gen. Virol. 35*:335–339, Cambridge University Press (1977).

Lee, K. et al., "Two–Dimensional Electrophoresis of Proteins as a Tool in the Metabolic Engineering of Cell Cycle Regulation," *Biotechnol. Bioeng. 50*:336–340, John Wiley & Sons, Inc. (1996).

Liljeström, P. and Garoff, H., "A New Generation of Animal Cell Expression Vectors Based on the Semliki Forest Virus Replicon," *Biotechnology* (*N Y*) *9*:1356–1361, Nature Publishing Company (1991).

Liljestroöm, P., "Alphavirus expression systems," *Curr. Opin. Biotechnol. 5*:495–500, Current Biology, Ltd. (1994).

Lindberg, F. et al., "PapD, a Periplasmic Transport Protein in P–Pilus Biogenesis," *J. Bacteriol. 171*:6052–6058, American Society for Microbiology/DC (1989).

Lo, K.K–W. et al., "Suface–modified mutants of cytochrome $p450_{cam}$: enzymatic properties and electrochemistry," *FEBS Lett. 451*:342–346, Elsevier Science Publishers B.V. (May 1999).

Lo–Man, R. et al., "A recombinant virus–like particle system derived from parvovirus as an efficient antigen carrier to elicit a polarized Th1 immune response without adjuvant," *Eur. J. Immunol. 28*:1401–1407, WILEY–VCH Verlag GmbH (1998).

Löpez, O. et al., "Direct formation of mixed micelles in the solubilization of phospholipid liposomes by Triton X–100," *FEBS Lett. 426*:314–318, Elsevier Science Publishers B.V.(1998).

Lundstrom, K., "Alphaviruses as expression vectors," *Curr. Opin. Biotechnol. 8*:578–582, Current Biology, Ltd. (1997).

Matsui, S.M. et al., "The Isolation and Characterization of a Norwalk Virus–specific cDNA," *J. Clin. Invest. 87*:1456–1461, Rockefeller University Press (1991).

McPherson, P.S., "Regulatory Role of SH3 Domain–mediated Protein–Protein Interactions in Synaptic Vesicle Endocytosis," *Cell. Signal. 11*:229–238. Elsevier Science, Inc. (Apr. 1999).

McReynolds, L. et al., "Sequence of chicken ovalbumin mRNA," *Nature 273*:723–728, Macmillan Magazines, Ltd. (1978).

Minenkova, O.O. et al., "Design of specific immunogens using filamentous phage as the carrier," *Gene 128*:85–88, Elsevier Publishers, B.V. (1993).

Morein, B. et al., "Iscom, a novel structure for antigenic presentation of membrane proteins from enveloped viruses," *Nature 308*:457–460, Macmillan Magazines, Ltd. (1984).

Neurath, A.R. et al., "Hepatitis B virus surface antigen (HbsAG) as carrier for synthetic peptides having an attached hydrophobic tail," *Mol. Immunol. 26*:53–62, Pergamon Press (1989).

O'Shea, E.K. et al., "Evidence That the Leucine Zipper Is a Coiled Coal," *Science 243*:538–542, American Association for the Advancement of Science (1989).

O'Shea, E.K. et al., "Mechanism of Specificity in the Fos–Jun Oncoprotein Heterodimer," *Cell 68*:699–708, Cell Press (1992).

Perham, R.N. et al., "Engineering a peptide epitope display system on filamentous bacteriophage," *FEMS Microbiol. Rev. 17*:28–31, Elsevier Science Publishers B.V. (1995).

Petrenko, V.A. et al., "A library of organic landscapes on filamentous phage," *Protein Eng. 9*:797–801, Oxford University Press (1996).

Pumpens, P. and Grens, E., "Hepatitis B core particles as a universal display model: a structure–function basis for development," *FEBS Lett. 442*:1–6, Elsevier Science Publishers B.V. (Jan. 1999).

Quash, G. et al., "The preparation of latex particles with covalently bound polyamines, IgG and measles agglutinins and their use in visual agglutination tests," *J. Immunol. Methods 22*:165–174, Elsevier/North–Holland Biomedical Press (1978).

Raychaudhuri, S. and Rock, K.L., "Fully mobilizing host defense: Building better vaccines," *Nat. Biotechnol. 16*:1025–1031, Nature America, Inc. (1998).

Redfield, R.R. et al., "Disseminated Vaccinia in a Miltary Recruit with Human Immunodeficiency Virus (HIV) Disease," *N. Engl. J. Med. 316*:673–676, New England Journal of Medicine (1987).

Renner, W.A. et al., "Recombinant Cyclin E Expression Activates Proliferation and Obviates Surface Attachment of Chinese Hamster Ovary (CHO) Cells in Protein–Free Medium," *Biotechnol. Bioeng. 4*:476–482, John Wiley & Sons, Inc. (1995).

Romagnani, S., "The Th1/Th2 paradigm," *Immunol. Today 18*:263–266, Elsevier Science, Ltd. (1997).

Rudolf, M.P. et al., "Molecular Basis for Nonanaphylactogenicity of a Monoclonal Anti–IgE Antibody," *J. Immunol. 165*:813–819, American Association of Immunologists (Jul. 2000).

Schelsinger, S., "Alphaviruses—vectors for the expression of heterologous genes," *Trends Biotechnol. 11*:18–22, Elsevier Science Publishers, Ltd. (1993).

Schenk, D. et al., "Immunization with amyloid–β attenuates Alzheimer–disease–like pathology in the PDAPP mouse," *Nature 400*:173–177, Macmillan Magazines, Ltd. (Jul. 1999).

Sedlik, C. et al., "Recombinant parovirus–like particles as an antigen carrier: A novel nonreplicative exogenous antigen to elicit protective antiviral cytotoxic T cells," *Proc. Natl. Acad. Sci. USA* 94:7503–7508, National Academy Press (1997).

Shen, L. et al., "Recombinant Virus Vaccine–Induced SIV–Specific $CD8^+$ Cytotoxic T Lymphocytes," *Science 252*:440–443, American Association for the Advancement of Science (1991).

Soto, G.E. et al., "Periplasmic chaperone recognition motif of subunits mediates quaternary interactions in the pilus," *EMBO J. 17*:6155–6167, Oxford University Press (1998).

Soto, G.E. and Hultgren, S.J., "Bacterial Adhesions: Common Themes and Variations in Architecture and Assembly," *J. Bacteriol. 181*:1059–1071, American Society for Microbiology/DC (Feb. 1999).

Stollar, V., "Togaviruses in Cultured Arthropod Cells," in *The Togaviruses: Biology, Structure, Replication*, Schlesinger, R.W. ed., Academic Press, Inc., New York, NY, pp. 612–615 (1980).

Strauss, J.H. and Strauss, E.G., "The Alphaviruses: Gene Expression, Replication, and Evolution," *Microbiol. Rev. 58*:491–562, American Society for Microbiology/DC (1994).

Tanimori, H. et al., "Enzyme Immunoassay of Neocarzinostatin Using β–Galactosidase as Label," *J. Pharm. Dyn. 4*:812–819, Pharmaceutical Society of Japan (1981).

Tewari, R. et al., "Neutrophil Activation by Nascent FimH Subunits of Type 1 Fimbriae Purified from the Periplasm of *Escherichia coli*," *J. Biol. Chem. 268*:3009–3015, American Society for Biochemistry and Molecular Biology, Inc. (1993).

Topchieva, I. and Karezin, K., "Self–Assembled Supramolecular Micellar Structures Based on Non–ionic Surfactants and Cyclodextrins," *J. Colloid Interface Sci.* 213:29–35, Academic Press, Inc. (May 1999).

Townsend, A. and Bodmer, H., "Antigen Recognition by Class I–Restricted T Lymphocytes," *Ann. Rev. Immunol. 7*:601–624, Annual Reviews, Inc. (1989).

Twomey, T. et al., "Structure and immunogenicity of experimental foot–and–mouth disease and poliomyelitis vaccines," *Vaccine 13*:1603–1610, Elsevier Science, Ltd. (1995).

Ulrich, R. et al., "Core Particles of Hepatitis B Virus as Carrier for Foreign Epitopes," *Adv. Virus Res. 50*:141–182, Academic Press, Inc. (1998).

VanCott, T.C. et al., "Antibodies with Specificity to Native gp120 and Neutralization Activity against Primary Human Immunodeficiency Virus Type 1 Isolates Elicited by Immunization with Oligomeric gp160," *J. Virol. 71*:4319–4330, American Society for Microbiology/DC (1997).

Warnes, A. et al., "Expression of the measles virus nucleoprotein gene in *Escherichia coli* and assembly of nucleocapsid–like structures," *Gene 160*:173–178, Elsevier Science Publishers B.V. (1995).

Watkins, S.J. et al., "The 'adenobody' approach to viral targeting: specific and enhanced adenoviral gene delivery," *Gene Ther 4*:1004–1012, Macmillan Magazine, Ltd. (1997).

Watson E. et al., "Structure determination of the intact major sialylated oligosaccharide chains of recombinant human erythropoietin expressed in Chinese hamster ovary cells," *Glycobiology 4*:227–237, Oxford University Press (1994).

Wild, C. et al., "Letter to the Editor: A Synthetic Peptide from HIV–1 gp41 Is a Potent Inhibitor of Virus–Mediated Cell–Cell Fusion," *AIDS Res. Hum. Retroviruses 9*:1051–1053, Mary Ann Liebert, Inc. (1993).

Willis, A.E. et al., "Immunological properties of foreign peptides in multiple display on a filamentous bacteriophage," *Gene 128*:79–83, Elsevier Science Publishers B.V. (1993).

Xiong, C. et al., "Sindbis Virus: An Efficient, Broad Host Range Vector for Gene Expression in Animal Cells," *Science* *243*:1188–1191, American Association for the Advancement of Science (1989).

Yuan, T.T–T. et al., "Subtype–Independent Immature Secretion and Subtype–Dependent Replication Deficiency of a Highly Frequent, Naturally Occurring Mutation of Human Hepatitis B Virus Core Antigen," *J. Virol.* *73*:10122–10128, American Society for Microbiology/DC (Dec. 1999).

Zang, M. et al., "Production of Recombinant Proteins in Chinese Hamster Ovary Cells Using A Protein–Free Cell Culture Medium," *Biotechnology* (*N Y*) *13*:389–392, Nature Publishing Company (1995).

Zhou, S. and Standring, D.N., "Cys Residues of the Hepatitis B Virus Capsid Protein Are Not Essential for the Assembly of Viral Core Particles but Can Influence Their Stability," *J. Virol.* *66*:5393–5398, American Society for Microbiology/DC (1992).

Invitrogen Manual, "Sindbis Expression System Version C," from internet web page http://www.invitrogen.com/manuals.html, Catalog No. K750–01 (1996).

International Preliminary Examination Report for International Application No. PCT/IB99/01925.

International Search Report for International Application No. PCT/IB99/01925 mailed Jun. 29, 2000.

International Search Report for International Application No. PCT/IB01/00741 mailed Mar. 5, 2002.

Copy of co–pending U.S. Appl. No. 10/050,902, Renner et al., filed Jan. 18, 2002.

Copy of co–pending U.S. Appl. No. 10/050,898, Renner et al., filed Jan. 18, 2002.

* cited by examiner

MOLECULAR ANTIGEN ARRAY

CROSS-REFERENCE TO RELATED APPLICATIONS

This application claims priority benefit of U.S. provisional application No. 60/202,341, filed May 5, 2000, which is incorporated by reference in its entirety.

BACKGROUND OF THE INVENTION

1. Field of the Invention

The present invention is related to the fields of molecular biology, virology, immunology and medicine. The invention provides a composition comprising an ordered and repetitive antigen or antigenic determinant array. The invention also provides a process for producing an antigen or antigenic determinant in an ordered and repetitive array. The ordered and repetitive antigen or antigenic determinant is useful in the production of vaccines for the treatment of infectious diseases, the treatment of allergies and as a pharmaccine to prevent or cure cancer and to generate defined self-specific antibodies and specific immune responses of the Th2 type.

2. Background Art

Vaccine development for the prevention of infectious disease has had the greatest impact on human health of any medical invention. It is estimated that three million deaths per year are prevented worldwide by vaccination (Hillemann, *Nature Medicine* 4:507 (1998)). The most common vaccination strategy, the use of attenuated (i.e., less virulent) pathogens or closely related organisms, was first demonstrated by Edward Jenner in 1796, who vaccinated against smallpox by the administration of a less dangerous cowpox virus. Although a number of live attenuated viruses (e.g., measles, mumps, rubella, varicella, adenovirus, polio, influenza) and bacteria (e.g., bacille Calmette-Guerin (BCG) against tuberculosis) are successfully administered for vaccination, there is a risk for the development of serious complications related to a reversion to virulence and infection by the 'vaccine' organism, in particular in immunocompromised individuals.

The specific design of attenuated viruses is now enabled by recombinant DNA technology (i.e., genetic engineering) through the generation of deletion or mutation variants. For example, the administration of an engineered Simian Immunodeficiency Virus (SIV) with a deletion within the nef gene was shown to protect macaques from subsequent infection with a pathogenic SIV strain (Daniel et al., *Science* 258:1938–1941 (1992)). However, the progression of acquired immunodeficiency syndrome (AIDS)-like symptoms in animals administered attenuated SIV raises safety concerns (Baba et al., *Science* 267:1820–1825 (1995)).

As an alternative approach, attenuated viruses or bacteria may be used as carriers for the antigen-encoding genes of a pathogen that is considered too unsafe to be administered in an attenuated form (e.g., Human Immunodeficiency Virus (HIV)). Upon delivery of the antigen-encoding gene to the host, the antigen is synthesized in situ. Vaccinia and related avipox viruses have been used as such carriers for various genes in preclinical and clinical studies for a variety of diseases (e.g., Shen et al., *Science* 252:440 (1991)). One disadvantage of this vaccination strategy is that it does not mimic the virion surface, because the recombinant protein is expressed on the surface of the host cell. Additionally, complications may develop in immunocompromised individuals, as evidenced by life-threatening disseminated vaccinia infections (Redfield, *N. Eng. J. Med.* 316:673 (1998)).

A fourth vaccination approach involves the use of isolated components of a pathogen, either purified from the pathogen grown in vitro (e.g., influenza hemagglutinin or neuraminidase) or after heterologous expression of a single viral protein (e.g., Hepatitis B surface antigen). For example, recombinant, mutated toxins (detoxified) are used for vaccination against diphtheria, tetanus, cholera and pertussis toxins (Levine et al., *New generation vaccines*, 2nd edn., Marcel Dekker, Inc., New York 1997), and recombinant proteins of HIV (gp120 and full-length gp160) were evaluated as a means to induce neutralizing antibodies against HIV with disappointing results (Connor et al., *J. Virol.* 72:1552 (1998)). Recently, promising results were obtained with soluble oligomeric gp160, that can induce CTL response and elicit antibodies with neutralizing activity against HIV-1 isolates (Van Cortt et al., *J. Virol.* 71:4319 (1997)). In addition, peptide vaccines may be used in which known B- or T-cell epitopes of an antigen are coupled to a carrier molecule designed to increase the immunogenicity of the epitope by stimulating T-cell help. However, one significant problem with this approach is that it provides a limited immune response to the protein as a whole. Moreover, vaccines have to be individually designed for different MHC haplotypes. The most serious concern for this type of vaccine is that protective antiviral antibodies recognize complex, three-dimensional structures that cannot be mimicked by peptides.

A more novel vaccination strategy is the use of DNA vaccines (Donnelly et al., *Ann. Rev. Immunol.* 15:617 (1997)), which may generate MHC Class I-restricted CTL responses (without the use of a live vector). This may provide broader protection against different strains of a virus by targeting epitopes from conserved internal proteins pertinent to many strains of the same virus. Since the antigen is produced with mammalian post-translational modification, conformation and oligomerization, it is more likely to be similar or identical to the wild-type protein produced by viral infection than recombinant or chemically modified proteins. However, this distinction may turn out to be a disadvantage for the application of bacterial antigens, since non-native post-translational modification may result in reduced immunogenicity. In addition, viral surface proteins are not highly organized in the absence of matrix proteins.

In addition to applications for the prevention of infectious disease, vaccine technology is now being utilized to address immune problems associated with allergies. In allergic individuals, antibodies of the IgE isotype are produced in an inappropriate humoral immune response towards particular antigens (allergens). The treatment of allergies by allergy immunotherapy requires weekly administration of successively increasing doses of the particular allergen over a period of up to 3–5 years. Presumably, 'blocking' IgG antibodies are generated that intercept allergens in nasal or respiratory secretions or in membranes before they react with IgE antibodies on mast cells. However, no constant relationship exists between IgG titers and symptom relief Presently, this is an extremely time- and cost-consuming process, to be considered only for patients with severe symptoms over an extended period each year.

It is well established that the administration of purified proteins alone is usually not sufficient to elicit a strong immune response; isolated antigen generally must be given together with helper substances called adjuvants. Within these adjuvants, the administered antigen is protected against rapid degradation, and the adjuvant provides an extended release of a low level of antigen.

Unlike isolated proteins, viruses induce prompt and efficient immune responses in the absence of any adjuvants both with and without T-cell help (Bachmann & Zinkernagel, *Ann. Rev. Immunol.* 15:235–270 (1997)). Although viruses often consist of few proteins, they are able to trigger much stronger immune responses than their isolated components. For B cell responses, it is known that one crucial factor for the immunogenicity of viruses is the repetitiveness and order of surface epitopes. Many viruses exhibit a quasi-crystalline surface that displays a regular array of epitopes which efficiently crosslinks epitope-specific immunoglobulins on B cells (Bachmann & Zinkernagel, *Immunol. Today* 17:553–558 (1996)). This crosslinking of surface immunoglobulins on B cells is a strong activation signal that directly induces cell-cycle progression and the production of IgM antibodies. Further, such triggered B cells are able to activate T helper cells, which in turn induce a switch from IgM to IgG antibody production in B cells and the generation of long-lived B cell memory—the goal of any vaccination (Bachmann & Zinkernagel, *Ann. Rev. Immunol.* 15:235–270 (1997)). Viral structure is even linked to the generation of anti-antibodies in autoimmune disease and as a part of the natural response to pathogens (see Fehr, T., et al., *J. Exp. Med.* 185:1785–1792 (1997)). Thus, antigens on viral particles that are organized in an ordered and repetitive array are highly immunogenic since they can directly activate B cells.

In addition to strong B cell responses, viral particles are also able to induce the generation of a cytotoxic T cell response, another crucial arm of the immune system. These cytotoxic T cells are particularly important for the elimination of non-cytopathic viruses such as HIV or Hepatitis B virus and for the eradication of tumors. Cytotoxic T cells do not recognize native antigens but rather recognize their degradation products in association with MHC class I molecules (Townsend & Bodmer, *Ann. Rev. Immunol.* 7:601–624 (1989)). Macrophages and dendritic cells are able to take up and process exogenous viral particles (but not their soluble, isolated components) and present the generated degradation product to cytotoxic T cells, leading to their activation and proliferation (Kovacsovics-Bankowski et al., *Proc. Natl. Acad. Sci. USA* 90:4942–4946 (1993); Bachmann et al., *Eur. J. Immunol.* 26:2595–2600 (1996)).

Viral particles as antigens exhibit two advantages over their isolated components: (1) Due to their highly repetitive surface structure, they are able to directly activate B cells, leading to high antibody titers and long-lasting B cell memory; and (2) Viral particles but not soluble proteins are able to induce a cytotoxic T cell response, even if the viruses are non-infectious and adjuvants are absent.

Several new vaccine strategies exploit the inherent immunogenicity of viruses. Some of these approaches focus on the particulate nature of the virus particle; for example see Harding, C. V. and Song, R., (*J. Immunology* 153:4925 (1994)), which discloses a vaccine consisting of latex beads and antigen; Kovacsovics-Bankowski, M., et al. (*Proc. Natl. Acad. Sci. USA* 90:4942–4946 (1993)), which discloses a vaccine consisting of iron oxide beads and antigen; U.S. Pat. No. 5,334,394 to Kossovsky, N., et al., which discloses core particles coated with antigen, U.S. Pat. No. 5,871,747, which discloses synthetic polymer particles carrying on the surface one or more proteins covalently bonded thereto; and a core particle with a non-covalently bound coating, which at least partially covers the surface of said core particle, and at least one biologically active agent in contact with said coated core particle (see, e.g., WO 94/15585).

However, a disadvantage of these viral mimicry systems is that they are not able to recreate the ordered presentation of antigen found on the viral surface. Antigens coupled to a surface in a random orientation are found to induce CTL response and no or only weak B-cell response. For an efficient vaccine, both arms of the immune system have to be strongly activated, as described above and in Bachmann & Zinkernagel, *Ann. Rev. Immunol.* 15:235 (1997).

In another example, recombinant viruses are being utilized for antigen delivery. Filamentous phage virus containing an antigen fused to a capsid protein has been found to be highly immunogenic (see Perham R. N., et al., *FEMS Microbiol. Rev.* 17:25–31 (1995); Willis et al., *Gene* 128:85–88 (1993); Minenkova et al., *Gene* 128:85–88 (1993)). However, this system is limited to very small peptides (5 or 6 amino acid residues) when the fusion protein is expressed at a high level (Iannolo et al., *J. Mol. Biol.* 248:835–844 (1995)) or limited to the low level expression of larger proteins (de la Cruz et al., *J. Biol. Chem.* 263:4318–4322 (1988)) For small peptides, so far only the CTL response is observed and no or only weak B-cell response.

In yet another system, recombinant alphaviruses are proposed as a means of antigen delivery (see U.S. Pat. Nos. 5,766,602; 5,792,462; 5,739,026; 5;789,245 and 5,814,482). Problems with the recombinant virus systems described so far include a low density expression of the heterologous protein on the viral surface and/or the difficulty of successfully and repeatedly creating a new and different recombinant viruses for different applications.

In a further development, virus-like particles (VLPs) are being exploited in the area of vaccine production because of both their structural properties and their non-infectious nature. VLPs are supermolecular structures built in a symmetric manner from many protein molecules of one or more types. They lack the viral genome and, therefore, are non-infectious. VLPs can often be produced in large quantities by heterologous expression and can be easily be purified.

Examples of VLPs include the capsid proteins of Hepatitis B virus (Ulrich, et al., *Virus Res.* 50:141–182 (1998)), measles virus (Warnes, et al., *Gene* 160:173–178 (1995)), Sindbis virus, rotavirus (U.S. Pat. Nos. 5,071,651 and 5,374,426), foot-and-mouth-disease virus (Twomey, et al., *Vaccine* 13:1603–1610, (1995)), Norwalk virus (Jiang, X., et al., *Science* 250: 1580–1583 (1990); Matsui, S. M., et al., *J. Clin. Invest.* 87:1456–1461(1991)), the retroviral GAG protein (PCT Patent Appl. No. WO 96/30523), the retrotransposon Ty protein p1, the surface protein of Hepatitis B virus (WO 92/11291) and human papilloma virus (WO 98/15631). In some instances, recombinant DNA technology may be utilized to fuse a heterologous protein to a VLP protein (Kratz, P. A., et al., *Proc. Natl. Acad. Sci. USA* 96: 19151920 (1999)).

Thus, there is a need in the art for the development of new and improved vaccines that promote a strong CTL and B-cell immune response as efficiently as natural pathogens.

BRIEF SUMMARY OF THE INVENTION

The invention provides a versatile new technology that allows production of particles or pili coated with any desired antigen. The technology allows the creation of highly efficient vaccines against infectious diseases and for the creation of vaccines for the treatment of allergies and cancers. The invention also provides compositions suited for the induction of Th type 2 T-helper cells (Th2 cells). Thus, efficient vaccines for the treatment of chronic diseases induced or accelerated by a Th1 type immune response, such as arthritis, colitis, diabetes and multiple sclerosis can be produced with the technology provided by this invention.

In a first embodiment, the invention provides a novel composition comprising (A) a non-natural molecular scaffold and (B) an antigen or antigenic determinant.

The non-natural molecular scaffold comprises, or alternatively consists of, (i) a core particle selected from the group consisting of (1) a core particle of non-natural origin and (2) a core particle of natural origin; and (ii) an organizer comprising at least one first attachment site, wherein said organizer is connected to said core particle by at least one covalent bond.

In certain specific embodiments, the core particle naturally contains an organizer. One example of an embodiment of the invention where the organizer is naturally occurring is the bacterial pilus or pilin protein. The antigenic determinant may be linked by a cysteine to a naturally occurring lysine residue of the bacterial pili or pilin protein.

The antigen or antigenic determinant has at least one second attachment site which is selected from the group consisting of (i) an attachment site not naturally occurring with said antigen or antigenic determinant; and (ii) an attachment site naturally occurring with said antigen or antigenic determinant.

The invention provides for an ordered and repetitive antigen array through an association of the second attachment site to the first attachment site by way of at least one non-peptide bond. Thus, the antigen or antigenic determinant and the non-natural molecular scaffold are brought together through this association of the first and the second attachment site to form an ordered and repetitive antigen array.

In another embodiment, the core particle of the aforementioned composition comprises a virus, a virus-like particle, a bacterial pilus, a structure formed from bacterial pilin, a bacteriophage, a viral capsid particle or a recombinant form thereof. Alternatively, the core particle may be a synthetic polymer or a metal.

In yet another embodiment, the core particle comprises, or alternatively consists of, one or more different Hepatitis core (capsid) proteins (HBcAgs). In a related embodiment, one or more cysteine residues of these HBcAgs are either deleted or substituted with another amino acid residue (e.g., a serine residue). In a specific embodiment, the cysteine residues of the HBcAg used to prepare compositions of the invention which correspond to amino acid residues 48 and 107 in SEQ ID NO:134 are either deleted or substituted with another amino acid residue (e.g., a serine residue).

Further, the HBcAg variants used to prepare compositions of the invention will generally be variants which retain the ability to associate with other HBcAgs to form dimeric or multimeric structures that present ordered and repetitive antigen or antigenic determinant arrays.

In another embodiment, the non-natural molecular scaffold comprises, or alternatively consists of, pili or pilus-like structures that have been either produced from pilin proteins or harvested from bacteria. When pili or pilus-like structures are used to prepare compositions of the invention, they may be formed from products of pilin genes which are naturally resident in the bacterial cells but have been modified by genetically engineered (e.g., by homologous recombination) or pilin genes which have been introduced into these cells.

In a related embodiment, the core particle comprises, or alternatively consists of, pili or pilus-like structures that have been either prepared from pilin proteins or harvested from bacteria. These core particles may be formed from products of pilin genes naturally resident in the bacterial cells Further, antigens or antigenic determinants may be linked to these core particles naturally containing an organizer. In such a case, the core particles will generally be linked to a second attachment site of the antigen or antigenic determinant. In most embodiments of the invention, the pili or pilus-like structures will be able to form an ordered and repetitive antigen array with the antigen or antigenic determinant linked to the core particle at a specific or preferred location (e.g., a specific amino acid residue).

In a particular embodiment, the organizer may comprise at least one first attachment site. The first and the second attachment sites are particularly important elements of compositions of the invention. In various embodiments of the invention, the first and/or the second attachment site may be an antigen and an antibody or antibody fragment thereto; biotin and avidin; strepavidin and biotin; a receptor and its ligand; a ligand-binding protein and its ligand; interacting leucine zipper polypeptides; an amino group and a chemical group reactive thereto; a carboxyl group and a chemical group reactive thereto; a sulfhydryl group and a chemical group reactive thereto; or a combination thereof.

In one embodiment, the invention provides the coupling of almost any antigen of choice to the surface of a virus, bacterial pilus, structure formed from bacterial pilin, bacteriophage, virus-like particle or viral capsid particle. By bringing an antigen into a quasi-crystalline 'virus-like' structure, the invention exploits the strong antiviral immune reaction of a host for the production of a highly efficient immune response, i.e., a vaccination, against the displayed antigen.

In another embodiment, the core particle may be selected from the group consisting of: recombinant proteins of Rotavirus, recombinant proteins of Norwalk virus, recombinant proteins of Alphavirus, recombinant proteins of Foot and Mouth Disease virus, recombinant proteins of Retrovirus, recombinant proteins of Hepatitis B virus, recombinant proteins of Tobacco mosaic virus, recombinant proteins of Flock House Virus, and recombinant proteins of human Papilomavirus.

In yet another embodiment, the antigen may be selected from the group consisting of: (1) a protein suited to induce an immune response against cancer cells; (2) a protein suited to induce an immune response against infectious diseases; (3) a protein suited to induce an immune response against allergens, and (4) a protein suited to induce an immune response in pets or farm animals.

In one embodiment, the invention relates to the induction of specific Th type 2 T-helper cells (Th2 cells) using antigens attached to Pili. The induction of Th2 responses may be beneficial for the treatment of a number of diseases. For example, many chronic diseases in humans an animals, such as arthritis, colitis, diabetes and multiple sclerosis are dominated by Th1 response, where T cells secrete $IFN_\gamma$ and other pro-inflammatory cytokines precipitating disease.

In a particularly embodiment of the invention, the first attachment site and/or the second attachment site comprise an interacting leucine zipper polypeptide. In a related embodiment, the first attachment site and/or the second attachment site are selected from the group comprising: (1) the JUN leucine zipper protein domain; and (2) the FOS leucine zipper protein domain.

In another embodiment, the first attachment site and/or the second attachment site are selected from the group comprising: (1) a genetically engineered lysine residue and (2) a genetically engineered cysteine residue, two residues that may be chemically linked together.

The invention also includes embodiments where the organizer particle has only a single first attachment site and the antigen or antigenic determinant has only a single second attachment site. Thus, when an ordered and repetitive antigen array is prepared using such embodiments, each organizer will be bound to a single antigen or antigenic determinant.

In one aspect, the invention provides compositions comprising, or alternatively consisting of, (a) a non-natural molecular scaffold comprising (i) a core particle selected from the group consisting of a core particle of non-natural origin and a core particle of natural origin, and (ii) an organizer comprising at least one first attachment site, wherein the core particle comprises, or alternatively consists of, a bacterial pilus, a pilus-like structure, or a modified HBcAg, or fragment thereof, and wherein the organizer is connected to the core particle by at least one covalent bond, and (b) an antigen or antigenic determinant with at least one second attachment site, the second attachment site being selected from the group consisting of (i) an attachment site not naturally occurring with the antigen or antigenic determinant and (ii) an attachment site naturally occurring with the antigen or antigenic determinant, wherein the second attachment site is capable of association through at least one non-peptide bond to the first attachment site, and wherein the antigen or antigenic determinant and the scaffold interact through the association to form an ordered and repetitive antigen array.

Other embodiments of the invention include processes for the production of compositions of the invention and a methods of medical treatment using vaccine compositions described herein.

It is to be understood that both the foregoing general description and the following detailed description are exemplary and explanatory only and are intended to provide further explanation of the invention as claimed.

DETAILED DESCRIPTION OF THE INVENTION

1. Definitions

Figure 1:
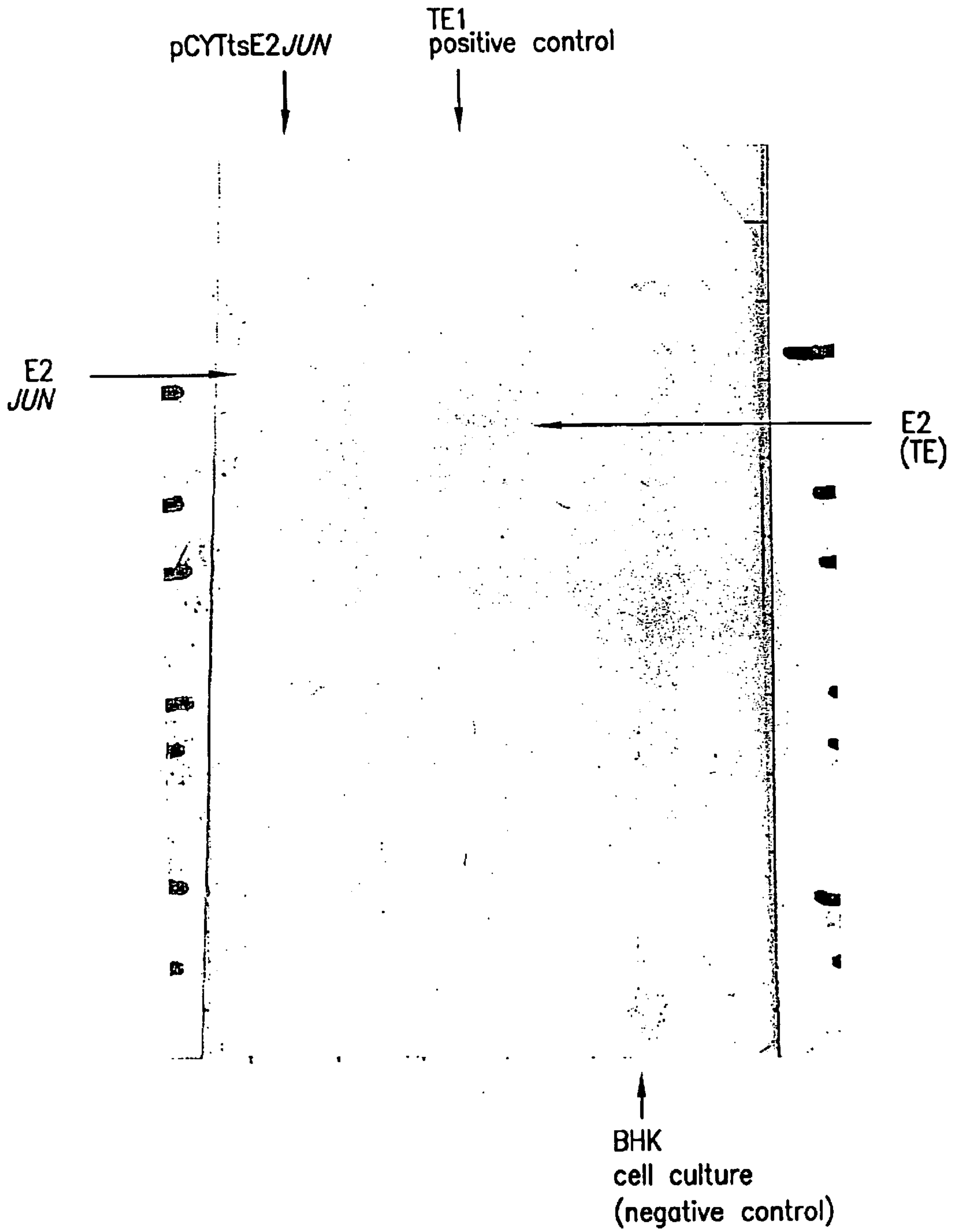
FIG. 1 shows a Western blot demonstrating the production of viral particles containing the E2-JUN fusion protein using the pCYTts::E2JUN expression vector.

The following definitions are provided to clarify the subject matter which the inventors consider to be the present invention.

Alphavirus: As used herein, the term "alphavirus" refers to any of the RNA viruses included within the genus *Alphavirus*. Descriptions of the members of this genus are contained in Strauss and Strauss, *Microbiol. Rev.*, 58:491–562 (1994). Examples of alphaviruses include Aura virus, Bebaru virus, Cabassou virus, Chikungunya virus, Easter equine encephalomyelitis virus, Fort morgan virus, Getah virus, Kyzylagach virus, Mayoaro virus, Middleburg virus, Mucambo virus, Ndumu virus, Pixuna virus, Tonate virus, Triniti virus, Una virus, Western equine encephalomyelitis virus, Whataroa virus, Sindbis virus (SIN), Semliki forest virus (SFV), Venezuelan equine encephalomyelitis virus (VEE), and Ross River virus.

Antigen: As used herein, the term "antigen" is a molecule capable of being bound by an antibody. An antigen is additionally capable of inducing a humoral immune response and/or cellular immune response leading to the production of B- and/or T-lymphocytes. An antigen may have one or more epitopes (B- and T-epitopes). The specific reaction referred to above is meant to indicate that the antigen will react, in a highly selective manner, with its corresponding antibody and not with the multitude of other antibodies which may be evoked by other antigens.

Antigenic determinant: As used herein, the term"antigenic determinant" is meant to refer to that portion of an antigen that is specifically recognized by either B- or T-lymphocytes. B-lymphocytes respond to foreign antigenic determinants via antibody production, whereas T-lymphocytes are the mediator of cellular immunity. Thus, antigenic determinants or epitopes are those parts of an antigen that are recognized by antibodies, or in the context of an MHC, by T-cell receptors.

Association: As used herein, the term "association" as it applies to the first and second attachment sites, is used to refer to at least one non-peptide bond. The nature of the association may be covalent, ionic, hydrophobic, polar or any combination thereof.

Attachment Site, First: As used herein, the phrase "first attachment site" refers to an element of the "organizer", itself bound to the core particle in a non-random fashion, to which the second attachment site located on the antigen or antigenic determinant may associate The first attachment site may be a protein, a polypeptide, an amino acid, a peptide, a sugar, a polynucleotide, a natural or synthetic polymer, a secondary metabolite or compound (biotin, fluorescein, retinol, digoxigenin, metal ions, phenylmethylsulfonylfluoride), or a combination thereof, or a chemically reactive group thereof Multiple first attachment sites are present on the surface of the non-natural molecular scaffold in a repetitive configuration.

Attachment Site, Second: As used herein, the phrase "second attachment site" refers to an element associated with the antigen or antigenic determinant to which the first attachment site of the "organizer" located on the surface of the non-natural molecular scaffold may associate. The second attachment site of the antigen or antigenic determinant may be a protein, a polypeptide, a peptide, a sugar, a polynucleotide, a natural or synthetic polymer, a secondary metabolite or compound (biotin, fluorescein, retinol, digoxigenin, metal ions, phenylmethylsulfonylfluoride), or a combination thereof, or a chemically reactive group thereof. At least one second attachment site is present on the antigen or antigenic determinant.

Core particle: As used herein, the term "core particle" refers to a rigid structure with an inherent repetitive organization that provides a foundation for attachment of an "organizer". A core particle as used herein may be the product of a synthetic process or the product of a biological process.

In certain embodiments of the invention, the antigens or antigenic determinants are directly linked to the core particle.

Cis-acting: As used herein, the phrase "cis-acting" sequence refers to nucleic acid sequences to which a replicase binds to catalyze the RNA-dependent replication of RNA molecules. These replication events result in the replication of the full-length and partial RNA molecules and, thus, the alpahvirus subgenomic promoter is also a "cis-acting" sequence. Cis-acting sequences may be located at or near the 5' end, 3' end, or both ends of a nucleic acid molecule, as well as internally.

Fusion: As used herein, the term "fusion" refers to the combination of amino acid sequences of different origin in one polypeptide chain by in-frame combination of their coding nucleotide sequences. The term "fusion" explicitly encompasses internal fusions, i.e., insertion of sequences of different origin within a polypeptide chain, in addition to fusion to one of its termini.

Heterologous sequence: As used herein, the term "heterologous sequence" refers to a second nucleotide sequence present in a vector of the invention. The term "heterologous sequence" also refers to any amino acid or RNA sequence encoded by a heterologous DNA sequence contained in a vector of the invention. Heterologous nucleotide sequences can encode proteins or RNA molecules normally expressed in the cell type in which they are present or molecules not normally expressed therein (e.g., Sindbis structural proteins).

Isolated: As used herein, when the term "isolated" is used in reference to a molecule, the term means that the molecule has been removed from its native environment. For example, a polynucleotide or a polypeptide naturally present in a living animal is not "isolated," but the same polynucleotide or polypeptide separated from the coexisting materials of its natural state is "isolated." Further, recombinant DNA molecules contained in a vector are considered isolated for the purposes of the present invention. Isolated RNA molecules include in vivo or in vitro RNA replication products of DNA and RNA molecules. Isolated nucleic acid molecules further include synthetically produced molecules. Additionally, vector molecules contained in recombinant host cells are also isolated. Thus, not all "isolated" molecules need be "purified."

Immunotherapeutic: As used herein, the term "immunotherapeutic" is a composition for the treatment of diseases or disorders. More specifically, the term is used to refer to a method of treatment for allergies or a method of treatment for cancer.

Individual: As used herein, the term "individual" refers to multicellular organisms and includes both plants and animals. Preferred multicellular organisms are animals, more preferred are vertebrates, even more preferred are mammals, and most preferred are humans.

Low or undetectable: As used herein, the phrase "low or undetectable," when used in reference to gene expression level, refers to a level of expression which is either significantly lower than that seen when the gene is maximally induced (e.g., at least five fold lower) or is not readily detectable by the methods used in the following examples section.

Lectin: As used herein, proteins obtained particularly from the seeds of leguminous plants, but also from many other plant and animal sources, that have binding sites for specific mono- or oligosaccharides. Examples include concanavalin A and wheat-germ agglutinin, which are widely used as analytical and preparative agents in the study of glycoprotein.

Natural origin: As used herein, the term "natural origin" means that the whole or parts thereof are not synthetic and exist or are produced in nature.

Non-natural: As used herein, the term generally means not from nature, more specifically, the term means from the hand of man.

Non-natural origin: As used herein, the term "non-natural origin" generally means synthetic or not from nature; more specifically, the term means from the hand of man.

Non-natural molecular scaffold: As used herein, the phrase "non-natural molecular scaffold" refers to any product made by the hand of man that may serve to provide a rigid and repetitive array of first attachment sites. Ideally but not necessarily, these first attachment sites are in a geometric order. The non-natural molecular scaffold may be organic or non-organic and may be synthesized chemically or through a biological process, in part or in whole. The non-natural molecular scaffold is comprised of: (a) a core particle, either of natural or non-natural origin; and (b) an organizer, which itself comprises at least one first attachment site and is connected to a core particle by at least one covalent bond. In a particular embodiment, the non-natural molecular scaffold may be a virus, virus-like particle, a bacterial pilus, a virus capsid particle, a phage, a recombinant form thereof, or synthetic particle.

Ordered and repetitive antigen or antigenic determinant array: As used herein, the term "ordered and repetitive antigen or antigenic determinant array" generally refers to a repeating pattern of antigen or antigenic determinant, characterized by a uniform spacial arrangement of the antigens or antigenic determinants with respect to the non-natural molecular scaffold. In one embodiment of the invention, the repeating pattern may be a geometric pattern. Examples of suitable ordered and repetitive antigen or antigenic determinant arrays are those which possess strictly repetitive paracrystalline orders of antigens or antigenic determinants with spacings of 5 to 15 nanometers.

Organizer: As used herein, the term "organizer" is used to refer to an element bound to a core particle in a non-random fashion that provides a nucleation site for creating an ordered and repetitive antigen array. An organizer is any element comprising at least one first attachment site that is bound to a core particle by at least one covalent bond. An organizer may be a protein, a polypeptide, a peptide, an amino acid (i.e., a residue of a protein, a polypeptide or peptide), a sugar, a polynucleotide, a natural or synthetic polymer, a secondary metabolite or compound (biotin, fluorescein, retinol, digoxigenin, metal ions, phenylmethylsulfonylfluoride), or a combination thereof, or a chemically reactive group thereof.

Permissive temperature: As used herein, the phrase "permissive temperature" refers to temperatures at which an enzyme has relatively high levels of catalytic activity.

Pili: As used herein, the term "pili" (singular being "pilus") refers to extracellular structures of bacterial cells composed of protein monomers (e.g., pilin monomers) which are organized into ordered and repetitive patterns. Further, pili are structures which are involved in processes such as the attachment of bacterial cells to host cell surface receptors, inter-cellular genetic exchanges, and cell-cell recognition. Examples of pili include Type-1 pili, P-pili, F1C pili, S-pili, and 987P-pili. Additional examples of pili are set out below.

Pilus-like structure: As used herein, the phrase "pilus-like structure" refers to structures having characteristics similar to that of pili and composed of protein monomers. One example of a "pilus-like structure" is a structure formed by a bacterial cell which expresses modified pilin proteins that do not form ordered and repetitive arrays that are essentially identical to those of natural pili.\

Purified: As used herein, when the term "purified" is used in reference to a molecule, it means that the concentration of the molecule being purified has been increased relative to molecules associated with it in its natural environment. Naturally associated molecules include proteins, nucleic acids, lipids and sugars but generally do not include water, buffers, and reagents added to maintain the integrity or facilitate the purification of the molecule being purified. For example, even if mRNA is diluted with an aqueous solvent during oligo dT column chromatography, mRNA molecules are purified by this chromatography if naturally associated nucleic acids and other biological molecules do not bind to the column and are separated from the subject mRNA molecules.

Receptor: As used herein, the term "receptor" refers to proteins or glycoproteins or fragments thereof capable of interacting with another molecule, called the ligand. The ligand may belong to any class of biochemical or chemical compounds. The receptor need not necessarily be a membrane-bound protein. Soluble protein, like e.g., maltose binding protein or retinol binding protein are receptors as well.

Residue: As used herein, the term "residue" is meant to mean a specific amino acid in a polypeptide backbone or side chain.

Temperature-sensitive: As used herein, the phrase "temperature-sensitive" refers to an enzyme which readily catalyzes a reaction at one temperature but catalyzes the same reaction slowly or not at all at another temperature. An example of a temperature-sensitive enzyme is the replicase protein encoded by the pCYTts vector, which has readily detectable replicase activity at temperatures below 34° C. and has low or undetectable activity at 37° C.

Transcription: As used herein, the term "transcription" refers to the production of RNA molecules from DNA templates catalyzed by RNA polymerase.

Recombinant host cell: As used herein, the term "recombinant host cell" refers to a host cell into which one ore more nucleic acid molecules of the invention have been introduced.

Recombinant virus: As used herein, the phrase "recombinant virus" refers to a virus that is genetically modified by the hand of man. The phrase covers any virus known in the art. More specifically, the phrase refers to a an alphavirus genetically modified by the hand of man, and most specifically, the phrase refers to a Sinbis virus genetically modified by the hand of man.

Restrictive temperature: As used herein, the phrase "restrictive temperature" refers to temperatures at which an enzyme has low or undetectable levels of catalytic activity. Both "hot" and "cold" sensitive mutants are known and, thus, a restrictive temperature may be higher or lower than a permissive temperature.

RNA-dependent RNA replication event: As used herein, the phrase "RNA-dependent RNA replication event" refers to processes which result in the formation of an RNA molecule using an RNA molecule as a template.

RNA-Dependent RNA polymerase: As used herein, the phrase "RNA-Dependent RNA polymerase" refers to a polymerase which catalyzes the production of an RNA molecule from another RNA molecule. This term is used herein synonymously with the term "replicase."

Untranslated RNA: As used herein, the phrase "untranslated RNA" refers to an RNA sequence or molecule which does not encode an open reading frame or encodes an open reading frame, or portion thereof, but in a format in which an amino acid sequence will not be produced (e.g., no initiation codon is present). Examples of such molecules are tRNA molecules, rRNA molecules, and ribozymes.

Vector: As used herein, the term "vector" refers to an agent (e.g., a plasmid or virus) used to transmit genetic material to a host cell. A vector may be composed of either DNA or RNA.

one, a, or an: When the terms "one," "a," or "an" are used in this disclosure, they mean "at least one" or "one or more," unless otherwise indicated.

2. Compositions of Ordered and Repetitive Antigen or Antigenic Determinant Arrays and Methods to Make the Same The disclosed invention provides compositions comprising an ordered and repetitive antigen or antigenic determinant. Furthermore, the invention conveniently enables the practitioner to construct ordered and repetitive antigen or antigenic determinant arrays for various treatment purposes, which includes the prevention of infectious diseases, the treatment of allergies and the treatment of cancers. The invention also enables the practitioner to construct compositions comprising Pili inducing Th2 immune responses, useful in the treatment of chronic diseases.

Compositions of the invention essentially comprise, or alternatively consist of, two elements: (1) a non-natural molecular scaffold; and (2) an antigen or antigenic determinant with at least one second attachment site capable of association through at least one non-peptide bond to said first attachment site.

The non-natural molecular scaffold comprises, or alternatively consists of: (a) a core particle selected from the group consisting of (1) a core particle of non-natural origin and (2) a core particle of natural origin; and (b) an organizer comprising at least one first attachment site, wherein said organizer is connected to said core particle by at least one covalent bond.

Compositions of the invention also comprise, or alternatively consist of, core particles to which antigens or antigenic determinants are directly linked.

The antigen or antigenic determinant has at least one second attachment site which is selected from the group consisting of (a) an attachment site not naturally occurring with said antigen or antigenic determinant; and (b) an attachment site naturally occurring with said antigen or antigenic determinant.

The invention provides for an ordered and repetitive antigen array through an association of the second attachment site to the first attachment site by way of at least one non-peptide bond. Thus, the antigen or antigenic determinant and the non-natural molecular scaffold are brought together through this association of the first and the second attachment site to form an ordered and repetitive antigen array.

The practioner may specifically design the antigen or antigenic determinant and the second attachment site such that the arrangement of all the antigens or antigenic determinants bound to the non-natural molecular scaffold or, in certain embodiments, the core particle will be uniform. For example, one may place a single second attachment site on the antigen or antigenic determinant at the carboxyl or amino terminus, thereby ensuring through design that all antigen or antigenic determinant molecules that are attached to the non-natural molecular scaffold are positioned in a uniform way. Thus, the invention provides a convenient means of placing any antigen or antigenic determinant onto a non-natural molecular scaffold in a defined order and in a manner which forms a repetitive pattern.

As will be clear to those skilled in the art, certain embodiments of the invention involve the use of recombinant nucleic acid technologies such as cloning, polymerase chain reaction, the purification of DNA and RNA, the expression of recombinant proteins in prokaryotic and eukaryotic cells, etc. Such methodologies are well known to those skilled in the art and may be conveniently found in published laboratory methods manuals (e.g., Sambrook, J. et al., eds., MOLECULAR CLONING, A LABORATORY MANUAL, 2nd. edition, Cold Spring Harbor Laboratory Press, Cold Spring Harbor, N.Y. (1989); Ausubel, F et al., eds., CURRENT PROTOCOLS IN MOLECULAR BIOLOGY, John H. Wiley & Sons, Inc. (1997)). Fundamental laboratory techniques for working with tissue culture cell lines (Celis, J., ed., CELL BIOLOGY, Academic Press, $2^{nd}$ edition, (1998)) and antibody-based technologies (Harlow, E. and Lane, D., "Antibodies: A Laboratory Manual," Cold Spring Harbor Laboratory, Cold Spring Harbor, N.Y. (1988); Deutscher, M. P., "Guide to Protein Purification," *Meth. Enzymol.* 128, Academic Press San Diego (1990); Scopes, R. K., "Protein Purification Principles and Practice," $3^{rd}$ ed., Springer-Verlag, New York (1994)) are also adequately described in the literature, all of which are incorporated herein by reference.

A. Construction of a Non-natural Molecular Scaffold

One element in compositions of the invention is a non-natural molecular scaffold comprising, or alternatively consisting of, a core particle and an organizer. As used herein, the phrase "non-natural molecular scaffold" refers to any product made by the hand of man that may serve to provide a rigid and repetitive array of first attachment sites. More specifically, the non-natural molecular scaffold comprises, or alternatively consists of, (a) a core particle selected from the group consisting of (1) a core particle of non-natural origin and (2) a core particle of natural origin; and (b) an organizer comprising at least one first attachment site, wherein said organizer is connected to said core particle by at least one covalent bond.

As will be readily apparent to those skilled in the art, the core particle of the non-natural molecular scaffold of the invention is not limited to any specific form. The core particle may be organic or non-organic and may be synthesized chemically or through a biological process.

In one embodiment, a non-natural core particle may be a synthetic polymer, a lipid micelle or a metal Such core particles are known in the art, providing a basis from which to build the novel non-natural molecular scaffold of the invention. By way of example, synthetic polymer or metal core particles are described in U.S. Pat. No. 5,770,380, which discloses the use of a calixarene organic scaffold to which is attached a plurality of peptide loops in the creation of an 'antibody mimic', and U.S. Pat. No. 5,334,394 describes nanocrystalline particles used as a viral decoy that are composed of a wide variety of inorganic materials, including metals or ceramics. Suitable metals include chromium, rubidium, iron, zinc, selenium, nickel, gold, silver, platinum. Suitable ceramic materials in this embodiment include silicon dioxide, titanium dioxide, aluminum oxide, ruthenium oxide and tin oxide. The core particles of this embodiment may be made from organic materials including carbon (diamond). Suitable polymers include polystyrene, nylon and nitrocellulose. For this type of nanocrystalline particle, particles made from tin oxide, titanium dioxide or carbon (diamond) are may also be used. A lipid micelle may be prepared by any means known in the art. For example micelles may be prepared according to the procedure of Baiselle and Millar (*Biophys. Chem.* 4:355–361 (1975)) or Corti et al. (*Chem. Phys. Lipids* 38:197–214 (1981)) or Lopez et al. (*FEBS Lett.* 426:314–318 (1998)) or Topchieva and Karezin (*J. Colloid Interface Sci.* 213:29–35 (1999)) or Morein et al., (*Nature* 308:457–460 (1984)), which are all incorporated herein by reference.

The core particle may also be produced through a biological process, which may be natural or non-natural. By way of example, this type of embodiment may includes a core particle comprising, or alternatively consisting of, a virus, virus-like particle, a bacterial pilus, a phage, a viral capsid particle or a recombinant form thereof. In a more specific embodiment, the core particle may comprise, or alternatively consist of, recombinant proteins of Rotavirus, recombinant proteins of Norwalk virus, recombinant proteins of Alphavirus, recombinant proteins which form bacterial pili or pilus-like structures, recombinant proteins of Foot and Mouth Disease virus, recombinant proteins of Retrovirus, recombinant proteins of Hepatitis B virus (e.g. a HBcAg), recombinant proteins of Tobacco mosaic virus, recombinant proteins of Flock House Virus, and recombinant proteins of human Papilomavirus.

Whether natural or non-natural, the core particle of the invention will generally have an organizer that is attached to the natural or non-natural core particle by at least one covalent bond. The organizer is an element bound to a core particle in a non-random fashion that provides a nucleation site for creating an ordered and repetitive antigen array. Ideally, but not necessarily, the organizer is associated with the core particle in a geometric order. Minimally, the organizer comprises a first attachment site.

In some embodiments of the invention, the ordered and repetitive array is formed by association between (1) either core particles or non-natural molecular scaffolds and (2) an antigen or antigenic determinant. For example, bacterial pili or pilus-like structures are formed from proteins which are organized into ordered and repetitive structures. Thus, in many instances, it will be possible to form ordered arrays of antigens or antigenic determinants by linking these constituents to bacterial pili or pili-like structures.

As previously stated, the organizer may be any element comprising at least one first attachment site that is bound to a core particle by at least one covalent bond. An organizer may be a protein, a polypeptide, a peptide, an amino acid (i.e., a residue of a protein, a polypeptide or peptide), a sugar, a polynucleotide, a natural or synthetic polymer, a secondary metabolite or compound (biotin, fluorescein, retinol, digoxigenin, metal ions, phenylmethylsulfonylfluoride), or a combination thereof, or a chemically reactive group thereof. In a more specific embodiment, the organizer may comprise a first attachment site comprising an antigen, an antibody or antibody fragment, biotin, avidin, strepavidin, a receptor, a receptor ligand, a ligand, a ligand-binding protein, an interacting leucine zipper polypeptide, an amino group, a chemical group reactive to an amino group; a carboxyl group, chemical group reactive to a carboxyl group, a sulfthydryl group, a chemical group reactive to a sulfhydryl group, or a combination thereof.

In one embodiment, the core particle of the non-natural molecular scaffold comprises a virus, a bacterial pilus, a structure formed from bacterial pilin, a bacteriophage, a virus-like particle, a viral capsid particle or a recombinant form thereof. Any virus known in the art having an ordered and repetitive coat and/or core protein structure may be selected as a non-natural molecular scaffold of the invention; examples of suitable viruses include: sindbis and other alphaviruses; vesicular somatitis virus; rhabdo-, (e.g. vesicular stomatitis virus), picorna-, toga-, orthomyxo-, polyoma-, parvovirus, rotavirus, Norwalk virus, foot and mouth disease virus, a retrovirus, Hepatitis B virus, Tobacco mosaic virus, flock house virus, human papilomavirus (for example, see Table 1 in Bachman, M. F. and Zinkernagel, R. M., *Immunol. Today* 17:553–558 (1996)).

In one embodiment, the invention utilizes genetic engineering of a virus to create a fusion between an ordered and repetitive viral envelope protein and an organizer comprising a heterologous protein, peptide, antigenic determinant or a reactive amino acid residue of choice. Other genetic manipulations known to those in the art may be included in the construction of the non-natural molecular scaffold; for example, it may be desirable to restrict the replication ability of the recombinant virus through genetic mutation. The viral protein selected for fusion to the organizer (i.e., first attachment site) protein should have an organized and repetitive structure. Such an organized and repetitive structure include paracrystalline organizations with a spacing of 5–15 nm on the surface of the virus. The creation of this type of fusion protein will result in multiple, ordered and repetitive organizers on the surface of the virus. Thus, the ordered and repetitive organization of the first attachment sites resulting therefrom will reflect the normal organization of the native viral protein.

As will be discussed in more detail herein, in another embodiment of the invention, the non-natural molecular scaffold is a recombinant alphavirus, and more specifically, a recombinant Sinbis virus. Alphaviruses are positive stranded RNA viruses that replicate their genomic RNA entirely in the cytoplasm of the infected cell and without a DNA intermediate (Strauss, J. and Strauss, E., *Microbiol. Rev.* 58:491–562 (1994)). Several members of the alphavirus family, Sindbis (Xiong, C. et al., *Science* 243:1188–1191 (1989); Schlesinger, S., *Trends Biotechnol.* 11:18–22 (1993)), Semliki Forest Virus (SFV) (Liljestrom, P. & Garoff, H., *Bio/Technology* 9:1356–1361 (1991)) and others (Davis, N. L. et al., *Virology* 171:189–204 (1989)), have received considerable attention for use as virus-based expression vectors for a variety of different proteins (Lundstrom, K., *Curr. Opin. Biotechnol.* 8:578–582 (1997); Liljeström, P., *Curr. Opin. Biotechnol.* 5:495–500 (1994)) and as candidates for vaccine development. Recently, a number of patents have issued directed to the use of alphaviruses for the expression of heterologous proteins and the development of vaccines (see U.S. Pat. Nos. 5,766,602; 5,792,462; 5,739,026; 5,789,245 and 5,814,482). The construction of the alphaviral scaffold of the invention may be done by means generally known in the art of recombinant DNA technology, as described by the aforementioned articles, which are incorporated herein by reference.

A variety of different recombinant host cells can be utilized to produce a viral-based core particle for antigen or antigenic determinant attachment. For example, Alphaviruses are known to have a wide host range; Sindbis virus infects cultured mammalian, reptilian, and amphibian cells, as well as some insect cells (Clark, H., *J. Natl. Cancer Inst.* 51:645 (1973); Leake, C., *J. Gen. Virol.* 35:335 (1977); Stollar, V. in THE TOGAVIRUSES, R. W Schlesinger, Ed., Academic Press, (1980), pp. 583–621). Thus, numerous recombinant host cells can be used in the practice of the invention. BHK, COS, Vero, HeLa and CHO cells are particularly suitable for the production of heterologous proteins because they have the potential to glycosylate heterologous proteins in a manner similar to human cells (Watson, E. et al., *Glycobiology* 4:227, (1994)) and can be selected (Zang, M. et al., *Bio/Technology* 13:389 (1995)) or genetically engineered (Renner W. et al., *Biotech. Bioeng.* 4:476 (1995); Lee K et al. *Biotech. Bioeng.* 50:336 (1996)) to grow in serum-free medium, as well as in suspension.

Introduction of the polynucleotide vectors into host cells can be effected by methods described in standard laboratory manuals (see, e.g., Sambrook, J. et al., eds, MOLECULAR CLONING, A LABORATORY MANUAL, 2nd. edition, Cold Spring Harbor Laboratory Press, Cold Spring Harbor, N.Y. (1989), Chapter 9; Ausubel, F. et al., eds., CURRENT PROTOCOLS IN MOLECULAR BIOLOGY, John H. Wiley & Sons, Inc. (1997), Chapter 16), including methods such as electroporation, DEAE-dextran mediated transfection, transfection, microinjection, cationic lipid-mediated transfection, transduction, scrape loading, ballistic introduction, and infection. Methods for the introduction of exogenous DNA sequences into host cells are discussed in Felgner, P. et al., U.S. Pat. No. 5,580,859.

Packaged RNA sequences can also be used to infect host cells. These packaged RNA sequences can be introduced to host cells by adding them to the culture medium. For example, the preparation of non-infective alpahviral particles is described in a number of sources, including "Sindbis Expression System", Version C (*Invitrogen* Catalog No. K750-1).

When mammalian cells are used as recombinant host cells for the production of viral-based core particles, these cells will generally be grown in tissue culture. Methods for growing cells in culture are well known in the art (see, e.g., Celis, J., ed., CELLBIOLOGY, AcademicPress, 2nd edition, (1998); Sambrook, J. et al., eds., MOLECULAR CLONING, A LABORATORY MANUAL, 2nd. edition, Cold Spring Harbor Laboratory Press, Cold Spring Harbor, N.Y. (1989); Ausubel, F. et al., eds., CURRENT PROTOCOLS IN MOLECULAR BIOLOGY, John H. Wiley & Sons, Inc. (1997); Freshney, R., CULTURE OF ANIMAL CELLS, Alan R. Liss, Inc. (1983)).

As will be understood by those in the art, the first attachment site may be or be a part of any suitable protein, polypeptide, sugar, polynucleotide, peptide (amino acid), natural or synthetic polymer, a secondary metabolite or combination thereof that may serve to specifically attach the antigen or antigenic determinant of choice to the non-natural molecular scaffold. In one embodiment, the attachment site is a protein or peptide that may be selected from those known in the art. For example, the first attachment site may selected from the following group: a ligand, a receptor, a lectin, avidin, streptavidin, biotin, an epitope such as an HA or T7 tag, Myc, Max, immunoglobulin domains and any other amino acid sequence known in the art that would be useful as a first attachment site.

It should be further understood by those in the art that with another embodiment of the invention, the first attachment site may be created secondarily to the organizer (i.e., protein or polypeptide) utilized in constructing the in-frame fusion to the capsid protein. For example, a protein may be utilized for fusion to the envelope protein with an amino acid sequence known to be glycosylated in a specific fashion, and the sugar moiety added as a result may then serve at the first attachment site of the viral scaffold by way of binding to a lectin serving as the secondary attachment site of an antigen. Alternatively, the organizer sequence may be biotinylated in vivo and the biotin moiety may serve as the first attachment site of the invention, or the organizer sequence may be subjected to chemical modification of distinct amino acid residues in vitro, the modification serving as the first attachment site.

One specific embodiment of the invention utilizes the Sinbis virus. The Sinbis virus RNA genome is packaged into a capsid protein that is surrounded by a lipid bilayer containing three proteins called E1, E2, and E3. These so-called envelope proteins are glycoproteins, and the glycosylated portions are located on the outside of the lipid bilayer, where complexes of these proteins form the "spikes" that can be seen in electron micrographs to project outward from the surface of the virus. In another embodiment of the invention, the first attachment site is selected to be the JUN or FOS leucine zipper protein domain that is fused in frame to the E2 envelope protein. However, it will be clear to all individuals in the art that other envelope proteins may be utilized in the fusion protein construct for locating the first attachment site in the non-natural molecular scaffold of the invention.

In a specific embodiment of the invention, the first attachment site is selected to be the JUN-FOS leucine zipper protein domain that is fused in frame to the Hepatitis B capsid (core) protein (HBcAg). However, it will be clear to all individuals in the art that other viral capsid proteins may be utilized in the fusion protein construct for locating the first attachment site in the non-natural molecular scaffold of the invention.

In another specific embodiment of the invention, the first attachment site is selected to be a lysine or cysteine residue that is fused in frame to the HBcAg. However, it will be clear to all individuals in the art that other viral capsid or virus-like particles may be utilized in the fusion protein construct for locating the first attachment in the non-natural molecular scaffold of the invention.

Example 1 is provided to demonstrate the construction of an in-frame fusion protein between the Sinbis virus E2 envelope protein and the JUN leucine zipper protein domain using the pTE5'2J vector of Hahn et al. (*Proc. Natl. Acad. Sci. USA* 89:2679–2683 (1992)). The JUN amino acid sequence utilized for the first attachment site is the following: CGGRIARLEEKVKTLKAQNSE LASTANML-REQVAQLKQKVMNHVGC (SEQ ID NO:59). In this instance, the anticipated second attachment site on the antigen would be the FOS leucine zipper protein domain and the amino acid sequence would be the following: CGGLT-DTLQAETDQVEDEKSALQTEIAN-LLKEKEKLEFILAAHGGC (SEQ ID NO:60)

These sequences are derived from the transcription factors JUN and FOS, each flanked with a short sequence containing a cysteine residue on both sides. These sequences are known to interact with each other. The original hypothetical structure proposed for the JUN-FOS dimer assumed that the hydrophobic side chains of one monomer interdigitate with the respective side chains of the other monomer in a zipper-like manner (Landschulz et al., *Science* 240:1759–1764 (1988)). However, this hypothesis proved to be wrong, and these proteins are known to form an α-helical coiled coil (O'Shea et al., *Science* 243:538–542 (1989); O'Shea et al., *Cell* 68:699–708 (1992); Cohen & Parry, *Trends Biochem. Sci*. 11:245–248 (1986)). Thus, the term "leucine zipper" is frequently used to refer to these protein domains for more historical than structural reasons. Throughout this patent, the term "leucine zipper" is used to refer to the sequences depicted above or sequences essentially similar to the ones depicted above. The terms JUN and FOS are used for the respective leucine zipper domains rather than the entire JUN and FOS proteins.

In one embodiment, the invention provides for the production of a Sinbis virus E2-JUN scaffold using the pCYTts expression system (WO 99/50432). The pCYTts expression system provides novel expression vectors which permit tight regulation of gene expression in eucaryotic cells. The DNA vectors of this system are transcribed to form RNA molecules which are then replicated by a temperature-sensitive replicase to form additional RNA molecules. The RNA molecules produced by replication contain a nucleotide sequence which may be translated to produce a protein of interest or which encode one or more untranslated RNA molecules. Thus the expression system enables the production of recombinant Sinbis virus particles.

Example 2 provides details on the production of the E2-JUN Sinbis non-natural molecular scaffold of the invention. Additionally provided in Example 3 is another method for the production of recombinant E2-JUN Sinbis virus scaffold using the pTE5'2JE2:JUN vector produced in Example 1. Thus the invention provides two means, the pCYTts expression system (Example 2) and the pTE5'2J vector system (Example 3) by which recombinant Sinbis virus E2-JUN non-natural molecular scaffold may be produced. An analysis of viral particles produced in each system is provided in FIG. 1 and FIG. 2.

As previously stated, the invention includes viral-based core particles which comprise, or alternatively consist of, a virus, virus-like particle, a phage, a viral capsid particle or a recombinant form thereof. Skilled artisans have the knowledge to produce such core particles and attach organizers thereto. By way of providing other examples, the invention provides herein for the production of Hepatitis B virus-like particles and measles viral capsid particles as core particles (Examples 17 to 22). In such an embodiment, the JUN leucine zipper protein domain or FOS leucine zipper protein domain may be used as an organizer, and hence as a first attachment site, for the non-natural molecular scaffold of the invention.

Examples 23–29 provide details of the production of Hepatitis B core particles carrying an in-frame fused peptide with a reactive lysine residue and antigens carrying a genetically fused cysteine residue, as first and second attachment site, respectively.

In other embodiments, the core particles used in compositions of the invention are composed of a Hepatitis B capsid (core) protein (HBcAg), or fragment thereof, which has been modified to either eliminate or reduce the number of free cysteine residues. Zhou et al. (*J. Virol.* 66:5393–5398 (1992)) demonstrated that HBcAgs which have been modified to remove the naturally resident cysteine residues retain the ability to associate and form multimeric structures. Thus, core particles suitable for use in compositions of the invention include those comprising modified HBcAgs, or fragments thereof, in which one or more of the naturally resident cysteine residues have been either deleted or substituted with another amino acid residue (e.g., a serine residue).

The HBcAg is a protein generated by the processing of a Hepatitis B core antigen precursor protein. A number of isotypes of the HBcAg have been identified. For example, the HBcAg protein having the amino acid sequence shown in SEQ ID NO:132 is 183 amino acids in length and is generated by the processing of a 212 amino acid Hepatitis B core antigen precursor protein. This processing results in the removal of 29 amino acids from the N-terminus of the Hepatitis B core antigen precursor protein. Similarly, the HBcAg protein having the amino acid sequence shown in SEQ ID NO:134 is 185 amino acids in length and is generated by the processing of a 214 amino acid Hepatitis B core antigen precursor protein. The amino acid sequence shown in SEQ ID NO:134, as compared to the amino acid sequence shown in SEQ ID NO:132, contains a two amino acid insert at positions 152 and 153 in SEQ ID NO:134.

In most instances, vaccine compositions of the invention will be prepared using the processed form of a HBcAg (i.e., a HBcAg from which the N-terminal leader sequence (e.g., the first 29 amino acid residues shown in SEQ ID NO:134) of the Hepatitis B core antigen precursor protein have been removed).

Further, when HBcAgs are produced under conditions where processing will not occur, the HBcAgs will generally be expressed in "processed" form. For example, bacterial systems, such as *E. coli*, generally do not remove the leader sequences of proteins which are normally expressed in eukaryotic cells. Thus, when an *E. coli* expression system is used to produce HBcAgs of the invention, these proteins will generally be expressed such that the N-terminal leader sequence of the Hepatitis B core antigen precursor protein is not present.

In one embodiment of the invention, a modified HBcAg comprising the amino acid sequence shown in SEQ ID NO:134, or subportion thereof, is used to prepare non-natural molecular scaffolds. In particular, modified HBcAgs suitable for use in the practice of the invention include proteins in which one or more of the cysteine residues at positions corresponding to positions 48, 61, 107 and 185 of a protein having the amino acid sequence shown in SEQ ID NO:134 have been either deleted or substituted with other amino acid residues (e.g., a serine residue). As one skilled in the art would recognize, cysteine residues at similar locations in HBcAg variants having amino acids sequences which differ from that shown in SEQ ID NO:134 could also be deleted or substituted with other amino acid residues. The modified HBcAg variants can then be used to prepare vaccine compositions of the invention.

The present invention also includes HBcAg variants which have been modified to delete or substitute one or more additional cysteine residues which are not found in polypeptides having the amino acid sequence shown in SEQ ID NO:134. Examples of such HBcAg variants have the amino acid sequences shown in SEQ ID NOs:90 and 132. These variant contain cysteines residues at a position corresponding to amino acid residue 147 in SEQ ID NO:134. Thus, the vaccine compositions of the invention include compositions comprising HBcAgs in which cysteine residues not present in the amino acid sequence shown in SEQ ID NO:134 have been deleted.

Under certain circumstances (e.g., when a heterobifunctional cross-linking reagent is used to attach antigens or antigenic determinants to the non-natural molecular scaffold), the presence of free cysteine residues in the HBcAg is believed to lead to covalent coupling of toxic components to core particles, as well as the cross-linking of monomers to form undefined species.

Further, in many instances, these toxic components may not be detectable with assays performed on compositions of the invention. This is so because covalent coupling of toxic components to the non-natural molecular scaffold would result in the formation of a population of diverse species in which toxic components are linked to different cysteine residues, or in some cases no cysteine residues, of the HBcAgs. In other words, each free cysteine residue of each HBcAg will not be covalently linked to toxic components. Further, in many instances, none of the cysteine residues of particular HBcAgs will be linked to toxic components. Thus, the presence of these toxic components may be difficult to detect because they would be present in a mixed population of molecules. The administration to an individual of HBcAg species containing toxic components, however, could lead to a potentially serious adverse reaction.

It is well known in the art that free cysteine residues can be involved in a number of chemical side reactions. These side reactions include disulfide exchanges, reaction with chemical substances or metabolites that are, for example, injected or formed in a combination therapy with other substances, or direct oxidation and reaction with nucleotides upon exposure to UV light. Toxic adducts could thus be generated, especially considering the fact that HBcAgs have a strong tendency to bind nucleic acids. Detection of such toxic products in antigen-capsid conjugates would be difficult using capsids prepared using HBcAgs containing free cysteines and heterobifunctional cross-linkers, since a distribution of products with a broad range of molecular weight would be generated. The toxic adducts would thus be distributed between a multiplicity of species, which individually may each be present at low concentration, but reach toxic levels when together.

In view of the above, one advantage to the use of HBcAgs in vaccine compositions which have been modified to remove naturally resident cysteine residues is that sites to which toxic species can bind when antigens or antigenic determinants are attached to the non-natural molecular scaffold would be reduced in number or eliminated altogether. Further, a high concentration of cross-linker can be used to produce highly decorated particles without the drawback of generating a plurality of undefined cross-linked species of HBcAg monomers (i.e., a diverse mixture of cross-linked monomeric HbcAgs).

A number of naturally occurring HBcAg variants suitable for use in the practice of the present invention have been identified. Yuan et al., (*J. Virol.* 73:10122–10128 (1999)), for example, describe variants in which the isoleucine residue at position corresponding to position 97 in SEQ ID NO:134 is replaced with either a leucine residue or a phenylalanine residue. The amino acid sequences of a number of HBcAg variants, as well as several Hepatitis B core antigen precursor variants, are disclosed in GenBank reports AAF121240 (SEQ ID NO:89), AF121239 (SEQ ID NO:90), X85297 (SEQ ID NO:91), X02496 (SEQ ID NO:92), X85305 (SEQ ID NO:93), X85303 (SEQ ID NO:94), AF151735 (SEQ ID NO:95), X85259 (SEQ ID NO:96), X85286 (SEQ ID NO:97), X85260 (SEQ ID NO:98), X85317 (SEQ ID NO:99), X85298 (SEQ ID NO:100), AF043593 (SEQ ID NO:101), M20706 (SEQ ID NO:102), X85295 (SEQ ID NO:103), X80925 (SEQ ID NO:104), X85284(SEQ ID NO:105), X85275 (SEQ ID NO:106), X72702 (SEQ ID NO:107), X85291 (SEQ ID NO:108), X65258 (SEQ ID NO:109), X85302 (SEQ ID NO:110), M32138 (SEQ ID NO:111), X85293 (SEQ ID NO:112), X85315 (SEQ ID NO:113), U95551 (SEQ ID NO:114), X85256 (SEQ ID NO:115), X85316 (SEQ ID NO:116), X85296 (SEQ ID NO:117), AB033559 (SEQ ID NO:118), X59795 (SEQ ID NO:119), X85299 (SEQ ID NO:120), X85307 (SEQ ID NO:121), X65257 (SEQ ID NO:122), X85311 (SEQ ID NO:123), X85301 (SEQ ID NO:124), X85314 (SEQ ID NO:125), X85287 (SEQ ID NO:126), X85272 (SEQ ID NO:127), X85319 (SEQ ID NO:128), AB010289 (SEQ ID NO:129), X85285 (SEQ ID NO:130), AB010289(SEQ ID NO:131), AF121242(SEQ ID NO:132), M90520(SEQ ID NO:135), P03153(SEQ ID NO:136), AF110999(SEQ ID NO:137), and M95589 (SEQ ID NO:138), the disclosures of each of which are incorporated herein by reference. These HBcAg variants differ in amino acid sequence at a number of positions, including amino acid residues which corresponds to the amino acid residues located at positions 12, 13, 21, 22, 24, 29, 32, 33, 35, 38, 40, 42, 44, 45, 49, 51, 57, 58, 59, 64, 66, 67, 69, 74, 77, 80, 81, 87, 92, 93, 97, 98, 100, 103, 105, 106, 109, 113, 116, 121, 126, 130, 133, 135, 141, 147, 149, 157, 176, 178, 182 and 183 in SEQ ID NO:134. The invention is also directed to amino acid sequences that are at least 65, 0, 75, 80, 85, 90 or 95% identical to the above Hepatitis B viral capsid protein sequences. HBcAgs suitable for use in the present invention may be derived from any organism so long as they are able to associate to form an ordered and repetitive antigen array.

As noted above, generally processed HBcAgs (i.e., those which lack leader sequences) will be used in the vaccine compositions of the invention. Thus, when HBcAgs having amino acid sequence shown in SEQ ID NOs:136, 137, or 138 are used to prepare vaccine compositions of the invention, generally 30, 35–43, or 35–43 amino acid residues at the N-terminus, respectively, of each of these proteins will be omitted.

The present invention includes vaccine compositions, as well as methods for using these compositions, which employ the above described variant HBcAgs for the preparation of non-natural molecular scaffolds.

Further included withing the scope of the invention are additional HBcAg variants which are capable of associating to form dimeric or multimeric structures. Thus, the invention further includes vaccine compositions comprising HBcAg polypeptides comprising, or alternatively consisting of, amino acid sequences which are at least 80%, 85%, 90%, 95%, 97%, or 99% identical to any of the amino acid sequences shown in SEQ ID NOs:89–132 and 134–138, and forms of these proteins which have been processed, where appropriate, to remove the N-terminal leader sequence.

Whether the amino acid sequence of a polypeptide has an amino acid sequence that is at least 80%, 85%, 90%, 95%, 97%, or 99% identical to one of the amino acid sequences shown in SEQ ID NOs:89–132 and 134–138, or a subportion thereof, can be determined conventionally using known computer programs such the Bestfit program. When using Bestfit or any other sequence alignment program to determine whether a particular sequence is, for instance, 95% identical to a reference amino acid sequence according to the present invention, the parameters are set such that the percentage of identity is calculated over the full length of the reference amino acid sequence and that gaps in homology of up to 5% of the total number of amino acid residues in the reference sequence are allowed.

The HBcAg variants and precursors having the amino acid sequences set out in SEQ ID NOs:89–132 and 134–136 are relatively similar to each other. Thus, reference to an amino acid residue of a HBcAg variant located at a position which corresponds to a particular position in SEQ ID NO:134, refers to the amino acid residue which is present at that position in the amino acid sequence shown in SEQ ID NO:134. The homology between these HBcAg variants is for the most part high enough among Hepatitis B viruses that infect mammals so that one skilled in the art would have little difficulty reviewing both the amino acid sequence shown in SEQ ID NO:134 and that of a particular HBcAg variant and identifying "corresponding" amino acid residues. For example, the HBcAg amino acid sequence shown in SEQ ID NO:135, which shows the amino acid sequence of a HBcAg derived from a virus which infect woodchucks, has enough homology to the HBcAg having the amino acid sequence shown in SEQ ID NO:134 that it is readily apparent that a three amino acid residue insert is present in SEQ ID NO:135 between amino acid residues 155 and 156 of SEQ ID NO:134.

The HBcAgs of Hepatitis B viruses which infect snow geese and ducks differ enough from the amino acid sequences of HBcAgs of Hepatitis B viruses which infect mammals that alignment of these forms of this protein with the amino acid sequence shown in SEQ ID NO:134 is difficult. However, the invention includes vaccine compositions which comprise HBcAg variants of Hepatitis B viruses which infect birds, as wells as vaccine compositions which comprise fragments of these HBcAg variants. HBcAg fragments suitable for use in preparing vaccine compositions of the invention include compositions which contain polypeptide fragments comprising, or alternatively consisting of, amino acid residues selected from the group consisting of 36–240, 36–269, 44–240, 44–269, 36–305, and 44–305 of SEQ ID NO:137 or 36–240, 36–269, 44–240, 44–269, 36–305, and 44–305 of SEQ ID NO:138. As one skilled in the art would recognize, one, two, three or more of the cysteine residues naturally present in these polypeptides (e.g., the cysteine residues at position 153 is SEQ ID NO:137 or positions 34, 43, and 196 in SEQ ID NO:138) could be either substituted with another amino acid residue or deleted prior to their inclusion in vaccine compositions of the invention.

In one embodiment, the cysteine residues at positions 48 and 107 of a protein having the amino acid sequence shown in SEQ ID NO:134 are deleted or substituted with another amino acid residue but the cysteine at position 61 is left in place. Further, the modified polypeptide is then used to prepare vaccine compositions of the invention.

As set out below in Example 31, the cysteine residues at positions 48 and 107, which are accessible to solvent, may be removed, for example, by site-directed mutagenesis. Further, the inventors have found that the Cys-48-Ser, Cys-107-Ser HBcAg double mutant constructed as described in Example 31 can be expressed in *E. coli.*

As discussed above, the elimination of free cysteine residues reduces the number of sites where toxic components can bind to the HBcAg, and also eliminates sites where cross-linking of lysine and cysteine residues of the same or of neighboring HBcAg molecules can occur. The cysteine at position 61, which is involved in dimer formation and forms a disulfide bridge with the cysteine at position 61 of another HBcAg, will normally be left intact for stabilization of HBcAg dimers and multimers of the invention.

As shown in Example 32, cross-linking experiments performed with (1) HBcAgs containing free cysteine residues and (2) HBcAgs whose free cysteine residues have been made unreactive with iodacetamide, indicate that free cysteine residues of the HBcAg are responsible for cross-linking between HBcAgs through reactions between heterobifunctional cross-linker derivatized lysine side chains, and free cysteine residues Example 32 also indicates that cross-linking of HBcAg subunits leads to the formation of high molecular weight species of undefined size which cannot be resolved by SDS-polyacrylamide gel electrophoresis.

When an antigen or antigenic determinant is linked to the non-natural molecular scaffold through a lysine residue, it may be advantageous to either substitute or delete one or both of the naturally resident lysine residues located at positions corresponding to positions 7 and 96 in SEQ ID NO:134, as well as other lysine residues present in HBcAg variants. The elimination of these lysine residues results in the removal of binding sites for antigens or antigenic determinants which could disrupt the ordered array and should improve the quality and uniformity of the final vaccine composition.

In many instances, when both of the naturally resident lysine residues at positions corresponding to positions 7 and 96 in SEQ ID NO:134 are eliminated, another lysine will be introduced into the HBcAg as an attachment site for an antigen or antigenic determinant. Methods for inserting such a lysine residue are set out, for example, in Example 23 below. It will often be advantageous to introduce a lysine residue into the HBcAg when, for example, both of the naturally resident lysine residues at positions corresponding to positions 7 and 96 in SEQ ID NO:134 are altered and one seeks to attach the antigen or antigenic determinant to the non-natural molecular scaffold using a heterobifunctional cross-linking agent.

The C-terminus of the HBcAg has been shown to direct nuclear localization of this protein (Eckhardt et al., *J. Virol.* 65:575–582 (1991).) Further, this region of the protein is also believed to confer upon the HBcAg the ability to bind nucleic acids.

In some embodiments, vaccine compositions of the invention will contain HBcAgs which have nucleic acid binding activity (e.g., which contain a naturally resident HBcAg nucleic acid binding domain). HBcAgs containing one or more nucleic acid binding domains are useful for preparing vaccine compositions which exhibit enhanced T-cell stimulatory activity. Thus, the vaccine compositions of the invention include compositions which contain HBcAgs having nucleic acid binding activity. Further included are vaccine compositions, as well as the use of such compositions in vaccination protocols, where HBcAgs are bound to nucleic acids. These HBcAgs may bind to the nucleic acids prior to administration to an individual or may bind the nucleic acids after administration.

In other embodiments, vaccine compositions of the invention will contain HBcAgs from which the C-terminal region (e.g., amino acid residues 145–185 or 150–185 of SEQ ID NO:134) has been removed and do not bind nucleic acids. Thus, additional modified HBcAgs suitable for use in the practice of the present invention include C-terminal truncation mutants. Suitable truncation mutants include HBcAgs where 1, 5, 10, 15, 20, 25, 30, 34, 35, 36, 37, 38, 39, 40, 41, 42 or 48 amino acids have been removed from the C-terminus.

HBcAgs suitable for use in the practice of the present invention also include N-terminal truncation mutants. Suitable truncation mutants include modified HBcAgs where 1, 2, 5, 7, 9, 10, 12, 14, 15, and 17 amino acids have been removed from the N-terminus.

Further HBcAgs suitable for use in the practice of the present invention include N- and C-terminal truncation mutants. Suitable truncation mutants include HBcAgs where 1, 2, 5, 7, 9, 10, 12, 14, 15, and 17 amino acids have been removed from the N-terminus and 1, 5, 10, 15, 20, 25, 30, 34, 35, 36, 37, 38, 39 40, 41, 42 or 48 amino acids have been removed from the C-terminus.

The invention further includes vaccine compositions comprising HBcAg polypeptides comprising, or alternatively consisting of, amino acid sequences which are at least 80%, 85%, 90%, 95%, 97%, or 99% identical to the above described truncation mutants.

As discussed above, in certain embodiments of the invention, a lysine residue is introduced as a first attachment site into a polypeptide which forms the non-natural molecular scaffold. In preferred embodiments, vaccine compositions of the invention are prepared using a HBcAg comprising, or alternatively consisting of, amino acids 1–144 or amino acids 1–149 of SEQ ID NO:134 which is modified so that the amino acids corresponding to positions 79 and 80 are replaced with a peptide having the amino acid sequence of Gly-Gly-Lys-Gly-Gly (SEQ ID NO:158) and the cysteine residues at positions 48 and 107 are either deleted or substituted with another amino acid residue, while the cysteine at position 61 is left in place. The invention further includes vaccine compositions comprising corresponding fragments of polypeptides having amino acid sequences shown in any of SEQ ID NOs:89–132 and 135–136 which also have the above noted amino acid alterations.

The invention further includes vaccine compositions comprising fragments of a HBcAg comprising, or alternatively consisting of, an amino acid sequence other than that shown in SEQ ID NO:134 from which a cysteine residue not present at corresponding location in SEQ ID NO:134 has been deleted. One example of such a fragment would be a polypeptide comprising, or alternatively consisting of, amino acids amino acids 1–149 of SEQ ID NO:132 where the cysteine residue at position 147 has been either substituted with another amino acid residue or deleted.

The invention further includes vaccine compositions comprising HBcAg polypeptides comprising, or alternatively consisting of, amino acid sequences which are at least 80%, 85%, 90%, 95%, 97%, or 99% identical to amino acids 1–144 or 1–149 of SEQ ID NO:134 and corresponding subportions of a polypeptide comprising an amino acid sequence shown in any of SEQ ID NOs:89–132 or 134–136, as well as to amino acids 1–147 or 1–152 of SEQ ID NO:158.

The invention also includes vaccine compositions comprising HBcAg polypeptides comprising, or alternatively consisting of, amino acid sequences which are at least 80%, 85%, 90%, 95%, 97%, or 99% identical to amino acids 36–240, 36–269, 44–240, 44–269, 36–305, and 44–305 of SEQ ID NO:137 or 36–240, 36–269, 44–240, 44–269, 36–305, and 44–305 of SEQ ID NO:138.

Vaccine compositions of the invention may comprise mixtures of different HBcAgs. Thus, these vaccine compositions may be composed of HBcAgs which differ in amino acid sequence. For example, vaccine compositions could be prepared comprising a "wild-type" HBcAg and a modified HBcAg in which one or more amino acid residues have been altered (e.g., deleted, inserted or substituted). In most applications, however, only one type of a HBcAg, or at least HBcAgs having essentially equivalent first attachment sites, will be used because vaccines prepared using such HBcAgs will present highly ordered and repetitive arrays of antigens or antigenic determinants. Further, preferred vaccine compositions of the invention are those which present highly ordered and repetitive antigen arrays.

The invention further includes vaccine compositions where the non-natural molecular scaffold is prepared using a HBcAg fused to another protein. As discussed above, one example of such a fusion protein is a HBcAg/FOS fusion. Other examples of HBcAg fusion proteins suitable for use in vaccine compositions of the invention include fusion proteins where an amino acid sequence has been added which aids in the formation and/or stabilization of HBcAg dimers and multimers. This additional amino acid sequence may be fused to either the N- or C-terminus of the HBcAg. One example, of such a fusion protein is a fusion of a HBcAg with the GCN4 helix region of *Saccharomyces cerevisiae* (GenBank Accession No. P03069 (SEQ ID NO:154)).

The helix domain of the GCN4 protein forms homodimers via non-covalent interactions which can be used to prepare and stabilize HBcAg dimers and multimers.

In one embodiment, the invention provides vaccine compositions prepared using HBcAg fusions proteins comprising a HBcAg, or fragment thereof, with a GCN4 polypeptide having the sequence of amino acid residues 227 to 276 in SEQ ID NO:154 fused to the C-terminus. This GCN4 polypeptide may also be fused to the N-terminus of the HbcAg.

HBcAg/src homology 3 (SH3) domain fusion proteins could also be used to prepare vaccine compositions of the invention. SH3 domains are relatively small domains found in a number of proteins which confer the ability to interact with specific proline-rich sequences in protein binding partners (see McPherson, *Cell Signal* 11:229–238 (1999). HBcAg/SH3 fusion proteins could be used in several ways. First, the SH3 domain could form a first attachment site which interacts with a second attachment site of the antigen or antigenic determinant. Similarly, a proline rich amino acid sequence could be added to the HBcAg and used as a first attachment site for an SH3 domain second attachment site of an antigen or antigenic determinant. Second, the SH3 domain could associate with proline rich regions introduced into HBcAgs. Thus, SH3 domains and proline rich SH3 interaction sites could be inserted into either the same or different HBcAgs and used to form and stabilized dimers and multimers of the invention.

In other embodiments, a bacterial pilin, a subportion of a bacterial pilin, or a fusion protein which contains either a bacterial pilin or subportion thereof is used to prepare vaccine compositions of the invention. Examples of pilin proteins include pilins produced by *Escherichia coli, Haemophilus influenzae, Neisseria meningitidis, Neisseria gonorrhoeae, Caulobacter crescentus, Pseudomonas stutzeri*, and *Pseudomonas aeruginosa*. The amino acid sequences of pilin proteins suitable for use with the present invention include those set out in GenBank reports AJ000636 (SEQ ID NO:139), AJ132364 (SEQ ID NO:140), AF229646 (SEQ ID NO:141), AF051814 (SEQ ID NO:142), AF051815 (SEQ ID NO:143), and X00981 (SEQ ID NO:155), the entire disclosures of which are incorporated herein by reference.

Bacterial pilin proteins are generally processed to remove N-terminal leader sequences prior to export of the proteins into the bacterial periplasm.

Further, as one skilled in the art would recognize, bacterial pilin proteins used to prepare vaccine compositions of the invention will generally not have the naturally present leader sequence.

One specific example of a pilin protein suitable for use in the present invention is the P-pilin of *E. coli* (GenBank report AF237482 (SEQ ID NO:144)). An example of a Type-1 *E. coli* pilin suitable for use with the invention is a pilin having the amino acid sequence set out in GenBank report P04128 (SEQ ID NO:146), which is encoded by nucleic acid having the nucleotide sequence set out in GenBank report M27603 (SEQ ID NO:145). The entire disclosures of these GenBank reports are incorporated herein by reference. Again, the mature form of the above referenced protein would generally be used to prepare vaccine compositions of the invention. Another example of a pilin protein is SEQ ID NO: 184, which is identical to SEQ ID NO: 146, except that in SEQ ID NO: 146, amino acid 20 is threonine, but in SEQ ID NO:184, amino acid 20 is alanine.

Bacterial pilins or pilin subportions suitable for use in the practice of the present invention will generally be able to associate to form non-natural molecular scaffolds.

Methods for preparing pili and pilus-like structures in vitro are known in the art. Bullitt et al., *Proc. Natl. Acad. Sci. USA* 93:12890–12895 (1996), for example, describe the in vitro reconstitution of *E. coli* P-pili subunits. Further, Eshdat et al., *J. Bacteriol.* 148:308–314 (1981) describe methods suitable for dissociating Type-1 pili of *E. coli* and the reconstitution of pili. In brief, these methods are as follows: pili are dissociated by incubation at 37° C. in saturated guanidine hydrochloride. Pilin proteins are then purified by chromatography, after which pilin dimers are formed by dialysis against 5 mM tris(hydroxymethyl)aminomethane hydrochloride (pH 8.0). Eshdat et al. also found that pilin dimers reassemble to form pili upon dialysis against the 5 mM tris(hydroxymethyl)aminomethane (pH 8.0) containing 5 mM $MgCl_2$.

Further, using, for example, conventional genetic engineering and protein modification methods, pilin proteins may be modified to contain a first attachment site to which an antigen or antigenic determinant is linked through a second attachment site. Alternatively, antigens or antigenic determinants can be directly linked through a second attachment site to amino acid residues which are naturally resident in these proteins. These modified pilin proteins may then be used in vaccine compositions of the invention.

Bacterial pilin proteins used to prepare vaccine compositions of the invention may be modified in a manner similar to that described herein for HBcAg. For example, cysteine and lysine residues may be either deleted or substituted with other amino acid residues and first attachment sites may be added to these proteins. Further, pilin proteins may either be expressed in modified form or may be chemically modified after expression. Similarly, intact pili may be harvested from bacteria and then modified chemically.

In another embodiment, pili or pilus-like structures are harvested from bacteria (e.g., *E. coli*) and used to form vaccine compositions of the invention. One example of pili suitable for preparing vaccine compositions is the Type-1 pilus of *E. coli*, which is formed from pilin monomers having the amino acid sequence set out in SEQ ID NO:146.

A number of methods for harvesting bacterial pili are known in the art. Bullitt and Makowski (*Biophys. J.* 74:623–632 (1998)), for example, describe a pilus purification method for harvesting P-pili from *E. coli*. According to this method, pili are sheared from hyperpiliated *E. coli* containing a P-pilus plasmid and purified by cycles of solubilization and $MgCl_2$ (1.0 M) precipitation. A similar purification method is set out below in Example 33.

Once harvested, pili or pilus-like structures may be modified in a variety of ways. For example, a first attachment site can be added to the pili to which antigens or antigen determinants may be attached through a second attachment site. In other words, bacterial pili or pilus-like structures can be harvested and modified to form non-natural molecular scaffolds.

Pili or pilus-like structures may also be modified by the attachment of antigens or antigenic determinants in the absence of a non-natural organizer. For example, antigens or antigenic determinants could be linked to naturally occurring cysteine resides or lysine residues. In such instances, the high order and repetitiveness of a naturally occurring amino acid residue would guide the coupling of the antigens or antigenic determinants to the pili or pilus-like structures. For example, the pili or pilus-like structures could be linked to the second attachment sites of the antigens or antigenic determinants using a heterobifunctional cross-linking agent.

When structures which are naturally synthesized by organisms (e.g., pili) are used to prepare vaccine compositions of the invention, it will often be advantageous to genetically engineer these organisms so that they produce structures having desirable characteristics. For example, when Type-1 pili of *E. coli* are used, the *E. coli* from which these pili are harvested may be modified so as to produce structures with specific characteristics. Examples of possible modifications of pilin proteins include the insertion of one or more lysine residues, the deletion or substitution of one or more of the naturally resident lysine residues, and the deletion or substitution of one or more naturally resident cysteine residues (e.g., the cysteine residues at positions 44 and 84 in SEQ ID NO:146).

Further, additional modifications can be made to pilin genes which result in the expression products containing a first attachment site other than a lysine residue (e.g., a FOS or JUN domain). Of course, suitable first attachment sites will generally be limited to those which do not prevent pilin proteins from forming pili or pilus-like structures suitable for use in vaccine compositions of the invention.

Pilin genes which naturally reside in bacterial cells can be modified in vivo (e.g., by homologous recombination) or pilin genes with particular characteristics can be inserted into these cells. For examples, pilin genes could be introduced into bacterial cells as a component of either a replicable cloning vector or a vector which inserts into the bacterial chromosome. The inserted pilin genes may also be linked to expression regulatory control sequences (e.g., a lac operator).

In most instances, the pili or pilus-like structures used in vaccine compositions of the invention will be composed of single type of a pilin subunit. Pili or pilus-like structures composed of identical subunits will generally be used because they are expected to form structures which present highly ordered and repetitive antigen arrays.

However, the compositions of the invention also include vaccines comprising pili or pilus-like structures formed from heterogenous pilin subunits. The pilin subunits which form these pili or pilus-like structures can be expressed from genes naturally resident in the bacterial cell or may be introduced into the cells. When a naturally resident pilin gene and an introduced gene are both expressed in a cell which forms pili or pilus-like structures, the result will generally be structures formed from a mixture of these pilin proteins. Further, when two or more pilin genes are expressed in a bacterial cell, the relative expression of each pilin gene will typically be the factor which determines the ratio of the different pilin subunits in the pili or pilus-like structures.

When pili or pilus-like structures having a particular composition of mixed pilin subunits is desired, the expression of at least one of the pilin genes can be regulated by a heterologous, inducible promoter. Such promoters, as well as other genetic elements, can be used to regulate the relative amounts of different pilin subunits produced in the bacterial cell and, hence, the composition of the pili or pilus-like structures.

In additional, while in most instances the antigen or antigenic determinant will be linked to bacterial pili or pilus-like structures by a bond which is not a peptide bond, bacterial cells which produce pili or pilus-like structures used in the compositions of the invention can be genetically engineered to generate pilin proteins which are fused to an antigen or antigenic determinant. Such fusion proteins which form pili or pilus-like structures are suitable for use in vaccine compositions of the invention.

The inventors surprisingly found that bacterial Pili induced an antibody response dominated by the IgG1 isotype in mince. This type of antibodies is indicative for a Th2 response. Moreover, antigens coupled to Pili also induced a IgG1 response indicating that coupling of antigens to Pili was sufficient for induction of antigen-specific Th2 responses.

B. Construction of an Antigen or Antigenic Determinant with a Second Attachment Site The second element in the compositions of the invention is an antigen or antigenic determinant possessing at least one second attachment site capable of association through at least one non-peptide bond to the first attachment site of the non-natural molecular scaffold. The invention provides for compositions that vary according to the antigen or antigenic determinant selected in consideration of the desired therapeutic effect. Other compositions are provided by varying the molecule selected for the second attachment site.

However, when bacterial pili, or pilus-like structures, pilin proteins are used to prepare vaccine compositions of the invention, antigens or antigenic determinants may be attached to pilin proteins by the expression of pilin/antigen fusion proteins. Antigen and antigenic determinants may also be attached to bacterial pili, or pilus-like structures, pilin proteins through non-peptide bonds.

Antigens of the invention may be selected from the group consisting of the following: (a) proteins suited to induce an immune response against cancer cells; (b) proteins suited to induce an immune response against infectious diseases; (c) proteins suited to induce an immune response against allergens, (d) proteins suited to induce an immune response in farm animals, and (e) fragments (e.g., a domain) of any of the proteins set out in (a)–(d).

In one specific embodiment of the invention, the antigen or antigenic determinant is one that is useful for the prevention of infectious disease. Such treatment will be useful to treat a wide variety of infectious diseases affecting a wide range of hosts, e.g., human, cow, sheep, pig, dog, cat, other mammalian species and non-mammalian species as well. Treatable infectious diseases are well known to those skilled in the art, examples include infections of viral etiology such as HIV, influenza, Herpes, viral hepatitis, Epstein Bar, polio, viral encephalitis, measles, chicken pox, etc.; or infections of bacterial etiology such as pneumonia, tuberculosis, syphilis, etc.; or infections of parasitic etiology such as malaria, trypanosomiasis, leishmaniasis, trichomoniasis, amoebiasis, etc. Thus, antigens or antigenic determinants selected for the compositions of the invention will be well known to those in the medical art; examples of antigens or antigenic determinants include the following: the HIV antigens gp140 and gp160; the influenaza antigens hemagglutinin and neuraminidase, Hepatitis B surface antigen, circumsporozoite protein of malaria.

In another specific embodiment, compositions of the invention are an immunotherapeutic that may be used for the treatment of allergies or cancer.

The selection of antigens or antigenic determinants for compositions and methods of treatment for allergies would be known to those skilled in the medical art treating such disorders; representative examples of this type of antigen or antigenic determinant include the following: bee venom phospholipase $A_2$, Bet v I (birch pollen allergen), 5 Dol m V (white-faced hornet venom allergen), Der p I (House dust mite allergen).

The selection of antigens or antigenic determinants for compositions and methods of treatment for cancer would be known to those skilled in the medical art treating such disorders; representative examples of this type of antigen or antigenic determinant include the following: Her2 (breast cancer), GD2 (neuroblastoma), EGF-R (malignant glioblastoma), CEA (medullary thyroid cancer), CD52 (leukemia).

In a particular embodiment of the invention, the antigen or antigenic determinant is selected from the group consisting of: (a) a recombinant protein of HIV, (b) a recombinant protein of Influenza virus, (c) a recombinant protein of Hepatitis B virus, (d) a recombinant protein of *Toxoplasma*, (e) a recombinant protein of *Plasmodium falciparum*, (f) a recombinant protein of *Plasmodium vivax*, (g) a recombinant protein of *Plasmodium ovale*, (h) a recombinant protein of *Plasmodium malariae*, (i) a recombinant protein of breast cancer cells, (j) a recombinant protein of kidney cancer cells, (k) a recombinant protein of prostate cancer cells, (l) a recombinant protein of skin cancer cells, (m) a recombinant protein of brain cancer cells, (n) a recombinant protein of leukemia cells, (o) a recombinant profiling, (p) a recombinant protein of bee sting allergy, (q) a recombinant proteins of nut allergy, (r) a recombinant proteins of food allergies, (s) recombinant proteins of asthma, (t) a recombinant protein of *Chlamydia*, and (u) a fragment of any of the proteins set out in (a)–(t).

Once the antigen or antigenic determinant of the composition is chosen, at least one second attachment site may be added to the molecule in preparing to construct the organized and repetitive array associated with the non-natural molecular scaffold of the invention. Knowledge of what will constitute an appropriate second attachment site will be known to those skilled in the art. Representative examples of second attachment sites include, but are not limited to, the following: an antigen, an antibody or antibody fragment, biotin, avidin, strepavidin, a receptor, a receptor ligand, a ligand, a ligand-binding protein, an interacting leucine zipper polypeptide, an amino group, a chemical group reactive to an amino group; a carboxyl group, chemical group reactive to a carboxyl group, a sulfhydryl group, a chemical group reactive to a sulfhydryl group, or a combination thereof.

The association between the first and second attachment sites will be determined by the characteristics of the respective molecules selected but will comprise at least one non-peptide bond. Depending upon the combination of first and second attachment sites, the nature of the association may be covalent, ionic, hydrophobic, polar, or a combination thereof.

In one embodiment of the invention, the second attachment site may be the FOS leucine zipper protein domain or the JUN leucine zipper protein domain.

In a more specific embodiment of the invention, the second attachment site selected is the FOS leucine zipper protein domain, which associates specifically with the JUN leucine zipper protein domain of the non-natural molecular scaffold of the invention. The association of the JUN and FOS leucine zipper protein domains provides a basis for the formation of an organized and repetitive antigen or antigenic determinant array on the surface of the scaffold. The FOS leucine zipper protein domain may be fused in frame to the antigen or antigenic determinant of choice at either the amino terminus, carboxyl terminus or internally located in the protein if desired.

Several FOS fusion constructs are provided for exemplary purposes. Human growth hormone (Example 4), bee venom phospholipase $A_2$ (PLA) (Example 9), ovalbumin (Example 10) and HIV gp140 (Example 12).

In order to simplify the generation of FOS fusion constructs, several vectors are disclosed that provide options for antigen or antigenic determinant design and construction (see Example 6). The vectors pAV1–4 were designed for the expression of FOS fusion in *E. coli*; the vectors pAV5 and pAV6 were designed for the expression of FOS fusion proteins in eukaryotic cells. Properties of these vectors are briefly described.

1. pAV1: This vector was designed for the secretion of fusion proteins with FOS at the C-terminus into the *E. coli* periplasmic space. The gene of interest (g.o.i.) may be ligated into the StuI/NotI sites of the vector.

2. pAV2: This vector was designed for the secretion of fusion proteins with FOS at the N-terminus into the *E. coli* periplasmic space. The gene of interest (g.o.i.) ligated into the NotI/EcoRV (or NotI/HindIII) sites of the vector.

3. pAV3: This vector was designed for the cytoplasmic production of fusion proteins with FOS at the C-terminus in *E. coli*. The gene of interest (g.o.i.) may be ligated into the EcoRV/NotI sites of the vector.

4. pAV4: This vector is designed for the cytoplasmic production of fusion proteins with FOS at the N-terminus in *E. coli*. The gene of interest (g.o.i.) may be ligated into the NotI/EcoRV (or NotI/HindIII) sites of the vector. The N-terminal methionine residue is proteolytically removed upon protein synthesis (Hirel et al., *Proc. Natl. Acad. Sci. USA* 86:8247–8251 (1989)).

5. pAV5: This vector was designed for the eukaryotic production of fusion proteins with FOS at the C-terminus. The gene of interest (g.o.i.) may be inserted between the sequences coding for the hGH signal sequence and the FOS domain by ligation into the Eco47III/NotI sites of the vector. Alternatively, a gene containing its own signal sequence may be fused to the FOS coding region by ligation into the StuI/NotI sites.

6. pAV6: This vector was designed for the eukaryotic production of fusion proteins with FOS at the N-terminus. The gene of interest (g.o.i.) may be ligated into the NotI/StuI (or NotI/HindIII) sites of the vector.

As will be understood by those skilled in the art, the construction of a FOS-antigen or -antigenic determinant fusion protein may include the addition of certain genetic elements to facilitate production of the recombinant protein. Example 4 provides guidance for the addition of certain *E. coli* regulatory elements for translation, and Example 7 provides guidance for the addition of a eukaryotic signal sequence. Other genetic elements may be selected, depending on the specific needs of the practioner.

The invention is also seen to include the production of the FOS-antigen or FOS-antigenic determinant fusion protein either in bacterial (Example 5) or eukaryotic cells (Example 8). The choice of which cell type in which to express the fusion protein is within the knowledge of the skilled artisan, depending on factors such as whether post-translational modifications are an important consideration in the design of the composition.

As noted previously, the invention discloses various methods for the construction of a FOS-antigen or FOS-antigenic determinant fusion protein through the use of the pAV vectors. In addition to enabling prokaryotic and eukaryotic expression, these vectors allow the practitioner to choose between N- and C-terminal addition to the antigen of the FOS leucine zipper protein domain. Specific examples are provided wherein N- and C-terminal FOS fusions are made to PLA (Example 9) and ovalbumin (Example 10). Example 11 demonstrates the purification of the PLA and ovalbumin FOS fusion proteins.

In a more specific embodiment, the invention is drawn to an antigen or antigenic determinant encoded by the HIV genome. More specifically, the HIV antigen is gp140. As provided for in Examples 11–15, HIV gp140 may be created with a FOS leucine zipper protein domain and the fusion protein synthesized and purified for attachment to the non-natural molecular scaffold of the invention. As one skilled in the art would know, other HIV antigens or antigenic determinants may be used in the creation of a composition of the invention.

In a more specific embodiment of the invention, the second attachment site selected is a cysteine residue, which associates specifically with a lysine residue of the non-natural molecular scaffold of the invention. The chemical linkage of the lysine residue (Lys) and cysteine residue (Cys) provides a basis for the formation of an organized and repetitive antigen or antigenic determinant array on the surface of the scaffold. The cysteine residue may be engineered in frame to the antigen or antigenic determinant of choice at either the amino terminus, carboxyl terminus or internally located in the protein if desired. By way of example, PLA and HIV gp140 are provided with a cysteine residue for linkage to a lysine residue first attachment site.

C. Preparation of the AlphaVaccine Particles

The invention provides novel compositions and methods for the construction of ordered and repetitive antigen arrays. As one of skill in the art would know, the conditions for the assembly of the ordered and repetitive antigen array depend to a large extent on the specific choice of the first attachment site of the non-natural molecular scaffold and the specific choice of the second attachment site of the antigen or antigenic determinant. Thus, practitioner choice in the design of the composition (i.e., selection of the first and second attachment sites, antigen and non-natural molecular scaffold) will determine the specific conditions for the assembly of the AlphaVaccine particle (the ordered and repetitive antigen array and non-natural molecular scaffold combined). Information relating to assembly of the AlphaVaccine particle is well within the working knowledge of the practitioner, and numerous references exist to aid the practitioner (e.g., Sambrook, J et al., eds, MOLECULAR CLONING, A LABORATORY MANUAL, 2nd. edition, Cold Spring Harbor Laboratory Press, Cold Spring Harbor, N.Y. (1989); Ausubel, F. et al., eds., CURRENT PROTOCOLS IN MOLECULAR BIOLOGY, John H. Wiley & Sons, Inc. (1997); Celis, J., ed., CELL BIOLGY, Academic Press, $2^{nd}$ edition, (1998); Harlow, E. and Lane, D., "Antibodies: A Laboratory Manual," Cold Spring Harbor Laboratory, Cold Spring Harbor, N.Y. (1988), all of which are incorporated herein by reference.

In a specific embodiment of the invention, the JUN and FOS leucine zipper protein domains are utilized for the first and second attachment sites of the invention, respectively. In the preparation of AlphaVaccine particles, antigen must be produced and purified under conditions to promote assembly of the ordered and repetitive antigen array onto the non-natural molecular scaffold. In the particular JUN/FOS leucine zipper protein domain embodiment, the FOS-antigen or FOS-antigenic determinant should be treated with a reducing agent (e.g., Dithiothreitol (DTT)) to reduce or eliminate the incidence of disulfide bond formation (Example 15).

For the preparation of the non-natural molecular scaffold (i.e., recombinant Sinbis virus) of the JUN/FOS leucine zipper protein domain embodiment, recombinant E2-JUN viral particles should be concentrated, neutralized and treated with reducing agent (see Example 16).

Assembly of the ordered and repetitive antigen array in the JUN/FOS embodiment is done in the presence of a redox shuffle. E2-JUN viral particles are combined with a 240 fold molar excess of FOS-antigen or FOS-antigenic determinant for 10 hours at 4° C. Subsequently, the AlphaVaccine particle is concentrated and purified by chromatography (Example 16).

In another embodiment of the invention, the coupling of the non-natural molecular scaffold to the antigen or antigenic determinant may be accomplished by chemical cross-linking. In a specific embodiment, the chemical agent is a heterobifunctional cross-linking agent such as ε-maleimidocaproic acid N-hydroxysuccinimide ester (Tanimori et al., *J. Pharm. Dyn.* 4:812 (1981); Fujiwara et al., *J. Immunol. Meth.* 45:195 (1981)), which contains (1) a succinimide group reactive with amino groups and (2) a maleimide group reactive with SH groups. A heterologous protein or polypeptide of the first attachment site may be engineered to contain one or more lysine residues that will serve as a reactive moiety for the succinimide portion of the heterobifunctional cross-linking agent. Once chemically coupled to the lysine residues of the heterologous protein, the maleimide group of the heterobifunctional cross-linking agent will be available to react with the SH group of a cysteine residue on the antigen or antigenic determinant. Antigen or antigenic determinant preparation in this instance may require the engineering of a cysteine residue into the protein or polypeptide chosen as the second attachment site so that it may be reacted to the free maleimide function on the cross-linking agent bound to the non-natural molecular scaffold first attachment sites. Thus, in such an instance, the heterobifunctional cross-linking agent binds to a first attachment site of the non-natural molecular scaffold and connects the scaffold to a second binding site of the antigen or antigenic determinant.

3. Compositions, Vaccines, and the Administration Thereof, and Methods of Treatment In one embodiment, the invention provides vaccines for the prevention of infectious diseases in a wide range of species, particularly mammalian species such as human, monkey, cow, dog, cat, horse, pig, etc. Vaccines may be designed to treat infections of viral etiology such as HIV, influenza, Herpes, viral hepatitis, Epstein Bar, polio, viral encephalitis, measles, chicken pox, etc.; or infections of bacterial etiology such as pneumonia, tuberculosis, syphilis, etc.; or infections of parasitic etiology such as malaria, trypanosomiasis, leishmaniasis, trichomoniasis, amoebiasis, etc.

In another embodiment, the invention provides vaccines for the prevention of cancer in a wide range of species, particularly mammalian species such as human, monkey, cow, dog, cat, horse, pig, etc. Vaccines may be designed to treat all types of cancer: lymphomas, carcinomas, sarcomas, melanomas, etc.

In another embodiment of the invention, compositions of the invention may be used in the design of vaccines for the treatment of allergies. Antibodies of the IgE isotype are important components in allergic reactions. Mast cells bind IgE antibodies on their surface and release histamines and other mediators of allergic response upon binding of specific antigen to the IgE molecules bound on the mast cell surface. Inhibiting production of IgE antibodies, therefore, is a promising target to protect against allergies. This should be possible by attaining a desired T helper cell response. T helper cell responses can be divided into type 1 ($T_H1$) and type 2 ($T_H2$) T helper cell responses (Romagnani, *Immunol. Today* 18:263–266 (1997)). $T_H1$ cells secrete interferon-gamma and other cytokines which trigger B cells to produce protective IgG antibodies. In contrast, a critical cytokine produced by $T_H2$ cells is IL-4, which drive B cells to produce IgE. In many experimental systems, the development of $T_H1$ and $T_H2$ responses is mutually exclusive since $T_H1$ cells suppress the induction of $T_H2$ cells and vice versa. Thus, antigens that trigger a strong $T_H1$ response simultaneously suppress the development of $T_H2$ responses and hence the production of IgE antibodies. Interestingly, virtually all viruses induce a $T_H1$ response in the host and fail to trigger the production of IgE antibodies (Coutelier et al., *J. Exp. Med.* 165:64–69 (1987)). This isotype pattern is not restricted to live viruses but has also been observed for inactivated or recombinant viral particles (Lo-Man et al., *Eur. J. Immunol.* 28:1401–1407 (1998)) Thus, by using the processes of the invention (e.g., Alpha Vaccine Technology), viral particles can be decorated with various allergens and used for immunization Due to the resulting "viral structure" of the allergen, a $T_H1$ response will be elicited, "protective" IgG antibodies will be produced, and the production of IgE antibodies which cause allergic reactions will be prevented. Since the allergen is presented by viral particles which are recognized by a different set of helper T cells than the allergen itself, it is likely that the allergen-specific IgG antibodies will be induced even in allergic individuals harboring pre-existing $T_H2$ cells specific for the allergen. The presence of high concentrations of IgG antibodies may prevent binding of allergens to mast cell bound IgE, thereby inhibiting the release of histamine. Thus, presence of IgG antibodies may protect from IgE mediated allergic reactions. Typical substances causing allergies include: grass, ragweed, birch or mountain cedar pollens, house dust, mites, animal danders, mold, insect venom or drugs (e.g., penicillin). Thus, immunization of individuals with allergen-decorated viral particles should be beneficial not only before but also after the onset of allergies. Food allergies are also very common, and immunization of subjects with particles decorated with food allergens should be useful for the treatment of these allergies.

In another embodiment, the invention relates to the induction of specific Th type 2 (Th2) cells. The inventors surprisingly found that bacterial Pili induce an antibody response dominated by the IgG1 isotype in mice, indicative of a Th2 response. Antigens coupled to Pili also induced a IgG1 response indicating that coupling of antigens to Pili was sufficient for induction of antigen-specific Th2 response. Many chronic diseases in humans an animals, such as arthritis, colitis, diabetes and multiple sclerosis are dominated by Th1 response, where T cells secrete IFNγ and other pro-inflammatory cytokines precipitating disease. By contrast, Th2 cells secrete Il-4, Il-13 and also Il-10. The latter cytokine is usually associated with immunosuppression and there is good evidence that specific Th2 cells can suppress chronic diseases, such as arthritis, colitis, diabetes and multiple sclerosis in vivo. Thus, induction of antigen-specific Th2 cells is desirable for the treatment of such chronic diseases.

It is known that induction of therapeutic self-specific antibodies may allow treating a variety of diseases. It is, e.g., known that anti-TNF antibodies can ameliorate symptoms in arthritis or colitis and antibodies specific for the Aβ-peptide may remove plaques from the brain of Alzheimers patients. It will usually be beneficial for the patient if such antibodies can be induced in the absence of a pro-inflammatory Th1 response. Thus, self antigens coupled to Pili that induce a strong antibody response but no Th1 response may be optimal for such immunotherapy.

In a preferred embodiment, the antigen is the amyloid beta peptide ($Aβ_{1-42}$) (DAEFRHDSGYEVHHQKL VFFAEDVGSNKGAIIGLMVGGVVIA (SEQ ID NO: 174), or a fragment thereof. The amyloid beta protein is SEQ ID NO: 172. The amyloid beta precursor protein is SEQ ID NO: 173.

The amyloid B peptide ($Aβ_{1-42}$) has a central role in the neuropathology of Alzheimers disease. Region specific, extracellular accumulation of Aβ peptide is accompanied by microgliosis, cytoskeletal changes, dystrophic neuritis and synaptic loss. These pathological alterations are thought to be linked to the cognitive decline that defines the disease.

In a mouse model of Alzheimer disease, transgenic animals engineered to produce $Aβ_{1-42}$ (PDAPP-mice), develop plaques and neuron damage in their brains. Recent work has shown immunization of young PDAPP-mice, using $Aβ_{1-42}$, resulted in inhibition of plaque formation and associated dystrophic neuritis (Schenk, D. et al., *Nature* 400:173–77 (1999)).

Furthermore immunization of older PDAPP mice that had already developed AD-like neuropathologies, reduced the extent and progression of the neuropathologies. The immunization protocol for these studies was as follows; peptide was dissolved in aqueous buffer and mixed 1:1 with complete Freunds adjuvant (for primary dose) to give a peptide concentration of 100 μg/dose. Subsequent boosts used incomplete Freunds adjuvant. Mice received 11 immunizations over an 11 month period. Antibodies titres greater than 1:10 000 were achieved and maintained. Hence, immunization may be an effective prophylactic and therapeutic action against Alzheimer disease.

In another study, peripherally administered antibodies raised against $Aβ_{1-42}$, were able to cross the blood-brain barrier, bind Aβ peptide, and induce clearance of pre-existing amyloid (Bard, F. et al., *Nature Medicine* 6: 916–19 (2000)). This study utilized either polyclonal antibodies raised against $Aβ_{1-42}$, or monoclonal antibodies raised against synthetic fragments derived from different regions of Aβ. Thus induction of antibodies can be considered as a potential therapeutic treatment for Alzheimer disease.

In another more specific embodiment, the invention is drawn to vaccine compositions comprising at least one antigen or antigenic determinant encoded by an Influenza viral nucleic acid, and the use of such vaccine compositions to elicit immune responses. In an even more specific embodiment, the Influenza antigen or antigenic determinant may be an M2 protein (e.g., an M2 protein having the amino acids shown in SEQ ID NO: 171, GenBank Accession No. P06821, or in SEQ ID NO: 170, PIR Accession No. MFIV62, or fragment thereof (e.g., amino acids from about 2 to about 24 in SEQ ID NO: 171, the amino acid sequence in SEQ ID NO: 170. Further, influenza antigens or antigenic determinants may be coupled to pili or pilus-like structures. Portions of an M2 protein (e.g., an M2 protein having the amino acid sequence in SEQ ID NO: 170), as well as other proteins against which an immunological response is sought, suitable for use with the invention may comprise, or alternatively consist of, peptides of any number of amino acids in length but will generally be at least 6 amino acids in length (e.g., peptides 6, 7, 8, 9, 10, 12, 15, 18, 20, 25, 30, 35, 40, 45, 50, 55, 60, 65, 70, 75, 80, 85, 90, 95, or 97 amino acids in length).

In an even more specific embodiment, the Influenza antigen or antigenic determinant may be an M2 protein (e.g., an M2 protein having the amino acids shown in SEQ ID NO: 170, GenBank Accession No. P06821, or in SEQ ID NO: 212, PIR Accession No. MFIV62, or fragment thereof (e.g., amino acids from about 2 to about 24 in SEQ ID NO: 171, the amino acid sequence in SEQ ID NO: 170).

As would be understood by one of ordinary skill in the art, when compositions of the invention are administered to an individual, they may be in a composition which contains salts, buffers, adjuvants, or other substances which are desirable for improving the efficacy of the composition. Examples of materials suitable for use in preparing pharmaceutical compositions are provided in numerous sources including REMINGTON'S PHARMACEUTICAL SCIENCES (Osol, A, ed., Mack Publishing Co., (1980)).

Compositions of the invention are said to be "pharmacologically acceptable" if their administration can be tolerated by a recipient individual. Further, the compositions of the invention will be administered in a "therapeutically effective amount" (i.e., an amount that produces a desired physiological effect).

The compositions of the present invention may be administered by various methods known in the art, but will normally be administered by injection, infusion, inhalation, oral administration, or other suitable physical methods. The compositions may alternatively be administered intramuscularly, intravenously, or subcutaneously. Components of compositions for administration include sterile aqueous (e.g., physiological saline) or non-aqueous solutions and suspensions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption.

The present invention also provides a composition comprising a bacterial pilin polypeptide to which an antigen or antigenic determinant has been attached by a covalent bond.

The present invention also provides a composition comprising a fragment of a bacteriophage coat protein to which an antigen or antigenic determinant has been attached by a covalent bond.

The present invention also provides a composition comprising (a) non-natural molecular scaffold comprising (i) a core particle selected from the group consisting of (1) a bacterial pilus or pilin protein; and (2) a recombinant form of a bacterial pilus or pilin protein; and (ii) an organizer comprising at least one first attachment site, wherein the organizer is connected to the core particle by at least one covalent bond; and (b) an antigen or antigenic determinant with at least one second attachment site, the second attachment site being selected from the group consisting of (i) an attachment site not naturally occurring with the antigen or antigenic determinant; and (ii) an attachment site naturally occurring with the antigen or antigenic determinant, wherein the second attachment site is capable of association through at least one non-peptide bond to the first attachment site; and wherein the antigen or antigenic determinant and the scaffold interact through the association to form an ordered and repetitive antigen array.

The present invention also provides a composition comprising (a) a non-natural molecular scaffold comprising (i) a core particle selected from the group consisting of: (1) a bacterial pilus; and (2) a recombinant form of a bacterial pilus; and (ii) an organizer comprising at least one first attachment site, wherein the organizer is connected to the core particle by at least one covalent bond; and (b) an antigen or antigenic determinant with at least one second attachment site, the second attachment site being selected from the group consisting of (i) an attachment site not naturally occurring with the antigen or antigenic determinant; and (ii) an attachment site naturally occurring with the antigen or antigenic determinant, wherein the second attachment site is capable of association through at least one non-peptide bond to the first attachment site; and wherein the antigen or antigenic determinant and the scaffold interact through the association to form an ordered and repetitive antigen array.

The present invention also provides a composition comprising (a) a non-natural molecular scaffold comprising (i) a virus-like particle that is a dimer or a multimer of a polypeptide comprising amino acids 1–147 of SEQ ID NO:158 as core particle; and (ii) an organizer comprising at least one first attachment site, wherein the organizer is connected to the core particle by at least one covalent bond; and (b) an antigen or antigenic determinant with at least one second attachment site, the second attachment site being selected from the group consisting of (i) an attachment site not naturally occurring with the antigen or antigenic determinant; and (ii) an attachment site naturally occurring with the antigen or antigenic determinant, wherein the second attachment site is capable of association through at least one non-peptide bond to the first attachment site; and wherein the antigen or antigenic determinant and the scaffold interact through the association to form an ordered and repetitive antigen array.

The present invention also provides a pharmaceutical composition comprising any of compositions of the present invention, and a pharmaceutically acceptable carrier.

The present invention also provides a vaccine composition comprising any of compositions of the present invention. The vaccine composition may further comprise at least one adjuvant. The present invention also provides a method of immunizing, comprising administering to a subject a vaccine composition of the present invention.

The present invention also provides a composition comprising (a) a non-natural molecular scaffold comprising (i) Hepatitis B virus capsid protein comprising an amino acid sequence selected from the group consisting of (1) the amino acid sequence of SEQ ID NO:89, (2) the amino acid sequence of SEQ ID NO:90 (3) the amino acid sequence of SEQ ID NO:93, (4) the amino acid sequence of SEQ ID NO:98, (5) the amino acid sequence of SEQ ID NO:99, (6) the amino acid sequence of SEQ ID NO:102, (7)the amino acid sequence of SEQ ID NO:104, (8) the amino acid sequence of SEQ ID NO:105, (9) the amino acid sequence of SEQ ID NO:106, (10) the amino acid sequence of SEQ ID NO:119, (11) the amino acid sequence of SEQ ID NO:120, (12) the amino acid sequence of SEQ ID NO:123, (13) the amino acid sequence of SEQ ID NO:125, (14) the amino acid sequence of SEQ ID NO:131, (15) the amino acid sequence of SEQ ID NO:132, (16) the amino acid sequence of SEQ ID NO:134, (17) the amino acid sequence of SEQ ID NO:157, and (18) the amino acid sequence of SEQ ID NO:158; and (ii) an organizer comprising at least one first attachment site, wherein the organizer is connected to the core particle by at least one covalent bond; and (b) an antigen or antigenic determinant with at least one second attachment site, the second attachment site being selected from the group consisting of (i) an attachment site not naturally occurring with the antigen or antigenic determinant; and (ii) an attachment site naturally occurring with the antigen or antigenic determinant, wherein the second attachment site is capable of association through at least one non-peptide bond to the first attachment site; and wherein the antigen or antigenic determinant and the scaffold interact through the association to form an ordered and repetitive antigen array. Preferably, the organizer is a polypeptide or residue thereof, wherein the second attachment site is a polypeptide or residue thereof, and wherein the first attachment site is a lysine residue and the second attachment site is a cysteine residue. Preferably, one or more cysteine residues of the Hepatitis B virus capsid protein have been either deleted or substituted with another amino acid residue. Preferably, the cysteine residues corresponding to amino acids 48 and 107 in SEQ ID NO:134 have been either deleted or substituted with another amino acid residue.

The present invention also provides a composition comprising: (1) a non-natural molecular scaffold comprising (i) a core particle selected from the group consisting of (1) a bacterial pilus, and (2) a recombinant form of a bacterial pilus or pilin protein; and (ii) an organizer comprising at least one first attachment site, wherein the organizer is connected to the core particle by at least one covalent bond; and (2) an antigen or antigenic determinant with at least one second attachment site, the second attachment site being selected from the group consisting of (i) an attachment site not naturally occurring with the antigen or antigenic determinant, and (ii) an attachment site naturally occurring with the antigen or antigenic determinant, wherein the second attachment site is capable of association through at least one non-peptide bond to the first attachment site, wherein the antigen or antigenic determinant and the scaffold interact through the association to form an ordered and repetitive antigen array, and wherein the antigen or antigenic determinant is selected from the group consisting of an influenza M2 peptide, the GRA2 polypeptide, the DP178c peptide, the tumor necrosis factor polypeptide, a tumor necrosis factor peptide, the B2 peptide, the D2 peptide, and the Aβ peptide.

In the compositions and vaccines of the present invention, for a covalent bond between a first and second attachment site, the covalent bond is preferably not a peptide bond.

If a bacterial pilus is present in a composition or vaccine of the present invention, the pilus is preferably a Type-1 pilus of *Eschericia coli*. More preferably, pilin subunits of the Type-1 pilus comprises the amino acid sequence shown in SEQ ID NO:146. Preferably, the bacterial pilus and the antigen or antigen determinant are attached via either a naturally or non-naturally occurring attachment. Preferably, the first attachment site will be a lysine residue, while the second attachment site will be a cysteine residue present or engineered on the antigen If the attachment comprises interacting leucine zipper polypeptides, the polypeptides are preferably JUN and/or FOS leucine zipper polypeptides.

In the compositions and vaccines of the present invention that comprise an organizer having a first attachment site, attached to the second attachment site on the antigen, the organizer is preferably a polypeptide or a residue thereof, and the second attachment site is preferably a polypeptide or a residue thereof. More preferably, the first and/or the second attachment sites comprise an antigen and an antibody or antibody fragment thereto, biotin and avidin, strepavidin and biotin, a receptor and its ligand, a ligand-binding protein and its ligand, interacting leucine zipper polypeptides, an amino group and a chemical group reactive thereto, a carboxyl group and a chemical group reactive thereto, a sulfhydryl group and a chemical group reactive thereto, or a combination thereof. More preferably, the first attachment site is an amino group, and the second attachment site is a sulfhydryl group.

In the compositions and vaccines of the present invention, the antigen is preferably selected from the group consisting of a protein suited to induce an immune response against cancer cells, a protein suited to induce an immune response against infectious diseases, a protein suited to induce an immune response against allergens, and a protein suited to induce an immune response in farm animals. Preferably, the antigen induces an immune response against one or more allergens. More preferably, the antigen is a recombinant protein of HIV, a recombinant protein of Influenza virus, a recombinant protein of Hepatitis C virus, a recombinant protein of Toxoplasma, a recombinant protein of *Plasmodium falciparum*, a recombinant protein of *Plasmodium vivax*, a recombinant protein of *Plasmodium ovale*, a recombinant protein of *Plasmodium malariae*, a recombinant protein of breast cancer cells, a recombinant protein of kidney cancer cells, a recombinant protein of prostate cancer cells, a recombinant protein of skin cancer cells, a recombinant protein of brain cancer cells, a recombinant protein of leukemia cells, a recombinant profiling, a recombinant protein of bee sting allergy, a recombinant protein of nut allergy, a recombinant protein of food allergies, or a recombinant protein of asthma, or a recombinant protein of Chlamydia.

In the method of immunizing provided by the present invention, the immunization produces an immune response in the subject. Preferably, the immunization produces a humoral immune response, a cellular immune response, a humoral and a cellular immune response, or a protective immune response.

In the compositions and vaccines of the present invention, the antigen or antigenic determinant is attached to the non-natural molecular scaffold through the first attachment site, to form an antigen array or antigenic determinant array. Preferably, the array is ordered and/or repetitive.

In the compositions and vaccines of the present invention, the first and/or the second attachment sites are preferably attached via either a non-naturally occurring attachment, or by an attachment comprising interacting leucine zipper polypeptides. More preferably, the interacting leucine zipper polypeptides are JUN and/or FOS leucine zipper polypeptides.

The present invention also provides a method for making the compositions and vaccines of the present invention, comprising combining the antigen or antigenic determinant with the non-natural molecular scaffold through the first attachment site and organizer present on the non-natural molecular scaffold.

In addition to vaccine technologies, other embodiments of the invention are drawn to methods of medical treatment for cancer, allergies, and chronic diseases.

Following is a protocol for analyzing pili by SDS-PAGE Analysis. Add trichloroacetic acid to a final concentration of 10% to the pili solution containing approx. 50 ug of pili. Vortex and incubate for 10 minutes on ice. Centrifuge at maximal speed for 5 minutes in a microcentrifuge. Discard the supernatant and resuspend the pellet in 50 ul of a 8.5 M guanidiniumhydrochloride, pH 3 solution. Heat the sample for 15 minutes at 70° C. Precipitate the protein by adding 1.5 ml of Ethanol precooled at −20° C., and centrifuge 5 minutes at RT at maximal speed. Resuspend the pellet in 15 ul of a 10 mM Tris, pH 8 buffer. Add SDS-PAGE sample buffer, vortex shortly and heat the sample 10 minutes at 100° C. Load the sample on a 12% gel.

EXAMPLES

Enzymes and reagents used in the experiments that follow included: T4 DNA ligase obtained from New England Biolabs; Taq DNA Polymerase, QIAprep Spin Plasmid Kit, QIAGEN Plasmid Midi Kit, QiaExII Gel Extraction Kit, QIAquick PCR Purification Kit obtained from QIAGEN; QuickPrep Micro mRNA Purification Kit obtained from Pharmacia; SuperScript One-step RT PCR Kit, fetal calf serum (FCS), bacto-tryptone and yeast extract obtained from Gibco BRL; Oligonucleotides obtained from Microsynth (Switzerland); restriction endonucleases obtained from Boehringer Mannheim, New England Biolabs or MBI Fermentas; Pwo polymerase and dNTPs obtained from Boehringer Mannheim. HP-1 medium was obtained from Cell culture technologies (Glattbrugg, Switzerland). All standard chemicals were obtained from Fluka-Sigma-Aldrich, and all cell culture materials were obtained from TPP.

DNA manipulations were carried out using standard techniques. DNA was prepared according to manufacturer instruction either from a 2 ml bacterial culture using the QIAprep Spin Plasmid Kit or from a 50 ml culture using the QIAGEN Plasmid Midi Kit. For restriction enzyme digestion, DNA was incubated at least 2 hours with the appropriate restriction enzyme at a concentration of 5–10 units (U) enzyme per mg DNA under manufacturer recommended conditions (buffer and temperature). Digests with more than one enzyme were performed simultaneously if reaction conditions were appropriate for all enzymes, otherwise consecutively. DNA fragments isolated for further manipulations were separated by electrophoresis in a 0.7 to 1.5% agarose gel, excised from the gel and purified with the QiaExII Gel Extraction Kit according to the instructions provided by the manufacturer. For ligation of DNA fragments, 100 to 200 pg of purified vector DNA were incubated overnight with a threefold molar excess of the insert fragment at 16° C. in the presence of 1 U T4 DNA ligase in the buffer provided by the manufacturer (total volume: 10–20 μl). An aliquot (0.1 to 0.5 μl) of the ligation reaction was used for transformation of *E. coli* XL1-Blue (Stratagene). Transformation was done by electroporation using a Gene Pulser (BioRAD) and 0.1 cm Gene Pulser Cuvettes (BioRAD) at 200 Ω, 25 μF, 1.7 kV. After electroporation, the cells were incubated with shaking for 1 h in 1 ml S.O.B. medium (Miller, 1972) before plating on selective S.O.B. agar.

Example 1

Insertion of the JUN Amphiphatic Helix Domain within E2

In the vector pTE5'2J (Hahn et al., *Proc. Natl. Acad. Sci. USA* 89:2679–2683, (1992)), MluI and a BstEII restriction enzyme sites were introduced between codons 71 (Gln) and 74 (Thr) of the structural protein E2 coding sequence, resulting in vector pTE5'2JBM. Introduction of these restriction enzymes sites was done by PCR using the following oligonucleotides:

```
Oligo 1:
E2insBstEII/BssHII:
5'-ggggACGCGTGCAGCAggtaaccaccgTTAAAG   (SEQ ID NO:1)
                            AAGGCACC-3'

Oligo 2:
E2insMluIStuI.
5'-cggtggttaccTGCTGCACGCGTTGCTTAAGCG   (SEQ ID NO:2)
                         ACATGTAGCGG-3'

Oligo 3:
E2insStuI:
5'-CCATGAGGCCTACGATACCC-3'             (SEQ ID NO:3)

Oligo4:
E2insBssHII:
5'-GGCACTCACGGCGCGCTTTACAGGC-3'        (SEQ ID NO:4)
```

For the PCR reaction, 100 pmol of each oligo was used with 5 ng of the template DNA in a 100 μl reaction mixture containing 4 units of Taq or Pwo polymerase, 0.1 mM dNTPs and 1.5 mM $MgSO_4$. All DNA concentrations were determined photometrically using the GeneQuant apparatus (Pharmacia). Polymerase was added directly before starting the PCR reaction (starting point was 95° C.). Temperature cycling was done in the following manner and order: 95° C. for 2 minutes; 5 cycles of 95° C. (45 seconds), 53° C. (60 seconds), 72° C. (80 seconds); and 25 cycles of 95° C. (45 seconds), 57° C. (60 seconds), 72° C. (80 seconds).

The two PCR fragments were analyzed and purified by agarose gelelectrophoresis. Assembly PCR of the two PCR fragments using oligo 3 and 4 for amplification was carried out to obtain the final construct.

For the assembly PCR reaction, 100 pmol of each oligo was used with 2 ng of the purified PCR fragments in a 100 μl reaction mixture containing 4 units of Taq or Pwo polymerase, 0.1 mM dNTPs and 1.5 mM $MgSO_4$. All DNA concentrations were determined photometrically using the GeneQuant apparatus (Pharmacia). Polymerase was added directly before starting the PCR reaction (starting point was 95° C.). Temperature cycling was done in the following manner and order: 95° C. for 2 minutes; 5 cycles of 95° C. (45 seconds), 57° C. (60 seconds), 72° C. (90 seconds); and 25 cycles of 95° C. (45 seconds), 59° C. (60 seconds), 72° C. (90 seconds).

The final PCR product was purified using Qia spin PCR columns (Qiagen) and digested in an appropriate buffer using 10 units each of BssHII and StuI restriction endonucleases for 12 hours at 37° C. The DNA fragments were gel-purified and ligated into BssHII/StuI digested and gel-purified pTE5'2J vector (Hahn et al., *Proc. Natl. Acad. Sci. USA* 89:2679–2683). The correct insertion of the PCR product was first analyzed by BstEII and MluI restriction analysis and then by DNA sequencing of the PCR fragment.

The DNA sequence coding for the JUN amphiphatic helix domain was PCR-amplified from vector pJuFo (Crameri and Suter, *Gene* 137:69 (1993)) using the following oligonucleotides:

```
Oligo 5:
JUNBstEII:
5'-CCTTCTTTAAcggtggttaccTGCTGGCAACCA   (SEQ ID NO:5)
                     ACGTGGTTCATGAC-3'

Oligo 6:
MluIJUN:
5'-AAGCATGCTGCacgcgtgTGCGGTGGTCGGATC   (SEQ ID NO:6)
                            GCCCGGC-3'
```

For the PCR reaction, 100 pmol of each oligo was used with 5 ng of the template DNA in a 100 μl reaction mixture containing 4 units of Taq or Pwo polymerase, 0.1 mM dNTPs and 1.5 mM $MgSO_4$. All DNA concentrations were determined photometrically using the GeneQuant apparatus (Pharmacia). Polymerase was added directly before starting the PCR reaction (starting point was 95° C.). Temperature cycling was done in the following order and manner: 95° C. for 2 minutes; 5 cycles of 95° C. (45 seconds), 60° C. (30 seconds), 72° C. (25 seconds); and 25 cycles of 95° C. (45 seconds), 68° C. (30 seconds), 72° C. (20 seconds).

The final PCR product was gel-purified and ligated into EcoRV digested and gel-purified pBluescript II($KS^-$). From the resulting vector, the JUN sequence was isolated by cleavage with MluI/BstEII purified with QiaExII and ligated into vector pTE5'2JBM (previously cut with the same restriction enzymes) to obtain the vector pTE5'2J:E2JUN.

Example 2

Production of Viral Particles Containing E2-JUN using the pCYTts System

The structural proteins were PCR amplified using pTE5'2J:E2JUN as template and the oligonucleotides XbaI-Struct (ctatcaTCTAGAATGAATAGAGGATTCTTTAAC (SEQ ID NO:12)) and StructBsp1201 (tcgaatGGGCCCTCATCTTCGTGTGCTAGTCAG (SEQ ID NO:87)). For the PCR 100 pmol of each loligo was used and 5 ng of the template DNA was used in the 100 μl reaction mixture, containing 4 units of Tac or Pwo polymerase, 0.1 mM dNTPs and 1.5 mM $MgSO_4$. All DNA concentrations were determined photometrically using the GeneQuant apparatus (Pharmacia). The polymerase was added directly before starting the PCR reaction (starting point was 95° C.). The temperature cycles were as follows: 95° C. for 3 minutes, followed by 5 cycles of 92° C. (30 seconds), 54° C. (35 seconds), 72° C. (270 seconds) and followed by 25 cycles of 92° C. (30 seconds), 63° C. (35 seconds), 72° C. (270 seconds. The PCR product was gel purified and digested with the restriction enzymes XbaI/Bsp1201 and ligated into vector pCYTts previously cleaved with the same enzymes (WO 99/50432).

Twenty μg of pCYTtsE2:JUN were incubated with 30 U of ScaI in an appropriate buffer for at least 4 hours at 37° C. The reaction was stopped by phenol/chloroform extraction, followed by an isopropanol precipitation of the linerized DNA. The restriction reaction was checked by agarose gel eletrophoresis. For the transfection, 5.4 μg of linearized pCYTtsE2:JUN was mixed with 0.6 μg of linearized pSV2Neo in 30 μl $H_2O$ and 30 μl of 1 M $CaCl_2$ solution were added. After addition of 60 μl phosphate buffer (50 mM HEPES, 280 mM NaCl, 1.5 mM $Na_2$ $HPO_4$, pH 7.05), the solution was vortexed for 5 seconds, followed by an incubation at room temperature for 25 seconds. The solution was immediately added to 2 ml HP-1 medium containing 2% FCS (2% FCS medium). The medium of an 80% confluent BHK21 cell culture in a 6-well plate was then replaced with the DNA containing medium. After an incubation for 5 hours at 37° C. in a $CO_2$ incubator, the DNA containing medium was removed and replaced by 2 ml of 15% glycerol in 2% FCS medium. The glycerol containing medium was removed after a 30 second incubation phase, and the cells were washed by rinsing with 5 ml of HP-1 medium containing 10% FCS. Finally 2 ml of fresh HP-1 medium containing 10% FCS was added.

Stably transfected cells were selected and grown in selection medium (HP-1 medium, supplemented with G418) at 37° C. in a $CO_2$ incubator. When the mixed population was grown to confluency, the culture was split to two dishes, followed by a 12 hours growth period at 37° C. One dish of the cells was shifted to 30° C. to induce the expression of the viral particles; the other dish was kept at 37° C.

The expression of viral particles was determined by Western blotting (FIG. 1). Culture medium (0.5 ml) was methanol/chloroform precipitated, and the pellet was resuspended in SDS-PAGE sample buffer. Samples were heated for 5 minutes at 95° C. before being applied to 15% acrylamide gel. After SDS-PAGE, proteins were transferred to Protan nitrocellulose membranes (Schleicher & Schuell, Germany) as described by Bass and Yang, in Creighton, T. E., ed., *Protein Function: A Practical Approach*, 2nd Edn., IRL Press, Oxford (1997), pp. 29–55. The membrane was blocked with 1% bovine albumin (Sigma) in TBS (10×TBS per liter: 87.7 g NaCl, 66.1 g Trizma hydrochloride (Sigma) and 9.7 g Trizma base (Sigma), pH 7.4) for 1 hour at room temperature, followed by an incubation with an anti-E1/E2antibody (polyclonal serum) for 1 hour. The blot was washed 3 times for 10 minutes with TBS-T (TBS with 0.05% Tween20), and incubated for 1 hour with an alkaline-phosphatase-anti-rabbit IgG conjugate (0.1 μg/ml, Amersham Life Science, England). After washing 2 times for 10 minutes with TBS-T and 2 times for 10 minutes with TBS, the development reaction was carried out using alkaline phosphatase detection reagents (10 ml AP buffer (100 mM Tris/HCl, 100 mM NaCl, pH 9.5) with 50 μl NBT solution (7.7% Nitro Blue Tetrazolium (Sigma) in 70% dimethylformamide) and 37 μl of X-Phosphate solution (5% of 5-bromo-4-chloro-3-indolyl phosphate in dimethylformamide).

The production of viral particles is shown in FIG. 1. The Western Blot pattern showed that E2-JUN (lane 1) migrated to a higher molecular weight in SDS-PAGE compared to wild type E2 (lane 2) and the BHK21 host cell line did not show any background.

Example 3

Production of Viral Particles Containing E2-JUN using the pTE5'2JE2:JUN Vector RNase-free vector (1.0 μg) was linerarized by PvuI digestion. Subsequently, in vitro transcription was carried out using an SP6 in vitro transcription kit (InvitroscripCAP by InvitroGen, Invitrogen BV, NV Leek, Netherlands). The resulting 5'-capped mRNA was analyzed on a reducing agarose-gel.

In vitro transcribed mRNA (5 μg) was electroporated into BHK 21 cells (ATCC: CCL10) according to Invitrogen's manual (Sindbis Expression system, Invitrogen BV, Netherlands). After 10 hours incubation at 37° C., the FCS containing medium was exchanged by HP-1 medium without FCS, followed by an additional incubation at 37° C. for 10 hours. The supernatant was harvested and analyzed by Western blot analysis for production of viral particles exactly as described in Example 2.

Figure 2:
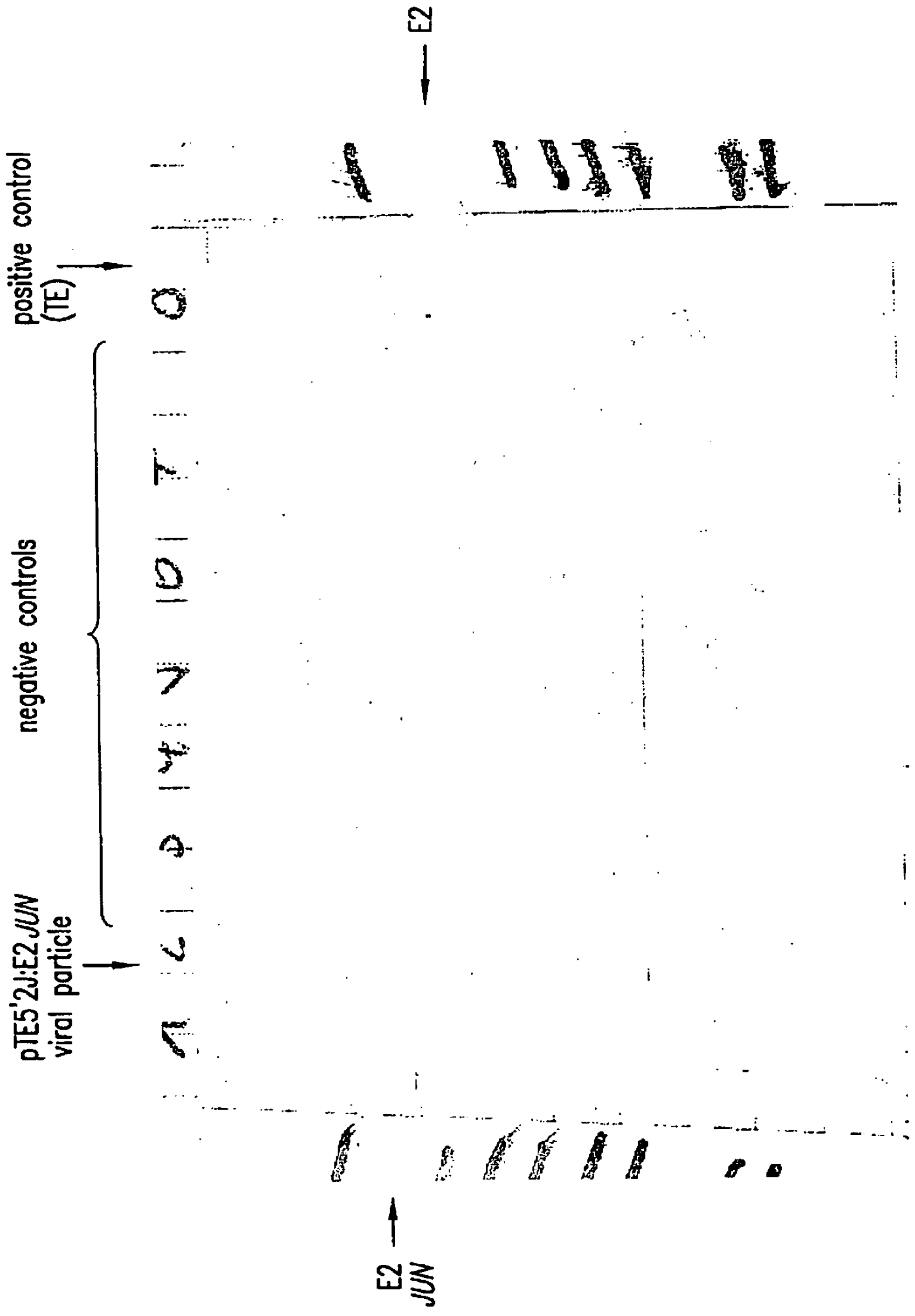
FIG. 2 shows a Western blot demonstrating the production of viral particles containing the E2-JUN fusion protein expressed from pTE5'2J::E2JUN expression vector.

The obtained result was identical to the one obtained with pCYTtsE2:JUN as shown in FIG. 2.

Example 4

Fusion of Human Growth Hormone (hGH) to the FOS Leucine Zipper Domain (OmpA signal sequence)

The hGH gene without the human leader sequence was amplified from the original plasmid (ATCC 31389) by PCR. Oligo 7 with an internal XbaI site was designed for annealing at the 5' end of the hGH gene, and oligo 9 with an internal EcoRI site primed at the 3' end of the hGH gene. For the PCR reaction, 100 pmol of each oligo and 5 ng of the template DNA was used in the 75 μl reaction mixture (4 units of Taq or Pwo polymerase, 0.1 mM dNTPs and 1.5 mM $MgSO_4$).

PCR cycling was performed in the following manner: 30 cycles with an annealing temperature of 60° C. and an elongation time of 1 minute at 72° C.

The gel purified and isolated PCR product was used as a template for a second PCR reaction to introduce the ompA signal sequence and the Shine-Dalgarno sequence. For the PCR reaction, 100 pmol of oligo 8 and 9 and 1 ng of the template PCR fragment was used in the 75 μl reaction mixture (4 units of Taq or Pwo polymerase, 0.1 mM dNTPs and 1.5 mM $MgSO_4$). The annealing temperature for the first five cycles was 55° C. with an elongation time of 60 seconds at 72° C.; another 25 cycles were performed with an annealing temperature of 65° C. and an elongation time of 60 seconds at 72° C.

Oligo7: gggtctagattcccaaccattcccttatccaggctttttgac aacgctatgctccgcgccc atcgtctgcaccagctggcctttgacacc (SEQ ID NO:7); olzgo 8: gggtctagaaggaggtaaaaaa cgatgaaaaagacagctatcgcgattgcagtggcactggctggtttcgctaccgtagcgcaggccttcccaac cattcccttatcc (SEQ ID NO:8); oligo 9: cccgaattcctagaagccacagctgccctcc (SEQ ID NO:9).

The resulting recombinant hGH gene was subcloned into pBluescript via XbaI/EcoRI. The correct sequence of both strands was confirmed by DNA sequencing.

The DNA sequence coding for the FOS amphiphatic helix domain was PCR-amplified from vector pJuFo (*Crameri & Suter Gene* 137:69 (1993)) using the oligonucleotides:

```
omp-FOS:
5'-ccTGCGGTGGTCTGACCGACACCC-3'                    (SEQ ID
                                                    NO:10)

FOS-hgh:
5'-ccgcggaagagccaccGCAACCACCGTGTGCCG               (SEQ ID
                                                    NO:11)
                              CCAGGATG-3'
```

For the PCR reaction, 100 pmol of each oligo and 5 ng of the template DNA was used in the 75 μl reaction mixture (4 units of Taq or Pwo polymerase, 0.1 mM dNTPs and 1.5 mM $MgSO_4$). The temperature cycles were as follows:

95° C. for 2 minutes, followed by 5 cycles of 95° C. (45 seconds), 60° C. (30 seconds), 72° C. (25 seconds) and followed by 25 cycles of 95° C. (45 seconds), 68° C. (30 seconds), 72° C. (20 seconds).

The PCR product was purified, isolated and cloned into the StuI digested pBluescript-ompA-hGH. The hybrid gene was then cloned into the pKK223-3 Plasmid (Pharmacia).

Example 5

Bacterial Expression of FOS-hGH

The ompA-FOS-hGH in pkk223-3 was expressed under the control of the inducible IPTG-dependend promoter using JM101 as *E. coli* host strain. Expression was performed in shaker flask. Cells were induced with 1 mM IPTG (final concentration) at an OD600 of 0.5. Expression was continued for 10 hours at 37° C. Cells were harvested by centrifugation at 3600 at 10° C. for 15 min. The cell pellet was frozen (−20° C. or liq. $N_2$) and stored for 16 hours. The pellet was then thawed at 4° C. and resuspended in 10 ml 10 mM Tris-HCl, pH 7.4 containing 600 mM sucrose. After stirring for 15 min at 4° C., periplasmic proteins were released by an osmotic shock procedure. Chilled (4° C.) deionized $H_2O$ was added, and the suspension was stirred for 30 min at 4° C. The sludge was diluted, resuspended, and lysozyme was added to degrade the cell wall of the bacteria. The cells and the periplasmic fraction spheroplasts were separated by centrifugation for 20 min at 11000×g at 4° C. The FOS-hGH-containing supernatant was analyzed by reducing and non-reducing SDS-Page and Dot Blot. Dot Blot was carried out as described in Example 8, using an anti-hGH antibody (Sigma) as the first antibody and an alkaline phosphatase (AP)-anti-mouse antibody conjugate as the second antibody.

Figure 3:
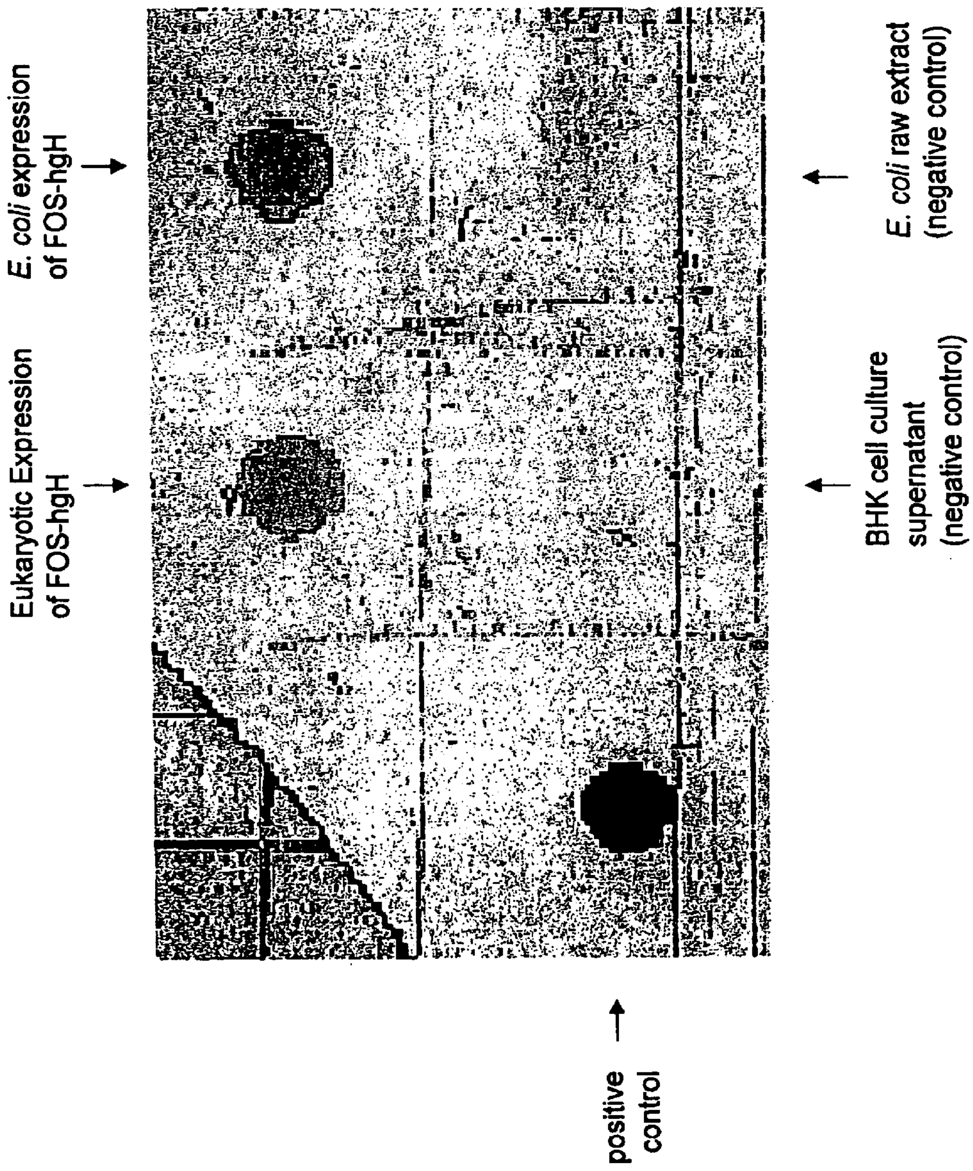
FIG. 3 shows a Western dot blot demonstrating bacterial and eukaryotic expression of the FOS-hgh antigen.

Full length, correctly processed FOS-hGH could be detected under reducing and non-reducing conditions. Part of FOS-hGH was bound to other, non-identified proteins due to the free cysteines present in the FOS amphiphatic helix. However, more than 50% of expressed FOS-hGH occurred in its native monomeric conformation (FIG. 3).

Purified FOS-hGH will be used to perform first doping experiments with JUN containing viral particles.

Example 6

Construction of the pAV Vector Series for Expression of FOS Fusion Proteins

A versatile vector system was constructed that allowed either cytplasmic production or secretion of N- or C-terminal FOS fusion proteins in *E. coli* or production of N- or C-terminal FOS fusion proteins in eukaryotic cells. The vectors pAV1–pAV4 which was designed for production of FOS fusion proteins in *E. coli*, encompasses the DNA cassettes listed below, which contain the following genetic elements arranged in different orders: (a) a strong ribosome binding site and 5'-untranslated region derived from the *E. coli* ompA gene (aggaggtaaaaaacg) (SEQ ID NO:13); (b) a sequence encoding the signal peptide of *E. coli* outer membrane protein OmpA (MKKTAIAIAVALAGFATVAQA) (SEQ ID NO:14); (c) a sequence coding for the FOS dimerization domain flanked on both sides by two glycine residues and a cystein residue (CGGLTDTLQAETDQVEDEKSALQTEIANLLKEKEKLEFILAAHGGC) (SEQ ID NO:15), and (d) a region encoding a short peptidic linker (AAASGG (SEQ ID NO:16) or GGSAAA (SEQ ID NO:17)) connecting the protein of interest to the FOS dimerization domain. Relevant coding regions are given in upper case letters. The arrangement of restriction cleavage sites allows easy construction of FOS fusion genes with or without a signal sequence. The cassettes are cloned into the EcoRI/HindIII restriction sites of expression vector pKK223-3 (Pharmacia) for expression of the fusion genes under control of the strong tac promotor.

pAV1

This vector was designed for the secretion of fusion proteins with FOS at the C-terminus into the *E. coli* periplasmic space. The gene of interest (g.o.i.) may be ligated into the StuI/NotI sites of the vector.

```
EcoRI                                       31/11
gaa ttc agg agg taa aaa acg ATG AAA AAG ACA GCT ATC GCG ATT GCA
GTG GCA CTG GCT
                            M   K   K   T   A   I   A   I   A
V   A   L   A

61/21                   StuI                NotI
GGT TTC GCT ACC GTA GCG CAG GCC tgg gtg ggg GCG GCC GCT TCT GGT
GGT TGC GGT GGT
G   F   A   T   V   A   Q   A     (goi)      A   A   A   S   G
G   C   G   G

121/41                                      151/51
CTG ACC GAC ACC CTG CAG GCG GAA ACC GAC CAG GTG GAA GAC GAA AAA
TCC GCG CTG CAA
L   T   D   T   L   Q   A   E   T   D   Q   V   E   D   E   K
S   A   L   Q

181/61                                      211/71
```

-continued

```
ACC GAA ATC GCG AAC CTG CTG AAA GAA AAA GAA AAG CTG GAG TTC ATC
CTG GCG GCA CAC
T   E   I   A   N   L   L   K   E   K   E   K   L    E   F   I
L   A   A   H

241/81       HindIII
GGT GGT TGC taa gct t (SEQ ID NO:18)
G   G   C   *   A     (SEQ ID NOs:14 and 19)
```

pAV2

This vector was designed for the secretion of fusion proteins with FOS at the N-terminus into the *E. coli* periplasmic space. The gene of interest (g.o.i.) ligated into the NotI/EcoRV (or NotI/HindIII) sites of the vector.

pAV4

This vector is designed for the cytoplasmic production of fusion proteins with FOS at the N-terminus in *E. coli*. The gene of interest (g.o.i.) may be ligated into the NotI/EcoRV

```
EcoRI                                   31/11
gaa ttc agg agg taa aaa acg ATG AAA AAG ACA GCT ATC GCG ATT GCA
GTG GCA CTG GCT
                            M   K   K   T   A   I   A    I   A
V   A   L   A

61/21                     StuI          91/31
GGT TTC GCT ACC GTA GCG CAG GCC TGC GGT GGT CTG ACC GAC ACC CTG
CAG GCG GAA ACC
G   F   A   T   V   A   Q   A   C   G   G   L    T   D   T   L
Q   A   E   T

121/41                                  151/51
GAC CAG GTG GAA GAC GAA AAA TCC GCG CTG CAA ACC GAA ATC GCG AAC
CTG CTG AAA GAA
D   Q   V   E   D   E   K   S   A    L   Q   T   E   I   A   N
L   L   K   E

181/61                                  211/71
   Not I
AAA GAA AAG CTG GAG TTC ATC CTG GCG GCA CAC GGT GGT TGC GGT GGT
TCT GCG GCC GCT
K   E   K   L   E   F   I   L   A   A   H   G   G   C    G   G
S   A   A   A

241/81      EcoRV   HindIII
ggg tgt ggg gat atc aag ctt (SEQ ID NO:20)
  (goi)                    (SEQ ID NO:21)
```

pAV3

This vector was designed for the cytoplasmic production of fusion proteins with FOS at the C-terminus in *E. coli*. The gene of interest (g.o.i.) may be ligated into the EcoRV/NotI sites of the vector.

(or NotI/HindIII) sites of the vector. The N-terminal methionine residue is proteolytically removed upon protein synthesis (Hirel et al., *Proc. Natl. Acad. Sci. USA* 86:8247–8251(1989)).

```
EcoRI                       EcoRV               NotI
gaa ttc agg agg taa aaa gat atc ggg tgt ggg GCG GCC GCT TCT GGT
GGT TGC GGT GGT
                                     (goi)    A   A   A    S   G
G   C   G   G

61/21                                   92/32
CTG ACC GAC ACC CTG CAG GCG GAA ACC GAC CAG GTG GAA GAC GAA AAA
TCC GCG CTG CAA
L   T   D   T   L   Q   A   E   T   D   Q   V   E    D   E   K
S   A   L   Q

121/41                                  151/51
ACC GAA ATC GCG AAC CTG CTG AAA GAA AAA GAA AAG CTG GAG TTC ATC
CTG GCG GCA CAC
T   E   I   A   N   L   L   K   E    K   E   K   L   E   F   I
L   A   A   H

181/61       HindIII
GGT GGT TGC taa gct t (SEQ ID NO:22)
G   G   C   *         (SEQ ID NO:23)
```

```
EcoRI                                         31/11
gaa ttc agg agg taa aaa acg ATG GCT TGC GGT GGT CTG ACC GAC ACC  (SEQ NO:24)
CTG CAG GCG GAA
E   F    R   R   *   K   T   M   A   C   G   G   L   T   D   T   (SEQ NOs:88 and 25)
L   Q   A   E

61/21                                         91/31
ACC GAC CAG GTG GAA GAC GAA AAA TCC GCG CTG CAA ACC GAA ATC GCG
AAC CTG CTG AAA
T   D   Q   V   E   D   E   K   S   A   L   Q   T   E   I   A
N   L   L   K

121/41                                        151/51
        NotI
GAA AAA GAA AAG CTG GAG TTC ATC CTG GCG GCA CAC GGT GGT TGC GGT
GGT TCT GCG GCC
E   K   E   K   L   E   F   I   L   A   A   H   G   G   C   G
G   S   A   A

181/61          EcoRV   HindIII
GCT ggg tgt ggg gat atc aag ctt
A     (goi)
```

The vectors pAV5 and pAV6, which are designed for eukaryotic production of FOS fusion proteins, encompasses the following genetic elements arranged in different orders: (a) a region coding for the leader peptide of human growth hormone (MATGSRTSLLLAFGLLCLPWLQEGSA) (SEQ ID NO:26);

(b) a sequence coding for the FOS dimerization domain flanked on both sides by two glycine residues and a cysteine residue (CGGLTDTLQAETDQVEDEKSALQTEIANLL-KEKEKLEFILAAHGGC) (SEQ ID NO:15); and (c) a region encoding a short peptidic linker (AAASGG (SEQ ID NO:16) or GGSAAA (SEQ ID NO:17)) connecting the protein of interest to the FOS dimerization domain. Relevant coding regions are given in upper case letters. The arrangement of restriction cleavage sites allows easy construction of FOS fusion genes. The cassettes are cloned into the EcoRI/HindIII restriction sites of the expression vector pMPSVEH (Artelt et al., *Gene* 68:213–219 (1988)).

pAV5 le;2qThis vector is designed for the eukaryotic production of fusion proteins with FOS at the C-terminus. The gene of interest (g.o.i.) may be inserted between the sequences coding for the hGH signal sequence and the FOS domain by ligation into the Eco47III/NotI sites of the vector. Alternatively, a gene containing its own signal sequence may be fused to the FOS coding region by ligation into the StuI/NotI sites.

```
EcoRI   StuI                                  31/11
gaa ttc agg cct ATG GCT ACA GGC TCC CGG ACG TCC CTG CTC CTG GCT  (SEQ ID NO:27)
TTT GGC CTG CTC
                M   A   T   G   S   R   T   S   L   L   L   A    (SEQ ID NO:28)
F   G   L   L

61/21                                     Eco47III        NotI
TGC CTG CCC TGG CTT CAA GAG GGC AGC GCT ggg tgt ggg GCG GCC GCT
TCT GGT GGT TGC
C   L   P   W   L   Q   E   G   S   A     (goi)     A   A   A
S   G   G   C

121/41                                        151/51
GGT GGT CTG ACC GAC ACC CTG CAG GCG GAA ACC GAC CAG GTG GAA GAC
GAA AAA TCC GCG
G   G   L   T   D   T   L   Q   A   E   T   D   Q   V   E   D
E   K   S   A

181/61                                        211/71
CTG CAA ACC GAA ATC GCG AAC CTG CTG AAA GAA AAA GAA AAG CTG GAG
TTC ATC CTG GCG
L   Q   T   E   I   A   N   L   L   K   E   K   E   K   L   E
F   I   L   A

241/81                HindIII
GCA CAC GGT GGT TGC taa gct t
A   H   G   G   C   *
```

pAV6

This vector is designed for the eukaryotic production of fusion proteins with FOS at the N-terminus. The gene of interest (g.o.i.) may be ligated into the NotI/StuI (or NotI/HindIII) sites of the vector.

```
EcoRI                                   31/11
gaa ttc ATG GCT ACA GGC TCC CGG ACG TCC CTG CTC CTG GCT TTT GGC
CTG CTC TGC CTG
        M   A   T   G   S   R   T   S   L   L   L   A   F   G
L   L   C   L

61/21             Eco47III         91/31
CCC TGG CTT CAA GAG GGC AGC GCT TGC GGT GGT CTG ACC GAC ACC CTG
CAG GCG GAA ACC
P   W   L   Q   E   G   S   A   C   G   G   L   T   D   T   L
Q   A   E   T

121/41           151/51
GAC CAG GTG GAA GAC GAA AAA TCC GCG CTG CAA ACC GAA ATC GCG AAC
CTG CTG AAA GAA
D   Q   V   E   D   E   K   S   A   L   Q   T   E   I   A   N
L   L   K   E

181/61                                  211/71
   Not I
AAA GAA AAG CTG GAG TTC ATC CTG GCG GCA CAC GGT GGT TGC GGT GGT
TCT GCG GCC GCT
K   E   K   L   E   F   I   L   A   A   H   G   G   C   G   G
S   A   A   A

241/81      StuI    HindIII
ggg tgt ggg agg cct aag ctt (SEQ ID NO:29)
  (goi)                     (SEQ ID NO:30)
```

Construction of Expression Vectors pAV1–pAV6

The following oligonucleotides have been synthesized for construction of expression vectors pAV1–pAV6:

FOS-FOR1:
CCTGGGTGGGGGCGGCCGCTTCTGGTGGTTGCGGT GGTCTGACC; (SEQ ID NO:31)

FOS-FOR2:
GGTGGGAATTCAGGAGGTAAAAAGATATCGGGTGT GGGGCGGCC; (SEQ ID NO:32)

FOS-FOR3:
GGTGGGAATTCAGGAGGTAAAAAACGATGGCTTGC GGTGGTCTGACC; (SEQ ID NO:33)

FOS-FOR4:
GCTTGCGGTGGTCTGACC; (SEQ ID NO:34)

FOS-REV1:
CCACCAAGCTTAGCAACCACCGTGTGC; (SEQ ID NO:35)

FOS-REV2:
CCACCAAGCTTGATATCCCCACACCCAGCGGCCGC AGAACCACCGCAACCACCG; (SEQ ID NO:36)

FOS-REV3:
CCACCAAGCTTAGGCCTCCCACACCCAGCGGC; (SEQ ID NO:37)

OmpA-FOR1:
GGTGGGAATTCAGGAGGTAAAAAACGATG; (SEQ ID NO:38)

hGH-FOR1:
GGTGGGAATTCAGGCCTATGGCTACAGGCTCC; (SEQ ID NO:39)

and hGH-FOR2:
GGTGGGAATTCATGGCTACAGGCTCCC. (SEQ ID NO:40)

For the construction of vector pAV2, the regions coding for the OmpA signal sequence and the FOS domain were amplified from the ompA-FOS-hGH fusion gene in vector pKK223-3 (see Example 5) using the primer pair OmpA-FOR1/FOS-REV2. The PCR product was digested with EcoRI/HindIII and ligated into the same sites of vector pKK223-3 (Pharmacia).

For the construction of vector pAV1, the FOS coding region was amplified from the ompA-FOS-hGH fusion gene in vector pKK223-3 (see Example 5) using the primer pair FOS-FOR1/FOS-REV1. The PCR product was digested with HindIII and ligated into StuI/HindIII digested vector pAV2.

For the construction of vector pAV3, the region coding for the FOS domain was amplified from vector pAV1 using the primer pair FOS-FOR2/FOS-REV1. The PCR product was digested with EcoRI/HindIII and ligated into the same sites of the vector pKK223-3 (Pharmacia).

For the construction of vector pAV4, the region coding for the FOS domain was amplified from the ompA-FOS-hGH fusion gene in vector pKK223-3 (see Example 5) using the primer pair FOS-FOR3/FOS-REV2. The PCR product was digested with EcoRI/HindIII and ligated into the same sites of the vector pKK223-3 (Pharmacia).

For the construction of vector pAV5, the region coding for the hGH signal sequence is amplified from the hGH-FOS-hGH fusion gene in vector pSINrep5 (see Example 7) using the primer pair hGH-FOR1/hGHREV1. The PCR product is digested with EcoRI/NotI and ligated into the same sites of the vector pAV1. The resulting cassette encoding the hGH signal sequence and the FOS domain is then isolated by EcoRI/HindIII digestion and cloned into vector pMPSVEH (Artelt et al., *Gene* 68:213–219 (1988)) digested with the same enzymes.

For the construction of vector pAV6, the FOS coding region is amplified from vector pAV2 using the primer pair FOS-FOR4/FOSREV3. The PCR product is digested with HindIII and cloned into Eco47III/HindIII cleaved vector pAV5. The entire cassette encoding the hGH signal sequence and the FOS domain is then reamplified from the resulting vector using the primer pair hGH-FOR2/FOSREV3, cleaved with EcoRI/HindIII and ligated into vector pMPSVEH (Artelt et al., *Gene* 68:213–219 (1988)) cleaved with the same enzymes.

Example 7

Construction of FOS-hGH with Human (hGH) Signal Sequence

For eukaryotic expression of the FOS-hGH fusion protein, the OmpA-FOS-hGH fusion gene was isolated from pBluescript::OmpA-FOS-hGH (see Example 4) by digestion with XbaI/Bsp120I and cloned into vector pSINrep5 (Invitrogen) cleaved with the same enzymes. The hGH signal sequence was synthesized by PCR (reaction mix: 50 pmol of each primer, dATP, dGTP, dTTP, dCTP (200 μM each), 2.5 U Taq DNA polymerase (Qiagen), 50 μl total volume in the buffer supplied by the manufacturer; amplification: 92° C. for 30 seconds, 55° C. for 30 seconds, 72° C. for 30 seconds, 30 cycles) using the overlapping oligonucleotides

```
Sig-hGH-FOR
(GGGTCTAGAATGGCTACAGGCTCCCGGACGTCCC    (SEQ ID NO:41)
       TGCTCCTGGCTTTTGGCCTGCTCTG) and

Sig-hGH-REV
(CGCAGGCCTCGGCACTGCCCTCTTGAAGCCAGGG    (SEQ ID NO:42)
           CAGGCAGAGCAGGCCAAAAGCCAG).
```

The PCR product was purified using the QiaExII Kit, digested with StuI/XbaI and ligated into vector pSINrep5::OmpA-FOS-hGH cleaved with the same enzymes.

Example 8

Eukaryotic Expression of FOS-hGH

RNase-free vector (1.0 μg) (pSINrep5::OmpA-FOS-hGH) and 1.0 μg of DHEB (Bredenbeek et al., *J. Virol.* 67:6439–6446 (1993)) were linerarized by ScaI restriction digest. Subsequently, in vitro transcription was carried out using an SP6 in vitro transcription kit (InvitroscripCAP by InvitroGen, Invitrogen BV, NV Leek, Netherlands). The resulting 5'-capped mRNA was analyzed on reducing agarose-gel.

In vitro, transcribed mRNA 5 μg was electroporated into BHK 21 cells (ATCC: CCL10) according to Invitrogen's manual (Sindbis Expression system, Invitrogen BV, Netherlands). After 10 hours incubation at 37° C. the FCS containing medium was exchanged by HP-1 medium without FCS, followed by an additional incubation at 37° C. for 10 hours. The supernatant was harvested and analyzed by dot-blot analysis for production of FOS-hgh.

Culture media (2.5 μl) was spotted on a nitrocellulose membrane and dried for 10 minutes at room temperature. The membrane was blocked with 1% bovine albumin (Sigma) in TBS (10×TBS per liter: 87.7 g NaCl, 66.1 g Trizma hydrochloride (Sigma) and 9.7 g Trizma base (Sigma), pH 7.4) for 1 hour at room temperature, followed by an incubation with 2 μg rabbit anti-human hGH antibody (Sigma) in 10 ml TBS-T (TBS with 0.05% Tween20) for 1 hour. The blot was washed 3 times for 10 minutes with TBS-T and incubated for 1 hour with alkaline phosphatase conjugated anti-rabbit IgG (Jackson ImmunoResearch Laboratories, Inc.) diluted 1:5000 in TBS-T. After washing 2 times for 10 minutes with TBS-T and 2 times for 10 minutes with TBS, the blot was developed by AP staining as described in Example 2. Results are shown in FIG. 3.

Example 9

Construction of FOS-PLA (N- and C-terminal)

The following gene is constructed by chemical gene synthesis coding for a catalytically inactive variant (Förster et al., *J. Allergy Clin. Immunol.* 95: 1229–1235 (1995)) of bee venom phospholipase $A_2$ (PLA).

```
1/1                                        31/11
ATC ATC TAC CCA GGT ACT CTG TGG TGT GGT CAC GGC AAC AAA TCT TCT  (SEQ ID NO:43)
GGT CCG AAC GAA
I   I   Y   P   G   T   L   W   C   G   H   G   N   K   S   S    (SEQ ID NO:44)
G   P   N   E

61/21                                      91/31
CTC GGC CGC TTT AAA CAC ACC GAC GCA TGC TGT CGC ACC CAG GAC ATG
TGT CCG GAC GTC
L   G   R   F   K   H   T   D   A   C   C   R   T   Q   D   M
C   P   D   V
121/41                                     151/51
ATG TCT GCT GGT GAA TCT AAA CAC GGG TTA ACT AAC ACC GCT TCT CAC
ACG CGT CTC AGC
M   S   A   G   E   S   K   H   G   L   T   N   T   A   S   H
T   R   L   S

181/61                                     211/71
TGC GAC TGC GAC GAC AAA TTC TAC GAC TGC CTT AAG AAC TCC GCC GAT
ACC ATC TCT TCT
C   D   C   D   D   K   F   Y   D   C   L   K   N   S   A   D
T   I   S   S

241/81                                     271/91
TAC TTC GTT GGT AAA ATG TAT TTC AAC CTG ATC GAT ACC AAA TGT TAC
AAA CTG GAA CAC
Y   F   V   G   K   M   Y   F   N   L   I   D   T   K   C   Y
K   L   E   H

301/101                                    331/111
CCG GTA ACC GGC TGC GGC GAA CGT ACC GAA GGT CGC TGC CTG CAC TAC
ACC GTT GAC AAA
P   V   T   G   C   G   E   R   T   E   G   R   C   L   H   Y
T   V   D   K

361/121                                    391/131
TCT AAA CCG AAA GTT TAC CAG TGG TTC GAC CTG CGC AAA TAC
S   K   P   K   V   Y   Q   W   F   D   L   R   K   Y
```

For fusion of PLA to the N-terminus of the FOS dimerization domain, the region is amplified using the oligonucleotides

```
PLA-FOR1 (CCATCATCTACCCAGGTAC)                (SEQ ID NO:45)
                                              and
PLA-REV1 (CCCACACCCAGCGGCCGCGTATTTGCGCAGGTCG) (SEQ ID NO:46).
```

The PCR product is cleaved with NotI and ligated into vector pAV1 previously cleaved with the restriction enzymes StuI/NotI. For fusion of PLA to the C-terminus of the FOS dimerization domain, the region is amplified using the oligonucleotides

```
PLA-FOR2 (CGGTGGTTCTGCGGCCGCTATCATCTACCCAGGTAC) (SEQ ID NO:47) and
PLA-REV2 (TTAGTATTTGCGCAGGTCG)                  (SEQ ID NO:48).
```

The PCR product is cleaved with NotI and ligated into vector pAV2 previously cleaved with the restriction enzymes NotI/EcoRV.

Example 10

Construction of FOS-Ovalbumin Fusion Gene (N- and C-terminal)

For cloning of the ovalbumin coding sequence, mRNA from chicken oviduct tissue is prepared using the QuickPrep™ Micro mRNA Purification Kit (Pharmacia) according to manufacturer instructions Using the SuperScript™ One-step RT PCR Kit (Gibco BRL), a cDNA encoding the mature part of ovalbumin (corresponding to nucleotides 68–1222 of the mRNA (McReynolds et al., *Nature* 273:723–728 (1978)) is synthesized using the primers

```
Ova-FOR1 (CCGGCTCCATCGGTGCAG)                 (SEQ ID NO:49) and
Ova-REV1 (ACCACCAGAAGCGGCCGCAGGGGAAACACATCTGCC) (SEQ ID NO:50).
```

The PCR product is digested with NotI and cloned into StuI/NotI digested vector pAV1 for expression of the fusion protein with the FOS dimerization domain at the C terminus. For production of a fusion protein with the FOS dimerization domain at the N terminus, the Ovalbumin coding region is amplified from the constructed vector (pAV1::Ova) using the primers

```
Ova-FOR2 (CGGTGGTTCTGCGGCCGCTGGCTCCATCGGTGCAG) (SEQ ID NO:51) and
Ova-REV2 (TTAAGGGGAAACACATCTGCC)              (SEQ ID NO:52).
```

The PCR product is digested with NotI and cloned into the NotI/EcoRV digested vector pAV2. Cloned fragments are verified by DNA sequence analysis.

Example 11

Production and Purification of FOS-PLA and FOS Ovalbumin Fusion Proteins

For cytoplasmic production of FOS fusion proteins, an appropriate *E. coli* strain was transformed with the vectors pAV3::PLA, pAV4::PLA, pAV3::Ova or pAV4::Ova. The culture was incubated in rich medium in the presence of ampicillin at 37° C. with shaking. At an optical density (550 nm) of 1, 1 mM IPTG was added and incubation was continued for another 5 hours. The cells were harvested by centrifugation, resuspended in an appropriate buffer (e.g., tris-HCl, pH 7.2, 150 mM NaCl) containing DNase, RNase and lysozyme, and disrupted by passage through a french pressure cell. After centrifugation (Sorvall RC-5C, SS34 rotor, 15000 rpm, 10 min, 4° C.), the pellet was resuspended in 25 ml inclusion body wash buffer (20 mM tris-HCl, 23% sucrose, 0.5% Triton X-100, 1 mM EDTA, pH8) at 4° C. and recentrifuged as described above. This procedure was repeated until the supernatant after centrifugation was essentially clear. Inclusion bodies were resuspended in 20 ml solubilization buffer (5.5 M guanidinium hydrochloride, 25 mM tris-HCl, pH 7.5) at room temperature and insoluble material was removed by centrifugation and subsequent passage of the supernatant through a sterile filter (0.45 μm). The protein solution was kept at 4° C. for at least 10 hours in the presence of 10 mM EDTA and 100 mM DTT and then dialyzed three times against 10 volumes of 5.5 M guanidinium hydrochloride, 25 mM tris-HCl, 10 mM EDTA, pH 6. The solution was dialyzed twice against 5 liters of 2 M urea, 4 mM EDTA, 0.1 M $NH_4Cl$, 20 mM sodium borate (pH 8.3) in the presence of an appropriate redox shuffle (oxidized glutathione/reduced glutathione; cystine/cysteine). The refolded protein was then applied to an ion exchange chromatography. The protein was stored in an appropriate buffer with a pH above 7 in the presence of 2–10 mM DTT to keep the cysteine residues flanking the FOS domain in a reduced form. Prior to coupling of the protein with the alphavirus particles, DTT was removed by passage of the protein solution through a Sephadex G-25 gel filtration column.

Example 12

Constructions of gp140-FOS jThe gp140 gene (Swiss-Prot:P03375) without the internal protease cleavage site was amplified by PCR from the original plasmid pAbT4674 (ATCC 40829) containing the full length gp160 gene using the following oligonucleotides:

```
HIV-1:
5'-ACTAGTCTAGAatgagagtgaaggagaaatatc-3'              (SEQ ID NO:53);

HIV-end:
5'-TAGCATGCTAGCACCGAAtttatctaattccaataattcttg-3'     (SEQ ID NO:54);

HIV-Cleav:
5'-gtagcacccaccaaggcaaagCTGAAAGCTACCCAGCTCGAGAAACTGgCa-3'  (SEQ ID NO:55); and

HIV-Cleav2:
5'-caaagctcctattcccactgcCAGTTTCTCGAGCTGGGTAGCTTTCAG-3'     (SEQ ID NO:56).
```

For PCR I, 100 pmol of oligo HIV-1 and HIV-Cleav2 and 5 ng of the template DNA were used in the 75 μl reaction mixture (4 units of Taq or Pwo polymerase, 0.1 mM dNTPs and 1.5 mM $MgSO_4$). PCR cycling was done in the following manner. 30 cycles with an annealing temperature of 60° C. and an elongation time of 2 minutes at 72° C.

For PCR II, 100 pmol of oligo HIV-end and HIV-Cleav and 5 ng of the template DNA were used in the 75 μl reaction mixture, (4 units of Taq or Pwo polymerase, 0.1 mM dNTPs and 1.5 mM $MgSO_4$). PCR cycling was done in the following manner: 30 cycles with an annealing temperature of 60° C. and an elongation time of 50 seconds at 72° C.

Both PCR fragments were purified, isolated and used in an assembly PCR reaction. For the assembly PCR reaction, 100 pmol of oligo HIV-1 and HIV-end and 2 ng of each PCR fragment (PCRI and PCR II) were used in the 75 μl (4 units of Taq or Pwo polymerase, 0.1 mM dNTPs and 1.5 mM $MgSO_4$). PCR cycling was done in the following manner: 30 cycles with an annealing temperature of 60° C. and an elongation time of 2.5 minutes at 72° C. The assembly PCR product was digested XbaI and NheI. The FOS amphiphatic helix was fused in frame to the C-terminal end of gp-140.

The DNA sequence coding for the FOS amphiphatic helix domain was PCR-amplified from vector pJuFo (Crameri & Suter *Gene* 137.69 (1993)) using the oligonucleotides:

```
FOS-HIV:
5'-ttcggtgctagcggtggcTGCGGTGGTCTGACCGAC-3'   (SEQ ID NO:57); and

FOS-Apa:
5'-gatgctgggcccttaaccGCAACCACCGTGTGCCGCC-3'  (SEQ ID NO:58).
```

For the PCR reaction, 100 pmol of each oligo and 5 ng of the template DNA was used in the 75 μl reaction mixture (4 units of Taq or Pwo polymerase, 0.1 mM dNTPs and 1.5 mM $MgSO_4$). Temperature cycling was done as follows: 95° C. for 2 minutes, followed by 5 cycles of 95° C. (45 seconds), 60° C. (30 seconds), 72° C. (25 seconds) and followed by 25 cycles of 95° C. (45 seconds), 68° C. (30 seconds), 72° C. (20 seconds). The obtained PCR fragment was digested with NheI and Bsp120L.

The final expression vector for GP140-FOS was obtained in a 3 fragment ligation of both PCR fragments into pSinRep5. The resultant vector pSinRep5-GP140-FOS was evaluated by restriction analysis and DNA sequencing.

GP140-FOS was also cloned into pCYTts via XbaI and Bsp120L to obtain a stable, inducible GP140-FOS expressing cell line.

Example 13

Expression of GP 140FOS using pSinRep5-GP 140FOS

RNase-free vector (1.0 μg) (pSinRep5-GP140-FOS) and 1.0 μg of DHEB (Bredenbeek et al., *J. Virol.* 67:6439–6446 (1993)) were linearized by restriction digestion. Subsequently, in vitro transcription was carried out using an SP6 in vitro transcription kit (InvitroscripCAP by InvitroGen, Invitrogen BV, NV Leek, Netherlands). The resulting 5'-capped mRNA was analyzed on a reducing agarose-gel.

In vitro transcribed mRNA (5 μg) was electroporated into BHK 21 cells (ATCC: CCL10) according to Invitrogen's manual (Sindbis Expression System, Invitrogen BV, Netherlands). After 10 hours incubation at 37° C., the FCS containing medium was exchanged by HP-1 medium without FCS, followed by an additional incubation at 37° C. for 10 hours. The supernatant was harvested and analyzed by Western blot analysis for production of soluble GP140-FOS exactly as described in Example 2.

Example 14

Expression of GP 140FOS using pCYTts-GP140FOS pCYT-GP 140-FOS 20 μg was linearized by restriction digestion. The reaction was stopped by phenol/chloroform extraction, followed by an isopropanol precipitation of the linearized DNA. The restriction digestion was evaluated by agarose gel eletrophoresis. For the transfection, 5.4 μg of linearized pCYTtsGP140-FOS was mixed with 0.6 μg of linearized pSV2Neo in 30 μl $H_2O$ and 30 μl of 1 M $CaCl_2$ solution was added. After addition of 60 μl phosphate buffer (50 mM HEPES, 280 mM NaCl, 1.5 mM $Na_2HPO_4$, pH 7.05), the solution was vortexed for 5 seconds, followed by an incubation at room temperature for 25 seconds. The solution was immediately added to 2 ml HP-1 medium containing 2% FCS (2% FCS medium). The medium of an 80% confluent BHK21 cell culture (6-well plate) was then replaced by the DNA containing medium. After an incubation for 5 hours at 37° C. in a $CO_2$ incubator, the DNA containing medium was removed and replaced by 2 ml of 15% glycerol in 2% FCS medium. The glycerol containing medium was removed after a 30 second incubation phase, and the cells were washed by rinsing with 5 ml of HP-1 medium containing 10% FCS. Finally 2 ml of fresh HP-1 medium containing 10% FCS was added.

Stably transfected cells were selected and grown in selection medium (HP-1 medium supplemented with G418) at 37° C. in a $CO_2$ incubator. When the mixed population was grown to confluency, the culture was split to two dishes, followed by a 12 h growth period at 37° C. One dish of the cells was shifted to 30° C. to induce the expression of soluble GP140-FOS. The other dish was kept at 37° C.

The expression of soluble GP 140-FOS was determined by Western blot analysis. Culture media (0.5 ml) was methanol/chloroform precipitated, and the pellet was resuspended in SDS-PAGE sample buffer. Samples were heated for 5 minutes at 95° C. before being applied to a 15% acrylamide gel. After SDS-PAGE, proteins were transferred to Protan nitrocellulose membranes (Schleicher & Schuell, Germany) as described by Bass and Yang, in Creighton, T. E., ed, *Protein Function: A Practical Approach*, 2nd Edn., IRL Press, Oxford (1997), pp. 29–55. The membrane was blocked with 1% bovine albumin (Sigma) in TBS (10×TBS per liter: 87 7 g NaCl, 66.1 g Trizma hydrochloride (Sigma) and 9.7 g Trizma base (Sigma), pH 7.4) for 1 hour at room temperature, followed by an incubation with an anti-GP140 or GP-160 antibody for 1 hour. The blot was washed 3 times for 10 minutes with TBS-T (TBS with 0.05% Tween20), and incubated for 1 hour with an alkaline-phosphatase-anti-mouse/rabbit/monkey/human IgG conjugate. After washing 2 times for 10 minutes with TBS-T and 2 times for 10 minutes with TBS, the development reaction was carried out using alkaline phosphatase detection reagents (10 ml AP buffer (100 mM Tris/HCl, 100 mM NaCl, pH 9.5) with 50 $\mu$l NBT solution (7.7% Nitro Blue Tetrazolium (Sigma) in 70% dimethylformamide) and 37 $\mu$l of X-Phosphate solution (5% of 5-bromo-4-chloro-3-indolyl phosphate in dimethylformamide).

Example 15

Production and Purification of GP140FOS

An anti-gp120 antibody was covalently coupled to a NHS/EDC activated dextran and packed into a chromatography column. The supernatant, containing GP140FOS is loaded onto the column and after sufficient washing, GP140FOS was eluted using 0.1 M HCl. The eluate was directly neutralized during collection using 1 M Tris pH 7.2 in the collection tubes.

Disulfide bond formation might occur during purification, therefore the collected sample is treated with 10 mM DTT in 10 mM Tris pH 7.5 for 2 hours at 25° C.

DTT is remove by subsequent dialysis against 10 mM Mes; 80 mM NaCl pH 6.0. Finally GP140FOS is mixed with alphavirus particles containing the JUN leucine zipper in E2 as described in Example 16.

Example 16

Preparation of the Alpha Vaccine Particles

Viral particles (see Examples 2 and 3) were concentrated using Millipore Ultrafree Centrifugal Filter Devices with a molecular weight cut-off of 100 kD according to the protocol supplied by the manufacturer. Alternatively, viral particles were concentrated by sucrose gradient centrifugation as described in the instruction manual of the Sindbis Expression System (Invitrogen, San Diego, Calif.). The pH of the virus suspension was adjusted to 7.5 and viral particles were incubated in the presence of 2–10 mM DTT for several hours. Viral particles were purified from contaminating protein on a Sephacryl S-300 column (Pharmacia) (viral particles elute with the void volume) in an appropriate buffer.

Purified virus particles were incubated with at least 240 fold molar excess of FOS-antigen fusion protein in an appropriate buffer (pH 7.5–8.5) in the presence of a redox shuffle (oxidized glutathione/reduced glutathione; cystine/cysteine) for at least 10 hours at 4° C. After concentration of the particles using a Millipore Ultrafree Centrifugal Filter Device with a molecular weight cut-off of 100 kD, the mixture was passed through a Sephacryl S-300 gel filtration column (Pharmacia). Viral particles were eluted with the void volume.

Example 17

Fusion of JUN Amphipathic Helix to the Amino Terminus of HBcAg(1–144)

The JUN helix was fused to the amino terminus of the HBcAg amino acid sequence 1 to 144 (JUN-HBcAg construct). For construction of the JUN-HBcAg DNA sequence, the sequences encoding the JUN helix and HBcAg(1–144) were amplified separately by PCR. The JUN sequence was amplified from the pJuFo plasmid using primers EcoRI-JUN(s) and JUN-SacII(as). The EcoRI-JUN(s) primer introduced an EcoRI site followed by a start ATG codon. The JUN-SacII(as) primer introduced a linker encoding the amino acid sequence GAAGS. The HBcAg (1–144) sequence was amplified from the pEco63 plasmid (obtained from ATCC No. 31518) using primers JUN-HBcAg(s) and HBcAg(1–144)Hind(as). JUN-HBcAg(s) contained a sequence corresponding to the 3' end of the sequence encoding the JUN helix followed by a sequence encoding the GAAGS linker and the 5' end of the HBcAg sequence. HBcAg(1–144)Hind(as) introduces a stop codon and a HindIII site after codon 144 of the HBcAg gene. For the PCR reactions, 100 pmol of each oligo and 50 ng of the template DNAs were used in the 50 $\mu$l reaction mixtures with 2 units of Pwo polymerase, 0.1 mM dNTPs and 2 mM $MgSO_4$. For both reactions, temperature cycling was carried out as follows: 94° C. for 2 minutes; and 30 cycles of 94° C. (1 minute), 50° C. (1 minute), 72° C. (2 minutes).

Primer Sequences:

```
EcoRI-JUN(s):
(5'-CCGGAATTCATGTGCGGTGGTCGGATCGCCCGG-3')                    (SEQ ID NO:61);

JUN-SacII(as):
(5'-GTCGCTACCCGCGGCTCCGCAACCAACGTGGTTCATGAC-3')              (SEQ ID NO:62);

JUN-HBcAg(s):
(5'-GTTGGTTGCGGAGCCGCGGGTAGCGACATTGACCCTTATAAAGAATTTGG-3')   (SEQ ID NO:63);

HBcAg(1-144)Hind(as):
(5'-CGCGTCCCAAGCTTCTACGGAAGCGTTGATAGGATAGG-3')               (SEQ ID NO:64).
```

Fusion of the two PCR fragments was performed by PCR using primers EcoRI-JUN(s) and HBcAg(1–144)Hind(as). 100 pmol of each oligo was used with 100 ng of the purified PCR fragments in a 50 $\mu$l reaction mixture containing 2 units of Pwo polymerase, 0.1 mM dNTPs and 2 mM $MgSO_4$. PCR cycling conditions were: 94° C. for 2 minutes; and 35 cycles of 94° C. (1 minute), 50° C. (1 minute), 72° C. (2 minutes). The final PCR product was analyzed by agarose gel electrophoresis, purified and digested for 16 hours in an appropriate buffer with EcoRI and HindIII restriction enzymes. The digested DNA fragment was ligated into EcoRI/HindIII-digested pKK vector to generate pKK-JUN-HBcAg expression vector. Insertion of the PCR product was analyzed by EcoRI/HindIII restriction analysis and by DNA sequencing of the insert.

Example 18

Fusion of JUN Amphipathic Helix to the Carboxy Terminus of HBcAg(1–144)

The JUN helix was fused to the carboxy terminus of the HBcAg amino acid sequence 1 to 144 (HBcAg-JUN construct). For construction of the HBcAg-JUN DNA sequence, the sequences encoding the JUN helix and HBcAg(1–144) were amplified separately by PCR. The JUN sequence was amplified from the pJuFo plasmid with primers SacII-JUN(s) and JUN-HindIII(as). SacII-JUN(s) introduced a linker encoding amino acids LAAG. This sequence also contains a SacII site. JUN-HindIII(as) introduced a stop codon (TAA) followed by a HindIII site. The HBcAg (1–144) DNA sequence was amplified from the pEco63 plasmid using primers EcoRI-HBcAg(s) and HBcAg (1–144)-JUN(as). EcoRI-HBcAg(s) introduced an EcoRI site prior to the Start ATG of the HBcAg coding sequence. HBcAg(1–144)-JUN(as) introduces a sequence encoding the peptide linker (LAAG), which also contains a SacII site. For the PCR reactions, 100 pmol of each oligo and 50 ng of the template DNAs were used in the 50 $\mu$l reaction mixtures with 2 units of Pwo polymerase, 0.1 mM dNTPs and 2 mM $MgSO_4$. Temperature cycling was carried out as follows: 94° C. for 2 minutes; and 30 cycles of 94° C. (1 minute), 50° C. (1 minute), 72° C. (2 minutes).

Primer Sequences

```
SacII-JUN(s):
(5'-CTAGCCGCGGGTTGCGGTGGTCGGATCGCCCGG-3')          (SEQ ID NO:65);

JUN-HindIII(as):
(5'-CGCGTCCCAAGCTTTTAGCAACCAACGTGGTTCATGAC -3')   (SEQ ID NO:66);

EcoRI-HBcAg(s):
(5'-CCGGAATTCATGGACATTGACCCTTATAAAG-3')            (SEQ ID NO:67); and

HBcAg-JUN(as):
(5'-CCGACCACCGCAACCCGCGGCTAGCGGAAGCGTTGATAGGATAGG-3')  (SEQ ID NO.68).
```

Fusion of the two PCR fragments was performed by PCR using primers EcoRI-HBcAg(s) and JUN-HindIII(as). For the PCR fusion, 100 pmol of each oligo was used with 100 ng of the purified PCR fragments in a 50 $\mu$l reaction mixture containing 2 units of Pwo polymerase, 0.1 mM dNTPs and 2 mM $MgSO_4$. PCR cycling conditions were: 94° C. for 2 minutes; and 35 cycles of 94° C. (1 minute), 50° C. (1 minute), 72° C. (2 minutes). The final PCR product was analyzed by agarose gel electrophoresis, and digested for 16 hours in an appropriate buffer with EcoRI and HindIII restriction enzymes. The DNA fragment was gel purified and ligated into EcoRI/HindIII-digested pKK vector to generate pKK-HBcAg-JUN expression vector. Insertion of the PCR product was analyzed by EcoRI/HindIII restriction analysis and by DNA sequencing of the insert.

Example 19

Insertion of JUN Amphipathic Helix into the c/e1 Epitope of HBcAg(1–144)

The c/e1 epitope (residues 72 to 88) of HBcAg is known to be located in the tip region on the surface of the Hepatitis B virus capsid. A part of this region (residues 76 to 82) of the protein was genetically replaced by the JUN helix to provide an attachment site for antigens (HBcAg-JUNIns construct). The HBcAg-JUNIns DNA sequence was generated by PCRs: The JUN helix sequence and two sequences encoding HBcAg fragments (amino acid residues 1 to 75 and 83 to 144) were amplified separately by PCR. The JUN sequence was amplified from the pJuFo plasmid with primers BamHI-JUN(s) and JUN-SacII(as). BamHI-JUN(s) introduced a linker sequence encoding the peptide sequence GSGGG that also contains a BamHI site. JUN-SacII(as) introduced a sequence encoding the peptide linker GAAGS followed by a sequence complementary to the 3' end of the JUN coding sequence. The HBcAg(1–75) DNA sequence was amplified from the pEco63 plasmid using primers EcoRIHBcAg(s) and HBcAg75-JUN(as). EcoRIHBcAg(s) introduced an EcoRI site followed by a sequence corresponding to the 5' end of the HBcAg sequence. HBcAg75-JUN(as) introduced a linker encoding the peptide GSGGG after amino acid 75 of HBcAg followed by a sequence complementary to the 5' end of the sequence encoding the JUN helix. The HBcAg (83–144) fragment was amplified using primers JUN-HBcAg83(s) and HBcAg(1–144)Hind (as). JUN-HBcAg83(s) contained a sequence corresponding to the 3' end of the JUN-encoding sequence followed by a linker encoding the peptide, GAAGS and a sequence corresponding to the 5' end of the sequence encoding HBcAg (83–144). HBcAg(1–144)Hind(as) introduced a stop codon and a HindIII site after codon 144 of the HBcAg gene. For the PCR reactions, 100 pmol of each oligo and 50 ng of the template DNAs were used in the 50 $\mu$l reaction mixtures (2 units of Pwo polymerase, 0 1 mM dNTPs and 2 mM $MgSO_4$). Temperature cycling was performed as follows: 94° C. for 2 minutes; and 35 cycles of 94° C. (1 minute), 50° C. (1 minute), 72° C. (2 minutes).

Primer Sequences:

```
BamHI-JUN(s):
(5'-CTAATGGATCCGGTGGGGGCTGCGGTGGTCGGATCGCCCGGCTCGAG-3')(SEQ ID NO:69);

JUN-SacII(as):
(5'-GTCGCTACCCGCGGCTCCGCAACCAACGTGGTTCATGAC-3')        (SEQ ID NO:70);

EcoRIHBcAg(s):
(5'-CCGGAATTCATGGACATTGACCCTTATAAAG-3')                (SEQ ID NO:71);

HBcAg75-JUN (as):
(5'-CCGACCACCGCAGCCCCCACCGGATCCATTAGTACCCACCCAGGTAGC-  (SEQ ID NO:72);
3')

JUN-HBcAg83(s):
(5'-GTTGGTTGCGGAGCCGCGGGTAGCGACCTAGTAGTCAGTTATGTC-3')  (SEQ ID NO:73); and

HBcAg(1-144)Hind(as):
(5'-CGCGTCCCAAGCTTCTACGGAAGCGTTGATAGGATAGG-3')         (SEQ ID NO:74).
```

Fusion of the three PCR fragments was performed as follows. First, the fragment encoding HBcAg 1–75 was fused with the sequence encoding JUN by PCR using primers EcoRIHBcAg(s) and JUN-SacII(as). Second, the product obtained was fused with the HBcAg(83–144) fragment by PCR using primers EcoRI HBcAg(s) and HBcAg HindIII(as). For PCR fusions, 100 pmol of each oligo was used with 100 ng of the purified PCR fragments in a 50 μl reaction mixture containing 2 units of Pwo polymerase, 0.1 mM dNTPs and 2 mM $MgSO_4$. The same PCR cycles were used as for generation of the individual fragments. The final PCR product was digested for 16 hours in an appropriate buffer with EcoRI and HindIII restriction enzymes. The DNA fragment was ligated into EcoRI/HindIII-digested pKK vector, yielding the pKK-HBcAg-JUNIns vector. Insertion of the PCR product was analyzed by EcoRI/HindIII restriction analysis and by DNA sequencing of the insert.

Example 20

Fusion of the JUN Amphipathic Helix to the Carboxy Terminus of the Measles Virus Nucleocapsid (N) Protein The JUN helix was fused to the carboxy terminus of the truncated measles virus N protein fragment comprising amino acid residues 1 to 473 (N473-JUN construct). For construction of the DNA sequence encoding N473-JUN the sequence encoding the JUN helix and the sequence encoding N473-JUN were amplified separately by PCR. The JUN sequence was amplified from the pJuFo plasmid with primers SacII-JUN(s) and JUN-HindIII(as). SacII-JUN(s) introduced a sequence encoding peptide linker LAAG. This sequence also contained a SacII site. The JUN-HindIII(as) anti-sense primer introduced a stop codon (TAA) followed by a HindIII site. The N (1–473) sequence was amplified from the pSC-N plasmid containing the complete measles virus N protein coding sequence (obtained from M. Billeter, Zurich) using primers EcoRI-Nmea(s) and Nmea-JUN(as). EcoRI-N(mea)(s) introduced an EcoRI site prior to the Start ATG of the N coding sequence. N(mea)-JUN(as) was complementary to the 3' end of the N(1–473) coding sequence followed by a sequence complementary to the coding sequence for the peptide linker (LAAG). For the PCR reactions, 100 pmol of each oligo and 50 ng of the template DNAs were used in the 50 μl reaction mixtures with 2 units of Pwo polymerase, 0.1 mM dNTPs and 2 mM $MgSO_4$. Temperature cycling was performed as follows: 94° C. for 2 minutes; and 35 cycles of 94° C. (1 minute), 55° C. (1 minute), 72° C. (2 minutes).

Primer Sequences:

```
SacII-JUN(s):
(5'-CTAGCCGCGGGTTGCGGTGGTCGGATCGCCCGG-3')      (SEQ ID NO:75);

JUN-HindIII(as):
(5'-CGCGTCCCAAGCTTTTAGCAACCAACGTGGTTCATGAC-3') (SEQ ID NO:76);

EcoRI-Nmea(s):
(5'-CCGGAATTCATGGCCACACTTTTAAGGAGC-3')         (SEQ ID NO:77); and

Nmea-JUN(as):
(5'-CGCGTCCCAAGCTTTTAGCAACCAACGTGGTTCATGAC-3') (SEQ ID NO:78).
```

Fusion of the two PCR fragments was performed in a further PCR using primers EcoRI-Nmea(s) and Nmea-JUN (as). For the PCR fusion, 100 pmol of each oligo was used with 100 ng of the purified PCR fragments in a 50 μl reaction mixture containing 2 units of Pwo polymerase, 0 1 mM dNTPs and 2 mM $MgSO_4$. Temperature cycling was performed as follows: 94° C. for 2 minutes; and 35 cycles of 94° C. (1 minute), 50° C. (1 minute), 72° C. (2 minutes). The PCR product was digested for 16 hours in an appropriate buffer with EcoRI and HindIII restriction enzymes. The DNA fragment was gel purified and ligated into EcoRI/HindIII-digested pKK vector, yielding the pKK-N473-JUN plasmid. Insertion of the PCR product was analyzed by EcoRI/HindIII restriction analysis and by DNA sequencing of the insert.

Example 21

Expression and Partial Purification of HBcAg-JUN

Figure 4:
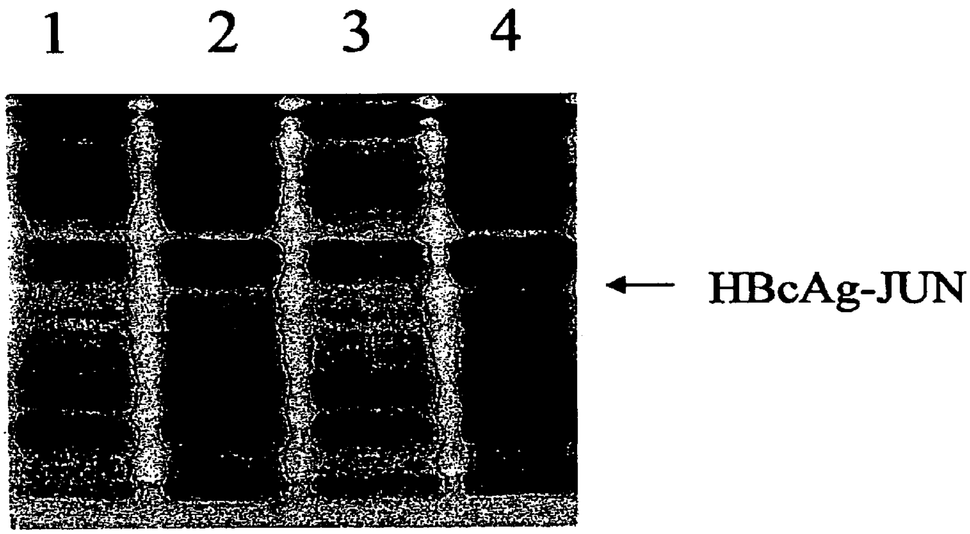
FIG. 4 shows the expression of HBcAg-JUN in *E. coli* cells.

*E. coli* strain XL-1 blue was transformed with pKK-HBcAg-JUN. 1 ml of an overnight culture of bacteria was used to innoculate 100 ml of LB medium containing 100 μg/ml ampicillin. This culture was grown for 4 hours at 37° C. until an OD at 600 nm of approximately 0.8 was reached. Induction of the synthesis of HBcAg-JUN was performed by addition of IPTG to a final concentration of 1 mM. After induction, bacteria were further shaken at 37° C. for 16 hours. Bacteria were harvested by centrifugation at 5000×g for 15 minutes. The pellet was frozen at −20° C. The pellet was thawed and resuspended in bacteria lysis buffer (10 mM $Na_2HPO_4$, pH 7.0, 30 mM NaCl, 0.25% Tween-20, 10 mM EDTA, 10 mM DTT) supplemented with 200 μg/ml lysozyme and 10 μl of Benzonase (Merck). Cells were incubated for 30 minutes at room temperature and disrupted using a French pressure cell. Triton X-100 was added to the lysate to a final concentration of 0.2%, and the lysate was incubated for 30 minutes on ice and shaken occasionally. FIG. 4 shows HBcAg-JUN protein expression in *E. coli* upon induction with IPTG. *E. coli* cells harboring pKK-HBcAg-JUN expression plasmid or a control plasmid were used for induction of HBcAg-JUN expression with IPTG. Prior to the addition of IPTG, a sample was removed from the bacteria culture carrying the pKK-HBcAg-JUN plasmid (lane 3) and from a culture carrying the control plasmid (lane 1). Sixteen hours after addition of IPTG, samples were again removed from the culture containing pKK-HBcAg-JUN (lane 4) and from the control culture (lane 2). Protein expression was monitored by SDS-PAGE followed by Coomassie staining.

Figure 5:
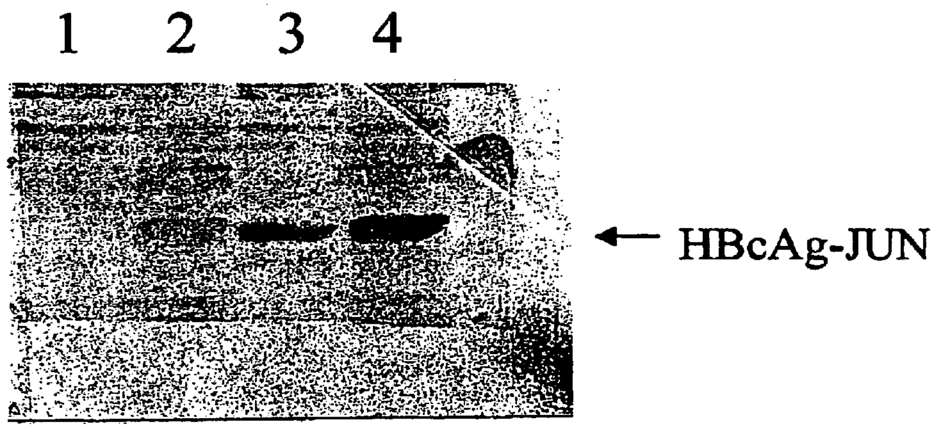
FIG. 5 shows a Western blot demonstrating that HBcAg-JUN is soluble in *E. coli* lysates.

The lysate was then centrifuged for 30 minutes at 12,000×g in order to remove insoluble cell debris. The supernatant and the pellet were analyzed by Western blotting using a monoclonal antibody against HBcAg (YVS1841, purchased from Accurate Chemical and Scientific Corp., Westbury, N.Y., USA), indicating that a significant amount of HBcAg-JUN protein was soluble (FIG. 5). Briefly, lysates from *E. coli* cells expressing HBcAg-JUN and from control cells were centrifuged at 14,000×g for 30 minutes. Supernatant (=soluble fraction) and pellet (=insoluble fraction) were separated and diluted with SDS sample buffer to equal volumes. Samples were analyzed by SDS-PAGE followed by Western blotting with anti-HBcAg monoclonal antibody YVS 1841. Lane 1: soluble fraction, control cells; lane 2: insoluble fraction, control cells; lane 3: soluble fraction, cells expressing HBcAg-JUN; lane 4: insoluble fraction, cells expressing HbcAg-JUN.

Figure 6:
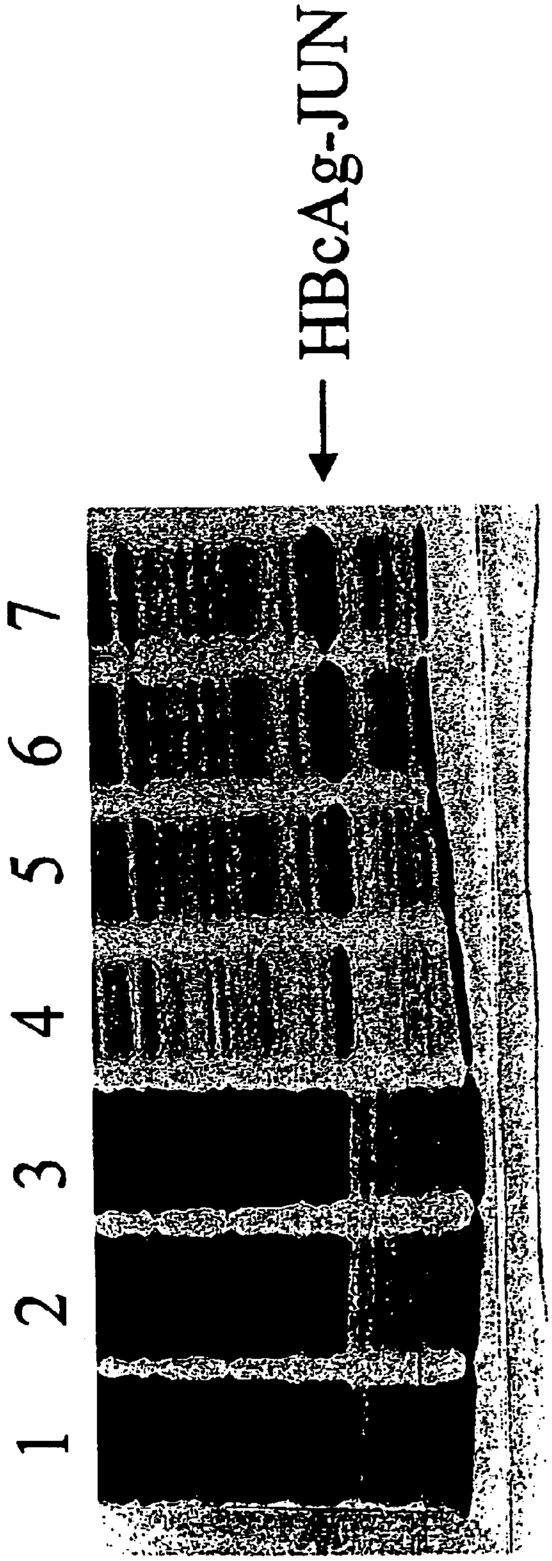
FIG. 6 shows an SDS-PAGE analysis of enrichment of HBcAg-JUN capsid particles on a sucrose density gradient.

The cleared cell lysate was used for step-gradient centrifugation using a sucrose step gradient consisting of a 4 ml 65% sucrose solution overlaid with 3 ml 15% sucrose solution followed by 4 ml of bacterial lysate. The sample was centrifuged for 3 hrs with 100,000×g at 4° C. After centrifugation, 1 ml fractions from the top of the gradient were collected and analyzed by SDS-PAGE followed by Coomassie staining. (FIG. 6). Lane 1: total *E. coli* lysate prior to centrifugation. Lane 1 and 2: fractions 1 and 2 from the top of the gradient. Lane 4 to 7: fractions 5 to 8 (15% sucrose). The HBcAg-JUN protein was detected by Coomassie staining.

The HBcAg-JUN protein was enriched at the interface between 15 and 65% sucrose indicating that it had formed a capsid particle. Most of the bacterial proteins remained in the sucrose-free upper layer of the gradient, therefore step-gradient centrifugation of the HBcAg-JUN particles led both to enrichment and to a partial purification of the particles.

Example 22

Covalent Coupling of hGH-FOS to HBcAg-JUN

Figure 7:
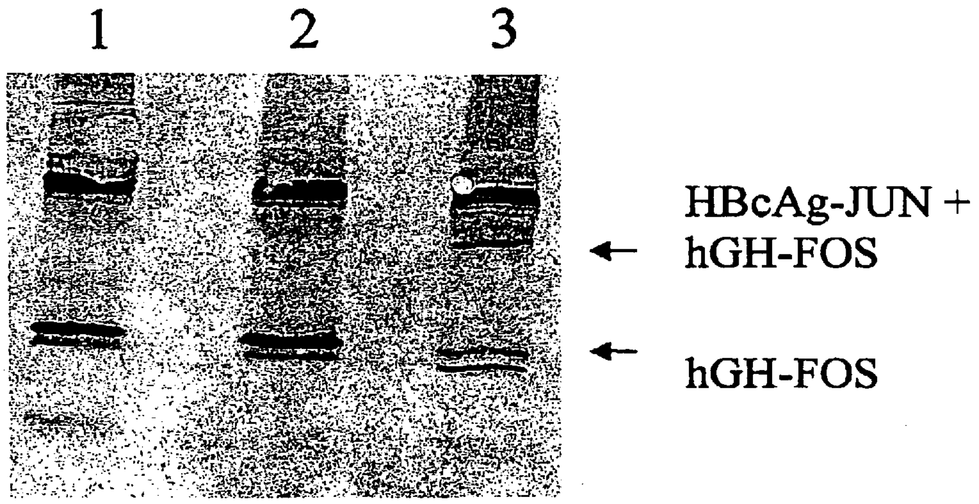
FIG. 7 shows a non-reducing SDS-PAGE analysis of the coupling of hGH-FOS and HBcAg-JUN particles.

In order to demonstrate binding of a protein to HBcAg-JUN particles, we chose human growth hormone (hGH) fused with its carboxy terminus to the FOS helix as a model protein (hGH-FOS). HBcAg-JUN particles were mixed with partially purified hGH-FOS and incubated for 4 hours at 4° C. to allow binding of the proteins. The mixture was then dialyzed overnight against a 3000-fold volume of dialysis buffer (150 mM NaCl, 10 mM Tris-HCl solution, pH 8.0) in order to remove DTT present in both the HBcAg-JUN solution and the hGH-FOS solution and thereby allow covalent coupling of the proteins through the establishment of disulfide bonds. As controls, the HBcAg-JUN and the hGH-FOS solutions were also dialyzed against dialysis buffer. Samples from all three dialyzed protein solutions were analyzed by SDS-PAGE under non-reducing conditions. Coupling of hGH-FOS to HBcAg-JUN was detected in an anti-hGH immunoblot (FIG. 7). hGH-FOS bound to HBcAg-JUN should migrate with an apparent molecular mass of approximately 53 kDa, while unbound hGH-FOS migrates with an apparent molecular mass of 31 kDa. The dialysate was analyzed by SDS-PAGE in the absence of reducing agent (lane 3) and in the presence of reducing agent (lane 2) and detected by Coomassie staining. As a control, hGH-FOS that had not been mixed with capsid particles was also loaded on the gel in the presence of reducing agent (lane 1).

A shift of hGH-FOS to a molecular mass of approximately 53 kDa was observed in the presence of HBcAg-JUN capsid protein, suggesting that efficient binding of hGH-FOS to HBcAg-JUN had taken place.

Example 23

Insertion of a Peptide Containing a Lysine Residue into the c/e1 Epitope of HBcAg(1–149)

The c/e1 epitope (residues 72 to 88) of HBcAg is located in the tip region on the surface of the Hepatitis B virus capsid (HBcAg). A part of this region (Proline 79 and Alanine 80) was genetically replaced by the peptide Gly-Gly-Lys-Gly-Gly (HBcAg-Lys construct). The introduced Lysine residue contains a reactive amino group in its side chain that can be used for intermolecular chemical crosslinking of HBcAg particles with any antigen containing a free cysteine group.

HBcAg-Lys DNA, having the amino acid sequence shown in SEQ ID NO:158, was generated by PCRs: The two fragments encoding HBcAg fragments (amino acid residues 1 to 78 and 81 to 149) were amplified separately by PCR. The primers used for these PCRs also introduced a DNA sequence encoding the Gly-Gly-Lys-Gly-Gly peptide. The HBcAg (1 to 78) fragment was amplified from pEco63 using primers EcoRIHBcAg(s) and Lys-HBcAg(as). The HBcAg (81 to 149) fragment was amplified from pEco63 using primers Lys-HBcAg(s) and HBcAg(1–149)Hind(as). Primers Lys-HBcAg(as) and Lys-HBcAg(s) introduced complementary DNA sequences at the ends of the two PCR products allowing fusion of the two PCR products in a subsequent assembly PCR. The assembled fragments were amplified by PCR using primers EcoRIHBcAg(s) and HbcAg(1–149)Hind(as).

For the PCRs, 100 pmol of each oligo and 50 ng of the template DNAs were used in the 50 μl reaction mixtures with 2 units of Pwo polymerase, 0.1 mM dNTPs and 2 mM MgSO4. For both reactions, temperature cycling was carried out as follows: 94° C. for 2 minutes; 30 cycles of 94° C. (1 minute), 50° C. (1 minute), 72° C. (2 minutes).

Primer Sequences:

```
EcoRIHBcAg(s):
(5'-CCGGAATTCATGGACATTGACCCTTATAAAG-3')                 (SEQ ID NO:79);

Lys-HBcAg(as):
(5'-CCTAGAGCCACCTTTGCCACCATCTTCTAAATTAGTACCCACCCAGGTAGC-3') (SEQ ID NO:80);

Lys-HBcAg(s):
(5'-GAAGATGGTGGCAAAGGTGGCTCTAGGGACCTAGTAGTCAGTTATGTC-3')    (SEQ ID NO:81);

HBcAg(1-149)Hind(as):
(5'-CGCGTCCCAAGCTTCTAAACAACAGTAGTCTCCGGAAG-3')           (SEQ ID NO:82).
```

For fusion of the two PCR fragments by PCR 100 pmol of primers EcoRIHBcAg(s) and HBcAg(1–149)Hind(as) were used with 100 ng of the two purified PCR fragments in a 50 μl reaction mixture containing 2 units of Pwo polymerase, 0.1 mM dNTPs and 2 mM $MgSO_4$. PCR cycling conditions were: 94° C. for 2 minutes; 30 cycles of 94° C. (1 minute), 50° C. (1 minute), 72° C. (2 minutes). The assembled PCR product was analyzed by agarose gel electrophoresis, purified and digested for 19 hours in an appropriate buffer with EcoRI and HindIII restriction enzymes. The digested DNA fragment was ligated into EcoRI/HindIII-digested pKK vector to generate pKK-HBcAg-Lys expression vector. Insertion of the PCR product into the vector was analyzed by EcoRI/HindIII restriction analysis and DNA sequencing of the insert.

The amino acid sequence of the HBcAg-Lys polypeptide is

```
MDIDPYKEFGATVELLSFLPSDFFPSVRDLLDTASALYREAIESPEHCSP  (SEQ ID NO:185).

HHTALRQAILCWGELMTLATWVGTNLEDGGKGGSRDLVVSYVNTNM

GLKIRQLLWFHISCLTFGRETVLEYLVSFGVWIRTPPAYRPPNAPILSTL

PETTVV
```

This sequence differs from SEQ ID NO:134 at amino acid 74 (N in SEQ ID NO:1314, T in SEQ ID NO:185) and at amino acid 87 (N in SEQ ID NO:134, S in SEQ ID NO: 185).

Example 24

Expression and Partial Purification of HBcAg-Lys

*E. coli* strain XL-1 blue was transformed with pKK-HBcAg-Lys. 1 ml of an overnight culture of bacteria was used to innoculate 100 ml of LB medium containing 100 μg/ml ampicillin. This culture was grown for 4 hours at 37° C. until an OD at 600 nm of approximately 0.8 was reached. Induction of the synthesis of HBcAg-Lys was performed by addition of IPTG to a final concentration of 1 mM. After induction, bacteria were further shaken at 37° C. for 16 hours. Bacteria were harvested by centrifugation at 5000×g for 15 minutes. The pellet was frozen at −20° C. The pellet was thawed and resuspended in bacteria lysis buffer (10 mM $Na_2HPO_4$, pH 7.0, 30 mM NaCl, 0.25% Tween-20, 10 mM EDTA, 10 mM DTT) supplemented with 200 μg/ml lysozyme and 10 μl of Benzonase (Merck). Cells were incubated for 30 minutes at room temperature and disrupted using a French pressure cell. Triton X-100 was added to the lysate to a final concentration of 0.2%, and the lysate was incubated for 30 minutes on ice and shaken occasionally. *E. coli* cells harboring pKK-HBcAg-Lys expression plasmid or a control plasmid were used for induction of HBcAg-Lys expression with IPTG. Prior to the addition of IPTG, a sample was removed from the bacteria culture carrying the pKK-HBcAg-Lys plasmid and from a culture carrying the control plasmid. Sixteen hours after addition of IPTG, samples were again removed from the culture containing pKK-HBcAg-Lys and from the control culture. Protein expression was monitored by SDS-PAGE followed by Coomassie staining.

The lysate was then centrifuged for 30 minutes at 12,000×g in order to remove insoluble cell debris. The supernatant and the pellet were analyzed by Western blotting using a monoclonal antibody against HBcAg (YVS1841, purchased from Accurate Chemical and Scientific Corp., Westbury, N.Y., USA), indicating that a significant amount of HBcAg-Lys protein was soluble. Briefly, lysates from *E. coli* cells expressing HBcAg-Lys and from control cells were centrifuged at 14,000×g for 30 minutes. Supernatant (=soluble fraction) and pellet (=insoluble fraction) were separated and diluted with SDS sample buffer to equal volumes. Samples were analyzed by SDS-PAGE followed by Western blotting with anti-HBcAg monoclonal antibody YVS 1841.

The cleared cell lysate was used for step-gradient centrifugation using a sucrose step gradient consisting of a 4 ml 65% sucrose solution overlaid with 3 ml 15% sucrose solution followed by 4 ml of bacterial lysate. The sample was centrifuged for 3 hrs with 100,000×g at 4° C. After centrifugation, 1 ml fractions from the top of the gradient were collected and analyzed by SDS-PAGE followed by Coomassie staining. The HBcAg-Lys protein was detected by Coomassie staining.

The HBcAg-Lys protein was enriched at the interface between 15 and 65% sucrose indicating that it had formed a capsid particle. Most of the bacterial proteins remained in the sucrose-free upper layer of the gradient, therefore step-gradient centrifugation of the HBcAg-Lys particles led both to enrichment and to a partial purification of the particles.

Example 25

Chemical Coupling of FLAG Peptide to HBcAg-Lys using the Heterobifunctional Cross-linker SPDP Synthetic FLAG peptide with a Cysteine residue at its amino terminus (amino acid sequence CGGDYKDDDDK (SEQ ID NO:147)) was coupled chemically to purified HBcAg-Lys particles in order to elicit an immune response against the FLAG peptide. 600 μl of a 95% pure solution of HBcAg-Lys particles (2 mg/ml) were incubated for 30 minutes at room temperature with the heterobifunctional cross-linker N-Succinimidyl 3-(2-pyridyldithio)propionate (SPDP) (0.5 mM). After completion of the reaction, the mixture was dialyzed overnight against 1 liter of 50 mM Phosphate buffer (pH 7.2) with 150 mM NaCl to remove free SPDP. Then 500 μl of derivatized HBcAg-Lys capsid (2 mg/ml) were mixed with 0.1 mM FLAG peptide (containing an amino-terminal cysteine) in the presence of 10 mM EDTA to prevent metal-catalyzed sulfhydryl oxidation. The reaction was monitored through the increase of the optical density of the solution at 343 nm due to the release of pyridine-2-thione from SPDP upon reaction with the free cysteine of the peptide. The reaction of derivatized Lys residues with the peptide was complete after approximately 30 minutes.

The FLAG decorated particles were injected into mice.

Example 26

Construction of pMPSV-gp 140 cys

The gp140 gene was amplified by PCR from pCytTSgp140FOS using oligos gp140 CysEcoRI and SalIgp140. For the PCRs, 100 pmol of each oligo and 50 ng of the template DNAs were used in the 50 μl reaction mixtures with 2 units of Pwo polymerase, 0.1 mM dNTPs and 2 mM MgSO4. For both reactions, temperature cycling was carried out as follows: 94° C. for 2 minutes; 30 cycles of 94° C. (0.5 minutes), 55° C. (0.5 minutes), 72° C. (2 minutes).

The PCR product was purified using QiaEXII kit, digested with SalI/EcoRI and ligated into vector pMPSVHE cleaved with the same enzymes.

| Oligo sequences: | |
|---|---|
| Gp140CysEcoRI: | |
| 5'-GCCGAATTCCTAGCAGCTAGCACCGAATTTATCTAA-3' | (SEQ ID NO:83); |
| SalIgp140: | |
| 5'-GGTTAAGTCGACATGAGAGTGAAGGAGAAATAT-3' | (SEQ ID NO:84). |

Example 27

Expression of pMPSVgp140Cys pMPSVgp140Cys (20 μg) was linearized by restriction digestion. The reaction was stopped by phenol/chloroform extraction, followed by an isopropanol precipitation of the linearized DNA. The restriction digestion was evaluated by agarose gel eletrophoresis. For the transfection, 5.4 μg of linearized pMPSVgp140-Cys was mixed with 0.6 μg of linearized pSV2Neo in 30 μl $H_2O$ and 30 μl of 1 M $CaCl_2$ solution was added. After addition of 60 μl phosphate buffer (50 mM HEPES, 280 mM NaCl, 1.5 mM $Na_2HPO_4$, pH 7.05), the solution was vortexed for 5 seconds, followed by an incubation at room temperature for 25 seconds. The solution was immediately added to 2 ml HP-1 medium containing 2% FCS (2% FCS medium). The medium of an 80% confluent BHK21 cell culture (6-well plate) was then replaced by the DNA containing medium. After an incubation for 5 hours at 37° C. in a $CO_2$ incubator, the DNA containing medium was removed and replaced by 2 ml of 15% glycerol in 2% FCS medium. The glycerol containing medium was removed after a 30 second incubation phase, and the cells were washed by rinsing with 5 ml of HP-1 medium containing 10% FCS. Finally 2 ml of fresh HP-1 medium containing 10% FCS was added.

Stably transfected cells were selected and grown in selection medium (HP-1 medium supplemented with G418) at 37° C. in a $CO_2$ incubator. When the mixed population was grown to confluency, the culture was split to two dishes, followed by a 12 h growth period at 37° C. One dish of the cells was shifted to 30° C. to induce the expression of soluble GP140-FOS. The other dish was kept at 37° C.

The expression of soluble GP140-Cys was determined by Western blot analysis. Culture media (0.5 ml) was methanol/chloroform precipitated, and the pellet was resuspended in SDS-PAGE sample buffer. Samples were heated for 5 minutes at 95° C. before being applied to a 15% acrylamide gel. After SDS-PAGE, proteins were transferred to Protan nitrocellulose membranes (Schleicher & Schuell, Germany) as described by Bass and Yang, in Creighton, T. E., ed., *Protein Function: A Practical Approach*, 2nd Edn., IRL Press, Oxford (1997), pp. 29–55. The membrane was blocked with 1% bovine albumin (Sigma) in TBS (10×TBS per liter: 87 7 g NaCl, 66.1 g Trizma hydrochloride (Sigma) and 9.7 g Trizma base (Sigma), pH 7.4) for 1 hour at room temperature, followed by an incubation with an anti-GP140 or GP-160 antibody for 1 hour. The blot was washed 3 times for 10 minutes with TBS-T (TBS with 0.05% Tween20), and incubated for 1 hour with an alkaline-phosphatase-anti-mouse/rabbit/monkey/human IgG conjugate. After washing 2 times for 10 minutes with TBS-T and 2 times for 10 minutes with TBS, the development reaction was carried out using alkaline phosphatase detection reagents (10 ml AP buffer (100 mM Tris/HCl, 100 mM NaCl, pH 9.5) with 50 μl NBT solution (7.7% Nitro Blue Tetrazolium (Sigma) in 70% dimethylformamide) and 37 μl of X-Phosphate solution (5% of 5-bromo-4-chloro-3-indolyl phosphate in dimethylformamide).

Example 28

Purification of gp140Cys

An anti-gp120 antibody was covalently coupled to a NHS/EDC activated dextran and packed into a chromatography column. The supernatant, containing GP140Cys is loaded onto the column and after sufficient washing, GP140Cys was eluted using 0.1 M HCl. The eluate was directly neutralized during collection using 1 M Tris pH 7.2 in the collection tubes.

Disulfide bond formation might occur during purification, therefore the collected sample is treated with 10 mM DTT in 10 mM Tris pH 7.5 for 2 hours at 25° C.

DTT is remove by subsequent dialysis against 10 mM Mes; 80 mM NaCl pH 6.0. Finally GP140Cys is mixed with alphavirus particles containing the JUN residue in E2 as described in Example 16.

Example 29

Construction of PLA2-Cys

The PLA2 gene was amplified by PCR from pAV3PLAfos using oligos EcoRIPLA and PLA-Cys-hind. For the PCRs, 100 pmol of each oligo and 50 ng of the template DNAs were used in the 50 μl reaction mixtures with 2 units of Pwo polymerase, 0.1 mM dNTPs and 2 mM MgSO4. For both reactions, temperature cycling was carried out as follows: 94° C. for 2 minutes; 30 cycles of 94° C. (0.5 minutes), 55° C. (0.5 minutes), 72° C. (2 minutes).

The PCR product was purified using QiaEXII kit, digested with EcoRI/HinDIII and ligated into vector pAV3 cleaved with the same enzymes.

| Oligos | |
|---|---|
| EcoRIPLA: | |
| 5'-TAACCGAATTCAGGAGGTAAAAAGATATGG-3' | (SEQ ID NO:85) |
| PLACys-hind: | |
| 5'-GAAGTAAAGCTTTTAACCACCGCAACCACCAGAAG-3' | (SEQ ID NO:86). |

Example 30

Expression and Purification of PLA-Cys

For cytoplasmic production of Cys tagged proteins, *E. coli* XL-1-Blue strain was transformed with the vectors pAV3::PLA and pPLA-Cys. The culture was incubated in rich medium in the presence of ampicillin at 37° C. with shaking. At an optical density (550 nm) of, 1 mM IPTG was added and incubation was continued for another 5 hours. The cells were harvested by centrifugation, resuspended in an appropriate buffer (e.g., Tris-HCl, pH 7.2, 150 mM NaCl) containing DNase, RNase and lysozyme, and disrupted by passage through a french pressure cell. After centrifugation (Sorvall RC-5C, SS34 rotor, 15000 rpm, 10 min, 4° C.), the pellet was resuspended in 25 ml inclusion body wash buffer (20 mM tris-HCl, 23% sucrose, 0.5% Triton X-100, 1 mM EDTA, pH8) at 4° C. and recentrifuged as described above. This procedure was repeated until the supernatant after centrifugation was essentially clear. Inclusion bodies were resuspended in 20 ml solubilization buffer (5.5 M guanidinium hydrochloride, 25 mM tris-HCl, pH 7.5) at room temperature and insoluble material was removed by centrifugation and subsequent passage of the supernatant through a sterile filter (0 45 μm). The protein solution was kept at 4° C. for at least 10 hours in the presence of 10 mM EDTA and 100 mM DTT and then dialyzed three times against 10 volumes of 5.5 M guanidinium hydrochloride, 25 mM tris-HCl, 10 mM EDTA, pH 6. The solution was dialyzed twice against 51 2 M urea, 4 mM EDTA, 0.1 M $NH_4Cl$, 20 mM sodium borate (pH 8.3) in the presence of an appropriate redox shuffle (oxidized glutathione/reduced glutathione; cystine/cysteine). The refolded protein was then applied to an ion exchange chromatography. The protein was stored in an appropriate buffer with a pH above 7 in the presence of 2–10 mM DTT to keep the cysteine residues in a reduced form. Prior to coupling of the protein with the alphavirus particles, DTT was removed by passage of the protein solution through a Sephadex G-25 gel filtration column.

Example 31

Construction of a HBcAg Devoid of Free Cysteine Residues and Containing an Inserted Lysine Residue A Hepatitis core Antigen (HBcAg), referred to herein as HBcAg-lys-2cys-Mut, devoid of cysteine residues at positions corresponding to 48 and 107 in SEQ ID NO:134 and containing an inserted lysine residue was constructed using the following methods.

The two mutations were introduced by first separately amplifying three fragments of the HBcAg-Lys gene prepared as described above in Example 23 with the following PCR primer combinations. PCR methods essentially as described in Example 1 and conventional cloning techniques were used to prepare the HBcAg-lys-2cys-Mut gene.

In brief, the following primers were used to prepare fragment 1:

```
In brief, the following primers were used to
prepare fragment 1:
Primer 1: EcoRIHBcAg(s)
CCGGAATTCATGGACATTGACCCTTATAAAG                (SEQ ID NO:148)

Primer 2: 48as
GTGCAGTATGGTGAGGTGAGGAATGCTCAGGAGACTC          (SEQ ID NO:149)

The following primers were used to
prepare fragment 2:
Primer 3: 48s
GSGTCTCCTGAGCATTCCTCACCTCACCATACTGCAC          (SEQ ID NO:150)
```

-continued

```
Primer 4: 107as
CTTCCAAAAGTGAGGGAAGAAATGTGAAACCAC             (SEQ ID NO:151)

The following primers were used to
prepare fragment 3:
Primer 5: HBcAg149hind-as
CGCGTCCCAAGCTTCTAAACAACAGTAGTCTCCGGAAGCGTTGATAG (SEQ ID NO:152)

Primer 6: 107s
GTGGTTTCACATTTCTTCCCTCACTTTTGGAAG             (SEQ ID NO:153)
```

Fragments 1 and 2 were then combined with PCR primers EcoRIHBcAg(s) and 107 as to give fragment 4. Fragment 4 and fragment 3 were then combined with primers EcoRIHBcAg(s) and HBcAg149hind-as to produce the full length gene. The full length gene was then digested with the EcoRI (GAATTC) and HindIII (AAGCTT) enzymes and cloned into the pKK vector (Pharmacia) cut at the same restriction sites. The amino acid sequence of the HBcAg-Lys-2cys-Mut polypeptide is

```
MDIDPYKEFGATVELLSFL                              (SEQ ID NO:186).

PSDFFPSVRDLLDTASALYREALESPEHSSPHHTALRQAILCWGELMTL

ATWVGTNLEDGGKGGSRDLVVSYVNTNMGLKIRQLLWFHISSLTFGR

ETVLEYLVSFGVWIRTPPAYRPPNAPILSTLPETTVV
```

Example 32

Blockage of Free Cysteine Residues of a HBcAg Followed by Cross-linking

The free cysteine residues of the HBcAg-Lys prepared as described above in Example 23 were blocked using lodacetamide. The blocked HBcAg-Lys was then cross-linked to the FLAG peptide with the hetero-bifunctional cross-linker m-maleimidonbenzoyl-N-hydroxysuccinimide ester (Sulfo-MBS).

The methods used to block the free cysteine residues and cross-link the HBcAg-Lys are as follows. HBcAg-Lys (550 $\mu$g/ml) was reacted for 15 minutes at room temperature with Iodacetamide (Fluka Chemie, Brugg, Switzerland) at a concentration of 50 mM in phosphate buffered saline (PBS) (50 mM sodium phosphate, 150 mM sodium chloride), pH 7.2, in a total volume of 1 ml. The so modified HBcAg-Lys was then reacted immediately with Sulfo-MBS (Pierce) at a concentration of 530 $\mu$M directly in the reaction mixture of step 1 for 1 hour at room temperature. The reaction mixture was then cooled on ice, and dialyzed against 1000 volumes of PBS pH 7.2. The dialyzed reaction mixture was finally reacted with 300 $\mu$M of the FLAG peptide (CGGDYKDDDDK (SEQ ID NO:147)) containing an N-terminal free cysteine for coupling to the activated HBcAg-Lys, and loaded on SDS-PAGE for analysis.

Figure 8:
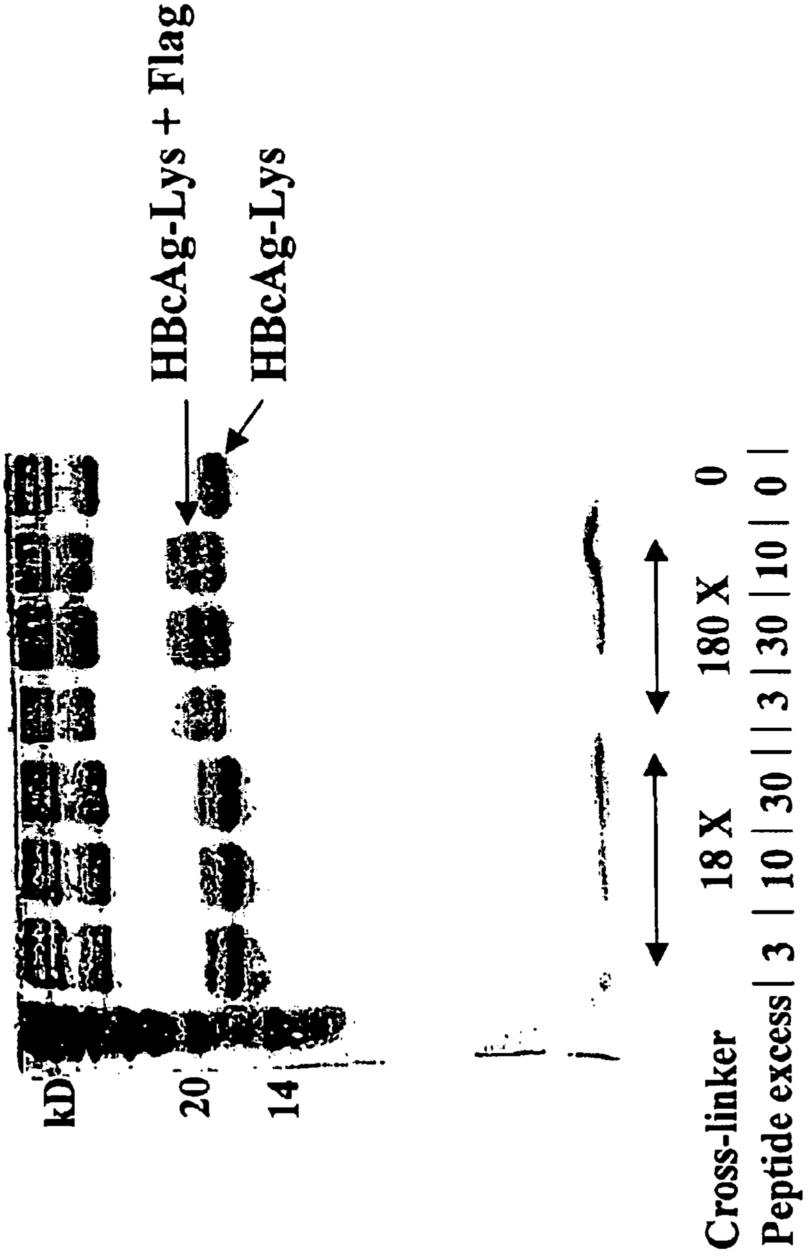
FIG. 8 depicts an analysis by SDS-PAGE of the coupling reaction of the FLAG peptide to HBcAG-Lys treated with iodacetamide and activated with Sulfo-MBS The excess of cross-linker and of peptide over HBcAg-Lys monomer is indicated below the figure.

As shown in FIG. 8, the resulting patterns of bands on the SDS-PAGE gel showed a clear additional band migrating slower than the control HBcAg-Lys derivatized with the cross-linker, but not reacted with the FLAG peptide. Reactions done under the same conditions without prior derivatization of the cysteines with Iodacetamide led to complete cross-linking of monomers of the HBcAg-Lys to higher molecular weight species.

Example 33

Isolation of Type-1 Pili and Chemical Coupling of FLAG Peptide to Type-1 Pili of *Escherichia coli* using a Heterobifunctional Cross-linker A. Introduction Bacterial pili or fimbriae are filamentous surface organelles produced by a wide range of bacteria. These organelles mediate the attachment of bacteria to surface receptors of host cells and are required for the establishment of many bacterial infections like cystitis, pyelonephritis, new born meningitis and diarrhea.

Pili can be divided in different classes with respect to their receptor specificity (agglutination of blood cells from different species), their assembly pathway (extracellular nucleation, general secretion, chaperone/usher, alternate chaperone) and their morphological properties (thick, rigid pili; thin, flexible pili; atypical structures including capsule; curli; etc). Examples of thick, rigid pili forming a right handed helix that are assembled via the so called chaperone/usher pathway and mediate adhesion to host glycoproteins include Type-1 pili, P-pili, S-pili, FIC-pili, and 987P-pili). The most prominent and best characterized members of this class of pili are P-pili and Type-1 pili (for reviews on adhesive structures, their assembly and the associated diseases see Soto, G. E. & Hultgren, S. J., *J. Bacteriol.* 181:1059–1071 (1999); Bullitt & Makowski, *Biophys. J.* 74:623–632 (1998); Hung, D. L. & Hultgren, S. J., *J. Struct, Biol.* 124:201–220 (1998)).

Type-1 pili are long, filamentous polymeric protein structures on the surface of *E. coli.* They possess adhesive properties that allow for binding to mannose-containing receptors present on the surface of certain host tissues. Type-1 pili can be expressed by 70–80% of all *E. coli* isolates and a single *E. coli* cell can bear up to 500 pili. Type-pili reach a length of typically 0.2 to 2 $\mu$M with an average number of 1000 protein subunits that associate to a right-handed helix with 3.125 subunits per turn with a diameter of 6 to 7 nm and a central hole of 2.0 to 2.5 nm.

The main Type-1 pilus component, FimA, which represents 98% of the total pilus protein, is a 15.8 kDa protein. The minor pilus components FimF, FimG and FimH are incorporated at the tip and in regular distances along the pilus shaft (Klemm, P & Krogfelt, K. A., "Type I fimbriae of *Escherichia coli*," in: *Fimbriae.* Klemm, P. (ed.), CRC Press Inc., (1994) pp. 9–26). FimH, a 29.1 kDa protein, was shown to be the mannose-binding adhesin of Type-1 pili (Krogfelt, K. A., et al., *Infect. Immun.* 58:1995–1998 (1990); Klemm, P., et al., *Mol. Microbiol.* 4:553–560 (1990); Hanson, M. S. & Brinton, C. C. J., *Nature* 17:265–268 (1988)), and its incorporation is probably facilitated by FimG and FimF (Klemm, P. & Christiansen, G., *Mol. Gen. Genetics* 208:439–445 (1987); Russell, P. W. & Orndorff, P. E., *J. Bacteriol.* 174:5923–5935 (1992)). Recently, it was shown that FimH might also form a thin tip-fibrillum at the end of the pili (Jones, C. H., et al., *Proc. Nat. Acad. Sci. USA* 92:2081–2085 (1995)). The order of major and minor components in the individual mature pili is very similar, indicating a highly ordered assembly process (Soto, G. E. & Hultgren, S. J., *J. Bacteriol.* 181:1059–1071 (1999)).

P-pili of *E. coli* are of very similar architecture, have a diameter of 6.8 nm, an axial hole of 1.5 nm and 3.28 subunits per turn (Bullitt & Makowski, *Biophys. J.* 74:623–632 (1998)). The 16.6 kDa PapA is the main component of this pilus type and shows 36% sequence identity and 59% similarity to FimA (see Table 1). As in Type-1 pili the 36.0 kDa P-pilus adhesin PapG and specialized adapter proteins make up only a tiny fraction of total pilus protein. The most obvious difference to Type-1 pili is the absence of the adhesin as an integral part of the pilus rod, and its exclusive localization in the tip fibrillium that is connected to the pilus rod via specialized adapter proteins that Type-1 pili lack (Hultgren, S. J., et al., *Cell* 73:887–901 (1993)).

helical structure and form an extended and flexible, 2 nm wide protein chain (Abraham, S. N., et al., *J. Bacteriol.* 174:5145–5148 (1992)).

P-pili and Type-1 pili are encoded by single gene clusters on the *E. coli* chromosome of approximately 10 kb (Klemm, P. & Krogfelt, K. A., "Type I fimbriae of *Escherichia coli*," in: *Fimbriae*. Klemm, P. (ed.), CRC Press Inc., (1994) pp. 9–26; Orndorff, P. E. & Falkow, S., *J. Bacteriol.* 160:61–66 (1984)). A total of nine genes are found in the Type-1 pilus gene cluster, and 11 genes in the P-pilus cluster (Hultgren, S. J., et al., *Adv. Prot. Chem.* 44:99–123 (1993)). Both clusters are organized quite similarly.

The first two fim-genes, fimB and fimE, code for recombinases involved in the regulation of pilus expression (McClain, M. S., et al., *J. Bacteriol.* 173:5308–5314 (1991)). The main structural pilus protein is encoded by the next gene of the cluster, fimA (Klemm, P., *Euro. J. Biochem.* 143:395–400 (1984); Orndorff, P. E. & Falkow, S., *J. Bacteriol.* 160:61–66 (1984); Orndorff, P. E. & Falkow, S., *J. Bacteriol.* 162:454–457 (1985)). The exact role of fimI is unclear. It has been reported to be incorporated in the pilus as well (Klemm, P. & Krogfelt, K. A., "Type I fimbriae of *Escherichia coli*," in: *Fimbriae*. Klemm, P. (ed.), CRC Press Inc., (1994) pp. 9–26). The adjacent fimC codes not for a structural component of the mature pilus, but for a so-called pilus chaperone that is essential for the pilus assembly

TABLE 1

Similarity and identity between several structural pilus proteins of Type-1 and P-pili (in percent). The adhesins were omitted.

| | | Similarity | | | | | | | | |
|---|---|---|---|---|---|---|---|---|---|---|
| | | FimA | PapA | FimI | FimF | FimG | PapE | PapK | PapH | PapF |
| Identity | FimA | | 59 | 57 | 56 | 44 | 50 | 44 | 46 | 46 |
| | PapA | 36 | | 49 | 48 | 41 | 45 | 49 | 49 | 47 |
| | FimI | 35 | 31 | | 56 | 46 | 40 | 47 | 48 | 48 |
| | FimF | 34 | 26 | 30 | | 40 | 47 | 43 | 49 | 48 |
| | FimG | 28 | 28 | 28 | 26 | | 39 | 39 | 41 | 45 |
| | PapE | 25 | 23 | 18 | 28 | 22 | | 43 | 47 | 54 |
| | PapK | 24 | 29 | 25 | 28 | 22 | 18 | | 49 | 53 |
| | PapH | 22 | 26 | 22 | 22 | 23 | 24 | 23 | | 41 |
| | PapF | 18 | 22 | 22 | 24 | 28 | 27 | 26 | 21 | |

Type-1 pili are extraordinary stable hetero-oligomeric complexes. Neither SDS-treatment nor protease digestions, boiling or addition of denaturing agents can dissociate Type-1 pili into their individual protein components. The combination of different methods like incubation at 100° C. at pH 1.8 was initially found to allow for the depolymerization and separation of the components (Eshdat, Y., et al., *J. Bacteriol.* 148:308–314 (1981); Brinton, C. C. J., *Trans, N. Y. Acad. Sci.* 27:1003–1054(1965); Hanson, A. S., et al., *J. Bacteriol.*, 170:3350–3358 (1988); Klemm, P. & Krogfelt, K. A., "Type I fimbriae of *Escherichia coli*," in: *Fimbriae*. Klemm, P. (ed.), CRC Press Inc., (1994) pp. 9–26). Interestingly, Type-1 pili show a tendency to break at positions where FimH is incorporated upon mechanical agitation, resulting in fragments that present a FimH adhesin at their tips. This was interpreted as a mechanism of the bacterium to shorten pili to an effective length under mechanical stress (Klemm, P. & Krogfelt, K. A., "Type I fimbriae of *Escherichia coli*," in: *Fimbriae*. Klemm, P. (ed.), CRC Press Inc., (1994) pp. 9–26). Despite their extraordinary stability, Type-1 pili have been shown to unravel partially in the presence of 50% glycerol; they lose their (Klemm, P., *Res. Microbiol.* 143:831–838 (1992); Jones, C. H., et al., *Proc. Nat. Acad Sci. USA* 90:8397–8401 (1993)).

The assembly platform in the outer bacterial membrane to which the mature pilus is anchored is encoded by fimD (Klemm, P. & Christiansen, G., *Mol. Gen, Genetics* 220:334–338 (1990)). The three minor components of the Type-1 pili, FimF, FimG and FimH are encoded by the last three genes of the cluster (Klemm, P. & Christiansen, G., *Mol. Gen. Genetics* 208:439–445 (1987)). Apart from fimB and fimE, all genes encode precursor proteins for secretion into the periplasm via the sec-pathway.

The similarities between different pili following the chaperone/usher pathway are not restricted to their morphological properties. Their genes are also arranged in a very similar manner. Generally the gene for the main structural subunit is found directly downstream of the regulatory elements at the beginning of the gene cluster, followed by a gene for an additional structural subunit (fimI in the case of Type-1 pili and papH in the case of P-pili). PapH was shown and FimI is supposed to terminate pilus assembly (Hultgren, S. J., et al., *Cell* 73:887–901 (1993)). The two proteins that guide the process of pilus formation, namely the specialized pilus chaperone and the outer membrane assembly platform, are located adjacently downstream. At the end of the clusters a variable number of minor pilus components including the adhesins are encoded. The similarities in morphological structure, sequence (see Table 1), genetic organization and regulation indicate a close evolutionary relationship and a similar assembly process for these cell organelles.

Bacteria producing Type-1 pili show a so-called phase-variation. Either the bacteria are fully piliated or bald. This is achieved by an inversion of a 314 bp genomic DNA fragment containing the fimA promoter, thereby inducing an "all on" or "all off" expression of the pilus genes (McClain, M. S., et al., *J. Bacteriol.* 173:5308–5314 (1991)). The coupling of the expression of the other structural pilus genes to fimA expression is achieved by a still unknown mechanism. However, a wide range of studies elucidated the mechanism that influences the switching between the two phenotypes.

The first two genes of the Type-1 pilus cluster, fimB and fimE encode recombinases that recognize 9 bp DNA segments of dyad symmetry that flank the invertable fimA promoter. Whereas FimB switches pilation "on", FimE turns the promoter in the "off" orientation. The up- or down-regulation of either fimB or fimE expression therefore controls the position of the so-called "fim-switch" (McClain, M. S., et al., *J. Bacteriol.* 173:5308–5314 (1991); Blomfield, I. C., et al., *J. Bacteriol.* 173:5298–5307 (1991)).

The two regulatory proteins fimB and fimE are transcribed from distinct promoters and their transcription was shown to be influenced by a wide range of different factors including the integration host factor (IHF) (Blomfield, I. C., et al., *Mol. Microbiol.* 23:705–717 (1997)) and the leucine-responsive regulatory protein (LRP) (Blomfield, I. C., et al., *J. Bacteriol.* 175:27–36 (1993); Gally, D. L., et al., *J. Bacteriol.* 175:6186–6193 (1993); Gally, D. L., et al., *Microbiol.* 21:725–738 (1996); Roesch, R. L. & Blomfield, I. C., *Mol. Microbiol*, 27:751–761 (1998)). Mutations in the former lock the bacteria either in "on" or "off" phase, whereas LRP mutants switch with a reduced frequency. In addition, an effect of leuX on pilus biogenesis has been shown. This gene is located in the vicinity of the fim-genes on the chromosome and codes for the minor leucine tRNA species for the UUG codon. Whereas fimB contains five UUG codons, fimE contains only two, and enhanced leuX transcription might favor FimB over FimE expression (Burghoff, R. L., et al., *Infect. Immun.* 61:1293–1300 (1993); Newman, J. V., et al., *FEMS Microbiol. Lett.* 122:281–287 (1994); Ritter, A., et al., *Mol. Microbial*, 25:871–882 (1997)).

Furthermore, temperature, medium composition and other environmental factors were shown to influence the activity of FimB and FimE. Finally, a spontaneous, statistical switching of the fimA promoter has been reported. The frequency of this spontaneous switching is approximately $10^{-3}$ per generation (Eisenstein, B. I., *Science* 214:337–339 (1981); Abraham, S. M., et al., *Proc. Nat. Acad. Sci, USA* 82:5724–5727 (1985)), but is strongly influenced by the above mentioned factors.

The genes fimI and fimC are also transcribed from the fimA promoter, but directly downstream of fimA a DNA segment with a strong tendency to form secondary structure was identified which probably represents a partial transcription terminator (Klemm, P., *Euro. J. Biochem.* 143:395–400 (1984)); and is therefore supposed to severely reduce fimI and fimC transcription. At the 3' end of fimC an additional promoter controls the fimD transcription; at the 3' end of fimD the last known fim promoter is located that regulates the levels of FimF, FimG, and FimH. Thus, all of the minor Type-1 pili proteins are transcribed as a single mRNA (Klemm, P. & Krogfelt, K. A., "Type I fimbriae of *Escherichia coli*," in: *Fimbriae* Klemm, P. (ed.), CRC Press Inc., (1994) pp. 9–26). This ensures a 1:1:1 stochiometry on mRNA-level, which is probably maintained on the protein level.

In the case of P-pili additional regulatory mechanisms were found when the half-life of mRNA was determined for different P-pilus genes. The mRNA for papA was extraordinarily long-lived, whereas the mRNA for papB, a regulatory pilus protein, was encoded by short-lived mRNA (Naureckiene, S. & Uhlin. B. E., *Mol. Microbiol.* 21:55–68 (1996); Nilsson, P., et al., *J. Bacterial.* 178:683–690 (1996)).

In the case of Type-1 pili, the gene for the Type-1 pilus chaperone FimC starts with a GTG instead of an ATG codon, leading to a reduced translation efficiency. Finally, analysis of the fimH gene revealed a tendency of the fimH mRNA to form a stem-loop, which might severely hamper translation. In summary, bacterial pilus biogenesis is regulated by a wide range of different mechanisms acting on all levels of protein biosynthesis.

Periplasmic pilus proteins are generally synthesized as precursors, containing a N-terminal signal-sequence that allows translocation across the inner membrane via the Sec-apparatus. After translocation the precursors are normally cleaved by signal-peptidase I. Structural Type-1 pilus subunits normally contain disulfide bonds, their formation is catalyzed by DsbA and possibly DsbC and DsbG gene products.

The Type-1 pilus chaperone FimC lacks cysteine residues. In contrast, the chaperone of P-pili, PapD, is the only member of the pilus chaperone family that contains a disulfide bond, and the dependence of P-pili on DsbA has been shown explicitly (Jacob-Dubuisson, F., et al., *Proc. Nat. Acad. Sci. USA* 91:11552–11556 (1994)). PapD does not accumulate in the periplasm of ΔdsbA strain, indicating that the disturbance of the P-pilus assembly machinery is caused by the absence of the chaperone (Jacob-Dubuisson, F., et al., *Proc. Nat. Acad. Sci. USA* 91:11552–11556 (1994)). This is in accordance with the finding that Type-1 pili are still assembled in a ΔdsbA strain, albeit to reduced level (Hultgren, S. J., et al., "Bacterial Adhesion and Their Assembly", in: *Escherichia coli* and *Salmonella*, Neidhardt, F. C. (ed.) ASM Press, (1996) pp. 2730–2756).

Type-1 pili as well as P-pili are to 98% made of a single or main structural subunit termed FimA and PapA, respectively. Both proteins have a size of ~15.5 kDa. The additional minor components encoded in the pilus gene clusters are very similar (see Table 1). The similarities in sequence and size of the subunits with the exception of the adhesins suggest that all share an identical folding motif, and differ only with respect to their affinity towards each other. Especially the N- and C-terminal regions of these proteins are well conserved and supposed to play an important role in chaperone/subunit interactions as well as in subunit/subunit interactions within the pilus (Soto, G. E. & Hultgren, S. J., *J. Bacteriol.* 181:1059–1071 (1999)). Interestingly, the conserved N-terminal segment can be found in the middle of the pilus adhesins, indicating a two-domain organization of the adhesins where the proposed C-terminal domain, starting with the conserved motif, corresponds to a structural pilus subunit whereas the N-terminal domain was shown to be responsible for recognition of host cell receptors (Hultgren, S. J., et al., *Proc. Nat. Acad. Sci. USA* 86:4357–4361 (1989); Haslam, D. B., et al., *Mol. Microbiol.* 14:399–409 (1994); Soto, G. E., et al., *EMBO J.* 17:6155–6167 (1998)). The different subunits were also shown to influence the morphological properties of the pili. The removal of several genes was reported to reduce the number of Type-1 or P-pili or to increase their length, (fimH, papG, papk fimf, fimG) (Russell, P. W. & Orndorff, P. E., *J. Bacteriol.* 174:5923–5935 (1992); Jacob-Dubuisson, R., et al., *EMBO J.* 12:837–847 (1993); Soto, G. E. & Hultgren, S. J., *J. Bacteriol.* 181:1059–1071 (1999)); combination of the gene deletions amplified these effects or led to a total loss of pilation (Jacob-Dubuisson, R., et al., *EMBO J.* 12:837–847 (1993)).

In non-fimbrial adhesive cell organelles also assembled via chaperones/usher systems such as Myf fimbriae and CS3 pili, the conserved C-terminal region is different. This indirectly proves the importance of these C-terminal subunit segments for quaternary interactions (Hultgren, S. J., et al., "Bacterial Adhesion and Their Assembly", in: *Escherichia coli* and *Salmonella*, Neidhardt, F. C. (ed.) ASM Press, (1996) pp. 2730–2756).

Gene deletion studies proved that removal of the pilus chaperones leads to a total loss of piliation in P-pili and Type-1 pili (Lindberg, F., et al., *J. Bacteriol.* 171:6052–6058 (1989); Klemm, P., *Res. Microbiol.* 143:831–838 (1992); Jones, C. H., et al., *Proc. Nat. Acad Sci. USA* 90:8397–8401 (1993)). Periplasmic extracts of a ΔfimC strain showed the accumulation of the main subunit FimA, but no pili could be detected (Klemm, P., *Res. Microbiol.* 143:831–838 (1992)). Attempts to over-express individual P-pilus subunits failed and only proteolytically degraded forms could be detected in the absence of PapD; in addition, the P-pilus adhesin was purified with the inner membrane fraction in the absence of the chaperone (Lindberg, F., et al., *J. Bacteriol.* 171:6052–6058 (1989)). However, co-expression of the structural pilus proteins and their chaperone allowed the detection of chaperone/subunit complexes from the periplasm in the case of the FimC/FimH complex as well as in the case of different Pap-proteins including the adhesin PapG and the main subunit PapA (Tewari, R., et al., *J. Biol. Chem.* 268:3009–3015 (1993); Lindberg, F., et al., *J. Bacteriol.* 171:6052–6058 (1989)). The affinity of chaperone/subunit complexes towards their assembly platform has also been investigated in vitro and was found to differ strongly (Dodson et al., *Proc. Natl. Acad. Sci. USA* 90:3670–3674 (1993)). From these results the following functions were suggested for the pilus chaperones:

They are assumed to recognize unfolded pilus subunits, prevent their aggregation and to provide a "folding template" that guides the formation of a native structure.

The folded subunits, which after folding display surfaces that allow subunit/subunit interactions, are then expected to be shielded from interacting with other subunits, and to be kept in a monomeric, assembly-competent state.

Finally, the pilus chaperones are supposed to allow a triggered release of the subunits at the outer membrane assembly location, and, by doing so with different efficiency, influence the composition and order of the mature pili (see also the separate section below).

After subunit release at the outer membrane, the chaperone is free for another round of substrate binding, folding assistance, subunit transport through the periplasm and specific delivery to the assembly site. Since the periplasm lacks energy sources, like ATP, the whole pilus assembly process must be thermodynamically driven (Jacob-Dubuisson, F., et al., *Proc. Nat. Acad. Sci. USA* 91:11552–11556 (1994)). The wide range of different functions attributed to the pilus chaperones would implicate an extremely fine tuned cascade of steps.

Several findings, however, are not readily explained with the model of pilus chaperone function outlined above. One example is the existence of multimeric chaperone/subunit complexes (Striker, R. T., et al., *J. Biol. Chem.* 269:12233–12239 (1994)), where one chaperone binds subunit dimers or trimers. It is difficult to imagine a folding template that can be "double-booked". The studies on the molecular details of chaperone/subunit interaction (see below) partially supported the functions summarized above, but also raised new questions.

All 31 periplasmic chaperones identified by genetic studies or sequence analysis so far are proteins of approximately 25 kDa with conspicuously high pI values around 10. Ten of these chaperones assist the assembly of rod-like pili, four are involved in the formation of thin pili, ten are important for the biogenesis of atypically thin structures (including capsule-like structures) and two adhesive structures have not been determined so far (Holmgren, A., et al., *EMBO J.* 11:1617–1622 (1992); Bonci, A., et al., *J. Mol. Evolution* 44:299–309 (1997); Smyth, C. J., et al., *FEMS Immun. Med Microbiol.* 16:127–139 (1996); Hung, D. L. & Hultgren, S. J., *J. Struct, Biol.* 124:201–220 (1998)). The pairwise sequence identity between these chaperones and PapD ranges from 25 to 56%, indicating an identical overall fold (Hung, D. L., et al., *EMBO J.* 15:3792–3805 (1996)).

The first studies on the mechanism of chaperone/substrate recognition was based on the observation that the C-termini of all known pilus chaperones are extremely similar. Synthetic peptides corresponding to the C-termini of the P-pilus proteins were shown to bind to PapD in ELISA assays (Kuehn, M. J., et al., *Science* 262:1234–1241 (1993)). Most importantly, the X-ray structures of two complexes were solved in which PapD was co-crystallized with 19-residue peptides corresponding to the C-termini of either the adhesin PapG or the minor pilus component PapK (Kuehn, M. J., et al., *Science* 262:1234–1241 (1993); Soto, G. E., et al., *EMBO J.* 17:6155–6167 (1998)). Both peptides bound in an extended conformation to a β-strand in the N-terminal chaperone domain that is oriented towards the inter-domain cleft, thereby extending a β-sheet by an additional strand. The C-terminal carboxylate groups of the peptides were anchored via hydrogen-bonds to Arg8 and Lys112, these two residues are invariant in the family of pilus chaperones. Mutagenesis studies confirmed their importance since their exchange against alanine resulted in accumulation of non-functional pilus chaperone in the periplasm (Slonim, L. N., et al., *EMBO J.* 11:4747–4756 (1992)). The crystal structure of PapD indicates that neither Arg8 nor Lys112 is involved in stabilization of the chaperone, but completely solvent exposed (Holmgren, A. & Branden, C. I., *Nature* 342:248–251 (1989)). On the substrate side the exchange of C-terminal PapA residues was reported to abolish P-pilus formation, and similar experiments on the conserved C-terminal segment of the P-pilus adhesin PapG prevented its incorporation into the P-pilus (Hultgren, S. J., et al., "Bacterial Adhesion and Their Assembly", in: *Escherichia coli* and *Salmonella*, Neidhardt, F. C. (ed.) ASM Press, (1996) pp. 2730–2756). All evidence therefore indicated pilus subunit recognition via the C-terminal segments of the subunits.

A more recent study on C-terminal amino acid exchanges of the P-pilus adhesin PapG gave a more detailed picture. A range of amino acid substitutions at the positions -2, -4, -6, and -8 relative to the C-terminus were tolerated, but changed pilus stability (Soto, G. E., et al., *EMBO J.* 17:6155–6167 (1998)).

Still, certain problems arise when this model is examined more closely. Adhesive bacterial structures not assembled to rigid, rod-like pili lack the conserved C-terminal segments (Hultgren, S. J., et al., "Bacterial Adhesion and Their Assembly", in: *Escherichia coli* and *Salmonella*, Neidhardt, F. C. (ed.) ASM Press, (1996) pp. 2730–2756), even though they are also dependent on the presence of related pilus chaperones. This indicates a different general role for the C-terminal segments of pilus subunits, namely the mediation of quaternary interactions in the mature pilus. Moreover, the attempt to solve the structure of a C-terminal peptide in complex with the chaperone by NMR was severely hampered by the weak binding of the peptide to the chaperone (Walse, B., et al., *FEBS Lett.* 412:115–120 (1997)); whereas an essential contribution of the C-terminal segments for chaperone recognition implies relatively high affinity interactions.

An additional problem arises if the variability between the different subunits are taken into account. Even though the C-terminal segments are conserved, a wide range of conservative substitutions is found. For example, 15 out of 19 amino acid residues differ between the two peptides co-crystallized with PapD (Soto, G. E., et al., *EMBO J.* 17:6155–6167 (1998)). This has been explained by the kind of interaction between chaperone and substrate, that occurs mainly via backbone interactions and not specifically via side-chain interactions. Then again, the specificity of the chaperone for certain substrates is not readily explained. On the contrary to the former argument, the conserved residues have been taken as a proof for the specificity (Hultgren, S. J., et al., "Bacterial Adhesion and Their Assembly", in: *Escherichia coli* and *Salmonella*, Neidhardt, F. C. (ed.) ASM Press, (1996) pp. 2730–2756).

The outer membrane assembly platform, also termed "usher" in the literature, is formed by homo-oligomers of FimD or PapC, in the case of Type-1 and P-pili, respectively (Klemm, P. & Christiansen, G., *Mol. Gen, Genetics* 220:334–338 (1990); Thanassi, D. G., et al., *Proc. Nat. Acad. Sei. USA* 95:3146–3151 (1998)). Studies on the elongation of Type-1 fimbriae by electron microscopy demonstrated an elongation of the pilus from the base (Lowe, M. A., et al., *J. Bacteriol.* 169:157–163 (1987)). In contrast to the secretion of unfolded subunits into the periplasmic space, the fully folded proteins have to be translocated through the outer membrane, possibly in an oligomeric form (Thanassi, D. G., et al., *Proc. Nat. Acad Sei. USA* 95:3146–3151 (1998)). This requires first a membrane pore wide enough to allow the passage and second a transport mechanism that is thermodynamically driven (Jacob-Dubuisson, F., et al., *J. Biol. Chem.* 269:12447–12455 (1994)).

FimD expression alone was shown to have a deleterious effect on bacterial growth, the co-expression of pilus subunits could restore normal growth behavior Klemm, P. & Christiansen, G., *Mol. Gen, Genetics* 220:334–338 (1990)). Based on this it can be concluded that the ushers probably form pores that are completely filled by the pilus. Electron microscopy on membrane vesicles in which PapC had been incorporated confirmed a pore-forming structure with an inner diameter of 2 nm (Thanassi, D. G., et al., *Proc. Nat. Acad. Sei. USA* 95:3146–3151 (1998)). Since the inner diameter of the pore is too small to allow the passage of a pilus rod, it has been suggested that the helical arrangement of the mature pilus is formed at the outside of the bacterial surface. The finding that glycerol leads to unraveling of pili which then form a protein chain of approximately 2 nm is in good agreement with this hypothesis, since an extended chain of subunits might be formed in the pore as a first step (Abraham, S. N., et al., *J. Bacteriol.* 174:5145–5148 (1992); Thanassi, D. G., et al., *Proc. Nat. Acad. Sei. USA* 95:3146–3151 (1998)). The formation of the helical pilus rod at the outside of the bacterial membrane might then be the driving force responsible for translocation of the growing pilus through the membrane.

It has also been demonstrated that the usher proteins of Type-1 and P-pili form ternary complexes with chaperone/subunit complexes with different affinities (Dodson, K. W., et al., *Proc. Nat. Acad. Sci. USA* 90:3670–3674 (1993); Saulino, E. T., et al., *EMBO J.* 17:2177–2185 (1998)). This was interpreted as "kinetic partitioning" that allows a defined order of pilus proteins in the pilus. Moreover, it has been suggested that structural proteins might present a binding surface only compatible with one other type of pilus protein; this would be another mechanism to achieve a highly defined order of subunits in the mature pilus (Saulino, E. T., et al., *EMBO J.* 17:2177–2185 (1998)).

B. Production of Type-1 pili from *Escherichia coli*

*E. coli* strain W3110 was spread on LB (10 g/L tryptone, 5 g/L yeast extract, 5 g/L NaCl, pH 7.5, 1% agar (w/v)) plates and incubated at 37° C. overnight. A single colony was then used to inoculate 5 ml of LB starter culture (10 g/L tryptone, 5 g/L yeast extract, 5 g/L NaCl, pH 7.5). After incubation for 24 hours under conditions that favor bacteria that produce Type-1 pili (37° C., without agitation) 5 shaker flasks containing 1 liter LB were inoculated with one milliliter of the starter culture. The bacterial cultures were then incubated for additional 48 to 72 hours at 37° C. without agitation. Bacteria were then harvested by centrifugation (5000 rpm, 4° C., 10 minutes) and the resulting pellet was resuspended in 250 milliliters of 10 mM Tris/HCl, pH 7.5. Pili were detached from the bacteria by 5 minutes agitation in a conventional mixer at 17.000 rpm. After centrifugation for 10 minutes at 10,000 rpm at 4° C. the pili containing supernatant was collected and 1 M MgCl2 was added to a final concentration of 100 mM. The solution was kept at 4° C. for 1 hour, and the precipitated pili were then pelleted by centrifugation (10,000 rpm, 20 minutes, 4° C.). The pellet was then resuspended in 10 mM HEPES, pH 7.5, and the pilus solution was then clarified by a final centrifugation step to remove residual cell debris.

C. Coupling of FLAG to Purified Type-1 Pili of *E. coli* using m-Maleimidonbenzoyl-N-hydroxysulfosuccinimide Ester (sulfo-MBS)

600 $\mu$l of a 95% pure solution of bacterial Type-1 pili (2 mg/ml) were incubated for 30 minutes at room temperature with the heterobifunctional cross-linker sulfo-MBS (0.5 mM). Thereafter, the mixture was dialyzed overnight against 1 liter of 50 mM Phosphate buffer (pH 7.2) with 150 mM NaCl to remove free sulfo-MBS. Then 500 $\mu$l of the derivatized pili (2 mg/ml) were mixed with 0.5 mM FLAG peptide (containing an amino-terminal Cysteine) in the presence of 10 mM EDTA to prevent metal-catalyzed sufhydryloxidation. The non-coupled peptide was removed by size-exclusion-chromatography.

Figure 9:
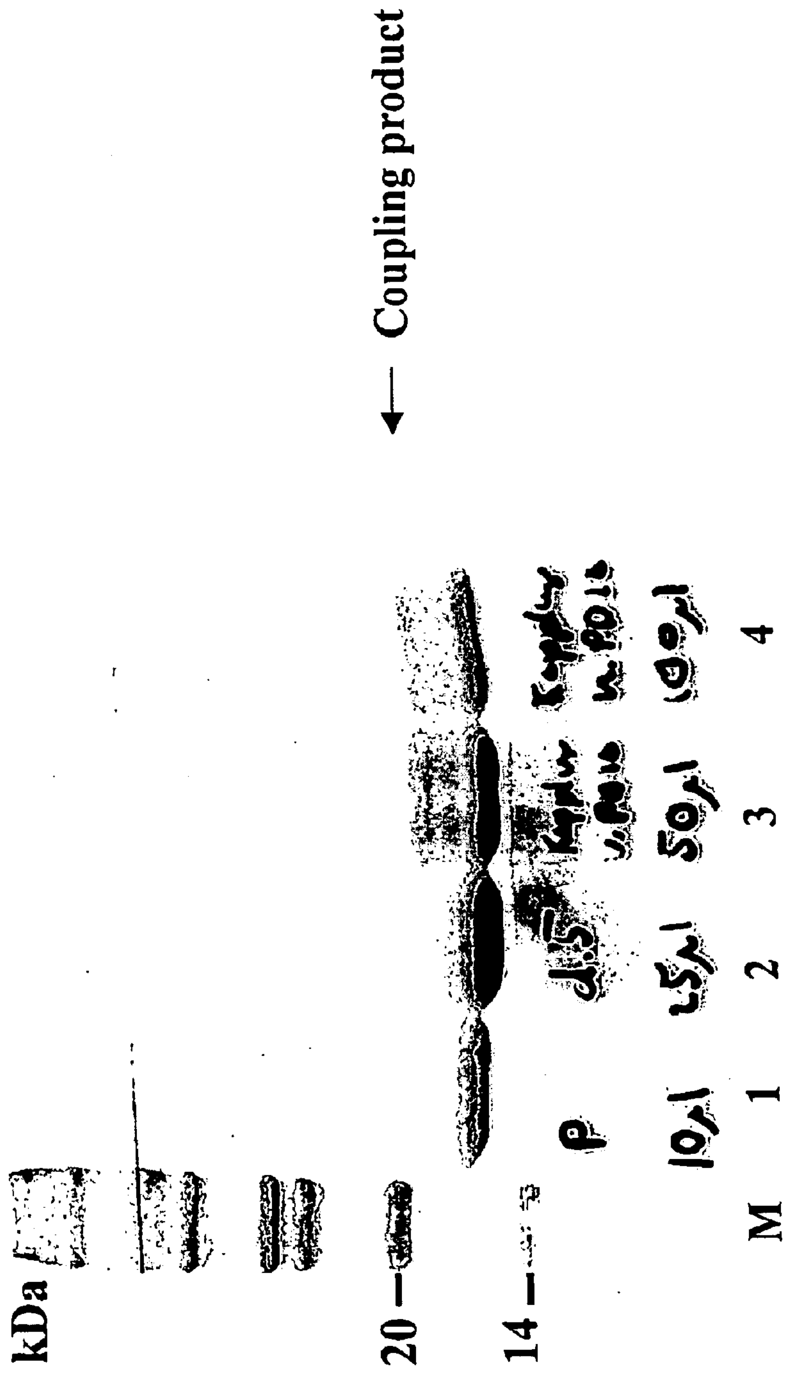
FIG. 9 depicts an analysis of coupling of the FLAG peptide to type-1 bacterial pili by SDS-PAGE. Lane 1 shows the unreacted pili subunit FimA. Lane 3 shows the purified reaction mixture of the pili with the FLAG peptide. The upper band corresponds to the coupled product, while the lower band corresponds to the unreached subunit.

FIG. 9 depicts an analysis of coupling of the FLAG peptide to type-1 bacterial pili by SDS-PAGE. Lane 1 shows the unreacted pili subunit FimA. Lane 3 shows the purified reaction mixture of the pili with the FLAG peptide. The upper band corresponds to the coupled product, while the lower band corresponds to the unreached subunit.

Example 34

Construction of an Expression Plasmid for the Expression of Type-1 Pili of *Escherichia coli*

The DNA sequence disclosed in GenBank Accession No. U14003, the entire disclosure of which is incorporated herein by reference, contains all of the *Escherichia coli* genes necessary for the production of type-1 pili from nucleotide number 233947 to nucleotide number 240543 (the fim gene cluster). This part of the sequences contains the sequences for the genes fimA, fimI, fimC, fimD, fimF, fimG, and fimH. Three different PCRs were employed for the amplification of this part of the *E. coli* genome and subsequent cloning into pUC19 (GenBank Accession Nos. L09137 and X02514) as described below.

The PCR template was prepared by mixing 10 ml of a glycerol stock of the *E. coli* strain W3110 with 90 ml of water and boiling of the mixture for 10 minutes at 95° C., subsequent centrifugation for 10 minutes at 14,000 rpm in a bench top centrifuge and collection of the supernatant.

Ten ml of the supernatant were then mixed with 50 pmol of a PCR primer one and 50 pmol of a PCR primer two as defined below. Then 5 ml of a 10×PCR buffer, 0.5 ml of Taq-DNA-Polymerase and water up to a total of 50 ml were added. All PCRs were carried out according to the following scheme: 94° C. for 2 minutes, then 30 cycles of 20 seconds at 94° C., 30 seconds at 55° C., and 2 minutes at 72° C. The PCR products were then purified by 1% agarose gel-electrophoresis.

Oligonucleotides with the following sequences with were used to amplify the sequence from nucleotide number 233947 to nucleotide number 235863, comprising the fimA, fimI, and fimC genes:

TAGATGATTACGCCAAGCTTATAATAGAAATAGTTTTTTGAAAGGAAAGCAGCATG (SEQ ID NO:196) and

GTCAAAGGCCTTGTCGACGTTATTCCATTACGCCCGTCATTTTGG (SEQ ID NO:197)

These two oligonucleotides also contained flanking sequences that allowed for cloning of the amplification product into puc19 via the restriction sites HindIII and SalI. The resulting plasmid was termed pFIMAIC (SEQ ID NO:198).

Oligonucleotides with the following sequences with were used to amplify the sequence from nucleotide number 235654 to nucleotide number 238666, comprising the fimD gene:

AAGATCTTAAGCTAAGCTTGAATTCTCTGACGCTGATTAACC (SEQ ID NO:199) and

ACGTAAAGCATTTCTAGACCGCGGATAGTAATCGTGCTATC (SEQ ID NO:200).

These two oligonucleotides also contained flanking sequences that allowed for cloning of the amplification product into pub19 via the restriction sites HindIII and XhaI, the resulting plasmid was termed pFIMD (SEQ ID NO:201).

Oligonucleotides with the following sequences with were used to amplify the sequence from nucleotide number 238575 nucleotide number 240543, comprising the fimF, fimG, and fimH gene:

AATTACGTGAGCAAGCTTATGAGAAACAAACCTTTTTATC (SEQ ID NO:202) and

GACTAAGGCCTTTCTAGATTATTGATAAACAAAAGTCACGC (SEQ ID NO:203).

These two oligonucleotides also contained flanking sequences that allowed for cloning of the amplification product into pub19 via the restriction sites HindIII and XbaI; the resulting plasmid was termed pFIMFGH. (SEQ ID NO:204).

The following cloning procedures were subsequently carried out to generate a plasmid containing all the above-mentioned fim-genes: pFIMAIC was digested EcoRI and HindIII (2237–3982), pFIMD was digested EcoRI and SstII (2267–5276), pFIMFGH was digested SstII and HindIII (2327–2231). The fragments were then ligated and the resulting plasmid, containing all the fim-genes necessary for pilus formation, was termed pFIMAICDFGH (SEQ ID NO:205).

Example 35

Construction of an Expression Plasmid for *Escherichia coli* type-1 Pili that Lacks the Adhesion FimH The plasmid pFIMAICDFGH (SEQ ID NO:205) was digested with KpnI, after which a fragment consisting of nucleotide numbers 8895–8509 was isolated by 0.7% agarose gelelectrophoresis and circularized by self-ligation. The resulting plasmid was termed pFIMAICDFG (SEQ ID NO: 206), lacks the fimH gene and can be used for the production of FIMH-free type-1 pili.

Example 36

Expression of Type-1 Pili using the Plasmid pFIMAICDFGH

*E. coli* strain W3110 was transformed with pFIMAICD-FGH (SEQ ID NO:205) and spread on LB (10 g/L tryptone, 5 g/L yeast extract, 5 g/L NaCl, pH 7.5, 1% agar (w/v)) plates containing 100 μg/ml ampicillin and incubated at 37° C. overnight. A single colony was then used to inoculate 50 ml of LB-glucose starter culture (10 g/L tryptone, 5 g/L yeast extract, 1% (w/v) glucose, 5 g/L NaCl, pH 7.5, 100 mg/ml ampicillin). After incubation for 12–16 hours at 37° C. at 150 rpm, a 5 liter shaker flasks containing 2 liter LB-glucose was inoculated with 20 milliliter of the starter culture. The bacterial cultures were then incubated for additional 24 hours at 37° C. with agitation (150 rpm). Bacteria were then harvested by centrifugation (5000 rpm, 4° C., 10 minutes) and the resulting pellet was resuspended in 250 milliliters of 10 mM Tris/HCl, pH 8. Pili were detached from the bacteria by agitation in a conventional mixer at 17,000 rpm for 5 minutes. After centrifugation for 10 minutes at 10,000 rpm, 1 hour, 4° C. the supernatant containing pili was collected and 1 M $MgCl_2$ was added to a final concentration of 100 mM. The solution was kept at 4° C. for 1 hour, and precipitated pili were then pelleted by centrifugation (10,000 rpm, 20 minutes, 4° C.). The pellet was then resuspended in 10 mM HEPES, 30 mM EDTA, pH 7.5, for 30 minutes at room temperature, and the pilus solution was then clarified by a final centrifugation step to remove residual cell debris. The preparation was then dialyzed against 20 mM HEPES, pH 74.

Example 37

Activation of HBcAg-Lys with SPDP

Figure 10:
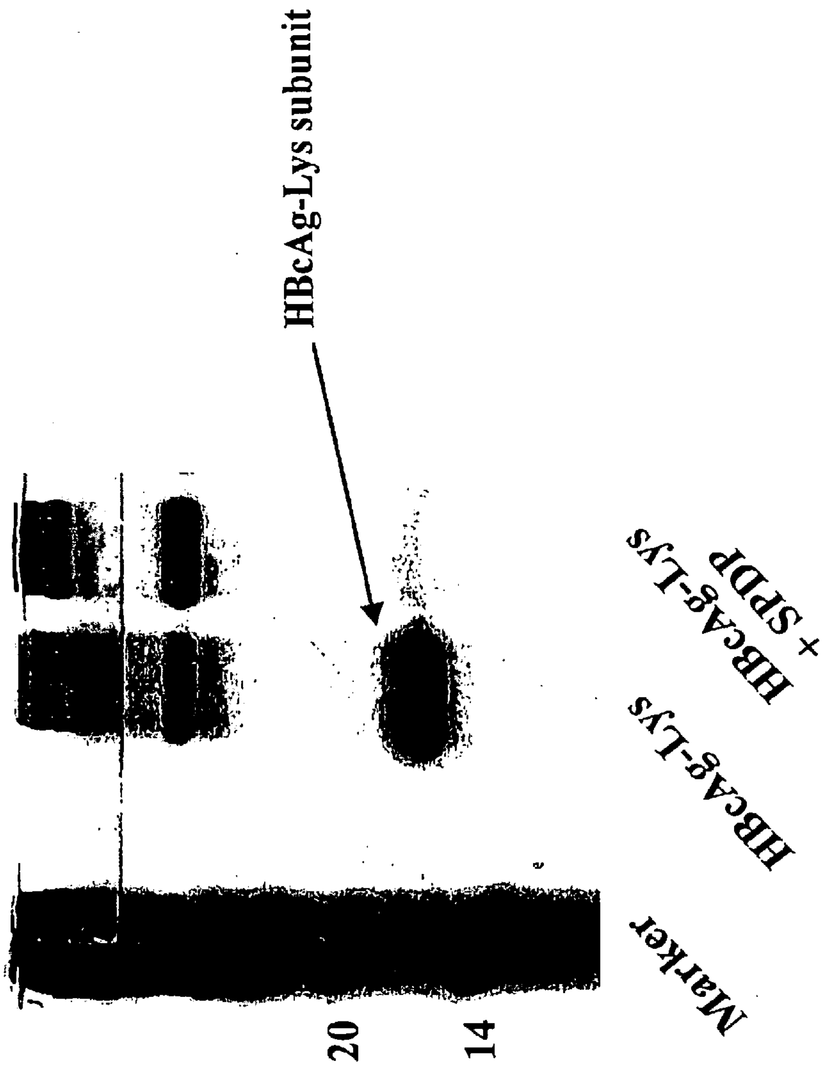
FIG. 10 depicts an analysis by SDS-PAGE of the derivatization of HBcAg-Lys with SPDP.

HBcAg-Lys at a concentration of 15 $\mu$M was reacted with SPDP at a concentration of 456 $\mu$M SPDP for 60 minutes at room temperature, resulting in a thirty-fold excess of cross-linker over capsid subunit. The reaction mixture was subsequently loaded on SDS-PAGE for analysis, as shown in FIG. 10. The gel shows that the monomer subunits are cross-linked to dimers and higher-order polymers during the reaction.

Example 38

Multimerization of HBcAg-Lys Upon Reaction with Sulfo-MBS

Figure 11:
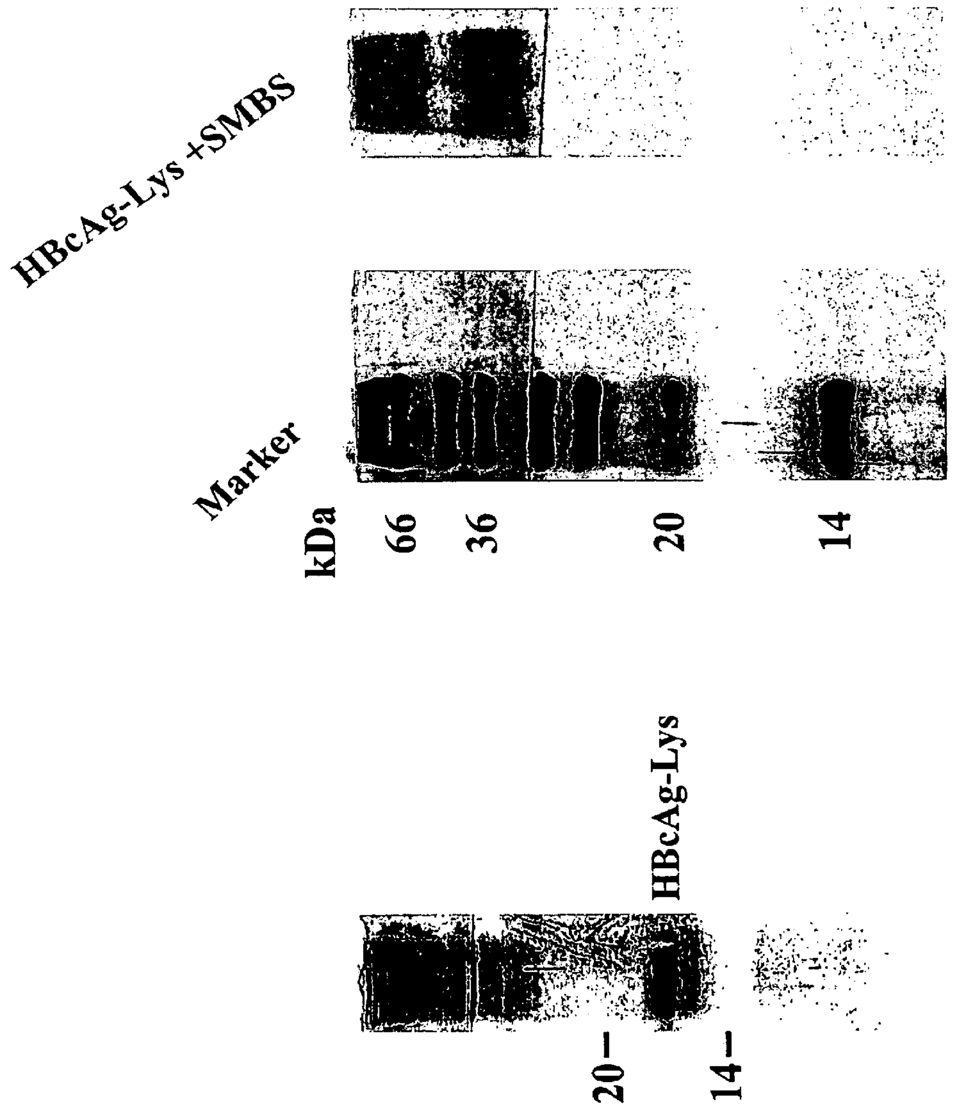
FIG. 11 depicts an analysis by SDS-PAGE of the derivatization of HBcAg-Lys with Sulfo-MBS.

HBcAg-Lys at a concentration of 118 $\mu$M was reacted with 20 mM Sulfo-MBS for 30 minutes at room temperature. As shown in FIG. 11, analysis of the reaction mixture by SDS-PAGE revealed that the HBcAg-Lys monomers internally cross-linked to multimers, as reflected in the absence of a band corresponding to the subunit monomer after cross-linking.

Example 39

Conjugation of HBcAg-Lys-2cys Mut to the FLAG Peptide

Figure 12:
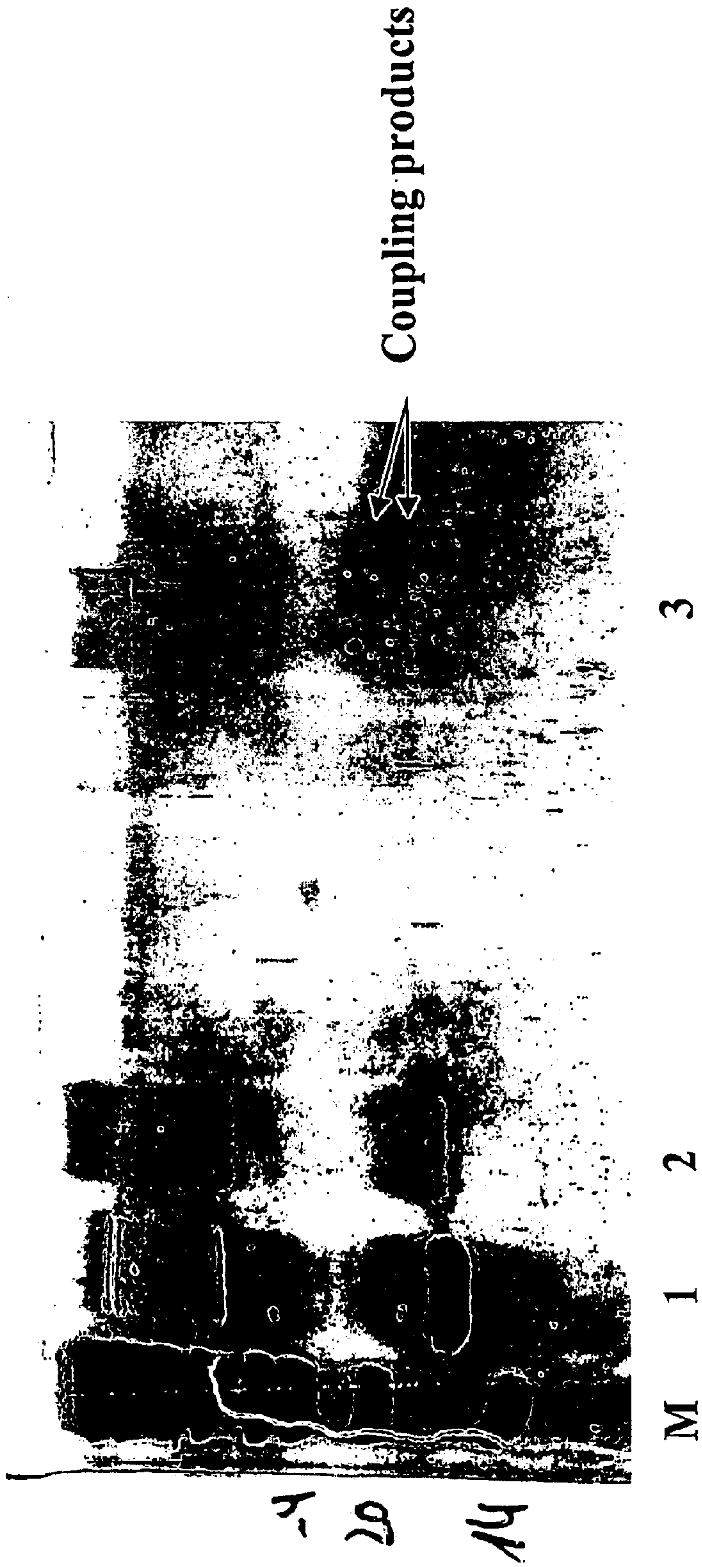
FIG. 12 depicts an analysis by SDS-PAGE of the coupling of HBcAg-Lys-2cyc-Mut to the FLAG peptide. The arrow shows the bands corresponding to the coupling of one and two FLAG peptides, respectively, to one subunit of HBcAgLys-2cyc-Mut. Lane M corresponds to the marker, lane 1 to the unreached HBcAg-Lys-2cyc-Mut, lane 2 to HBcAg-Lys-2cyc-Mut activated with Sulfo-MBS, and lane 3 activated HBcAg-Lys-2cyc-Mut after reaction with the FLAG peptide containing an N-terminal cysteine.

HBcAg-Lys-2cys-Mut at a concentration of 80 $\mu$M was reacted with sulfa-MBS at a concentration of 8.8 mM for 30 minutes at room temperature, resulting in a 110-fold excess of cross-linker over capsid subunit. The reaction mixture was precipitated two times with 50% ammoniumsulfate and resuspended in 20 mM Hepes, 150 mM NaCl, pH 7.4, in a volume equivalent to the reaction volume before precipitation. FLAG peptide containing an N-terminal cysteine was added at a concentration of 1.6 mM and the reaction was allowed to proceed for four hours at room temperature. The reaction mixture was subsequently loaded on SDS-PAGE for analysis, and the coupling products are shown in FIG. 12.

Example 40

Conjugation of Pili to the p33 Peptide

Figure 13:
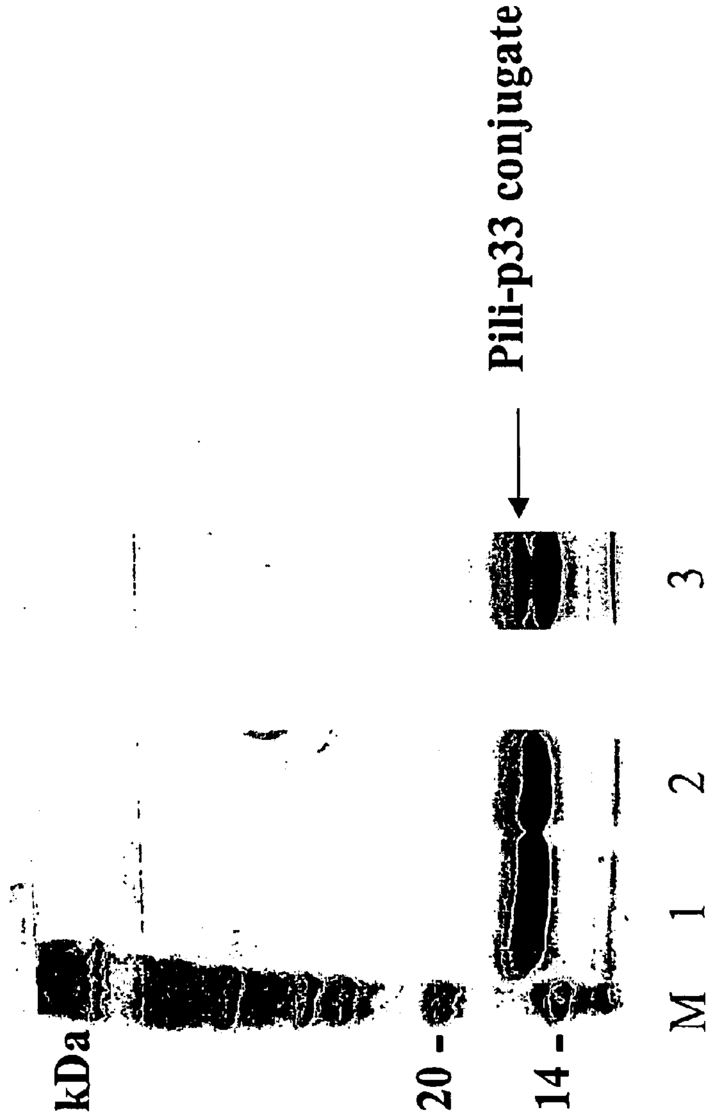
FIG. 13 depicts an analysis by SDS-PAGE of the coupling of pili to the p33 peptide.

A solution of 1 ml pili at a concentration of 1.5 mg/ml (concentration of the subunit) was reacted with 750 $\mu$l of a 100 mM Sulfo-MBS solution in 20 mM Hepes, pH 7.4, for 45 minutes at room temperature. The reaction mixture was desalted over a Sephadex G25 column equilibrated with 20 mM Hepes, pH 7.4. Fractions containing pili protein were pooled after analysis by dot blot stained with amidoblack, and 0.6 $\mu$l of a solution of 100 mM p33 peptide (CGGKAVYNFATM, SEQ ID NO: 175), containing an N-terminal cysteine, in DMSO was added to 100 $\mu$l of the desalted activated pili and reaction allowed to proceed for four hours at room temperature. The reaction mixture was subsequently analyzed by SDS-PAGE, as shown in FIG. 13.

Example 41

Expression of HBcAg-Lys-2cys-Mut

The plasmid coding for HBcAg-Lys-2cys-Mut was transformed into *E. coli* K802. A single colony was inoculated into 50 ml LB containing 100 mg/ml ampicillin. The next day, the overnight culture was diluted into 2 L LB medium containing 100 mg/ml ampicillin and grown until $ID_{600}$=0.6 at 37° C. Cells were induced with 1 mM IPTG, and grown for another 4 hours at 37° C. The cells were then harvested, and the pellet resuspended in 5 ml of 10 mM $Na_2HPO_4$, 03 mM NaCl, 10 mM EDTA, 0.25% Tween, pH 7.0. Cells were then disrupted by sonification, and ammoniumsulfate was added to a concentration of 20%. The pellet was resuspended in 3 ml PBS buffer, and loaded onto a Sephacryl S-400 column. The protein peak containing the capsid protein corresponding to the size of assembled capsid was collected and loaded onto a hydoxyapatite column for subsequent purification. The protein was eluted in the path-through fraction.

Example 42

Coupling of DP178c Peptide, Immunization of Mice and Determination of the IgG Subtypes DP178c peptide is a fragment of the gp41 protein of HIV virus (Kilby, J. M. et al., *Nature Medicine* 4: 1302–07 (1998)); Wild, C. et al., *Aids Res. Hum. Retroviruses* 9: 1051–53 (1993)).

A. Coupling of DP178c to Pili

Figure 14A:
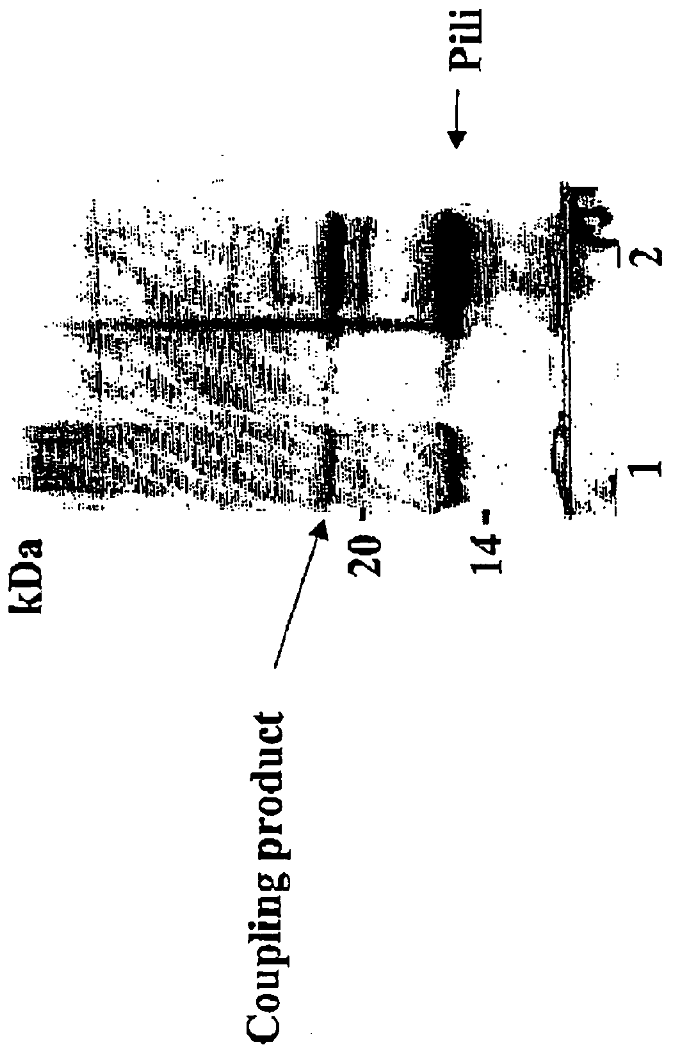
FIG. 14A shows an analysis of coupling of DP178c peptide by SDS-PAGE analysis and Coomassie staining. Lane 1 corresponds to the supernatant of the coupling reaction after centrifugation, while lane 2 corresponds to the pellet.

A solution of 3 ml Pili (2.5 mg/ml) produced as described in Example 33 B was reacted with 500 $\mu$l of a 100 mM Sulfo-MBS solution for 45 minutes at RT. The reaction mixture was desalted on a Sephadex G25 column equilibrated with 20 mM hepes pH 74, and fractions containing pili were pooled. An aliquot of 750 $\mu$l of the activated pili was diluted in 750 $\mu$l DMSO, and 2–5 $\mu$l of a 100 mM DP 178c solution in DMSO was added. The reaction was left to react 4 hours at RT, and glucose was added to the reaction mixture to give a final concentration of 0.2%. This solution was then dialyzed against 20 mM Hepes, 0.1% glucose, pH 7.4. The dialyzed coupled pili were centrifuged and loaded on SDS-PAGE for analysis. The result of the coupling reaction is depicted on FIG. 14A. The sequence of the DP178c peptide (fragment of the HIV gp14 protein) is CYTSLIHSLIEESQNQQEKNEQELLELDKWAS-LWNWF (SEQ ID No: 176).

B. Immunization of Mice and IgG Subtype Determination

Figure 14B:
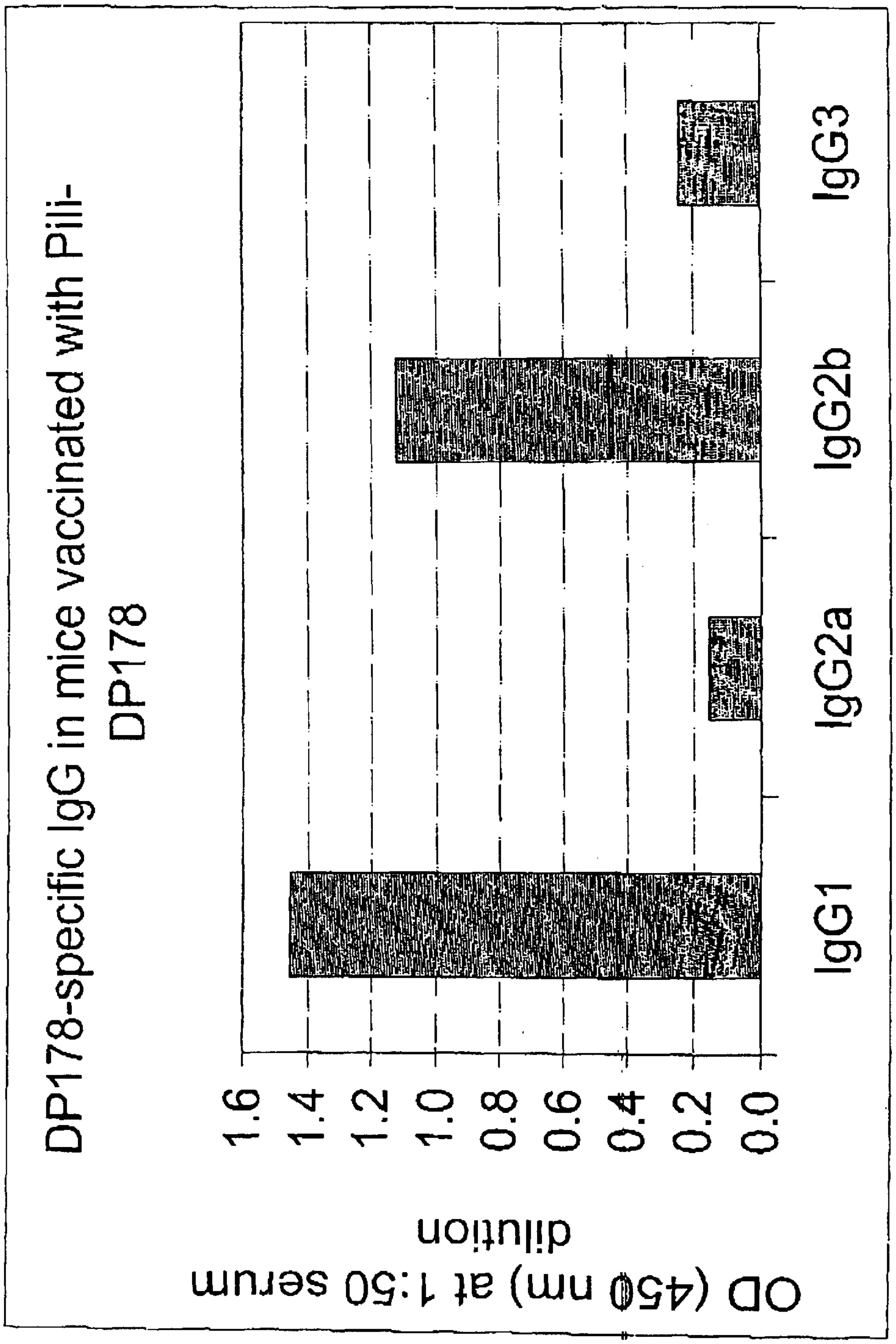
FIG. 14B show an ELISA data and subtype analysis of mice, sera immunized with Pili-DP178c. The OD (450 nm) of the ELISA signal obtained at a fifty-fold dilution of the sera is shown in the diagram. For each subtype determination, mice sera were titrated from a fifty-fold dilution in two-fold dilution steps. The ELISA titer of the IgG1 subtype (OD50 dilution) was 1:400, while the titer of the IgG2b subtype was 1:100. The other subtypes all had titers inferior to 1:50. The IgG isotype pattern is characteristic of a Th2 response, with a high IgG1 titer and a low IgG2a titer.

80 $\mu$g of Pili-DP178c was injected in saline intravenously into female Balb/c mice. These mice were boosted with the same amount of vaccine on day 14 and bled on day 24. DP178-specific IgG in serum was determined on day 24 in a DP178 peptide specific ELISA (DP178c peptide was conjugated to Ribonuclease A using the cross-linker SPDP). In FIG. 14B, average results from two mice are shown as optical densities obtained with a 1:50 dilution of the serum.

Example 43

Expression and Purification of GRA2 Polypeptide

Gra2 is an antigen of Toxoplasma Gondii. The 59 c-terminal amino acids acids of GRA2 with a c-terminal linker of 6 amino acids (GSGGCG, SEQ ID No. 177) were cloned into the pGEX-2T vector (Pharmacia, 27-4801-01). Expression and purification of the GST-fusion protein was carried out as described in the instructions. GST was cleaved from GRA2 with thrombin while the fusion protein was bound to glutathione-sepharose-beads and the reaction stopped after 20 min. with 1 mM PMSF. The sepharose beads were then pelleted by centrifugation and the supernatant containing the GRA2-polypeptide was collected. The solution was then concentrated 10-fold with a Ultrafree-4 centrifugal filter-5K (Millipore, UFV4BCC25). To reduce disulfide bonds which might eventually have formed, the solution was treated with 20 mM DTT 1 h on ice. DTT was removed by loading the protein solution on a PD10 column (Pharmacia). Protein concentration was determined by the Lowry test and concentration of free cysteines in an Ellmann's test. The protein was subsequently analyzed by SDS-PAGE. The GRA2 protein can however not be detected by Commassie staining. A yield of 9 mg GRA2 was obtained from an 8 L culture. The GRA2 amino acid sequence is KEAAGRGMVT VGKKLANVES DRSTTTTQAP DSPNGLAETE VPVEPQQRAA HVPVPDFSQGSGGCG (SEQ ID No. 178)

Example 44

Coupling of GRA2 to Pili

A. Coupling of GRA2 to Pili.

Figure 15A:
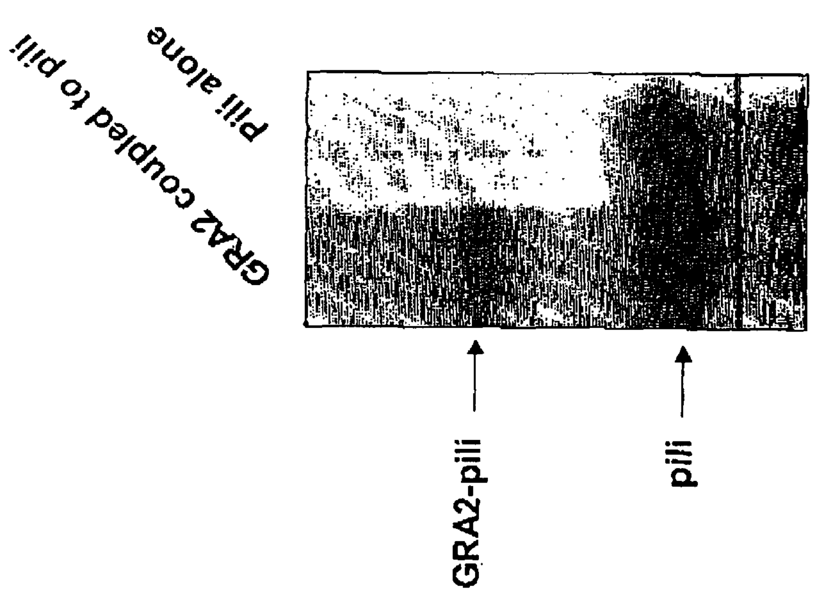
FIG. 15A shows an analysis of Coupling of GRA2 to Pili by SDS-PAGE analysis and Coomassie staining.

6 ml of a 2.5 mg/ml Pili protein solution (produced as described in Example 33 B) were reacted with a 50 fold molar excess of Sulfo-MBS, and desalted over a PD10 column (Pharmacia). 1.5 ml of the reaction mixture were loaded on one column, 1 ml was added and the first 1.5 ml were collected. Fractions containing Pili were identified on a dot blot stained with amidoblack. A 300 μg/ml solution of GRA2 was concentrated 100 fold, and 100 μl were reacted with 1.2 ml of the desalted activated Pili solution for 4 hours at RT. The reaction mixture was then dialyzed against 21 of a 20 mM Hepes, 150 mM NaCl, pH 7.2 overnight. FIG. 15A shows an analysis of the coupling reaction.

B. Immunization of Mice with Pili-GRA2 and IgG Subtype Determination.

Figure 15B:
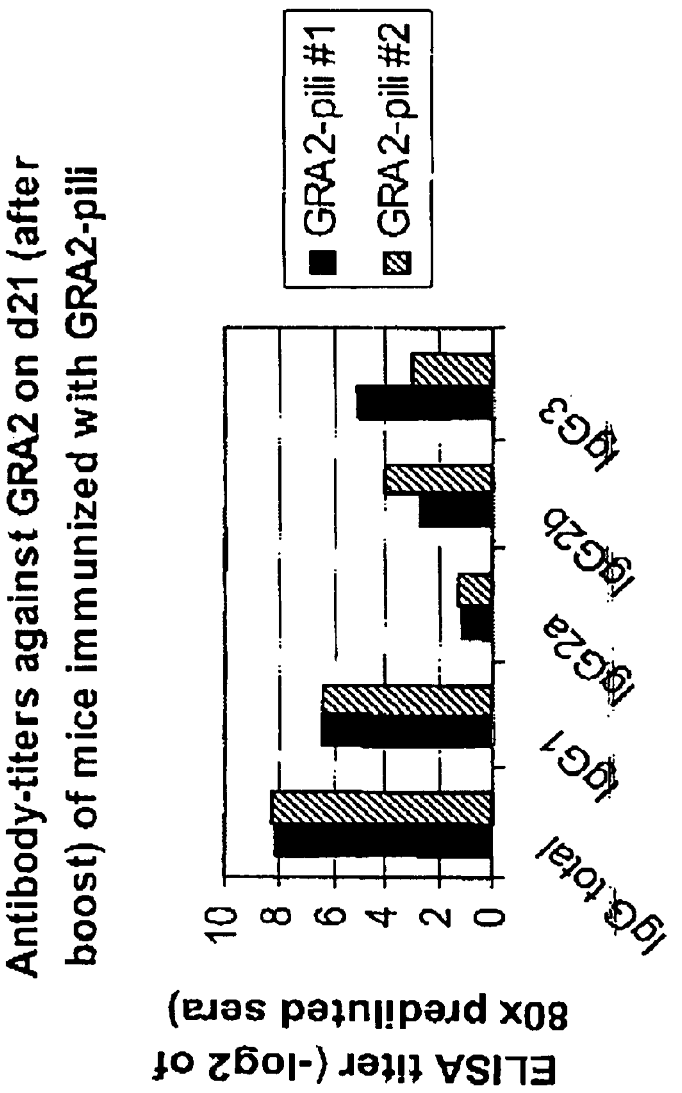
FIG. 15B relates to immunization of mice with Pili-GRA2 and IgG subtype determination. Depicted is an analysis of total IgG titer and IgG subtype titers by ELISA. The ELISA titer is given by the dilution of sera at which OD50 is obtained. The result of the immunization of two individual mice is shown. A high IgG1 titer and a low IgG2a titer is characteristic of a Th2 response.

Mice, were immunized with 50 4 g of Pili-GRA2 and boosted on day 14, with the same amount of vaccine. Serum samples were taken on day 0,6,14 and 21 after the first immunization. GRA2 specific IgG in serum was determined on day 21 in a GRA2 specific ELISA. Results of two individual mice in each group are shown in FIG. 15B. The titer was determined as the dilution of sera resulting in half-maximal optical density ($OD_{50}$).

Example 45

Coupling of B2- and D2-peptide to Pili

D2 and B2 peptides are sequences from the OmpC protein of *Salmonella typhi*. It is an outer membrane porin. High level of antiporin antibodies have been detected in the sera of patients with typhoid fever (Arocklasamy, A. and Krishnaswamy, S., *FEBS Letters* 453: 380–82 (1999)).

Figure 16A:
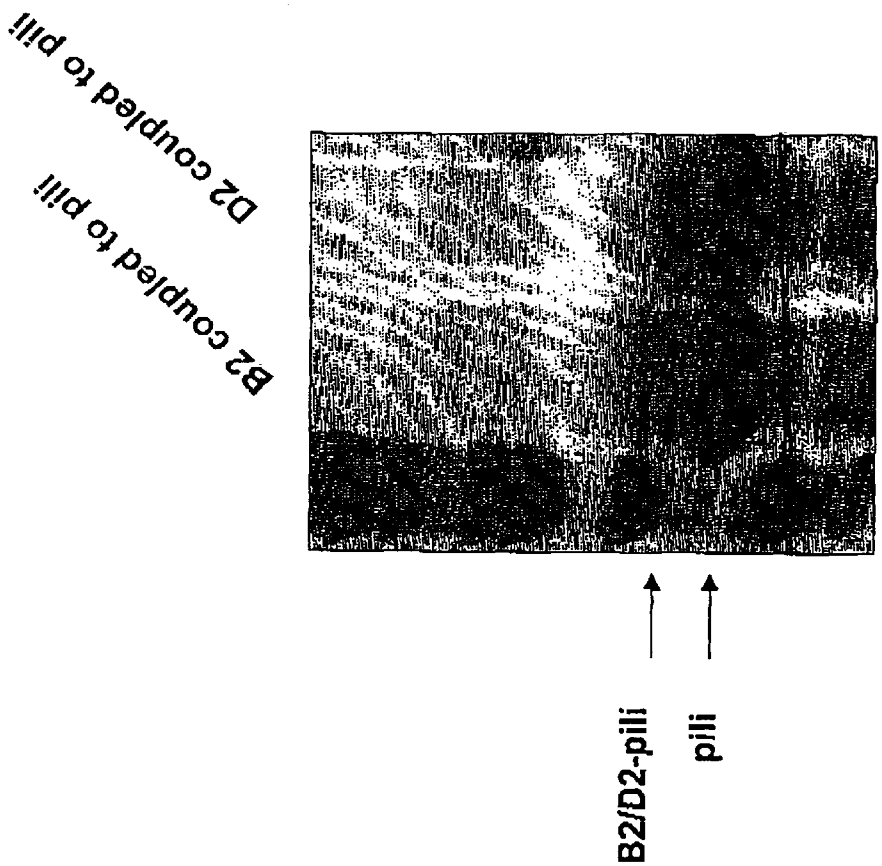
FIG. 16A shows an analysis of coupling of B2 and D2 peptides to Pili by SDS-PAGE analysis and Coomassie staining.

A. Coupling of B2- or D2-peptides of the ompC Protein of *Salmonella typhi* to Pili 6 ml of a 2.5 mg/ml Pili protein solution (produced as described in Example 33 B) were reacted with a 50 fold molar excess of Sulfo-MBS, and desalted over a PD10 column (Pharmacia). 1.5 ml of the reaction mixture were loaded on one column, 1 ml was added, and the first 1.5 ml were collected. Fractions containing Pili were identified on a dot blot stained with amidoblack. An aliquot of 5 μl of a 100 mM solution of peptide was reacted with 2.6 ml of the desalted activated Pili solution for 4 hours at RT. The reaction mixture was then dialyzed against 21 of a 20 mM Hepes, 150 mM NaCl, pH 7.2 overnight. FIG. 16A shows an analysis of the coupling reaction. The sequence of the D2 peptide is CGG TSN GSN PST SYG FAN (SEQ ID No. 179). The sequence of the B2 peptide is CGG DIS NGY GAS YGD NDI (SEQ ID No. 180).

B Immunization of Mice with Pili-B2 and IgG Subtype Determination.

Figure 16B:
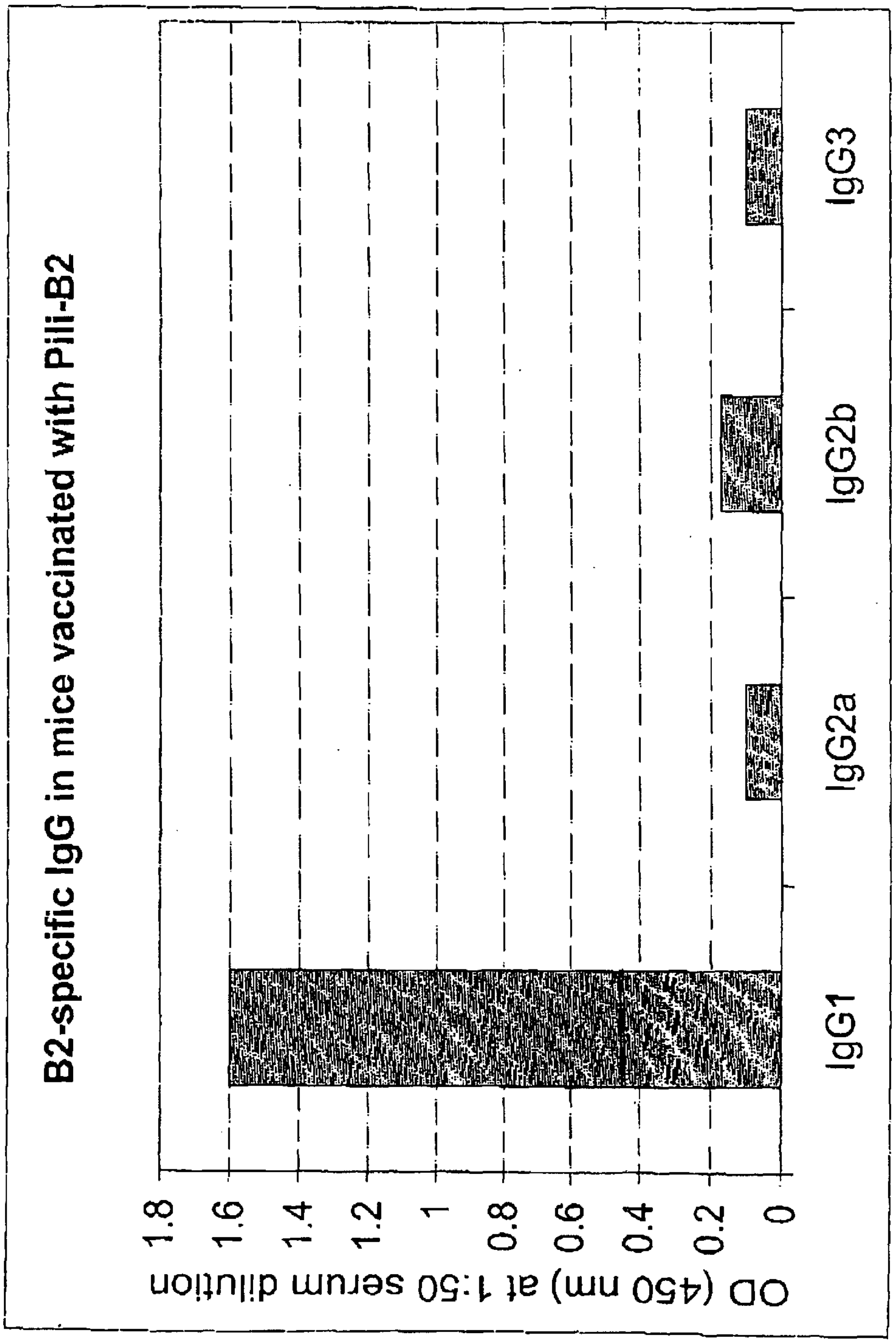
FIG. 16B relates to immunization of mice with Pili-B2 and IgG subtype determination. The OD (450 nm) of the ELISA signal obtained at a fifty-fold dilution of the sera is shown in the diagram. For each subtype determination, mice sera were titrated from a fifty-fold dilution in two-fold dilution steps. The titer of the IgG1 subtype (dilution at which the signal corresponds to OD 50) was 1:250, while the other subtypes all had titers inferior to 1:50. The titer of the IgG1 subtype is much higher than the titer of the IgG2a subtype, a pattern typical for a Th2 response.

Mice were immunized interaperitoneally in female Balb/c mice with 50 μg of Pili-B2 in saline and boosted on day 14 with the same amount of vaccine, and bled on day 33. B2-peptide specific IgG in serum was determined on day 33 in a B2-specific ELISA (B2 peptide was conjugated to Ribonuclease A with the cross-linker SPDP). Average of the results of two individual mice are shown in FIG. 16B.

Example 46

Figure 17:
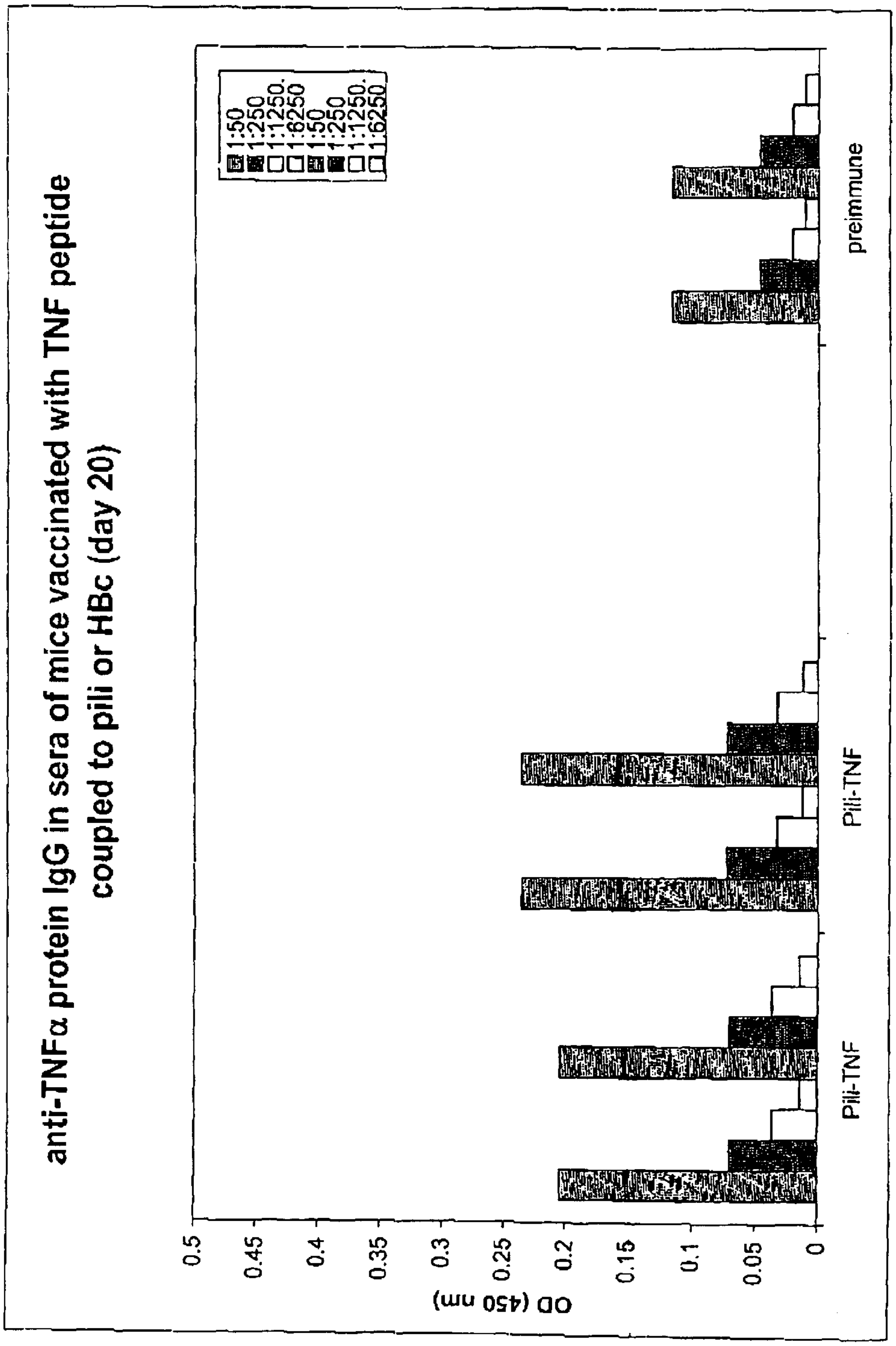
FIG. 17 relates to the measurement of antibodies specific for TNFα protein in the serum of mice immunized with the muTNFα peptide coupled to type-1 Pili. As a control, preimmune sera of two mice were assayed for binding to TNFα protein. Sera were added at three different dilutions (1:50, 1:100 and 1:200), and bound IgG was detected with a horseradish peroxidase-conjugated anti-murine IgG antibody. Results from four individual mice are shown on day 21 and day 43. OD (450 nm): optical density at 450 nm.

The muTNFa peptide, comprising amino acids 22–33 of TNFα protein was coupled to Pili as described in Example 42, except that no glucose was addedduring the final dialysis step, where the reaction solution was dialyzed against 20 mM Hepes, pH 7.4 only. Two Balb/c female mice, 8 days of age were immunized intravenously with 100 μg of Pili-muTNFa each. These mice were boosted at day 14 with the same amount of vaccine, and bled on day 20. IgG specific for native TNFα protein in serum was detected at day 20 in an ELISA. As a control, preimmune sera of two mice were assayed for binding to TNFα protein. See FIG. 17. The sequence of the muTNFa peptide was CGGVEEQLEWLSQR (SEQ ID No. 181).

Example 47

A. Preparation of Bacterial Type-1 Pili Coupled to TNF Peptides

Figure 18A:
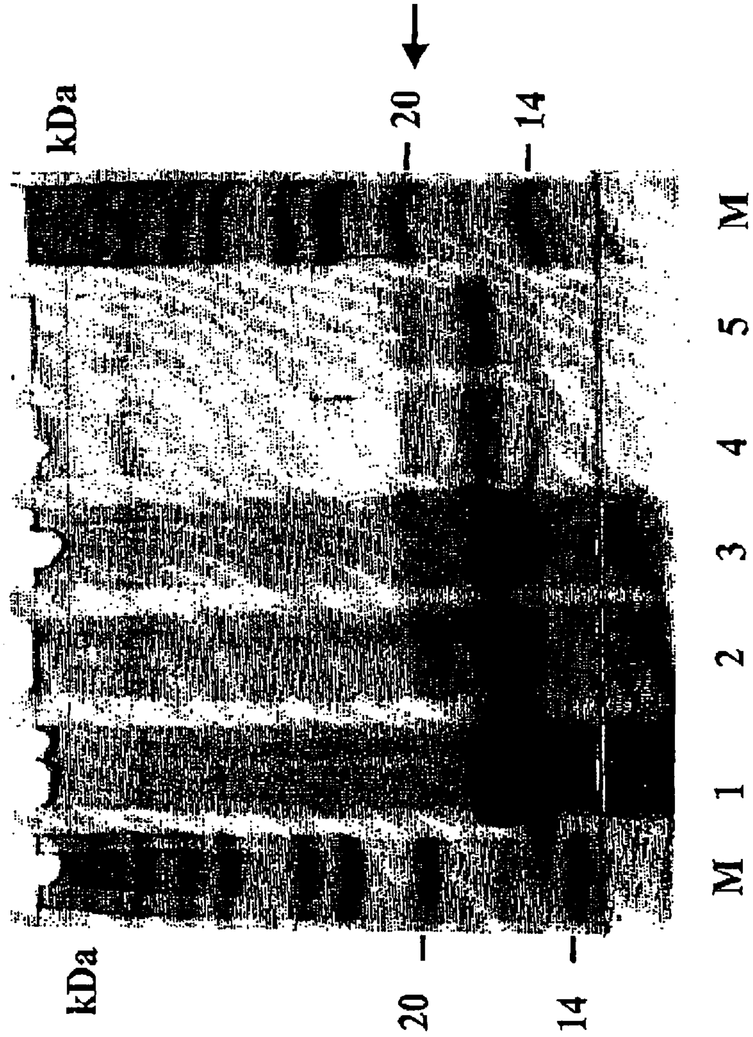
FIG. 18A shows an analysis of coupling of 5'-TNF II and 3'-TNF II by SDS-PAGE and Coomassie staining. Lane M is the marker lane. Untreated Pili were loaded on lane 1, Pili-5'-TNF II before dialysis on lane 2, Pili-3'-TNF II before dialysis on lane 3, Pili-5'-TNF II after dialysis on lane 4, pili-3'-TNF II after dialysis on lane 5. The arrow indicates the size at which the coupled product migrates.

Two peptides comprising murine TNFα sequences were designed. Peptide 3' murine TNFaII (3'-TNFaII) was SSQNSSDKPVAHVVANHGVGGC (SEQ ID No. 182). Peptide 5' murine TNFa II (5' TNFa II) was CSSQNSSDKPVAHVVANHGV (SEQ ID No. 183). The peptides 5'-TNFa II and 3'-TNFa II were coupled to bacterial type-1 pili as follows. An aliquot of 1 ml of a Pili solution (2.5 mg/ml) was reacted with 503 μl of a 100 mM Sulfo-NMS solution for 45 minutes at RT. The reaction mixture was desalted over a desalting column previously saturated with Pili protein and equilibrated in 20 mM Hepes, pH 7.4. The fractions containing protein were pooled. Art aliquot of 1 ml of desalted Pili was mixed with 1.56 μl of peptide (100 mM in DMSO), and the reaction left to proceed for 4 hours at RT. The reaction solution was then dialyzed overnight against 20 mM Hepes, 150 mM NaCl, pH 7.4 in the cold. See FIG. 18A.

Figure 18B:
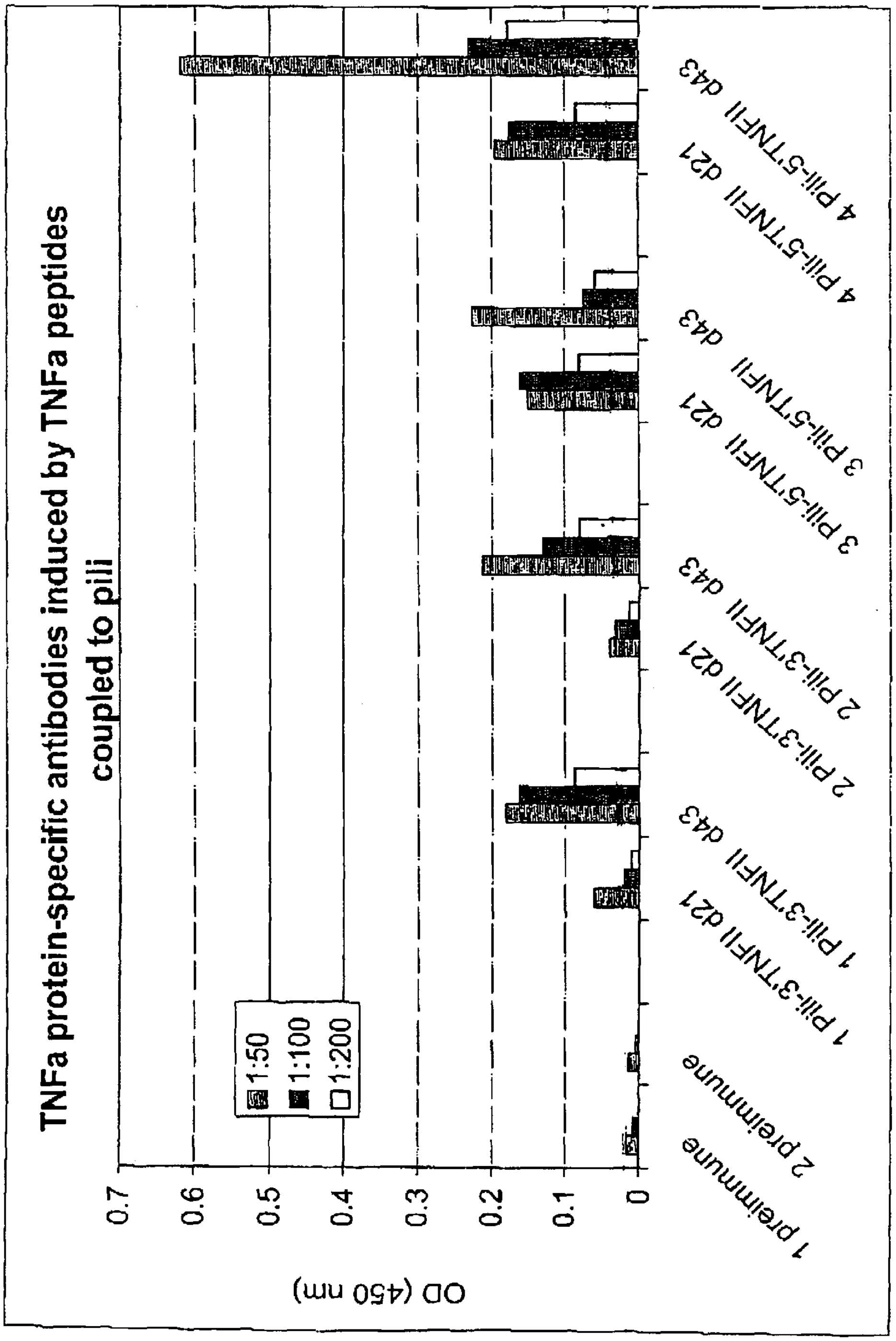
FIG. 18B shows an ELISA analysis of sera of mice immunized with Pili-5'-TNF II and Pili-3'-TNF II: Anti-TNFα ELISA. IgG antibodies specific for native TNFα protein were measured in a specific ELISA. 2 μg/ml native TNFα protein was coated on ELISA plates. Sera were added at different dilutions and bound IgG was detected with a horseradish peroxidase-conjugated anti-murine IgG antibody. Results from four individual mice are shown on day 21 and day 43 OD (450 nm): optical density at 450 nm. The data show that mice immunized with the TNF peptides coupled to pili mount an antibody response against native TNFα protein, thus breaking self-tolerance.
Figure 18C:
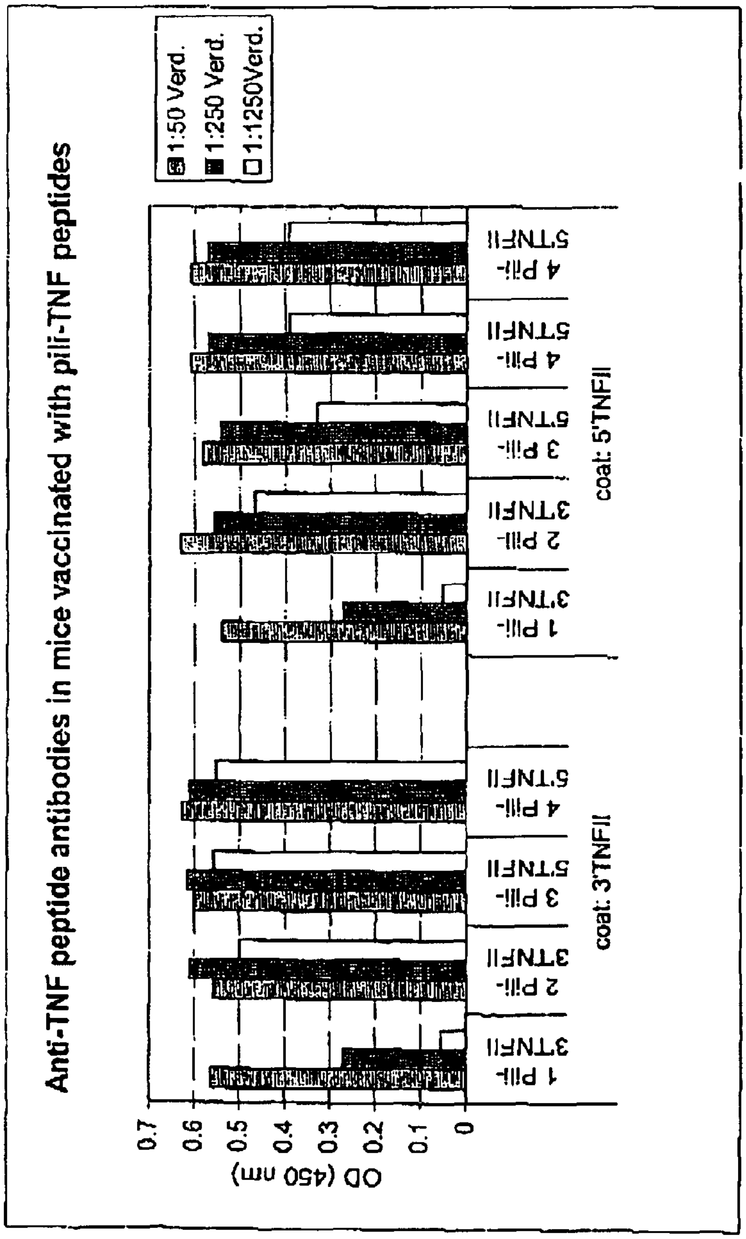
FIG. 18C shows an ELISA analysis of sera of mice immunized with Pili-5'-TNF II and Pili-3'-TNF II: Anti-TNFα peptide ELISA. IgG antibodies specific for the 5'TNF II and 3'TNF II peptides were measured in a specific ELISA: 10 μg/ml Ribonuclease A coupled to 5'TNF II or 3'TNF II peptide was coated on ELISA plates. Sera were added at different dilutions and bound IgG was detected with a horseradish peroxidaseconjugated anti-murine IgG antibody. Results from four individual mice are shown on day 21.

B. Immunization and Detection of Antibodies Specific for Native TNFα and the 3' TNFII and 5' TNFII Peptides Balb/c mice were vaccinated intraperitoneally with 30 μg protein in saline, on day 0, 14 and 33. IgG antibodies specific for native TNFα protein (FIG. 18B) and for the 3' TNFII and 5' TNFII peptides (FIG. 18C) were measured in a specific ELISA.

1. Native TNFα ELISA

2 μg/ml native TNFα protein was coated on ELISA plates. Sera were added at different dilutions and bound IgG was detected with a horseradish peroxidase-conjugated anti-murine IgG antibody. Results from four individual mice are shown on day 21 and day 43.

2. Anti Peptide ELISA

IgG antibodies specific for the 3' TNFII and 5' TNFII peptides were measured in a specific ELISA 10 ug/ml Ribonuclease A coupled to 3' TNFII or 5'TNFII peptide was coated on ELISA plates. Sera were added at different dilutions and bound IgG was detected with a horseradish peroxidase-conjugated anti-murine IgG antibody. Results from four individual mice are shown on day 21.

C. Analysis of Sera from Mice Immunized Under B.: IgG Subtype Determination

Figure 18D:
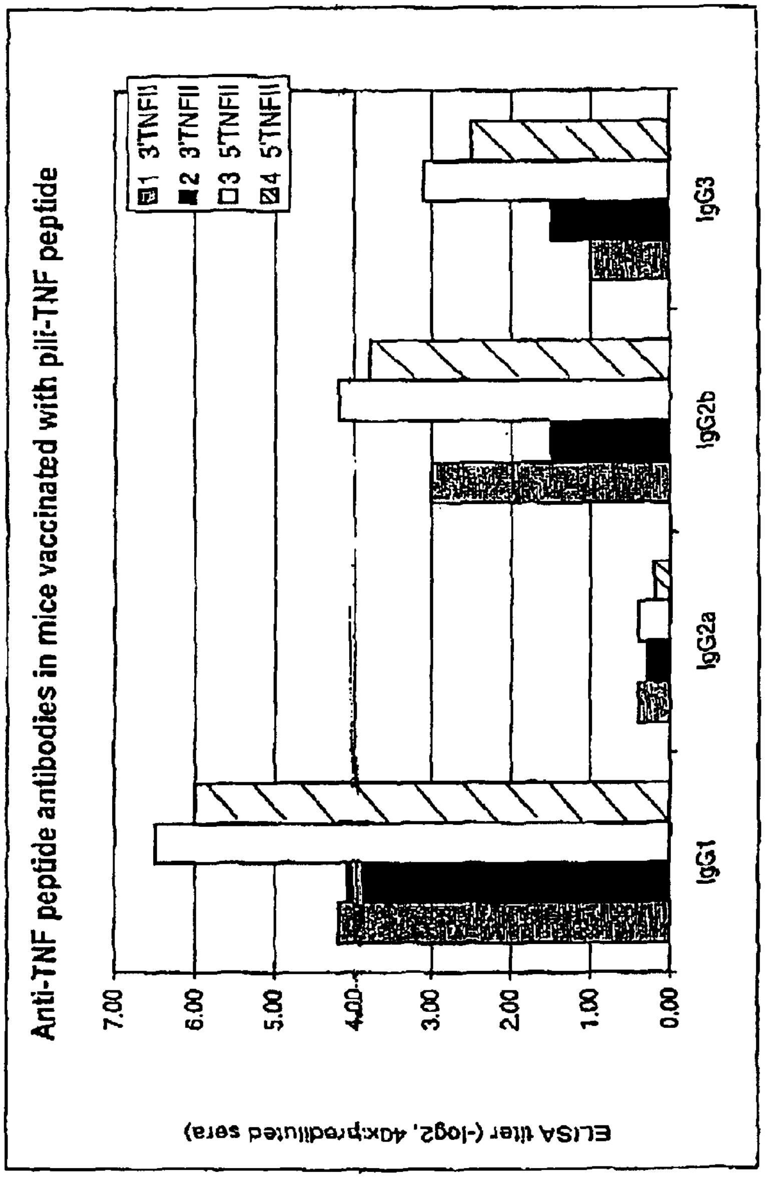
FIG. 18D shows that IgG subtype analysis of anti-TNF peptide antibodies in mice vaccinated with the corresponding TNF-peptides coupled to Pili. Results from four individual mice (no. 1–4) are shown on day 50. ELISA titer: dilution step at which half-maximal optical density was reached (−log 2 of 40-fold prediluted sera). The high IgG1 titer obtained as compared to the very low IgG2a titer is typical of a Th2 response.

Sera from the immunized mice described under B. were taken on day 50. Antibodies specific for the TNF peptides described under A. were measured in a specific ELISA on day 50. RNAse coupled to the corresponding TNF peptide was coated on ELISA plates at a concentration of 10 μg/ml. Sera were added at different dilutions and bound antibody was detected with horse radish peroxidase-conjugated anti-murine antibodies. See FIG. 18D.

Example 48

Figure 19A:
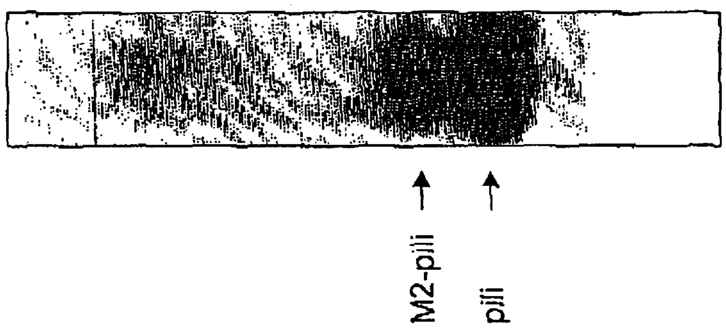
FIG. 19A shows an analysis of coupling of M2 peptide to Pili by SDS-PAGE analysis and Coomassie staining. The bands corresponding to non-coupled Pili and to the coupling product, Pili-M2, are indicated by arrows.
Figure 19B:
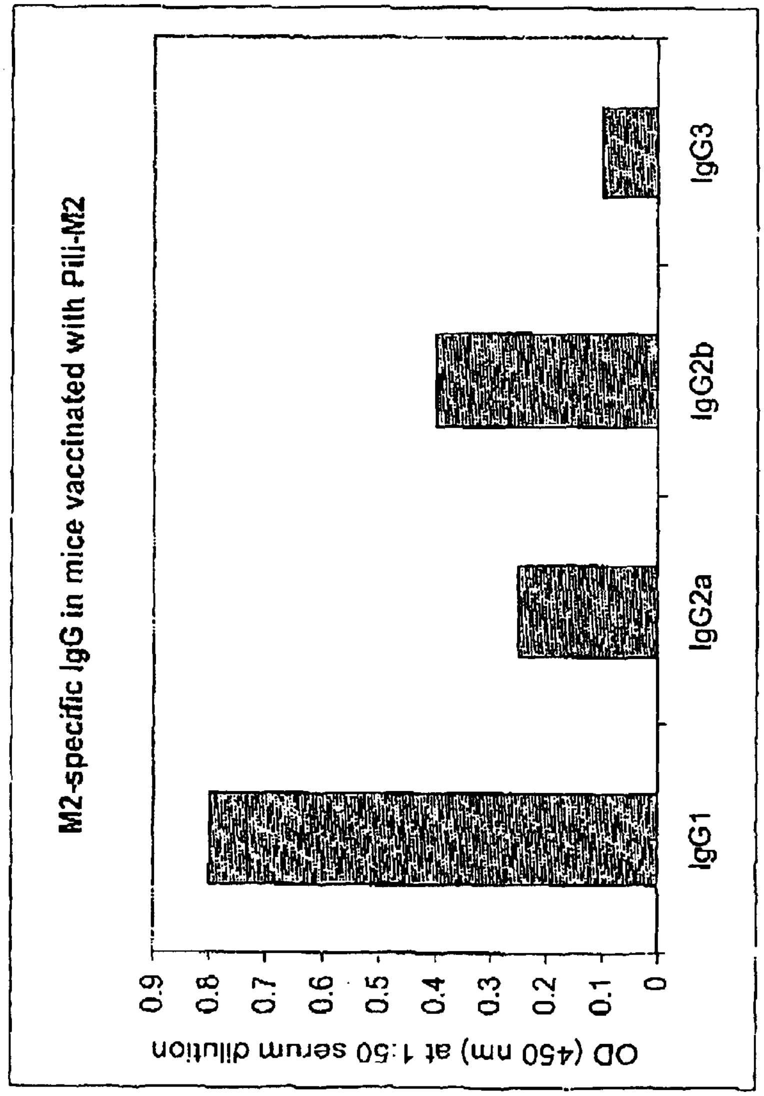
FIG. 19B shows an ELISA analysis and IgG subtype determination of mice vaccinated with Pili-M2. Sera were diluted eighty-fold, and titrated down in two-fold dilution steps. For the IgG1 subtype, a titer of 1:2560 was obtained, while for the IgG2a and IgG2b subtypes, titers below 1:100 were obtained. The titer for the IgG3 subtype was below 1:80. Titers were calculated as the serum dilution resulting in half-maximal optical density ($OD_{50}$). A strong IgG1 titer in conjunction with a low IgG2a titer is characteristic for a Th2 type response. Average results from two mice are shown as optical densities obtained with a 1:80 dilution of the serum.

Coupling of Pili to M2 Peptide, Immunization of Mice, and IgG Subtype Determination M2 peptide was coupled to pili as described in Example 47. The peptide was reacted at a fivefold molar excess with the activated Pili. Female Balb/c mice were injected with 50 μg Pili-M2 in saline subcutaneously. Mice were boosted with the same amount of vaccine on day 14 and bled on day 27, M2 specific IgG in serum was determined on day 27 in a M2-specific ELISA (peptide conjugated to Ribonuclease A with the cross-linker SPDP for coating). See FIGS. 19A and 19B.

Example 49

Figure 20:
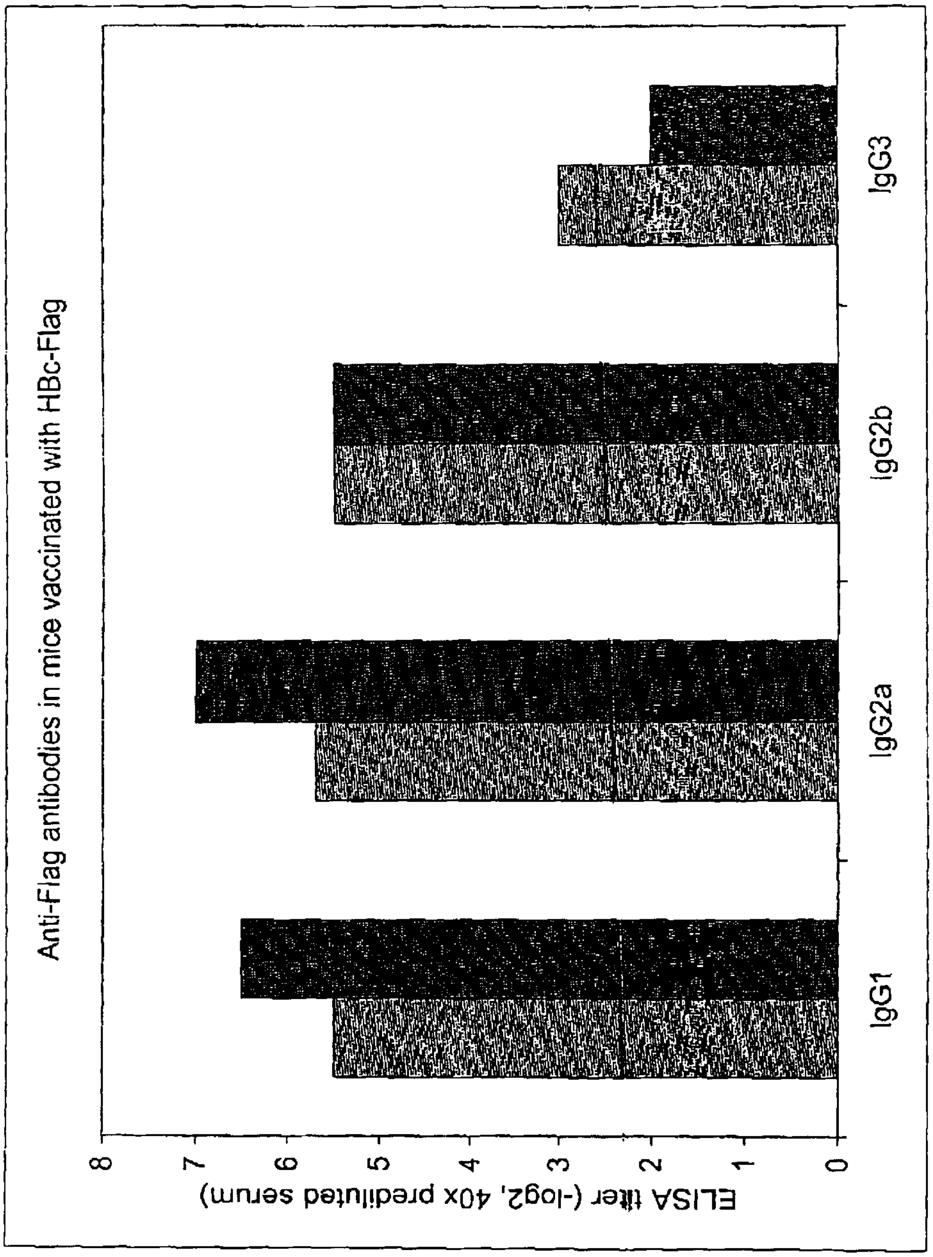
FIG. 20 shows an ELISA analysis and IgG subtype determination of sera from mice immunized with HBcAg-Lys-2cys-Mut coupled to the Flag peptide. Ribonuclease A coupled to Flag peptide was coated at 10 μg/ml, and serum was added at a 1:40 dilution. In contrast to experiments where mice were immunized with antigens coupled to Pili, there is no predominance of the IgG1 subtype over the other IgG subtypes.

Immunization of Mice with HbcAg-Lys-2cys-Mut Coupled to the Flag Peptide, and IgG Subtype Determination Flag peptide (SEQ ID NO: 147) was coupled to HBcAg-Lys-2cvs-Mut as described in Example 39. Two Balb/c mice were vaccinated intravenously with 50 μg HBc-Ag-Lys-2cys-Mut-Flag. On day 14 mice were boosted with the same amount of vaccine and bled on day 40, Flag-specific antibodies (Flag peptide was conjugated to Ribonuclease A with the cross-linker SPDP for coating) in serum were measured on day 40 in a specific ELISA. ELISA plates were coated with 10 μg/ml RNAse coupled to Flag peptide and serum was added at a 1:40 dilution. Bound antibodies were detected with peroxidase conjugate isotype-specific IgG. Results from the two mice are shown as ELISA titers in FIG. 20.

Example 50

Purification of Type-1 Pili of *Eschericia coli*

Isolated Type-1 pili of *Eschericia coil* prepared as described in Example 33B were precipitated with ammonium sulfate, added to a final concentration of 0.5 M, at 4° C. for 30 minutes. The pili were then pelleted by centrifugation at 20,000 rpm for 15 min at 4° C. and the pellet was resuspended in 25 ml of 20 mM HEPES buffer, pH 7.3. The precipitation step was repeated once, and the final sample was resuspended in 9 ml of 20 mM HEPES, pH 7.3 and finally dialyzed against the same buffer to remove residual ammonium sulfate. The pili were subsequently purified on an SR-400 size exclusion chromatography column (20 mM HEPES, pH 7.3) and the pili containing fractions were collected and pooled.

All patents and publications referred to herein are expressly incorporated by reference.

The entire disclosure of U.S. application Ser. No. 09/449,631, filed Nov. 30, 1999, is herein incorporated by reference. All publications and patents mentioned hereinabove are hereby incorporated in their entireties by reference.

What is claimed is:

1. A composition comprising:

(a) a non-natural molecular scaffold comprising:

(i) a virus-like particle that is a dimer or a multimer of a polypeptide comprising, as a core particle, a polypeptide having the amino acid sequence of SEQ ID NO:158, modified such that the cysteine residues at positions 48 and 110 of SEQ ID NO:158 (corresponding to positions 48 and 107 of SEQ ID NO:134) are either deleted or substituted with another amino acid, or a sequence having at least 90% sequence identity to said polypeptide sequence and in which the cysteine residues at positions 48 and 110 of SEQ ID NO:158 are either deleted or substituted with another amino acid; and (ii) an organizer comprising at least one first attachment site, wherein said organizer is connected to said core particle by at least one covalent bond; and (b) an antigen or antigenic determinant with at least one second attachment site, said second attachment site being selected from the group consisting of:

(i) an attachment site not naturally occurring with said antigen or antigenic determinant; and (ii) an attachment site naturally occurring with said antigen or antigenic determinant, wherein said second attachment site is capable of association through at least one non-peptide bond to said first attachment site; and wherein said antigen or antigenic determinant and said scaffold interact through said association to form an ordered and repetitive antigen array.

2. The composition of claim 1, wherein said organizer is a polypeptide or residue thereof; and wherein said second attachment site is a polypeptide or residue thereof.

3. The composition of claim 1, wherein said first and/or said second attachment sites comprise:

(a) an antigen and an antibody or antibody fragment thereto;

(b) biotin and avidin;

(c) strepavidin and biotin;

(d) a receptor and its ligand;

(e) a ligand-binding protein and its ligand;

(f) interacting leucine zipper polypeptides;

(g) an amino group and a chemical group reactive thereto;

(h) a carboxyl group and a chemical group reactive thereto;

(i) a sulfhydryl group and a chemical group reactive thereto; or (j) a combination thereof.

4. The composition of claim 3, wherein said first attachment site is an amino group and said second attachment site is a sulfhydryl group.

5. The composition of claim 1, wherein said antigen or antigenic determinant is selected from the group consisting of:

(a) an antigen suited to induce an immune response against bacteria;

(b) an antigen suited to induce an immune response against viruses;

(c) an antigen suited to induce an immune response against parasites;

(d) an antigen suited to induce an immune response against cancer cells;

(e) an antigen suited to induce an immune response against allergens;

(f) an antigen suited to induce an immune response in a farm animals; and (g) a protein suited to induce an immune response in a pet.

6. The composition of claim 5, wherein the antigen or antigenic determinant is a protein, polypeptide, or a fragment thereof.

7. The composition of claim 5, wherein said antigen or antigenic determinant induces an immune response against one or more allergens.

8. The composition of claim 5, wherein said antigen or antigenic determinant is selected from the group consisting of:

(a) a recombinant protein of HIV;

(b) a recombinant protein of Influenza virus;

(c) a recombinant protein of Hepatitis C virus;

(d) a recombinant protein of Toxoplasma;

(e) a recombinant protein of *Plasmodium falciparum;*

(f) a recombinant protein of *Plasmodium vivax;*

(g) a recombinant protein of *Plasmodium ovale;*

(h) a recombinant protein of *Plasmodium malariae;*

(i) a recombinant protein of breast cancer cells;

(j) a recombinant protein of kidney cancer cells;

(k) a recombinant protein of prostate cancer cells;

(l) a recombinant protein of skin cancer cells;

(m) a recombinant protein of brain cancer cells;

(n) a recombinant protein of leukemia cells;

(o) a recombinant protein of bee sting allergy;

(p) a recombinant protein of nut allergy;

(q) a recombinant protein of food allergies;

(r) a recombinant protein of asthma; and (s) a recombinant protein of Chlamydia.

9. A pharmaceutical composition comprising the composition of claim 1, and a pharmaceutically acceptable carrier.

10. An immunogenic composition comprising the composition of claim 1.

11. The immunogenic composition of claim 10, further comprising at least one adjuvant.

12. A method of immunizing, comprising administering to a subject the immunogenic composition of claim 10.

13. The method of claim 12, wherein said administering produces an immune response.

14. The method of claim 13, wherein said administering produces a humoral immune response.

15. The method of claim 13, wherein said administering produces a cellular immune response.

16. The method of claim 13, wherein said administering produces a humoral immune response and a cellular immune response.

17. The method of claim 13, wherein said administering produces a protective immune response.

18. A method of making the composition of claim 1, comprising combining said non-natural molecular scaffold and said antigen or antigenic determinant, wherein said non-natural molecular scaffold and said antigen or antigenic determinant interact to form an antigen array.

19. The method of claim 18, wherein said antigen array is ordered and/or repetitive.

20. A method of immunizing, comprising administering the composition of claim 1, or the immunogenic composition of claim 10, to a subject, wherein said administering produces a Th2 response that is specific for said antigen or antigenic determinant.

21. The method of claim 20, wherein antibodies specific for said antigen or antigenic determinant of a subtype corresponding to the Th2 subtype are induced in the subject.

22. The method of claim 20, wherein the subject does not generate a Th1 response that is specific for said antigen or antigenic determinant.

23. A vaccine composition comprising the composition of claim 1.

24. The vaccine composition of claim 23, further comprising at least one adjuvant.

* * * * *

SEQUENCE LISTING

```
<160> NUMBER OF SEQ ID NOS: 186

<210> SEQ ID NO 1
<211> LENGTH: 41
<212> TYPE: DNA
<213> ORGANISM: Artificial Sequence
<220> FEATURE:
<223> OTHER INFORMATION: Primer

<400> SEQUENCE: 1

ggggacgcgt gcagcaggta accaccgtta aagaaggcac c                          41


<210> SEQ ID NO 2
<211> LENGTH: 44
<212> TYPE: DNA
<213> ORGANISM: Artificial Sequence
<220> FEATURE:
<223> OTHER INFORMATION: Primer

<400> SEQUENCE: 2

cggtggttac ctgctgcacg cgttgcttaa gcgacatgta gcgg                       44
```

-continued

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
ccatgaggcc tacgataccc 20

<210> SEQ ID NO 4
<211> LENGTH: 25
<212> TYPE: DNA
<213> ORGANISM: Artificial Sequence
<220> FEATURE:
<223> OTHER INFORMATION: Primer

<400> SEQUENCE: 4
ggcactcacg gcgcgcttta caggc 25

<210> SEQ ID NO 5
<211> LENGTH: 47
<212> TYPE: DNA
<213> ORGANISM: Artificial Sequence
<220> FEATURE:
<223> OTHER INFORMATION: Primer

<400> SEQUENCE: 5
ccttctttaa cggtggttac ctgctggcaa ccaacgtggt tcatgac 47

<210> SEQ ID NO 6
<211> LENGTH: 40
<212> TYPE: DNA
<213> ORGANISM: Artificial Sequence
<220> FEATURE:
<223> OTHER INFORMATION: Primer

<400> SEQUENCE: 6
aagcatgctg cacgcgtgtg cggtggtcgg atcgcccggc 40

<210> SEQ ID NO 7
<211> LENGTH: 90
<212> TYPE: DNA
<213> ORGANISM: Artificial Sequence
<220> FEATURE:
<223> OTHER INFORMATION: Primer

<400> SEQUENCE: 7
gggtctagat tcccaaccat tcccttatcc aggctttttg acaacgctat gctccgcgcc 60
catcgtctgc accagctggc ctttgacacc 90

<210> SEQ ID NO 8
<211> LENGTH: 108
<212> TYPE: DNA
<213> ORGANISM: Artificial Sequence
<220> FEATURE:
<223> OTHER INFORMATION: Primer

<400> SEQUENCE: 8
gggtctagaa ggaggtaaaa aacgatgaaa aagacagcta tcgcgattgc agtggcactg 60
gctggtttcg ctaccgtagc gcaggccttc ccaaccattc ccttatcc 108

<210> SEQ ID NO 9

-continued

<211> LENGTH: 31
<212> TYPE: DNA
<213> ORGANISM: Artificial Sequence
<220> FEATURE:
<223> OTHER INFORMATION: Primer

<400> SEQUENCE: 9
cccgaattcc tagaagccac agctgccctc c 31

<210> SEQ ID NO 10
<211> LENGTH: 24
<212> TYPE: DNA
<213> ORGANISM: Artificial Sequence
<220> FEATURE:
<223> OTHER INFORMATION: Primer

<400> SEQUENCE: 10
cctgcggtgg tctgaccgac accc 24

<210> SEQ ID NO 11
<211> LENGTH: 41
<212> TYPE: DNA
<213> ORGANISM: Artificial Sequence
<220> FEATURE:
<223> OTHER INFORMATION: Primer

<400> SEQUENCE: 11
ccgcggaaga gccaccgcaa ccaccgtgtg ccgccaggat g 41

<210> SEQ ID NO 12
<211> LENGTH: 33
<212> TYPE: DNA
<213> ORGANISM: Artificial Sequence
<220> FEATURE:
<223> OTHER INFORMATION: Primer

<400> SEQUENCE: 12
ctatcatcta gaatgaatag aggattcttt aac 33

<210> SEQ ID NO 13
<211> LENGTH: 15
<212> TYPE: DNA
<213> ORGANISM: Artificial Sequence
<220> FEATURE:
<223> OTHER INFORMATION: Modified ribosome
binding site

<400> SEQUENCE: 13
aggaggtaaa aaacg 15

<210> SEQ ID NO 14
<211> LENGTH: 21
<212> TYPE: PRT
<213> ORGANISM: Artificial Sequence
<220> FEATURE:
<223> OTHER INFORMATION: signal peptide

<400> SEQUENCE: 14

Met Lys Lys Thr Ala Ile Ala Ile Ala Val Ala Leu Ala Gly Phe Ala
1 5 10 15

Thr Val Ala Gln Ala
20

<210> SEQ ID NO 15
<211> LENGTH: 46
<212> TYPE: PRT

-continued

<213> ORGANISM: Artificial Sequence
<220> FEATURE:
<223> OTHER INFORMATION: modified Fos
construct

<400> SEQUENCE: 15

Cys Gly Gly Leu Thr Asp Thr Leu Gln Ala Glu Thr Asp Gln Val Glu
1 5 10 15

Asp Glu Lys Ser Ala Leu Gln Thr Glu Ile Ala Asn Leu Leu Lys Glu
20 25 30

Lys Glu Lys Leu Glu Phe Ile Leu Ala Ala His Gly Gly Cys
35 40 45

<210> SEQ ID NO 16
<211> LENGTH: 6
<212> TYPE: PRT
<213> ORGANISM: Artificial Sequence
<220> FEATURE:
<223> OTHER INFORMATION: peptide linker

<400> SEQUENCE: 16

Ala Ala Ala Ser Gly Gly
1 5

<210> SEQ ID NO 17
<211> LENGTH: 6
<212> TYPE: PRT
<213> ORGANISM: Artificial Sequence
<220> FEATURE:
<223> OTHER INFORMATION: peptide linker

<400> SEQUENCE: 17

Gly Gly Ser Ala Ala Ala
1 5

<210> SEQ ID NO 18
<211> LENGTH: 256
<212> TYPE: DNA
<213> ORGANISM: Artificial Sequence
<220> FEATURE:
<223> OTHER INFORMATION: Fos fusion construct

<400> SEQUENCE: 18
gaattcagga ggtaaaaaac gatgaaaaag acagctatcg cgattgcagt ggcactggct 60
ggtttcgcta ccgtagcgca ggcctgggtg ggggcggccg cttctggtgg ttgcggtggt 120
ctgaccgaca ccctgcaggc ggaaaccgac caggtggaag acgaaaaatc cgcgctgcaa 180
accgaaatcg cgaacctgct gaaagaaaaa gaaaagctgg agttcatcct ggcggcacac 240
ggtggttgct aagctt 256

<210> SEQ ID NO 19
<211> LENGTH: 52
<212> TYPE: PRT
<213> ORGANISM: Artificial Sequence
<220> FEATURE:
<223> OTHER INFORMATION: Fos fusion construct

<400> SEQUENCE: 19

Ala Ala Ala Ser Gly Gly Cys Gly Gly Leu Thr Asp Thr Leu Gln Ala
5 10 15

Glu Thr Asp Gln Val Glu Asp Glu Lys Ser Ala Leu Gln Thr Glu Ile
20 25 30

Ala Asn Leu Leu Lys Glu Lys Glu Lys Leu Glu Phe Ile Leu Ala Ala

-continued

```
        35                  40                  45

His Gly Gly Cys
    50


<210> SEQ ID NO 20
<211> LENGTH: 261
<212> TYPE: DNA
<213> ORGANISM: Artificial Sequence
<220> FEATURE:
<223> OTHER INFORMATION: Fos fusion
      construct
<221> NAME/KEY: CDS
<222> LOCATION: (22)..(240)

<400> SEQUENCE: 20

gaattcagga ggtaaaaaac g atg aaa aag aca gct atc gcg att gca gtg       51
                        Met Lys Lys Thr Ala Ile Ala Ile Ala Val
                          1               5                  10

gca ctg gct ggt ttc gct acc gta gcg cag gcc tgc ggt ggt ctg acc       99
Ala Leu Ala Gly Phe Ala Thr Val Ala Gln Ala Cys Gly Gly Leu Thr
                15                  20                  25

gac acc ctg cag gcg gaa acc gac cag gtg gaa gac gaa aaa tcc gcg      147
Asp Thr Leu Gln Ala Glu Thr Asp Gln Val Glu Asp Glu Lys Ser Ala
            30                  35                  40

ctg caa acc gaa atc gcg aac ctg ctg aaa gaa aaa gaa aag ctg gag      195
Leu Gln Thr Glu Ile Ala Asn Leu Leu Lys Glu Lys Glu Lys Leu Glu
        45                  50                  55

ttc atc ctg gcg gca cac ggt ggt tgc ggt ggt tct gcg gcc gct          240
Phe Ile Leu Ala Ala His Gly Gly Cys Gly Gly Ser Ala Ala Ala
    60                  65                  70

gggtgtgggg atatcaagct t                                              261


<210> SEQ ID NO 21
<211> LENGTH: 73
<212> TYPE: PRT
<213> ORGANISM: Artificial Sequence
<220> FEATURE:
<223> OTHER INFORMATION: Fos fusion
      construct

<400> SEQUENCE: 21

Met Lys Lys Thr Ala Ile Ala Ile Ala Val Ala Leu Ala Gly Phe Ala
  1               5                  10                  15

Thr Val Ala Gln Ala Cys Gly Gly Leu Thr Asp Thr Leu Gln Ala Glu
            20                  25                  30

Thr Asp Gln Val Glu Asp Glu Lys Ser Ala Leu Gln Thr Glu Ile Ala
        35                  40                  45

Asn Leu Leu Lys Glu Lys Glu Lys Leu Glu Phe Ile Leu Ala Ala His
    50                  55                  60

Gly Gly Cys Gly Gly Ser Ala Ala Ala
 65                  70


<210> SEQ ID NO 22
<211> LENGTH: 196
<212> TYPE: DNA
<213> ORGANISM: Artificial Sequence
<220> FEATURE:
<223> OTHER INFORMATION: Fos fusion
      construct
<221> NAME/KEY: CDS
<222> LOCATION: (34)..(189)

<400> SEQUENCE: 22
```

-continued

```
gaattcagga ggtaaaaaga tatcgggtgt ggg gcg gcc gct tct ggt ggt tgc      54
                                     Ala Ala Ala Ser Gly Gly Cys
                                      1               5

ggt ggt ctg acc gac acc ctg cag gcg gaa acc gac cag gtg gaa gac      102
Gly Gly Leu Thr Asp Thr Leu Gln Ala Glu Thr Asp Gln Val Glu Asp
         10                  15                  20

gaa aaa tcc gcg ctg caa acc gaa atc gcg aac ctg ctg aaa gaa aaa      150
Glu Lys Ser Ala Leu Gln Thr Glu Ile Ala Asn Leu Leu Lys Glu Lys
     25                  30                  35

gaa aag ctg gag ttc atc ctg gcg gca cac ggt ggt tgc taagctt          196
Glu Lys Leu Glu Phe Ile Leu Ala Ala His Gly Gly Cys
 40                  45                  50
```

```
<210> SEQ ID NO 23
<211> LENGTH: 52
<212> TYPE: PRT
<213> ORGANISM: Artificial Sequence
<220> FEATURE:
<223> OTHER INFORMATION: Fos fusion
      construct

<400> SEQUENCE: 23

Ala Ala Ala Ser Gly Gly Cys Gly Gly Leu Thr Asp Thr Leu Gln Ala
  1               5                  10                  15

Glu Thr Asp Gln Val Glu Asp Glu Lys Ser Ala Leu Gln Thr Glu Ile
             20                  25                  30

Ala Asn Leu Leu Lys Glu Lys Glu Lys Leu Glu Phe Ile Leu Ala Ala
         35                  40                  45

His Gly Gly Cys
     50
```

```
<210> SEQ ID NO 24
<211> LENGTH: 204
<212> TYPE: DNA
<213> ORGANISM: Artificial Sequence
<220> FEATURE:
<223> OTHER INFORMATION: Fos fusion
      construct

<400> SEQUENCE: 24

gaattcagga ggtaaaaaac gatggcttgc ggtggtctga ccgacaccct gcaggcggaa     60

accgaccagg tggaagacga aaaatccgcg ctgcaaaccg aaatcgcgaa cctgctgaaa    120

gaaaaagaaa agctggagtt catcctggcg gcacacggtg gttgcggtgg ttctgcggcc    180

gctgggtgtg gggatatcaa gctt                                           204
```

```
<210> SEQ ID NO 25
<211> LENGTH: 56
<212> TYPE: PRT
<213> ORGANISM: Artificial Sequence
<220> FEATURE:
<223> OTHER INFORMATION: Fos fusion
      construct

<400> SEQUENCE: 25

Lys Thr Met Ala Cys Gly Gly Leu Thr Asp Thr Leu Gln Ala Glu Thr
  1               5                  10                  15

Asp Gln Val Glu Asp Glu Lys Ser Ala Leu Gln Thr Glu Ile Ala Asn
             20                  25                  30

Leu Leu Lys Glu Lys Glu Lys Leu Glu Phe Ile Leu Ala Ala His Gly
         35                  40                  45

Gly Cys Gly Gly Ser Ala Ala Ala
```

-continued

```
 50                  55


<210> SEQ ID NO 26
<211> LENGTH: 26
<212> TYPE: PRT
<213> ORGANISM: Homo sapiens

<400> SEQUENCE: 26

Met Ala Thr Gly Ser Arg Thr Ser Leu Leu Leu Ala Phe Gly Leu Leu
  1               5                  10                  15

Cys Leu Pro Trp Leu Gln Glu Gly Ser Ala
            20                  25


<210> SEQ ID NO 27
<211> LENGTH: 262
<212> TYPE: DNA
<213> ORGANISM: Artificial Sequence
<220> FEATURE:
<223> OTHER INFORMATION: Fos fusion
      construct

<400> SEQUENCE: 27

gaattcaggc ctatggctac aggctcccgg acgtccctgc tcctggcttt tggcctgctc     60

tgcctgccct ggcttcaaga gggcagcgct gggtgtgggg cggccgcttc tggtggttgc    120

ggtggtctga ccgacaccct gcaggcggaa accgaccagg tggaagacga aaaatccgcg    180

ctgcaaaccg aaatcgcgaa cctgctgaaa gaaaaagaaa agctggagtt catcctggcg    240

gcacacggtg gttgctaagc tt                                             262


<210> SEQ ID NO 28
<211> LENGTH: 52
<212> TYPE: PRT
<213> ORGANISM: Artificial Sequence
<220> FEATURE:
<223> OTHER INFORMATION: Fos fusion
      construct

<400> SEQUENCE: 28

Ala Ala Ala Ser Gly Gly Cys Gly Gly Leu Thr Asp Thr Leu Gln Ala
                 5                  10                  15

Glu Thr Asp Gln Val Glu Asp Glu Lys Ser Ala Leu Gln Thr Glu Ile
            20                  25                  30

Ala Asn Leu Leu Lys Glu Lys Glu Lys Leu Glu Phe Ile Leu Ala Ala
        35                  40                  45

His Gly Gly Cys
    50


<210> SEQ ID NO 29
<211> LENGTH: 261
<212> TYPE: DNA
<213> ORGANISM: Artificial Sequence
<220> FEATURE:
<223> OTHER INFORMATION: Fos fusion
      construct
<221> NAME/KEY: CDS
<222> LOCATION: (7)..(240)

<400> SEQUENCE: 29

gaattc atg gct aca ggc tcc cgg acg tcc ctg ctc ctg gct ttt ggc        48
       Met Ala Thr Gly Ser Arg Thr Ser Leu Leu Leu Ala Phe Gly
         1               5                  10

ctg ctc tgc ctg ccc tgg ctt caa gag ggc agc gct tgc ggt ggt ctg        96
Leu Leu Cys Leu Pro Trp Leu Gln Glu Gly Ser Ala Cys Gly Gly Leu
```

-continued

```
 15                  20                  25                  30

acc gac acc ctg cag gcg gaa acc gac cag gtg gaa gac gaa aaa tcc      144
Thr Asp Thr Leu Gln Ala Glu Thr Asp Gln Val Glu Asp Glu Lys Ser
                 35                  40                  45

gcg ctg caa acc gaa atc gcg aac ctg ctg aaa gaa aaa gaa aag ctg      192
Ala Leu Gln Thr Glu Ile Ala Asn Leu Leu Lys Glu Lys Glu Lys Leu
             50                  55                  60

gag ttc atc ctg gcg gca cac ggt ggt tgc ggt ggt tct gcg gcc gct      240
Glu Phe Ile Leu Ala Ala His Gly Gly Cys Gly Gly Ser Ala Ala Ala
         65                  70                  75

gggtgtggga ggcctaagct t                                              261


<210> SEQ ID NO 30
<211> LENGTH: 78
<212> TYPE: PRT
<213> ORGANISM: Artificial Sequence
<220> FEATURE:
<223> OTHER INFORMATION: Fos fusion
      construct

<400> SEQUENCE: 30

Met Ala Thr Gly Ser Arg Thr Ser Leu Leu Leu Ala Phe Gly Leu Leu
  1               5                  10                  15

Cys Leu Pro Trp Leu Gln Glu Gly Ser Ala Cys Gly Gly Leu Thr Asp
             20                  25                  30

Thr Leu Gln Ala Glu Thr Asp Gln Val Glu Asp Glu Lys Ser Ala Leu
         35                  40                  45

Gln Thr Glu Ile Ala Asn Leu Leu Lys Glu Lys Glu Lys Leu Glu Phe
     50                  55                  60

Ile Leu Ala Ala His Gly Gly Cys Gly Gly Ser Ala Ala Ala
 65                  70                  75


<210> SEQ ID NO 31
<211> LENGTH: 44
<212> TYPE: DNA
<213> ORGANISM: Artificial Sequence
<220> FEATURE:
<223> OTHER INFORMATION: Primer

<400> SEQUENCE: 31

cctgggtggg ggcggccgct tctggtggtt gcggtggtct gacc                      44


<210> SEQ ID NO 32
<211> LENGTH: 44
<212> TYPE: DNA
<213> ORGANISM: Artificial Sequence
<220> FEATURE:
<223> OTHER INFORMATION: Primer

<400> SEQUENCE: 32

ggtgggaatt caggaggtaa aaagatatcg ggtgtggggc ggcc                      44


<210> SEQ ID NO 33
<211> LENGTH: 47
<212> TYPE: DNA
<213> ORGANISM: Artificial Sequence
<220> FEATURE:
<223> OTHER INFORMATION: Primer

<400> SEQUENCE: 33

ggtgggaatt caggaggtaa aaaacgatgg cttgcggtgg tctgacc                   47
```

-continued

<210> SEQ ID NO 34
<211> LENGTH: 18
<212> TYPE: DNA
<213> ORGANISM: Artificial Sequence
<220> FEATURE:
<223> OTHER INFORMATION: Primer

<400> SEQUENCE: 34
gcttgcggtg gtctgacc 18

<210> SEQ ID NO 35
<211> LENGTH: 27
<212> TYPE: DNA
<213> ORGANISM: Artificial Sequence
<220> FEATURE:
<223> OTHER INFORMATION: Primer

<400> SEQUENCE: 35
ccaccaagct tagcaaccac cgtgtgc 27

<210> SEQ ID NO 36
<211> LENGTH: 54
<212> TYPE: DNA
<213> ORGANISM: Artificial Sequence
<220> FEATURE:
<223> OTHER INFORMATION: Primer

<400> SEQUENCE: 36
ccaccaagct tgatatcccc acacccagcg gccgcagaac caccgcaacc accg 54

<210> SEQ ID NO 37
<211> LENGTH: 32
<212> TYPE: DNA
<213> ORGANISM: Artificial Sequence
<220> FEATURE:
<223> OTHER INFORMATION: Primer

<400> SEQUENCE: 37
ccaccaagct taggcctccc acacccagcg gc 32

<210> SEQ ID NO 38
<211> LENGTH: 29
<212> TYPE: DNA
<213> ORGANISM: Artificial Sequence
<220> FEATURE:
<223> OTHER INFORMATION: Primer

<400> SEQUENCE: 38
ggtgggaatt caggaggtaa aaaacgatg 29

<210> SEQ ID NO 39
<211> LENGTH: 32
<212> TYPE: DNA
<213> ORGANISM: Artificial Sequence
<220> FEATURE:
<223> OTHER INFORMATION: Primer

<400> SEQUENCE: 39
ggtgggaatt caggcctatg gctacaggct cc 32

<210> SEQ ID NO 40
<211> LENGTH: 27
<212> TYPE: DNA
<213> ORGANISM: Artificial Sequence
<220> FEATURE:
<223> OTHER INFORMATION: Primer -continued

<400> SEQUENCE: 40
ggtgggaatt catggctaca ggctccc 27

<210> SEQ ID NO 41
<211> LENGTH: 59
<212> TYPE: DNA
<213> ORGANISM: Artificial Sequence
<220> FEATURE:
<223> OTHER INFORMATION: Primer

<400> SEQUENCE: 41
gggtctagaa tggctacagg ctcccggacg tccctgctcc tggcttttgg cctgctctg 59

<210> SEQ ID NO 42
<211> LENGTH: 58
<212> TYPE: DNA
<213> ORGANISM: Artificial Sequence
<220> FEATURE:
<223> OTHER INFORMATION: Primer

<400> SEQUENCE: 42
cgcaggcctc ggcactgccc tcttgaagcc agggcaggca gagcaggcca aaagccag 58

<210> SEQ ID NO 43
<211> LENGTH: 402
<212> TYPE: DNA
<213> ORGANISM: Artificial Sequence
<220> FEATURE:
<223> OTHER INFORMATION: Modified bee
venom phospholipase A2
<221> NAME/KEY: CDS
<222> LOCATION: (1)..(402)

<400> SEQUENCE: 43

```
atc atc tac cca ggt act ctg tgg tgt ggt cac ggc aac aaa tct tct       48
Ile Ile Tyr Pro Gly Thr Leu Trp Cys Gly His Gly Asn Lys Ser Ser
  1               5                  10                  15

ggt ccg aac gaa ctc ggc cgc ttt aaa cac acc gac gca tgc tgt cgc       96
Gly Pro Asn Glu Leu Gly Arg Phe Lys His Thr Asp Ala Cys Cys Arg
             20                  25                  30

acc cag gac atg tgt ccg gac gtc atg tct gct ggt gaa tct aaa cac      144
Thr Gln Asp Met Cys Pro Asp Val Met Ser Ala Gly Glu Ser Lys His
         35                  40                  45

ggg tta act aac acc gct tct cac acg cgt ctc agc tgc gac tgc gac      192
Gly Leu Thr Asn Thr Ala Ser His Thr Arg Leu Ser Cys Asp Cys Asp
     50                  55                  60

gac aaa ttc tac gac tgc ctt aag aac tcc gcc gat acc atc tct tct      240
Asp Lys Phe Tyr Asp Cys Leu Lys Asn Ser Ala Asp Thr Ile Ser Ser
 65                  70                  75                  80

tac ttc gtt ggt aaa atg tat ttc aac ctg atc gat acc aaa tgt tac      288
Tyr Phe Val Gly Lys Met Tyr Phe Asn Leu Ile Asp Thr Lys Cys Tyr
                 85                  90                  95

aaa ctg gaa cac ccg gta acc ggc tgc ggc gaa cgt acc gaa ggt cgc      336
Lys Leu Glu His Pro Val Thr Gly Cys Gly Glu Arg Thr Glu Gly Arg
            100                 105                 110

tgc ctg cac tac acc gtt gac aaa tct aaa ccg aaa gtt tac cag tgg      384
Cys Leu His Tyr Thr Val Asp Lys Ser Lys Pro Lys Val Tyr Gln Trp
        115                 120                 125

ttc gac ctg cgc aaa tac                                              402
Phe Asp Leu Arg Lys Tyr
    130
```

<210> SEQ ID NO 44

-continued

<211> LENGTH: 134
<212> TYPE: PRT
<213> ORGANISM: Artificial Sequence
<220> FEATURE:
<223> OTHER INFORMATION: Modified bee venom phospholipase A2

<400> SEQUENCE: 44

```
Ile Ile Tyr Pro Gly Thr Leu Trp Cys Gly His Gly Asn Lys Ser Ser
  1               5                  10                  15

Gly Pro Asn Glu Leu Gly Arg Phe Lys His Thr Asp Ala Cys Cys Arg
             20                  25                  30

Thr Gln Asp Met Cys Pro Asp Val Met Ser Ala Gly Glu Ser Lys His
         35                  40                  45

Gly Leu Thr Asn Thr Ala Ser His Thr Arg Leu Ser Cys Asp Cys Asp
     50                  55                  60

Asp Lys Phe Tyr Asp Cys Leu Lys Asn Ser Ala Asp Thr Ile Ser Ser
 65                  70                  75                  80

Tyr Phe Val Gly Lys Met Tyr Phe Asn Leu Ile Asp Thr Lys Cys Tyr
                 85                  90                  95

Lys Leu Glu His Pro Val Thr Gly Cys Gly Glu Arg Thr Glu Gly Arg
            100                 105                 110

Cys Leu His Tyr Thr Val Asp Lys Ser Lys Pro Lys Val Tyr Gln Trp
        115                 120                 125

Phe Asp Leu Arg Lys Tyr
    130
```

<210> SEQ ID NO 45
<211> LENGTH: 19
<212> TYPE: DNA
<213> ORGANISM: Artificial Sequence
<220> FEATURE:
<223> OTHER INFORMATION: Primer

<400> SEQUENCE: 45
ccatcatcta cccaggtac 19

<210> SEQ ID NO 46
<211> LENGTH: 34
<212> TYPE: DNA
<213> ORGANISM: Artificial Sequence
<220> FEATURE:
<223> OTHER INFORMATION: Primer

<400> SEQUENCE: 46
cccacaccca gcggccgcgt atttgcgcag gtcg 34

<210> SEQ ID NO 47
<211> LENGTH: 36
<212> TYPE: DNA
<213> ORGANISM: Artificial Sequence
<220> FEATURE:
<223> OTHER INFORMATION: Primer

<400> SEQUENCE: 47
cggtggttct gcggccgcta tcatctaccc aggtac 36

<210> SEQ ID NO 48
<211> LENGTH: 19
<212> TYPE: DNA
<213> ORGANISM: Artificial Sequence
<220> FEATURE:
<223> OTHER INFORMATION: Primer -continued

<400> SEQUENCE: 48
ttagtatttg cgcaggtcg 19

<210> SEQ ID NO 49
<211> LENGTH: 18
<212> TYPE: DNA
<213> ORGANISM: Artificial Sequence
<220> FEATURE:
<223> OTHER INFORMATION: Primer

<400> SEQUENCE: 49
ccggctccat cggtgcag 18

<210> SEQ ID NO 50
<211> LENGTH: 36
<212> TYPE: DNA
<213> ORGANISM: Artificial Sequence
<220> FEATURE:
<223> OTHER INFORMATION: Primer

<400> SEQUENCE: 50
accaccagaa gcggccgcag gggaaacaca tctgcc 36

<210> SEQ ID NO 51
<211> LENGTH: 35
<212> TYPE: DNA
<213> ORGANISM: Artificial Sequence
<220> FEATURE:
<223> OTHER INFORMATION: Primer

<400> SEQUENCE: 51
cggtggttct gcggccgctg gctccatcgg tgcag 35

<210> SEQ ID NO 52
<211> LENGTH: 21
<212> TYPE: DNA
<213> ORGANISM: Artificial Sequence
<220> FEATURE:
<223> OTHER INFORMATION: Primer

<400> SEQUENCE: 52
ttaaggggaa acacatctgc c 21

<210> SEQ ID NO 53
<211> LENGTH: 33
<212> TYPE: DNA
<213> ORGANISM: Artificial Sequence
<220> FEATURE:
<223> OTHER INFORMATION: Primer

<400> SEQUENCE: 53
actagtctag aatgagagtg aaggagaaat atc 33

<210> SEQ ID NO 54
<211> LENGTH: 42
<212> TYPE: DNA
<213> ORGANISM: Artificial Sequence
<220> FEATURE:
<223> OTHER INFORMATION: Primer

<400> SEQUENCE: 54
tagcatgcta gcaccgaatt tatctaattc caataattct tg 42

<210> SEQ ID NO 55

-continued

<211> LENGTH: 51
<212> TYPE: DNA
<213> ORGANISM: Artificial Sequence
<220> FEATURE:
<223> OTHER INFORMATION: Primer

<400> SEQUENCE: 55
gtagcaccca ccaaggcaaa gctgaaagct acccagctcg agaaactggc a 51

<210> SEQ ID NO 56
<211> LENGTH: 48
<212> TYPE: DNA
<213> ORGANISM: Artificial Sequence
<220> FEATURE:
<223> OTHER INFORMATION: Primer

<400> SEQUENCE: 56
caaagctcct attcccactg ccagtttctc gagctgggta gctttcag 48

<210> SEQ ID NO 57
<211> LENGTH: 36
<212> TYPE: DNA
<213> ORGANISM: Artificial Sequence
<220> FEATURE:
<223> OTHER INFORMATION: Primer

<400> SEQUENCE: 57
ttcggtgcta gcggtggctg cggtggtctg accgac 36

<210> SEQ ID NO 58
<211> LENGTH: 37
<212> TYPE: DNA
<213> ORGANISM: Artificial Sequence
<220> FEATURE:
<223> OTHER INFORMATION: Primer

<400> SEQUENCE: 58
gatgctgggc ccttaaccgc aaccaccgtg tgccgcc 37

<210> SEQ ID NO 59
<211> LENGTH: 46
<212> TYPE: PRT
<213> ORGANISM: Artificial Sequence
<220> FEATURE:
<223> OTHER INFORMATION: JUN amino acid
sequence

<400> SEQUENCE: 59

```
Cys Gly Gly Arg Ile Ala Arg Leu Glu Glu Lys Val Lys Thr Leu Lys
  1               5                  10                  15

Ala Gln Asn Ser Glu Leu Ala Ser Thr Ala Asn Met Leu Arg Glu Gln
             20                  25                  30

Val Ala Gln Leu Lys Gln Lys Val Met Asn His Val Gly Cys
         35                  40                  45
```

<210> SEQ ID NO 60
<211> LENGTH: 46
<212> TYPE: PRT
<213> ORGANISM: Artificial Sequence
<220> FEATURE:
<223> OTHER INFORMATION: FOS amino
acid sequence

<400> SEQUENCE: 60

```
Cys Gly Gly Leu Thr Asp Thr Leu Gln Ala Glu Thr Asp Gln Val Glu
  1               5                  10                  15
```

-continued

```
Asp Glu Lys Ser Ala Leu Gln Thr Glu Ile Ala Asn Leu Leu Lys Glu
            20                  25                  30

Lys Glu Lys Leu Glu Phe Ile Leu Ala Ala His Gly Gly Cys
        35                  40                  45


<210> SEQ ID NO 61
<211> LENGTH: 33
<212> TYPE: DNA
<213> ORGANISM: Artificial Sequence
<220> FEATURE:
<223> OTHER INFORMATION: Primer

<400> SEQUENCE: 61

ccggaattca tgtgcggtgg tcggatcgcc cgg                                  33


<210> SEQ ID NO 62
<211> LENGTH: 39
<212> TYPE: DNA
<213> ORGANISM: Artificial Sequence
<220> FEATURE:
<223> OTHER INFORMATION: Primer

<400> SEQUENCE: 62

gtcgctaccc gcggctccgc aaccaacgtg gttcatgac                            39


<210> SEQ ID NO 63
<211> LENGTH: 50
<212> TYPE: DNA
<213> ORGANISM: Artificial Sequence
<220> FEATURE:
<223> OTHER INFORMATION: Primer

<400> SEQUENCE: 63

gttggttgcg gagccgcggg tagcgacatt gacccttata aagaatttgg                50


<210> SEQ ID NO 64
<211> LENGTH: 38
<212> TYPE: DNA
<213> ORGANISM: Artificial Sequence
<220> FEATURE:
<223> OTHER INFORMATION: Primer

<400> SEQUENCE: 64

cgcgtcccaa gcttctacgg aagcgttgat aggatagg                             38


<210> SEQ ID NO 65
<211> LENGTH: 33
<212> TYPE: DNA
<213> ORGANISM: Artificial Sequence
<220> FEATURE:
<223> OTHER INFORMATION: Primer

<400> SEQUENCE: 65

ctagccgcgg gttgcggtgg tcggatcgcc cgg                                  33


<210> SEQ ID NO 66
<211> LENGTH: 38
<212> TYPE: DNA
<213> ORGANISM: Artificial Sequence
<220> FEATURE:
<223> OTHER INFORMATION: Primer

<400> SEQUENCE: 66

cgcgtcccaa gcttttagca accaacgtgg ttcatgac                             38
```

-continued

<210> SEQ ID NO 67
<211> LENGTH: 31
<212> TYPE: DNA
<213> ORGANISM: Artificial Sequence
<220> FEATURE:
<223> OTHER INFORMATION: Primer

<400> SEQUENCE: 67
ccggaattca tggacattga cccttataaa g 31

<210> SEQ ID NO 68
<211> LENGTH: 45
<212> TYPE: DNA
<213> ORGANISM: Artificial Sequence
<220> FEATURE:
<223> OTHER INFORMATION: Primer

<400> SEQUENCE: 68
ccgaccaccg caacccgcgg ctagcggaag cgttgatagg atagg 45

<210> SEQ ID NO 69
<211> LENGTH: 47
<212> TYPE: DNA
<213> ORGANISM: Artificial Sequence
<220> FEATURE:
<223> OTHER INFORMATION: Primer

<400> SEQUENCE: 69
ctaatggatc cggtgggggc tgcggtggtc ggatcgcccg gctcgag 47

<210> SEQ ID NO 70
<211> LENGTH: 39
<212> TYPE: DNA
<213> ORGANISM: Artificial Sequence
<220> FEATURE:
<223> OTHER INFORMATION: Primer

<400> SEQUENCE: 70
gtcgctaccc gcggctccgc aaccaacgtg gttcatgac 39

<210> SEQ ID NO 71
<211> LENGTH: 31
<212> TYPE: DNA
<213> ORGANISM: Artificial Sequence
<220> FEATURE:
<223> OTHER INFORMATION: Primer

<400> SEQUENCE: 71
ccggaattca tggacattga cccttataaa g 31

<210> SEQ ID NO 72
<211> LENGTH: 48
<212> TYPE: DNA
<213> ORGANISM: Artificial Sequence
<220> FEATURE:
<223> OTHER INFORMATION: Primer

<400> SEQUENCE: 72
ccgaccaccg cagcccccac cggatccatt agtacccacc caggtagc 48

<210> SEQ ID NO 73
<211> LENGTH: 45
<212> TYPE: DNA
<213> ORGANISM: Artificial Sequence
<220> FEATURE:
<223> OTHER INFORMATION: Primer -continued

<400> SEQUENCE: 73
gttggttgcg gagccgcggg tagcgaccta gtagtcagtt atgtc 45

<210> SEQ ID NO 74
<211> LENGTH: 38
<212> TYPE: DNA
<213> ORGANISM: Artificial Sequence
<220> FEATURE:
<223> OTHER INFORMATION: Primer

<400> SEQUENCE: 74
cgcgtcccaa gcttctacgg aagcgttgat aggatagg 38

<210> SEQ ID NO 75
<211> LENGTH: 33
<212> TYPE: DNA
<213> ORGANISM: Artificial Sequence
<220> FEATURE:
<223> OTHER INFORMATION: Primer

<400> SEQUENCE: 75
ctagccgcgg gttgcggtgg tcggatcgcc cgg 33

<210> SEQ ID NO 76
<211> LENGTH: 38
<212> TYPE: DNA
<213> ORGANISM: Artificial Sequence
<220> FEATURE:
<223> OTHER INFORMATION: Primer

<400> SEQUENCE: 76
cgcgtcccaa gcttttagca accaacgtgg ttcatgac 38

<210> SEQ ID NO 77
<211> LENGTH: 30
<212> TYPE: DNA
<213> ORGANISM: Artificial Sequence
<220> FEATURE:
<223> OTHER INFORMATION: Primer

<400> SEQUENCE: 77
ccggaattca tggccacact tttaaggagc 30

<210> SEQ ID NO 78
<211> LENGTH: 38
<212> TYPE: DNA
<213> ORGANISM: Artificial Sequence
<220> FEATURE:
<223> OTHER INFORMATION: Primer

<400> SEQUENCE: 78
cgcgtcccaa gcttttagca accaacgtgg ttcatgac 38

<210> SEQ ID NO 79
<211> LENGTH: 31
<212> TYPE: DNA
<213> ORGANISM: Artificial Sequence
<220> FEATURE:
<223> OTHER INFORMATION: Primer

<400> SEQUENCE: 79
ccggaattca tggacattga cccttataaa g 31

<210> SEQ ID NO 80

-continued

<211> LENGTH: 51
<212> TYPE: DNA
<213> ORGANISM: Artificial Sequence
<220> FEATURE:
<223> OTHER INFORMATION: Primer

<400> SEQUENCE: 80
cctagagcca cctttgccac catcttctaa attagtaccc acccaggtag c 51

<210> SEQ ID NO 81
<211> LENGTH: 48
<212> TYPE: DNA
<213> ORGANISM: Artificial Sequence
<220> FEATURE:
<223> OTHER INFORMATION: Primer

<400> SEQUENCE: 81
gaagatggtg gcaaaggtgg ctctagggac ctagtagtca gttatgtc 48

<210> SEQ ID NO 82
<211> LENGTH: 38
<212> TYPE: DNA
<213> ORGANISM: Artificial Sequence
<220> FEATURE:
<223> OTHER INFORMATION: Primer

<400> SEQUENCE: 82
cgcgtcccaa gcttctaaac aacagtagtc tccggaag 38

<210> SEQ ID NO 83
<211> LENGTH: 36
<212> TYPE: DNA
<213> ORGANISM: Artificial Sequence
<220> FEATURE:
<223> OTHER INFORMATION: Primer

<400> SEQUENCE: 83
gccgaattcc tagcagctag caccgaattt atctaa 36

<210> SEQ ID NO 84
<211> LENGTH: 33
<212> TYPE: DNA
<213> ORGANISM: Artificial Sequence
<220> FEATURE:
<223> OTHER INFORMATION: Primer

<400> SEQUENCE: 84
ggttaagtcg acatgagagt gaaggagaaa tat 33

<210> SEQ ID NO 85
<211> LENGTH: 30
<212> TYPE: DNA
<213> ORGANISM: Artificial Sequence
<220> FEATURE:
<223> OTHER INFORMATION: Primer

<400> SEQUENCE: 85
taaccgaatt caggaggtaa aaagatatgg 30

<210> SEQ ID NO 86
<211> LENGTH: 35
<212> TYPE: DNA
<213> ORGANISM: Artificial Sequence
<220> FEATURE:
<223> OTHER INFORMATION: Primer

<400> SEQUENCE: 86

-continued

```
gaagtaaagc ttttaaccac cgcaaccacc agaag                           35


<210> SEQ ID NO 87
<211> LENGTH: 33
<212> TYPE: DNA
<213> ORGANISM: Artificial Sequence
<220> FEATURE:
<223> OTHER INFORMATION: Primer

<400> SEQUENCE: 87

tcgaatgggc cctcatcttc gtgtgctagt cag                             33


<210> SEQ ID NO 88
<211> LENGTH: 4
<212> TYPE: PRT
<213> ORGANISM: Artificial Sequence
<220> FEATURE:
<223> OTHER INFORMATION: Fos fusion
      construct

<400> SEQUENCE: 88

Glu Phe Arg Arg
  1


<210> SEQ ID NO 89
<211> LENGTH: 183
<212> TYPE: PRT
<213> ORGANISM: Hepatitis B virus

<400> SEQUENCE: 89

Met Asp Ile Asp Pro Tyr Lys Glu Phe Gly Ala Thr Val Glu Leu Leu
  1               5                  10                  15

Ser Phe Leu Pro Ser Asp Phe Phe Pro Ser Val Arg Asp Leu Leu Asp
             20                  25                  30

Thr Ala Ser Ala Leu Tyr Arg Glu Ala Leu Glu Ser Pro Glu His Cys
         35                  40                  45

Ser Pro His His Thr Ala Leu Arg Gln Ala Ile Leu Cys Trp Gly Glu
     50                  55                  60

Leu Met Thr Leu Ala Thr Trp Val Gly Gly Asn Leu Glu Asp Pro Ile
 65                  70                  75                  80

Ser Arg Asp Leu Val Val Ser Tyr Val Asn Thr Asn Met Gly Leu Lys
                 85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Gly Ser Gln Cys
            180


<210> SEQ ID NO 90
<211> LENGTH: 183
<212> TYPE: PRT
<213> ORGANISM: Hepatitis B virus
```

-continued

<400> SEQUENCE: 90

Met Asp Ile Asp Pro Tyr Lys Glu Phe Gly Ala Thr Val Glu Leu Leu
1 5 10 15

Ser Phe Leu Pro Ser Asp Phe Phe Pro Ser Val Arg Asp Leu Leu Asp
20 25 30

Thr Ala Ser Ala Leu Tyr Arg Glu Ala Leu Glu Ser Pro Glu His Cys
35 40 45

Ser Pro His His Thr Ala Leu Arg Gln Ala Ile Leu Cys Trp Gly Glu
50 55 60

Leu Met Thr Leu Ala Thr Trp Val Gly Gly Asn Leu Glu Asp Pro Thr
65 70 75 80

Ser Arg Asp Leu Val Val Ser Tyr Val Asn Thr Asn Met Gly Leu Lys
85 90 95

Phe Arg Gln Leu Leu Trp Phe His Ile Ser Cys Leu Thr Phe Gly Arg
100 105 110

Glu Thr Val Ile Glu Tyr Leu Val Ser Phe Gly Val Trp Ile Arg Thr
115 120 125

Pro Pro Ala Tyr Arg Pro Thr Asn Ala Pro Ile Leu Ser Thr Leu Pro
130 135 140

Glu Thr Cys Val Ile Arg Arg Arg Gly Arg Ser Pro Arg Arg Arg Thr
145 150 155 160

Pro Ser Pro Arg Arg Arg Arg Ser Gln Ser Pro Arg Arg Arg Arg Ser
165 170 175

Gln Ser Arg Gly Ser Gln Cys
180

<210> SEQ ID NO 91
<211> LENGTH: 212
<212> TYPE: PRT
<213> ORGANISM: Hepatitis B virus

<400> SEQUENCE: 91

Met Gln Leu Phe His Leu Cys Leu Ile Ile Ser Cys Ser Cys Pro Thr
1 5 10 15

Val Gln Ala Ser Lys Leu Cys Leu Gly Trp Leu Trp Gly Met Asp Ile
20 25 30

Asp Pro Tyr Lys Glu Phe Gly Ala Thr Val Glu Leu Leu Ser Phe Leu
35 40 45

Pro Ser Asp Phe Phe Pro Ser Val Arg Asp Leu Leu Asp Thr Ala Ser
50 55 60

Ala Leu Tyr Arg Glu Ala Leu Glu Ser Pro Glu His Cys Ser Pro His
65 70 75 80

His Thr Ala Leu Arg Gln Ala Ile Leu Cys Trp Gly Glu Leu Met Thr
85 90 95

Leu Ala Thr Trp Val Gly Gly Asn Leu Glu Asp Pro Ile Ser Arg Asp
100 105 110

Leu Val Val Ser Tyr Val Asn Thr Asn Met Gly Leu Lys Phe Arg Gln
115 120 125

Leu Leu Trp Phe His Ile Ser Cys Leu Thr Phe Gly Arg Glu Thr Val
130 135 140

Ile Glu Tyr Leu Val Ser Phe Gly Val Trp Ile Arg Thr Pro Pro Ala
145 150 155 160

Tyr Arg Pro Pro Asn Ala Pro Ile Leu Ser Thr Leu Pro Glu Thr Thr
165 170 175

-continued

```
Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 92
<211> LENGTH: 212
<212> TYPE: PRT
<213> ORGANISM: Hepatitis B virus

<400> SEQUENCE: 92

Met Gln Leu Phe His Leu Cys Leu Ile Ile Ser Cys Ser Cys Pro Thr
  1               5                  10                  15

Val Gln Ala Ser Lys Leu Cys Leu Gly Trp Leu Trp Gly Met Asp Ile
             20                  25                  30

Asp Pro Tyr Lys Glu Phe Gly Ala Thr Val Glu Leu Leu Ser Phe Leu
         35                  40                  45

Pro Ser Asp Phe Phe Pro Ser Val Arg Asp Leu Leu Asp Asn Ala Ser
     50                  55                  60

Ala Leu Tyr Arg Glu Ala Leu Glu Ser Pro Glu His Cys Ser Pro His
 65                  70                  75                  80

His Thr Ala Leu Arg Gln Ala Ile Leu Cys Trp Gly Glu Leu Met Thr
                 85                  90                  95

Leu Ala Thr Trp Val Gly Gly Asn Leu Glu Asp Pro Ile Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 93
<211> LENGTH: 183
<212> TYPE: PRT
<213> ORGANISM: Hepatitis B virus

<400> SEQUENCE: 93

Met Asp Ile Asp Pro Tyr Lys Glu Phe Gly Ala Thr Val Glu Leu Leu
  1               5                  10                  15

Ser Phe Leu Pro Thr Asp Phe Phe Pro Ser Val Arg Asp Leu Leu Asp
             20                  25                  30

Thr Ala Ser Ala Leu Tyr Arg Glu Ala Leu Glu Ser Pro Glu His Cys
         35                  40                  45

Ser Pro His His Thr Ala Leu Arg Gln Ala Ile Leu Cys Trp Gly Glu
     50                  55                  60
```

-continued

```
Leu Met Thr Leu Ala Thr Trp Val Gly Val Asn Leu Glu Asp Pro Ala
 65                  70                  75                  80

Ser Arg Asp Leu Val Val Ser Tyr Val Asn Thr Asn Met Gly Leu Lys
                 85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Cys Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180


<210> SEQ ID NO 94
<211> LENGTH: 212
<212> TYPE: PRT
<213> ORGANISM: Hepatitis B virus

<400> SEQUENCE: 94

Met Gln Leu Phe His Leu Cys Leu Ile Ile Ser Cys Ser Cys Pro Thr
  1               5                  10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
 65                  70                  75                  80

His Thr Ala Leu Arg Gln Ala Ile Leu Cys Trp Gly Asp Leu Met Thr
                 85                  90                  95

Leu Ala Thr Trp Val Gly Gly Asn Leu Glu Asp Pro Val Ser Arg Asp
            100                 105                 110

Leu Val Val Ser Tyr Val Asn Thr Asn Val Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 95
<211> LENGTH: 212
<212> TYPE: PRT
<213> ORGANISM: Hepatitis B virus
```

-continued

<400> SEQUENCE: 95

Met Gln Leu Phe His Leu Cys Leu Ile Ile Ser Cys Ser Cys Pro Thr
1 5 10 15

Val Gln Ala Ser Lys Leu Cys Leu Gly Trp Leu Trp Asp Met Asp Ile
20 25 30

Asp Pro Tyr Lys Glu Phe Gly Ala Thr Val Glu Leu Leu Ser Phe Leu
35 40 45

Pro Ser Asp Phe Phe Pro Ser Val Arg Asp Leu Leu Asp Thr Ala Ser
50 55 60

Ala Leu Tyr Arg Glu Ala Leu Glu Ser Pro Glu His Cys Ser Pro His
65 70 75 80

His Thr Ala Leu Arg Gln Ala Ile Leu Cys Trp Gly Asp Leu Met Thr
85 90 95

Leu Ala Thr Trp Val Gly Gly Asn Leu Glu Asp Pro Val Ser Arg Asp
100 105 110

Leu Val Val Ser Tyr Val Asn Thr Asn Val Gly Leu Lys Phe Arg Gln
115 120 125

Leu Leu Trp Phe His Ile Ser Cys Leu Thr Phe Gly Arg Glu Thr Val
130 135 140

Ile Glu Tyr Leu Val Ser Phe Gly Val Trp Ile Arg Thr Pro Pro Ala
145 150 155 160

Tyr Arg Pro Pro Asn Ala Pro Ile Leu Ser Thr Leu Pro Glu Thr Thr
165 170 175

Val Val Arg Arg Arg Gly Arg Ser Pro Arg Arg Arg Thr Pro Ser Pro
180 185 190

Arg Arg Arg Arg Ser Gln Ser Pro Arg Arg Arg Arg Ser Gln Ser Arg
195 200 205

Glu Ser Gln Cys
210

<210> SEQ ID NO 96
<211> LENGTH: 212
<212> TYPE: PRT
<213> ORGANISM: Hepatitis B virus

<400> SEQUENCE: 96

Met Gln Leu Phe His Leu Cys Leu Ile Ile Ser Cys Ser Cys Pro Thr
1 5 10 15

Val Gln Ala Ser Lys Leu Cys Leu Gly Trp Leu Trp Gly Met Asp Ile
20 25 30

Asp Pro Tyr Lys Glu Phe Gly Ala Thr Val Glu Leu Leu Ser Phe Leu
35 40 45

Pro Ser Asp Phe Phe Pro Ser Val Arg Asp Leu Leu Asp Thr Ala Ser
50 55 60

Ala Leu Tyr Arg Glu Ala Leu Glu Ser Pro Glu His Cys Ser Pro Gln
65 70 75 80

His Thr Ala Leu Arg Gln Ala Ile Leu Cys Trp Gly Glu Leu Met Thr
85 90 95

Leu Ala Thr Trp Val Gly Gly Asn Leu Glu Asp Pro Ile Ser Arg Asp
100 105 110

Leu Val Val Ser Tyr Val Asn Thr Asn Met Gly Leu Lys Phe Arg Gln
115 120 125

Leu Leu Trp Phe His Ile Ser Cys Leu Thr Phe Gly Arg Glu Thr Val
130 135 140

-continued

```
Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 97
<211> LENGTH: 212
<212> TYPE: PRT
<213> ORGANISM: Hepatitis B virus

<400> SEQUENCE: 97

Met Gln Leu Phe His Leu Cys Leu Ile Ile Ser Cys Ser Cys Pro Thr
  1               5                  10                  15

Val Gln Ala Ser Lys Leu Cys Leu Gly Trp Leu Trp Gly Met Asp Ile
             20                  25                  30

Asp Pro Tyr Lys Glu Phe Gly Ala Thr Val Glu Leu Leu Ser Phe Leu
         35                  40                  45

Pro Ser Asp Phe Phe Pro Ser Val Arg Asp Leu Leu Asp Thr Ala Ser
     50                  55                  60

Ala Leu Tyr Arg Glu Ala Leu Glu Ser Pro Glu His Cys Ser Pro His
 65                  70                  75                  80

His Thr Ala Leu Arg Gln Ala Ile Leu Cys Trp Gly Glu Leu Met Thr
                 85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Lys Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Gly Ser Gln Cys
    210


<210> SEQ ID NO 98
<211> LENGTH: 183
<212> TYPE: PRT
<213> ORGANISM: Hepatitis B virus

<400> SEQUENCE: 98

Met Asp Ile Asp Pro Tyr Lys Glu Phe Gly Ala Thr Val Glu Leu Leu
  1               5                  10                  15

Ser Phe Leu Pro Ser Asp Phe Phe Pro Ser Val Arg Asp Leu Leu Asp
             20                  25                  30
```

-continued

```
Thr Ala Ser Ala Leu Phe Arg Asp Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Gly Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Asp Thr Val Ile Glu Tyr Leu Val Ser Phe Gly Val Trp Ile Arg Thr
        115                 120                 125

Pro Pro Ala Tyr Arg Pro Ser Asn Ala Pro Ile Leu Ser Thr Leu Pro
    130                 135                 140

Glu Thr Cys Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180


<210> SEQ ID NO 99
<211> LENGTH: 183
<212> TYPE: PRT
<213> ORGANISM: Hepatitis B virus

<400> SEQUENCE: 99

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180


<210> SEQ ID NO 100
<211> LENGTH: 212
<212> TYPE: PRT
```

<213> ORGANISM: Hepatitis B virus

<400> SEQUENCE: 100

Met Gln Leu Phe His Leu Cys Leu Ile Ile Ser Cys Ser Cys Pro Thr
1 5 10 15

Val Gln Ala Ser Lys Leu Cys Leu Gly Trp Leu Trp Gly Met Asp Ile
20 25 30

Asp Pro Tyr Lys Glu Phe Gly Ala Thr Val Glu Leu Leu Ser Phe Leu
35 40 45

Pro Ser Asp Phe Phe Pro Ser Val Arg Asp Leu Leu Asp Thr Ala Ser
50 55 60

Ala Leu Tyr Arg Glu Ala Leu Glu Ser Pro Glu His Cys Ser Pro His
65 70 75 80

His Thr Ala Leu Arg His Ala Ile Leu Cys Trp Gly Asp Leu Arg Thr
85 90 95

Leu Ala Thr Trp Val Gly Gly Asn Leu Glu Asp Pro Ile Ser Arg Asp
100 105 110

Leu Val Val Ser Tyr Val Asn Thr Asn Met Gly Leu Lys Phe Arg Gln
115 120 125

Leu Leu Trp Phe His Ile Ser Cys Leu Thr Phe Gly Arg Glu Thr Val
130 135 140

Ile Glu Tyr Leu Val Ser Phe Gly Val Trp Ile Arg Thr Pro Pro Ala
145 150 155 160

Tyr Arg Pro Pro Asn Ala Pro Ile Leu Ser Thr Leu Pro Glu Thr Thr
165 170 175

Val Val Arg Arg Arg Gly Arg Ser Pro Arg Arg Arg Thr Pro Ser Pro
180 185 190

Arg Arg Arg Arg Ser Gln Ser Pro Arg Arg Arg Arg Ser Gln Ser Arg
195 200 205

Glu Ser Gln Cys
210

<210> SEQ ID NO 101
<211> LENGTH: 212
<212> TYPE: PRT
<213> ORGANISM: Hepatitis B virus

<400> SEQUENCE: 101

Met Gln Leu Phe His Leu Cys Leu Ile Ile Ser Cys Ser Cys Pro Thr
1 5 10 15

Val Gln Ala Ser Lys Leu Cys Leu Gly Trp Leu Trp Asp Met Asp Ile
20 25 30

Asp Pro Tyr Lys Glu Phe Gly Ala Thr Val Glu Leu Leu Ser Phe Leu
35 40 45

Pro Ser Asp Phe Phe Pro Ser Val Arg Asp Leu Leu Asp Thr Ala Ser
50 55 60

Ala Leu Phe Arg Asp Ala Leu Glu Ser Pro Glu His Cys Ser Pro His
65 70 75 80

His Thr Ala Leu Arg Gln Ala Ile Leu Cys Trp Gly Glu Leu Met Thr
85 90 95

Leu Ala Thr Trp Val Gly Ala Asn Leu Glu Asp Pro Ala Ser Arg Asp
100 105 110

Leu Val Val Ser Tyr Val Asn Thr Asn Met Gly Leu Lys Phe Arg Gln
115 120 125

Leu Leu Trp Phe His Ile Ser Cys Leu Thr Phe Gly Arg Glu Thr Val

-continued

```
    130                 135                 140

Ile Glu Tyr Leu Val Ser Phe Gly Val Trp Ile Arg Thr Pro Gln Ala
145                 150                 155                 160

Tyr Arg Pro Pro Asn Ala Pro Ile Leu Ser Thr Leu Pro Glu Thr Cys
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 102
<211> LENGTH: 183
<212> TYPE: PRT
<213> ORGANISM: Artificial Sequence
<220> FEATURE:
<223> OTHER INFORMATION: synthetic
      human Hepatitus B construct

<400> SEQUENCE: 102

Met Asp Ile Asp Pro Tyr Lys Glu Phe Gly Ala Thr Val Glu Leu Leu
  1               5                  10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
     50                  55                  60

Leu Met Thr Leu Ala Thr Trp Val Gly Val Asn Leu Glu Asp Pro Ala
 65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180


<210> SEQ ID NO 103
<211> LENGTH: 212
<212> TYPE: PRT
<213> ORGANISM: Hepatitis B virus

<400> SEQUENCE: 103

Met Gln Leu Phe His Leu Cys Leu Ile Ile Ser Cys Ser Cys Pro Thr
  1               5                  10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
```

-continued

```
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Asp Leu Met Ser
                85                  90                  95

Leu Ala Thr Trp Val Gly Val Asn Leu Glu Asp Pro Ile Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 104
<211> LENGTH: 183
<212> TYPE: PRT
<213> ORGANISM: Hepatitis B virus

<400> SEQUENCE: 104

Met Asp Ile Asp Pro Tyr Lys Glu Phe Gly Ala Thr Val Glu Leu Leu
  1               5                  10                  15

Ser Phe Leu Pro Ser Asp Phe Phe Pro Ser Val Arg Asp Leu Leu Asp
            20                  25                  30

Thr Ala Ser Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180
```

-continued

<210> SEQ ID NO 105
<211> LENGTH: 183
<212> TYPE: PRT
<213> ORGANISM: Hepatitis B virus

<400> SEQUENCE: 105

```
Met Asp Ile Asp Pro Tyr Lys Glu Phe Gly Ala Thr Val Glu Leu Leu
  1               5                  10                  15

Ser Phe Leu Pro Ser Asp Phe Phe Pro Ser Val Arg Asp Leu Leu Asp
             20                  25                  30

Thr Ala Ser Ala Leu Tyr Arg Glu Ala Leu Glu Ser Pro Glu His Cys
         35                  40                  45

Ser Pro His His Thr Ala Leu Arg Gln Ala Ile Leu Cys Trp Gly Asp
     50                  55                  60

Leu Met Thr Leu Ala Thr Trp Val Gly Val Asn Leu Glu Asp Pro Ala
 65                  70                  75                  80

Ser Arg Asp Leu Val Val Ser Tyr Val Asn Thr Asn Met Gly Leu Lys
                 85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180
```

<210> SEQ ID NO 106
<211> LENGTH: 183
<212> TYPE: PRT
<213> ORGANISM: Hepatitis B virus

<400> SEQUENCE: 106

```
Met Asp Ile Asp Pro Tyr Lys Glu Phe Gly Ala Thr Val Glu Leu Leu
  1               5                  10                  15

Ser Phe Leu Pro Ser Asp Phe Phe Pro Ser Val Arg Asp Leu Leu Asp
             20                  25                  30

Thr Ala Ser Ala Leu Tyr Arg Asp Ala Leu Glu Ser Pro Glu His Cys
         35                  40                  45

Ser Pro His His Thr Ala Leu Arg Gln Ala Ile Leu Cys Trp Gly Glu
     50                  55                  60

Leu Met Thr Leu Ala Thr Trp Val Gly Ala Asn Leu Glu Asp Pro Ala
 65                  70                  75                  80

Ser Arg Asp Leu Val Val Ser Tyr Val Asn Thr Asn Met Gly Leu Lys
                 85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140
```

-continued

```
Glu Thr Thr Val Val Arg Arg Arg Gly Arg Thr Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180


<210> SEQ ID NO 107
<211> LENGTH: 212
<212> TYPE: PRT
<213> ORGANISM: Hepatitis B virus

<400> SEQUENCE: 107

Met Gln Leu Phe His Leu Cys Leu Ile Ile Ser Cys Ser Cys Pro Thr
  1               5                  10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
     50                  55                  60

Ala Leu Tyr Arg Asp Ala Leu Glu Ser Pro Glu His Cys Ser Pro His
 65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 108
<211> LENGTH: 212
<212> TYPE: PRT
<213> ORGANISM: Hepatitis B virus

<400> SEQUENCE: 108

Met Gln Leu Phe His Leu Cys Leu Ile Ile Ser Cys Ser Cys Pro Thr
  1               5                  10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
     50                  55                  60
```

-continued

```
Ala Leu Tyr Arg Glu Ala Leu Glu Ser Pro Glu His Cys Ser Pro His
 65                  70                  75                  80

His Thr Ala Leu Arg Gln Ala Ile Leu Cys Trp Gly Asp Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 109
<211> LENGTH: 212
<212> TYPE: PRT
<213> ORGANISM: Hepatitis B virus

<400> SEQUENCE: 109

Met Gln Leu Phe His Leu Cys Leu Ile Ile Ser Cys Thr Cys Pro Thr
  1               5                  10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
     50                  55                  60

Ala Leu Tyr Arg Glu Ala Leu Glu Ser Pro Glu His Cys Ser Pro His
 65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ala Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210
```

<210> SEQ ID NO 110
<211> LENGTH: 212
<212> TYPE: PRT
<213> ORGANISM: Hepatitis B virus

<400> SEQUENCE: 110

```
Met Gln Leu Phe His Leu Cys Leu Ile Ile Ser Cys Ser Cys Pro Thr
  1               5                  10                  15

Val Gln Ala Ser Lys Leu Cys Leu Gly Trp Leu Trp Gly Met Asp Ile
             20                  25                  30

Asp Pro Tyr Lys Glu Phe Gly Ala Thr Val Glu Leu Leu Ser Phe Leu
         35                  40                  45

Pro Ser Asp Phe Phe Pro Ser Val Arg Asp Leu Leu Asp Thr Ala Ser
     50                  55                  60

Ala Leu Tyr Arg Glu Ala Phe Glu Cys Ser Glu His Cys Ser Pro His
 65                  70                  75                  80

His Thr Ala Leu Arg Gln Ala Ile Leu Cys Trp Gly Glu Leu Met Thr
                 85                  90                  95

Leu Ala Thr Trp Val Gly Gly Asn Leu Glu Asp Pro Ile Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210
```

<210> SEQ ID NO 111
<211> LENGTH: 212
<212> TYPE: PRT
<213> ORGANISM: Hepatitis B virus
<220> FEATURE:
<221> NAME/KEY: UNSURE
<222> LOCATION: (28)..(28)
<223> OTHER INFORMATION: May be any amino acid.

<400> SEQUENCE: 111

```
Met Gln Leu Phe His Leu Cys Leu Ile Ile Ser Cys Ser Cys Pro Thr
  1               5                  10                  15

Val Gln Ala Ser Lys Leu Cys Leu Gly Trp Leu Xaa Asp Met Asp Ile
             20                  25                  30

Asp Pro Tyr Lys Glu Phe Gly Ala Thr Val Glu Leu Leu Ser Phe Leu
         35                  40                  45

Pro Ser Asp Phe Phe Pro Ser Val Arg Asp Leu Leu Asp Thr Ala Ser
     50                  55                  60

Ala Leu Tyr Arg Glu Ala Leu Glu Ser Pro Glu His Cys Ser Pro His
 65                  70                  75                  80

His Thr Ala Leu Arg Gln Ala Ile Leu Cys Trp Gly Asp Leu Ile Thr
```

-continued

```
                85                  90                  95

Leu Ser Thr Trp Val Gly Gly Asn Leu Glu Asp Pro Thr Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Thr Gln Ser Arg
        195                 200                 205

Glu Ser Gln Cys
    210


<210> SEQ ID NO 112
<211> LENGTH: 212
<212> TYPE: PRT
<213> ORGANISM: Hepatitis B virus

<400> SEQUENCE: 112

Met Gln Leu Phe His Leu Cys Leu Ile Ile Ser Cys Ser Cys Pro Thr
  1               5                  10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Asn Ala Ser
    50                  55                  60

Ala Leu Tyr Arg Glu Ala Leu Glu Ser Pro Glu His Cys Ser Pro His
 65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 113
<211> LENGTH: 212
```

-continued

<212> TYPE: PRT
<213> ORGANISM: Hepatitis B virus

<400> SEQUENCE: 113

```
Met Gln Leu Phe His Leu Cys Leu Ile Ile Ser Cys Ser Cys Pro Thr
  1               5                  10                  15

Val Gln Ala Ser Lys Leu Cys Leu Gly Trp Leu Trp Gly Met Asp Ile
             20                  25                  30

Asp Pro Tyr Lys Glu Phe Gly Ala Thr Val Glu Leu Leu Ser Phe Leu
         35                  40                  45

Pro Ser Asp Phe Phe Pro Ser Val Arg Asp Leu Leu Asp Thr Ala Ser
     50                  55                  60

Ala Leu Tyr Arg Glu Ala Leu Glu Ser Pro Glu His Cys Ser Pro His
 65                  70                  75                  80

His Thr Ala Leu Arg Gln Ala Ile Leu Cys Trp Gly Glu Leu Met Thr
                 85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Cys Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210
```

<210> SEQ ID NO 114
<211> LENGTH: 212
<212> TYPE: PRT
<213> ORGANISM: Hepatitis B virus

<400> SEQUENCE: 114

```
Met Gln Leu Phe His Leu Cys Leu Ile Ile Ser Cys Ser Cys Pro Thr
  1               5                  10                  15

Val Gln Ala Ser Lys Leu Cys Leu Gly Trp Leu Trp Gly Met Asp Ile
             20                  25                  30

Asp Pro Tyr Lys Glu Phe Gly Ala Thr Val Glu Leu Leu Ser Phe Leu
         35                  40                  45

Pro Ser Asp Phe Phe Pro Ser Val Arg Asp Leu Leu Asp Thr Ala Ser
     50                  55                  60

Ala Leu Tyr Arg Glu Ala Leu Glu Ser Pro Glu His Cys Ser Pro His
 65                  70                  75                  80

His Thr Ala Leu Arg Gln Ala Ile Leu Cys Trp Gly Glu Leu Met Thr
                 85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125
```

-continued

```
Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Pro Gln Cys
    210


<210> SEQ ID NO 115
<211> LENGTH: 212
<212> TYPE: PRT
<213> ORGANISM: Hepatitis B virus

<400> SEQUENCE: 115

Met Gln Leu Phe His Leu Cys Leu Ile Ile Ser Cys Ser Cys Pro Thr
  1               5                  10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Ser Thr Ala Ser
     50                  55                  60

Ala Leu Tyr Arg Glu Ala Leu Glu Ser Pro Glu His Cys Ser Pro His
 65                  70                  75                  80

His Thr Ala Leu Arg Gln Ala Ile Leu Cys Trp Gly Glu Leu Met Thr
                 85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 116
<211> LENGTH: 212
<212> TYPE: PRT
<213> ORGANISM: Hepatitis B virus

<400> SEQUENCE: 116

Met Gln Leu Phe His Leu Cys Leu Ile Ile Ser Cys Ser Cys Pro Thr
  1               5                  10                  15
```

-continued

```
Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Leu Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 117
<211> LENGTH: 212
<212> TYPE: PRT
<213> ORGANISM: Hepatitis B virus

<400> SEQUENCE: 117

Met Gln Leu Phe His Leu Cys Leu Ile Ile Ser Cys Ser Cys Pro Thr
  1               5                  10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Asp Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Lys Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175
```

-continued

```
Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210
```

<210> SEQ ID NO 118
<211> LENGTH: 212
<212> TYPE: PRT
<213> ORGANISM: Hepatitis B virus

<400> SEQUENCE: 118

```
Met Gln Leu Phe His Leu Cys Leu Ile Ile Ser Cys Ser Cys Pro Thr
  1               5                  10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ala
     50                  55                  60

Ala Leu Tyr Arg Asp Ala Leu Glu Ser Pro Glu His Cys Ser Pro His
 65                  70                  75                  80

His Thr Ala Leu Arg Gln Ala Ile Leu Cys Trp Gly Glu Leu Met Thr
                 85                  90                  95

Leu Ala Thr Trp Val Gly Thr Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Leu Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210
```

<210> SEQ ID NO 119
<211> LENGTH: 183
<212> TYPE: PRT
<213> ORGANISM: Hepatitis B virus

<400> SEQUENCE: 119

```
Met Asp Ile Asp Pro Tyr Lys Glu Phe Gly Ala Ser Met Glu Leu Leu
  1               5                  10                  15

Ser Phe Leu Pro Ser Asp Phe Tyr Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Thr Pro His His Thr Ala Leu Arg Gln Ala Ile Leu Cys Trp Gly Glu
     50                  55                  60
```

-continued

```
Leu Met Thr Leu Ala Thr Trp Val Gly Gly Asn Leu Gln Asp Pro Thr
 65                  70                  75                  80

Ser Arg Asp Leu Val Val Ser Tyr Val Asn Thr Asn Met Gly Leu Lys
                 85                  90                  95

Phe Arg Gln Leu Leu Trp Phe His Val Ser Cys Leu Thr Phe Gly Arg
            100                 105                 110

Glu Thr Val Val Glu Tyr Leu Val Ser Phe Gly Val Trp Ile Arg Thr
        115                 120                 125

Pro Gln Ala Tyr Arg Pro Pro Asn Ala Pro Ile Leu Ser Thr Leu Pro
    130                 135                 140

Glu Thr Cys Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180


<210> SEQ ID NO 120
<211> LENGTH: 183
<212> TYPE: PRT
<213> ORGANISM: Hepatitis B virus

<400> SEQUENCE: 120

Met Asp Ile Asp Pro Tyr Lys Glu Phe Gly Ala Thr Val Glu Leu Leu
  1               5                  10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg His Val Phe Leu Cys Trp Gly Asp
     50                  55                  60

Leu Met Thr Leu Ala Thr Trp Val Gly Gly Asn Leu Glu Asp Pro Thr
 65                  70                  75                  80

Ser Arg Asp Leu Val Val Ser Tyr Val Asn Thr Asn Met Gly Leu Lys
                 85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180


<210> SEQ ID NO 121
<211> LENGTH: 212
<212> TYPE: PRT
<213> ORGANISM: Hepatitis B virus

<400> SEQUENCE: 121

Met Gln Leu Phe His Leu Cys Leu Ile Ile Ser Cys Ser Cys Pro Thr
  1               5                  10                  15
```

-continued

```
Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Asp Leu Thr Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 122
<211> LENGTH: 212
<212> TYPE: PRT
<213> ORGANISM: Hepatitis B virus

<400> SEQUENCE: 122

Met Gln Leu Phe His Leu Cys Leu Ile Ile Ser Cys Ser Cys Pro Thr
  1               5                  10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Asp Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Ile Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
```

-continued

```
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 123
<211> LENGTH: 183
<212> TYPE: PRT
<213> ORGANISM: Hepatitis B virus

<400> SEQUENCE: 123

Met Asp Ile Asp Pro Tyr Lys Glu Phe Gly Ala Thr Val Glu Leu Leu
  1               5                  10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Asp
     50                  55                  60

Leu Met Thr Leu Ala Thr Trp Val Gly Val Asn Leu Glu Asp Pro Val
 65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Ala Arg Arg Arg Ser Gln Ser Pro Arg Arg Arg Arg Ser
                165                 170                 175

Gln Ser Arg Glu Ser Gln Cys
            180


<210> SEQ ID NO 124
<211> LENGTH: 212
<212> TYPE: PRT
<213> ORGANISM: Hepatitis B virus

<400> SEQUENCE: 124

Met Gln Leu Phe His Leu Cys Leu Ile Ile Ser Cys Ser Cys Pro Thr
  1               5                  10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
     50                  55                  60

Ala Leu Tyr Arg Glu Ala Leu Glu Ser Pro Glu His Cys Ser Pro His
 65                  70                  75                  80

His Thr Ala Leu Arg Gln Ala Ile Leu Cys Trp Gly Asp Leu Met Asn
```

-continued

```
                85                  90                  95

Leu Ala Thr Trp Val Gly Gly Asn Leu Glu Asp Pro Val Ser Arg Asp
            100                 105                 110

Leu Val Val Gly Tyr Val Asn Thr Thr Val Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 125
<211> LENGTH: 183
<212> TYPE: PRT
<213> ORGANISM: Hepatitis B virus

<400> SEQUENCE: 125

Met Asp Ile Asp Pro Tyr Lys Glu Phe Gly Ala Thr Val Glu Leu Leu
  1               5                  10                  15

Ser Phe Leu Pro Ser Asp Phe Phe Pro Ser Val Arg Asp Leu Leu Asp
            20                  25                  30

Thr Ala Ser Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
     50                  55                  60

Leu Met Thr Leu Ala Thr Trp Val Gly Val Asn Leu Glu Asp Pro Ala
 65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Thr Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180


<210> SEQ ID NO 126
<211> LENGTH: 212
<212> TYPE: PRT
<213> ORGANISM: Hepatitis B virus

<400> SEQUENCE: 126

Met Gln Leu Phe His Leu Cys Leu Ile Ile Ser Cys Ser Cys Pro Thr
```

-continued

```
  1               5                  10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Ala Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Ile Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 127
<211> LENGTH: 212
<212> TYPE: PRT
<213> ORGANISM: Hepatitis B virus

<400> SEQUENCE: 127

Met Gln Leu Phe His Leu Cys Leu Ile Ile Ser Cys Ser Cys Pro Thr
  1               5                  10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Asp Leu Met Thr
                85                  90                  95

Leu Ala Thr Trp Val Gly Val Asn Leu Glu Asp Pro Ala Thr Arg Asp
            100                 105                 110

Leu Val Val Ser Tyr Val Asn Thr Asn Val Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160
```

-continued

```
Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 128
<211> LENGTH: 212
<212> TYPE: PRT
<213> ORGANISM: Hepatitis B virus

<400> SEQUENCE: 128

Met Gln Leu Phe His Leu Cys Leu Ile Ile Ser Cys Ser Cys Pro Thr
  1               5                  10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
     50                  55                  60

Ala Leu Tyr Arg Glu Ala Leu Glu Ser Pro Glu His Cys Ser Pro His
 65                  70                  75                  80

His Thr Ala Leu Arg Gln Arg Ile Leu Cys Trp Gly Glu Leu Met Thr
                 85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Thr Arg Ser Gln Ser Arg
        195                 200                 205

Glu Ser Gln Cys
    210


<210> SEQ ID NO 129
<211> LENGTH: 212
<212> TYPE: PRT
<213> ORGANISM: Hepatitis B virus

<400> SEQUENCE: 129

Met Gln Leu Phe His Leu Cys Leu Val Ile Ser Cys Ser Cys Pro Thr
  1               5                  10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45
```

-continued

```
Pro Ser Asp Phe Phe Pro Ser Val Arg Asp Leu Leu Asp Thr Ala Ala
     50                  55                  60

Ala Leu Tyr Arg Glu Ala Leu Glu Ser Pro Glu His Cys Ser Pro His
 65                  70                  75                  80

His Thr Ala Leu Arg Gln Ala Ile Leu Cys Trp Gly Glu Leu Met Thr
                 85                  90                  95

Leu Ala Thr Trp Val Gly Asn Asn Leu Glu Asp Pro Ala Ser Arg Asp
            100                 105                 110

Leu Val Val Asn Tyr Val Asn Thr Asn Met Gly Leu Lys Ile Arg Gln
        115                 120                 125

Leu Leu Trp Phe His Ile Ser Cys Leu Thr Phe Gly Arg Glu Thr Val
    130                 135                 140

Leu Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210


<210> SEQ ID NO 130
<211> LENGTH: 212
<212> TYPE: PRT
<213> ORGANISM: Hepatitis B virus

<400> SEQUENCE: 130

Met Gln Leu Phe His Leu Cys Leu Ile Ile Ser Cys Ser Cys Pro Thr
  1               5                  10                  15

Val Gln Ala Ser Lys Leu Cys Leu Gly Trp Leu Trp Gly Met Asp Ile
             20                  25                  30

Asp Pro Tyr Lys Glu Phe Gly Ala Thr Val Glu Leu Leu Ser Phe Leu
         35                  40                  45

Pro Ser Ala Phe Phe Pro Ser Val Arg Asp Leu Leu Asp Thr Ala Ser
     50                  55                  60

Ala Leu Tyr Arg Glu Ala Leu Glu Ser Pro Glu His Cys Ser Pro His
 65                  70                  75                  80

His Thr Ala Leu Arg Gln Ala Ile Leu Cys Trp Gly Asp Leu Met Thr
                 85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205
```

-continued

```
Glu Ser Gln Cys
    210


<210> SEQ ID NO 131
<211> LENGTH: 183
<212> TYPE: PRT
<213> ORGANISM: Hepatitis B virus

<400> SEQUENCE: 131

Met Asp Ile Asp Pro Tyr Lys Glu Phe Gly Ala Thr Val Glu Leu Leu
  1               5                  10                  15

Ser Phe Leu Pro Ser Asp Phe Phe Pro Ser Val Arg Asp Leu Leu Asp
             20                  25                  30

Thr Ala Ala Ala Leu Tyr Arg Glu Ala Leu Glu Ser Pro Glu His Cys
         35                  40                  45

Ser Pro His His Thr Ala Leu Arg Gln Ala Ile Leu Cys Trp Gly Glu
     50                  55                  60

Leu Met Thr Leu Ala Thr Trp Val Gly Asn Asn Leu Glu Asp Pro Ala
 65                  70                  75                  80

Ser Arg Asp Leu Val Val Asn Tyr Val Asn Thr Asn Met Gly Leu Lys
                 85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180


<210> SEQ ID NO 132
<211> LENGTH: 183
<212> TYPE: PRT
<213> ORGANISM: Hepatitis B virus

<400> SEQUENCE: 132

Met Asp Ile Asp Pro Tyr Lys Glu Phe Gly Ala Thr Val Glu Leu Leu
  1               5                  10                  15

Ser Phe Leu Pro Ser Asp Phe Phe Pro Ser Val Arg Asp Leu Leu Asp
             20                  25                  30

Thr Ala Ser Ala Leu Tyr Arg Glu Ala Leu Glu Ser Pro Glu His Cys
         35                  40                  45

Ser Pro His His Thr Ala Leu Arg Gln Ala Ile Leu Cys Trp Gly Glu
     50                  55                  60

Leu Met Thr Leu Ala Thr Trp Val Gly Gly Asn Leu Glu Asp Pro Ile
 65                  70                  75                  80

Ser Arg Asp Leu Val Val Ser Tyr Val Asn Thr Asn Met Gly Leu Lys
                 85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125
```

-continued

```
Pro Pro Ala Tyr Arg Pro Pro Asn Ala Pro Ile Leu Ser Thr Leu Pro
    130                 135                 140

Glu Thr Cys Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Gly Ser Gln Cys
            180


<210> SEQ ID NO 133
<211> LENGTH: 3221
<212> TYPE: DNA
<213> ORGANISM: Hepatitis B virus
<220> FEATURE:
<221> NAME/KEY: CDS
<222> LOCATION: (1901)..(2458)

<400> SEQUENCE: 133

ttccactgcc ttccaccaag ctctgcagga ccccagagtc aggggtctgt attttcctgc     60

tggtggctcc agttcaggaa cagtaaaccc tgctccgaat attgcctctc acatctcgtc    120

aatctccgcg aggactgggg accctgtgac gaacatggag aacatcacat caggattcct    180

aggacccctg ctcgtgttac aggcggggtt tttattgttg acaagaatcc tcacaatacc    240

gcagagtcta gactcgtggt ggacttctct caattttata gggggatcac ccgtgtgtct    300

tggccaaaat tcgcagtccc caacctccaa tcactcacca acctcctgtc ctccaatttg    360

tcctggttat cgctggatgt gtctgcggcg ttttatcata ttcctcttca tcctgctgct    420

atgcctcatc ttcttattgg ttcttctgga ttatcaaggt atgttgcccg tttgtcctct    480

aattccagga tcaacaacaa ccagtacggg accatgcaaa acctgcacga ctcctgctca    540

aggcaactct atgtttccct catgttgctg tacaaaacct acggttggaa attgcacctg    600

tattcccatc ccatcgtcct gggctttcgc aaaataccta tgggagtggg cctcagtccg    660

tttctcttgg ctcagtttac tagtgccatt tgttcagtgg ttcgtagggc tttcccccac    720

tgtttggctt tcagctatat ggatgatgtg gtattggggg ccaagtctgt acagcatcgt    780

gagtcccttt ataccgctgt taccaatttt cttttgtctc tgggtataca tttaaaccct    840

aacaaaacaa aaagatgggg ttattcccta aacttcatgg gttacataat tggaagttgg    900

ggaacattgc cacaggatca tattgtacaa aagatcaaac actgttttag aaaacttcct    960

gttaacaggc ctattgattg gaaagtatgt caaagaattg tgggtctttt gggctttgct   1020

gctccattta cacaatgtgg atatcctgcc ttaatgcctt tgtatgcatg tatacaggct   1080

aaacaggctt tcactttctc gccaacttac aaggcctttc taagtaaaca gtacatgaac   1140

ctttaccccg ttgctcggca acggcctggt ctgtgccaag tgtttgctga cgcaaccccc   1200

actggttggg gcttggccat aggccatcag cgcatgagtg gaacctttgt ggctcctctg   1260

ccgatccata ctgcggaact cctagccgct tgtattgctc gcagccggtc tggagcaaag   1320

ctcatcggaa ctgacaattc tgtcgtcctc tcgcggaaat atacatcgtt tccatggctg   1380

ctaggctgta ctgccaactg gatccttcgc gggacgtcct ttgtttacgt cccgtcggcg   1440

ctgaatcccg cggacgaccc ctctcggggc cgcttgggac tctatcgtcc ccttctccgt   1500

ctgccgttcc agccgaccac ggggcgcacc tctctttacg cggtctcccc gtctgtgcct   1560

tctcatctgc cggtccgtgt gcacttcgct tcacctctgc acgttgcatg gagaccaccg   1620

tgaacgccca tcagatcctg cccaaggtct tacataagag gactcttgga ctcccagcaa   1680
```

-continued

```
tgtcaacgac cgaccttgag gcctacttca aagactgtgt gtttaaggac tgggaggagc   1740

tgggggagga gattaggtta aaggtctttg tattaggagg ctgtaggcat aaattggtct   1800

gcgcaccagc accatgcaac tttttcacct ctgcctaatc atctcttgta catgtcccac   1860

tgttcaagcc tccaagctgt gccttgggtg gctttggggc atg gac att gac cct     1915
                                            Met Asp Ile Asp Pro
                                              1               5

tat aaa gaa ttt gga gct act gtg gag tta ctc tcg ttt ttg cct tct     1963
Tyr Lys Glu Phe Gly Ala Thr Val Glu Leu Leu Ser Phe Leu Pro Ser
                 10                  15                  20

gac ttc ttt cct tcc gtc aga gat ctc cta gac acc gcc tca gct ctg     2011
Asp Phe Phe Pro Ser Val Arg Asp Leu Leu Asp Thr Ala Ser Ala Leu
             25                  30                  35

tat cga gaa gcc tta gag tct cct gag cat tgc tca cct cac cat act     2059
Tyr Arg Glu Ala Leu Glu Ser Pro Glu His Cys Ser Pro His His Thr
         40                  45                  50

gca ctc agg caa gcc att ctc tgc tgg ggg gaa ttg atg act cta gct     2107
Ala Leu Arg Gln Ala Ile Leu Cys Trp Gly Glu Leu Met Thr Leu Ala
     55                  60                  65

acc tgg gtg ggt aat aat ttg gaa gat cca gca tcc agg gat cta gta     2155
Thr Trp Val Gly Asn Asn Leu Glu Asp Pro Ala Ser Arg Asp Leu Val
 70                  75                  80                  85

gtc aat tat gtt aat act aac atg ggt tta aag atc agg caa cta ttg     2203
Val Asn Tyr Val Asn Thr Asn Met Gly Leu Lys Ile Arg Gln Leu Leu
                 90                  95                 100

tgg ttt cat ata tct tgc ctt act ttt gga aga gag act gta ctt gaa     2251
Trp Phe His Ile Ser Cys Leu Thr Phe Gly Arg Glu Thr Val Leu Glu
            105                 110                 115

tat ttg gtc tct ttc gga gtg tgg att cgc act cct cca gcc tat aga     2299
Tyr Leu Val Ser Phe Gly Val Trp Ile Arg Thr Pro Pro Ala Tyr Arg
        120                 125                 130

cca cca aat gcc cct atc tta tca aca ctt ccg gaa act act gtt gtt     2347
Pro Pro Asn Ala Pro Ile Leu Ser Thr Leu Pro Glu Thr Thr Val Val
    135                 140                 145

aga cga cgg gac cga ggc agg tcc cct aga aga aga act ccc tcg cct     2395
Arg Arg Arg Asp Arg Gly Arg Ser Pro Arg Arg Arg Thr Pro Ser Pro
150                 155                 160                 165

cgc aga cgc aga tct caa tcg ccg cgt cgc aga aga tct caa tct cgg     2443
Arg Arg Arg Arg Ser Gln Ser Pro Arg Arg Arg Arg Ser Gln Ser Arg
                170                 175                 180

gaa tct caa tgt tag tattccttgg actcataagg tgggaaactt tactgggctt     2498
Glu Ser Gln Cys
            185

tattcctcta cagtacctat ctttaatcct gaatggcaaa ctccttcctt tcctaagatt   2558

catttacaag aggacattat tgataggtgt caacaatttg tgggccctct cactgtaaat   2618

gaaaagagaa gattgaaatt aattatgcct gctagattct atcctaccca cactaaatat   2678

ttgcccttag acaaaggaat taaaccttat tatccagatc aggtagttaa tcattacttc   2738

caaaccagac attatttaca tactctttgg aaggctggta ttctatataa gagggaaacc   2798

acacgtagcg catcattttg cgggtcacca tattcttggg aacaagagct acagcatggg   2858

aggttggtca ttaaaacctc gcaaaggcat ggggacgaat ctttctgttc ccaaccctct   2918

gggattcttt cccgatcatc agttggaccc tgcattcgga gccaactcaa acaatccaga   2978

ttgggacttc aaccccatca aggaccactg gccagcagcc aaccaggtag gagtgggagc   3038

attcgggcca gggctcaccc ctccacacgg cggtattttg ggtggagcc ctcaggctca   3098
```

-continued

```
gggcatattg accacagtgt caacaattcc tcctcctgcc tccaccaatc ggcagtcagg   3158

aaggcagcct actcccatct ctccacctct aagagacagt catcctcagg ccatgcagtg   3218

gaa                                                                 3221


<210> SEQ ID NO 134
<211> LENGTH: 185
<212> TYPE: PRT
<213> ORGANISM: Hepatitis B virus

<400> SEQUENCE: 134

Met Asp Ile Asp Pro Tyr Lys Glu Phe Gly Ala Thr Val Glu Leu Leu
  1               5                  10                  15

Ser Phe Leu Pro Ser Asp Phe Phe Pro Ser Val Arg Asp Leu Leu Asp
             20                  25                  30

Thr Ala Ser Ala Leu Tyr Arg Glu Ala Leu Glu Ser Pro Glu His Cys
         35                  40                  45

Ser Pro His His Thr Ala Leu Arg Gln Ala Ile Leu Cys Trp Gly Glu
     50                  55                  60

Leu Met Thr Leu Ala Thr Trp Val Gly Asn Asn Leu Glu Asp Pro Ala
 65                  70                  75                  80

Ser Arg Asp Leu Val Val Asn Tyr Val Asn Thr Asn Met Gly Leu Lys
                 85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Asp Arg Gly Arg Ser Pro Arg Arg
145                 150                 155                 160

Arg Thr Pro Ser Pro Arg Arg Arg Arg Ser Gln Ser Pro Arg Arg Arg
                165                 170                 175

Arg Ser Gln Ser Arg Glu Ser Gln Cys
            180                 185


<210> SEQ ID NO 135
<211> LENGTH: 188
<212> TYPE: PRT
<213> ORGANISM: Woodchuck hepatitis B virus

<400> SEQUENCE: 135

Met Asp Ile Asp Pro Tyr Lys Glu Phe Gly Ser Ser Tyr Gln Leu Leu
  1               5                  10                  15

Asn Phe Leu Pro Leu Asp Phe Phe Pro Asp Leu Asn Ala Leu Val Asp
             20                  25                  30

Thr Ala Thr Ala Leu Tyr Glu Glu Glu Leu Thr Gly Arg Glu His Cys
         35                  40                  45

Ser Pro His His Thr Ala Ile Arg Gln Ala Leu Val Cys Trp Asp Glu
     50                  55                  60

Leu Thr Lys Leu Ile Ala Trp Met Ser Ser Asn Ile Thr Ser Glu Gln
 65                  70                  75                  80

Val Arg Thr Ile Ile Val Asn His Val Asn Asp Thr Trp Gly Leu Lys
                 85                  90                  95

Val Arg Gln Ser Leu Trp Phe His Leu Ser Cys Leu Thr Phe Gly Gln
            100                 105                 110
```

-continued

```
His Thr Val Gln Glu Phe Leu Val Ser Phe Gly Val Trp Ile Arg Thr
        115                 120                 125

Pro Ala Pro Tyr Arg Pro Pro Asn Ala Pro Ile Leu Ser Thr Leu Pro
    130                 135                 140

Glu His Thr Val Ile Arg Arg Arg Gly Gly Ala Arg Ala Ser Arg Ser
145                 150                 155                 160

Pro Arg Arg Arg Thr Pro Ser Pro Arg Arg Arg Arg Ser Gln Ser Pro
                165                 170                 175

Arg Arg Arg Arg Ser Gln Ser Pro Ser Thr Asn Cys
            180                 185


<210> SEQ ID NO 136
<211> LENGTH: 217
<212> TYPE: PRT
<213> ORGANISM: Ground squirrel hepatitis virus

<400> SEQUENCE: 136

Met Tyr Leu Phe His Leu Cys Leu Val Phe Ala Cys Val Pro Cys Pro
  1               5                  10                  15

Thr Val Gln Ala Ser Lys Leu Cys Leu Gly Trp Leu Trp Asp Met Asp
             20                  25                  30

Ile Asp Pro Tyr Lys Glu Phe Gly Ser Ser Tyr Gln Leu Leu Asn Phe
         35                  40                  45

Leu Pro Leu Asp Phe Phe Pro Asp Leu Asn Ala Leu Val Asp Thr Ala
     50                  55                  60

Ala Ala Leu Tyr Glu Glu Glu Leu Thr Gly Arg Glu His Cys Ser Pro
 65                  70                  75                  80

His His Thr Ala Ile Arg Gln Ala Leu Val Cys Trp Glu Glu Leu Thr
                 85                  90                  95

Arg Leu Ile Thr Trp Met Ser Glu Asn Thr Thr Glu Glu Val Arg Arg
            100                 105                 110

Ile Ile Val Asp His Val Asn Asn Thr Trp Gly Leu Lys Val Arg Gln
        115                 120                 125

Thr Leu Trp Phe His Leu Ser Cys Leu Thr Phe Gly Gln His Thr Val
    130                 135                 140

Gln Glu Phe Leu Val Ser Phe Gly Val Trp Ile Arg Thr Pro Ala Pro
145                 150                 155                 160

Tyr Arg Pro Pro Asn Ala Pro Ile Leu Ser Thr Leu Pro Glu His Thr
                165                 170                 175

Val Ile Arg Arg Arg Gly Gly Ser Arg Ala Ala Arg Ser Pro Arg Arg
            180                 185                 190

Arg Thr Pro Ser Pro Arg Arg Arg Arg Ser Gln Ser Pro Arg Arg Arg
        195                 200                 205

Arg Ser Gln Ser Pro Ala Ser Asn Cys
    210                 215


<210> SEQ ID NO 137
<211> LENGTH: 262
<212> TYPE: PRT
<213> ORGANISM: Snow Goose Hepatitis B Virus

<400> SEQUENCE: 137

Met Asp Val Asn Ala Ser Arg Ala Leu Ala Asn Val Tyr Asp Leu Pro
  1               5                  10                  15

Asp Asp Phe Phe Pro Lys Ile Glu Asp Leu Val Arg Asp Ala Lys Asp
             20                  25                  30
```

-continued

```
Ala Leu Glu Pro Tyr Trp Lys Ser Asp Ser Ile Lys Lys His Val Leu
        35                  40                  45

Ile Ala Thr His Phe Val Asp Leu Ile Glu Asp Phe Trp Gln Thr Thr
    50                  55                  60

Gln Gly Met His Glu Ile Ala Glu Ala Ile Arg Ala Val Ile Pro Pro
65                  70                  75                  80

Thr Thr Ala Pro Val Pro Ser Gly Tyr Leu Ile Gln His Asp Glu Ala
                85                  90                  95

Glu Glu Ile Pro Leu Gly Asp Leu Phe Lys Glu Gln Glu Glu Arg Ile
            100                 105                 110

Val Ser Phe Gln Pro Asp Tyr Pro Ile Thr Ala Arg Ile His Ala His
        115                 120                 125

Leu Lys Ala Tyr Ala Lys Ile Asn Glu Glu Ser Leu Asp Arg Ala Arg
    130                 135                 140

Arg Leu Leu Trp Trp His Tyr Asn Cys Leu Leu Trp Gly Glu Ala Thr
145                 150                 155                 160

Val Thr Asn Tyr Ile Ser Arg Leu Arg Thr Trp Leu Ser Thr Pro Glu
                165                 170                 175

Lys Tyr Arg Gly Arg Asp Ala Pro Thr Ile Glu Ala Ile Thr Arg Pro
            180                 185                 190

Ile Gln Val Ala Gln Gly Gly Arg Lys Thr Ser Thr Ala Thr Arg Lys
        195                 200                 205

Pro Arg Gly Leu Glu Pro Arg Arg Arg Lys Val Lys Thr Thr Val Val
    210                 215                 220

Tyr Gly Arg Arg Arg Ser Lys Ser Arg Glu Arg Arg Ala Ser Ser Pro
225                 230                 235                 240

Gln Arg Ala Gly Ser Pro Leu Pro Arg Ser Ser Ser Ser His His Arg
                245                 250                 255

Ser Pro Ser Pro Arg Lys
            260


<210> SEQ ID NO 138
<211> LENGTH: 305
<212> TYPE: PRT
<213> ORGANISM: Duck hepatitis B virus

<400> SEQUENCE: 138

Met Trp Asp Leu Arg Leu His Pro Ser Pro Phe Gly Ala Ala Cys Gln
  1               5                  10                  15

Gly Ile Phe Thr Ser Ser Leu Leu Leu Phe Leu Val Thr Val Pro Leu
            20                  25                  30

Val Cys Thr Ile Val Tyr Asp Ser Cys Leu Cys Met Asp Ile Asn Ala
        35                  40                  45

Ser Arg Ala Leu Ala Asn Val Tyr Asp Leu Pro Asp Asp Phe Phe Pro
    50                  55                  60

Lys Ile Asp Asp Leu Val Arg Asp Ala Lys Asp Ala Leu Glu Pro Tyr
65                  70                  75                  80

Trp Arg Asn Asp Ser Ile Lys Lys His Val Leu Ile Ala Thr His Phe
                85                  90                  95

Val Asp Leu Ile Glu Asp Phe Trp Gln Thr Thr Gln Gly Met His Glu
            100                 105                 110

Ile Ala Glu Ala Leu Arg Ala Ile Ile Pro Ala Thr Thr Ala Pro Val
        115                 120                 125

Pro Gln Gly Phe Leu Val Gln His Glu Glu Ala Glu Glu Ile Pro Leu
    130                 135                 140
```

-continued

Gly Glu Leu Phe Arg Tyr Gln Glu Glu Arg Leu Thr Asn Phe Gln Pro
145 150 155 160

Asp Tyr Pro Val Thr Ala Arg Ile His Ala His Leu Lys Ala Tyr Ala
165 170 175

Lys Ile Asn Glu Glu Ser Leu Asp Arg Ala Arg Arg Leu Leu Trp Trp
180 185 190

His Tyr Asn Cys Leu Leu Trp Gly Glu Pro Asn Val Thr Asn Tyr Ile
195 200 205

Ser Arg Leu Arg Thr Trp Leu Ser Thr Pro Glu Lys Tyr Arg Gly Lys
210 215 220

Asp Ala Pro Thr Ile Glu Ala Ile Thr Arg Pro Ile Gln Val Ala Gln
225 230 235 240

Gly Gly Arg Asn Lys Thr Gln Gly Val Arg Lys Ser Arg Gly Leu Glu
245 250 255

Pro Arg Arg Arg Arg Val Lys Thr Thr Ile Val Tyr Gly Arg Arg Arg
260 265 270

Ser Lys Ser Arg Glu Arg Arg Ala Pro Thr Pro Gln Arg Ala Gly Ser
275 280 285

Pro Leu Pro Arg Thr Ser Arg Asp His His Arg Ser Pro Ser Pro Arg
290 295 300

Glu
305

<210> SEQ ID NO 139
<211> LENGTH: 212
<212> TYPE: PRT
<213> ORGANISM: Haemophilus influenzae

<400> SEQUENCE: 139

Met Lys Lys Thr Leu Leu Gly Ser Leu Ile Leu Leu Ala Phe Ala Gly
1 5 10 15

Asn Val Gln Ala Ala Ala Asn Ala Asp Thr Ser Gly Thr Val Thr Phe
20 25 30

Phe Gly Lys Val Val Glu Asn Thr Cys Gln Val Asn Gln Asp Ser Glu
35 40 45

Tyr Glu Cys Asn Leu Asn Asp Val Gly Lys Asn His Leu Ser Gln Gln
50 55 60

Gly Tyr Thr Ala Met Gln Thr Pro Phe Thr Ile Thr Leu Glu Asn Cys
65 70 75 80

Asn Val Thr Thr Thr Asn Asn Lys Pro Lys Ala Thr Lys Val Gly Val
85 90 95

Tyr Phe Tyr Ser Trp Glu Ile Ala Asp Lys Asp Asn Lys Tyr Thr Leu
100 105 110

Lys Asn Ile Lys Glu Asn Thr Gly Thr Asn Asp Ser Ala Asn Lys Val
115 120 125

Asn Ile Gln Leu Leu Glu Asp Asn Gly Thr Ala Glu Ile Lys Val Val
130 135 140

Gly Lys Thr Thr Thr Asp Phe Thr Ser Glu Asn His Asn Gly Ala Gly
145 150 155 160

Ala Asp Pro Val Ala Thr Asn Lys His Ile Ser Ser Leu Thr Pro Leu
165 170 175

Asn Asn Gln Asn Ser Ile Asn Leu His Tyr Ile Ala Gln Tyr Tyr Ala
180 185 190

Thr Gly Val Ala Glu Ala Gly Lys Val Pro Ser Ser Val Asn Ser Gln

-continued

```
        195                 200                 205

Ile Ala Tyr Glu
    210


<210> SEQ ID NO 140
<211> LENGTH: 139
<212> TYPE: PRT
<213> ORGANISM: Pseudomonas stutzeri

<400> SEQUENCE: 140

Met Lys Ala Gln Met Gln Lys Gly Phe Thr Leu Ile Glu Leu Met Ile
  1               5                  10                  15

Val Val Ala Ile Ile Gly Ile Leu Ala Ala Ile Ala Leu Pro Ala Tyr
             20                  25                  30

Gln Asp Tyr Thr Val Arg Ser Asn Ala Ala Ala Ala Leu Ala Glu Ile
         35                  40                  45

Thr Pro Gly Lys Ile Gly Phe Glu Gln Ala Ile Asn Glu Gly Lys Thr
     50                  55                  60

Pro Ser Leu Thr Ser Thr Asp Glu Gly Tyr Ile Gly Ile Thr Asp Ser
 65                  70                  75                  80

Thr Ser Tyr Cys Asp Val Asp Leu Asp Thr Ala Ala Asp Gly His Ile
                 85                  90                  95

Glu Cys Thr Ala Lys Gly Gly Asn Ala Gly Lys Phe Asp Gly Lys Thr
            100                 105                 110

Ile Thr Leu Asn Arg Thr Ala Asp Gly Glu Trp Ser Cys Ala Ser Thr
        115                 120                 125

Leu Asp Ala Lys Tyr Lys Pro Gly Lys Cys Ser
    130                 135


<210> SEQ ID NO 141
<211> LENGTH: 59
<212> TYPE: PRT
<213> ORGANISM: Caulobacter crescentus

<400> SEQUENCE: 141

Met Thr Lys Phe Val Thr Arg Phe Leu Lys Asp Glu Ser Gly Ala Thr
  1               5                  10                  15

Ala Ile Glu Tyr Gly Leu Ile Val Ala Leu Ile Ala Val Val Ile Val
             20                  25                  30

Thr Ala Val Thr Thr Leu Gly Thr Asn Leu Arg Thr Ala Phe Thr Lys
         35                  40                  45

Ala Gly Ala Ala Val Ser Thr Ala Ala Gly Thr
     50                  55


<210> SEQ ID NO 142
<211> LENGTH: 173
<212> TYPE: PRT
<213> ORGANISM: Escherichia coli

<400> SEQUENCE: 142

Met Ala Val Val Ser Phe Gly Val Asn Ala Ala Pro Thr Ile Pro Gln
  1               5                  10                  15

Gly Gln Gly Lys Val Thr Phe Asn Gly Thr Val Val Asp Ala Pro Cys
             20                  25                  30

Ser Ile Ser Gln Lys Ser Ala Asp Gln Ser Ile Asp Phe Gly Gln Leu
         35                  40                  45

Ser Lys Ser Phe Leu Glu Ala Gly Gly Val Ser Lys Pro Met Asp Leu
     50                  55                  60
```

-continued

Asp Ile Glu Leu Val Asn Cys Asp Ile Thr Ala Phe Lys Gly Gly Asn
65 70 75 80

Gly Ala Gln Lys Gly Thr Val Lys Leu Ala Phe Thr Gly Pro Ile Val
85 90 95

Asn Gly His Ser Asp Glu Leu Asp Thr Asn Gly Gly Thr Gly Thr Ala
100 105 110

Ile Val Val Gln Gly Ala Gly Lys Asn Val Val Phe Asp Gly Ser Glu
115 120 125

Gly Asp Ala Asn Thr Leu Lys Asp Gly Glu Asn Val Leu His Tyr Thr
130 135 140

Ala Val Val Lys Lys Ser Ser Ala Val Gly Ala Ala Val Thr Glu Gly
145 150 155 160

Ala Phe Ser Ala Val Ala Asn Phe Asn Leu Thr Tyr Gln
165 170

<210> SEQ ID NO 143
<211> LENGTH: 173
<212> TYPE: PRT
<213> ORGANISM: Escherichia coli

<400> SEQUENCE: 143

Met Ala Val Val Ser Phe Gly Val Asn Ala Ala Pro Thr Ile Pro Gln
1 5 10 15

Gly Gln Gly Lys Val Thr Phe Asn Gly Thr Val Val Asp Ala Pro Cys
20 25 30

Ser Ile Ser Gln Lys Ser Ala Asp Gln Ser Ile Asp Phe Gly Gln Leu
35 40 45

Ser Lys Ser Phe Leu Glu Ala Gly Gly Val Ser Lys Pro Met Asp Leu
50 55 60

Asp Ile Glu Leu Val Asn Cys Asp Ile Thr Ala Phe Lys Gly Gly Asn
65 70 75 80

Gly Ala Gln Lys Gly Thr Val Lys Leu Ala Phe Thr Gly Pro Ile Val
85 90 95

Asn Gly His Ser Asp Glu Leu Asp Thr Asn Gly Gly Thr Gly Thr Ala
100 105 110

Ile Val Val Gln Gly Ala Gly Lys Asn Val Val Phe Asp Gly Ser Glu
115 120 125

Gly Asp Ala Asn Thr Leu Lys Asp Gly Glu Asn Val Leu His Tyr Thr
130 135 140

Ala Val Val Lys Lys Ser Ser Ala Val Gly Ala Ala Val Thr Glu Gly
145 150 155 160

Ala Phe Ser Ala Val Ala Asn Phe Asn Leu Thr Tyr Gln
165 170

<210> SEQ ID NO 144
<211> LENGTH: 172
<212> TYPE: PRT
<213> ORGANISM: Escherichia coli

<400> SEQUENCE: 144

Met Ala Val Val Ser Phe Gly Val Asn Ala Ala Pro Thr Thr Pro Gln
1 5 10 15

Gly Gln Gly Arg Val Thr Phe Asn Gly Thr Val Val Asp Ala Pro Cys
20 25 30

Ser Ile Ser Gln Lys Ser Ala Asp Gln Ser Ile Asp Phe Gly Gln Leu
35 40 45

-continued

```
Ser Lys Ser Phe Leu Ala Asn Asp Gly Gln Ser Lys Pro Met Asn Leu
     50                  55                  60

Asp Ile Glu Leu Val Asn Cys Asp Ile Thr Ala Phe Lys Asn Gly Asn
 65                  70                  75                  80

Ala Lys Thr Gly Ser Val Lys Leu Ala Phe Thr Gly Pro Thr Val Ser
                 85                  90                  95

Gly His Pro Ser Glu Leu Ala Thr Asn Gly Gly Pro Gly Thr Ala Ile
            100                 105                 110

Met Ile Gln Ala Ala Gly Lys Asn Val Pro Phe Asp Gly Thr Glu Gly
        115                 120                 125

Asp Pro Asn Leu Leu Lys Asp Gly Asp Asn Val Leu His Tyr Thr Thr
    130                 135                 140

Val Gly Lys Lys Ser Ser Asp Gly Asn Ala Gln Ile Thr Glu Gly Ala
145                 150                 155                 160

Phe Ser Gly Val Ala Thr Phe Asn Leu Ser Tyr Gln
                165                 170


<210> SEQ ID NO 145
<211> LENGTH: 853
<212> TYPE: DNA
<213> ORGANISM: Escherichia coli
<220> FEATURE:
<221> NAME/KEY: CDS
<222> LOCATION: (281)..(829)

<400> SEQUENCE: 145

acgtttctgt ggctcgacgc atcttcctca ttcttctctc caaaaaccac ctcatgcaat      60

ataaacatct ataaataaag ataacaaata gaatattaag ccaacaaata aactgaaaaa     120

gtttgtccgc gatgctttac ctctatgagt caaaatggcc ccaatgtttc atcttttggg     180

ggaaactgtg cagtgttggc agtcaaactc gttgacaaac aaagtgtaca gaacgactgc     240

ccatgtcgat ttagaaatag ttttttgaaa ggaaagcagc atg aaa att aaa act       295
                                            Met Lys Ile Lys Thr
                                            1               5

ctg gca atc gtt gtt ctg tcg gct ctg tcc ctc agt tct acg acg gct       343
Leu Ala Ile Val Val Leu Ser Ala Leu Ser Leu Ser Ser Thr Thr Ala
                 10                  15                  20

ctg gcc gct gcc acg acg gtt aat ggt ggg acc gtt cac ttt aaa ggg       391
Leu Ala Ala Ala Thr Thr Val Asn Gly Gly Thr Val His Phe Lys Gly
             25                  30                  35

gaa gtt gtt aac gcc gct tgc gca gtt gat gca ggc tct gtt gat caa       439
Glu Val Val Asn Ala Ala Cys Ala Val Asp Ala Gly Ser Val Asp Gln
         40                  45                  50

acc gtt cag tta gga cag gtt cgt acc gca tcg ctg gca cag gaa gga       487
Thr Val Gln Leu Gly Gln Val Arg Thr Ala Ser Leu Ala Gln Glu Gly
     55                  60                  65

gca acc agt tct gct gtc ggt ttt aac att cag ctg aat gat tgc gat       535
Ala Thr Ser Ser Ala Val Gly Phe Asn Ile Gln Leu Asn Asp Cys Asp
 70                  75                  80                  85

acc aat gtt gca tct aaa gcc gct gtt gcc ttt tta ggt acg gcg att       583
Thr Asn Val Ala Ser Lys Ala Ala Val Ala Phe Leu Gly Thr Ala Ile
                 90                  95                 100

gat gcg ggt cat acc aac gtt ctg gct ctg cag agt tca gct gcg ggt       631
Asp Ala Gly His Thr Asn Val Leu Ala Leu Gln Ser Ser Ala Ala Gly
            105                 110                 115

agc gca aca aac gtt ggt gtg cag atc ctg gac aga acg ggt gct gcg       679
Ser Ala Thr Asn Val Gly Val Gln Ile Leu Asp Arg Thr Gly Ala Ala
        120                 125                 130
```

-continued

```
ctg acg ctg gat ggt gcg aca ttt agt tca gaa aca acc ctg aat aac      727
Leu Thr Leu Asp Gly Ala Thr Phe Ser Ser Glu Thr Thr Leu Asn Asn
    135                 140                 145

gga acc aat acc att ccg ttc cag gcg cgt tat ttt gca acc ggg gcc      775
Gly Thr Asn Thr Ile Pro Phe Gln Ala Arg Tyr Phe Ala Thr Gly Ala
150                 155                 160                 165

gca acc ccg ggt gct gct aat gcg gat gcg acc ttc aag gtt cag tat      823
Ala Thr Pro Gly Ala Ala Asn Ala Asp Ala Thr Phe Lys Val Gln Tyr
                170                 175                 180

caa taa cctacctagg ttcagggacg ttca                                   853
Gln


<210> SEQ ID NO 146
<211> LENGTH: 182
<212> TYPE: PRT
<213> ORGANISM: Escherichia coli

<400> SEQUENCE: 146

Met Lys Ile Lys Thr Leu Ala Ile Val Val Leu Ser Ala Leu Ser Leu
  1               5                  10                  15

Ser Ser Thr Thr Ala Leu Ala Ala Ala Thr Thr Val Asn Gly Gly Thr
             20                  25                  30

Val His Phe Lys Gly Glu Val Val Asn Ala Ala Cys Ala Val Asp Ala
         35                  40                  45

Gly Ser Val Asp Gln Thr Val Gln Leu Gly Gln Val Arg Thr Ala Ser
     50                  55                  60

Leu Ala Gln Glu Gly Ala Thr Ser Ser Ala Val Gly Phe Asn Ile Gln
 65                  70                  75                  80

Leu Asn Asp Cys Asp Thr Asn Val Ala Ser Lys Ala Ala Val Ala Phe
                 85                  90                  95

Leu Gly Thr Ala Ile Asp Ala Gly His Thr Asn Val Leu Ala Leu Gln
            100                 105                 110

Ser Ser Ala Ala Gly Ser Ala Thr Asn Val Gly Val Gln Ile Leu Asp
        115                 120                 125

Arg Thr Gly Ala Ala Leu Thr Leu Asp Gly Ala Thr Phe Ser Ser Glu
    130                 135                 140

Thr Thr Leu Asn Asn Gly Thr Asn Thr Ile Pro Phe Gln Ala Arg Tyr
145                 150                 155                 160

Phe Ala Thr Gly Ala Ala Thr Pro Gly Ala Ala Asn Ala Asp Ala Thr
                165                 170                 175

Phe Lys Val Gln Tyr Gln
            180


<210> SEQ ID NO 147
<211> LENGTH: 11
<212> TYPE: PRT
<213> ORGANISM: Artificial Sequence
<220> FEATURE:
<223> OTHER INFORMATION: FLAG peptide

<400> SEQUENCE: 147

Cys Gly Gly Asp Tyr Lys Asp Asp Asp Asp Lys
  1               5                  10


<210> SEQ ID NO 148
<211> LENGTH: 31
<212> TYPE: DNA
<213> ORGANISM: Artificial Sequence
<220> FEATURE:
```

-continued

<223> OTHER INFORMATION: primer

<400> SEQUENCE: 148
ccggaattca tggacattga cccttataaa g 31

<210> SEQ ID NO 149
<211> LENGTH: 37
<212> TYPE: DNA
<213> ORGANISM: Artificial Sequence
<220> FEATURE:
<223> OTHER INFORMATION: primer

<400> SEQUENCE: 149
gtgcagtatg gtgaggtgag gaatgctcag gagactc 37

<210> SEQ ID NO 150
<211> LENGTH: 37
<212> TYPE: DNA
<213> ORGANISM: Artificial Sequence
<220> FEATURE:
<223> OTHER INFORMATION: primer

<400> SEQUENCE: 150
gsgtctcctg agcattcctc acctcaccat actgcac 37

<210> SEQ ID NO 151
<211> LENGTH: 33
<212> TYPE: DNA
<213> ORGANISM: Artificial Sequence
<220> FEATURE:
<223> OTHER INFORMATION: primer

<400> SEQUENCE: 151
cttccaaaag tgagggaaga aatgtgaaac cac 33

<210> SEQ ID NO 152
<211> LENGTH: 47
<212> TYPE: DNA
<213> ORGANISM: Artificial Sequence
<220> FEATURE:
<223> OTHER INFORMATION: primer

<400> SEQUENCE: 152
cgcgtcccaa gcttctaaac aacagtagtc tccggaagcg ttgatag 47

<210> SEQ ID NO 153
<211> LENGTH: 33
<212> TYPE: DNA
<213> ORGANISM: Artificial Sequence
<220> FEATURE:
<223> OTHER INFORMATION: primer

<400> SEQUENCE: 153
gtggtttcac atttcttccc tcacttttgg aag 33

<210> SEQ ID NO 154
<211> LENGTH: 281
<212> TYPE: PRT
<213> ORGANISM: Saccharomyces cerevisiae

<400> SEQUENCE: 154

Met Ser Glu Tyr Gln Pro Ser Leu Phe Ala Leu Asn Pro Met Gly Phe
1 5 10 15

Ser Pro Leu Asp Gly Ser Lys Ser Thr Asn Glu Asn Val Ser Ala Ser
20 25 30

-continued

Thr Ser Thr Ala Lys Pro Met Val Gly Gln Leu Ile Phe Asp Lys Phe
35 40 45

Ile Lys Thr Glu Glu Asp Pro Ile Ile Lys Gln Asp Thr Pro Ser Asn
50 55 60

Leu Asp Phe Asp Phe Ala Leu Pro Gln Thr Ala Thr Ala Pro Asp Ala
65 70 75 80

Lys Thr Val Leu Pro Ile Pro Glu Leu Asp Asp Ala Val Val Glu Ser
85 90 95

Phe Phe Ser Ser Ser Thr Asp Ser Thr Pro Met Phe Glu Tyr Glu Asn
100 105 110

Leu Glu Asp Asn Ser Lys Glu Trp Thr Ser Leu Phe Asp Asn Asp Ile
115 120 125

Pro Val Thr Thr Asp Asp Val Ser Leu Ala Asp Lys Ala Ile Glu Ser
130 135 140

Thr Glu Glu Val Ser Leu Val Pro Ser Asn Leu Glu Val Ser Thr Thr
145 150 155 160

Ser Phe Leu Pro Thr Pro Val Leu Glu Asp Ala Lys Leu Thr Gln Thr
165 170 175

Arg Lys Val Lys Lys Pro Asn Ser Val Val Lys Lys Ser His His Val
180 185 190

Gly Lys Asp Asp Glu Ser Arg Leu Asp His Leu Gly Val Val Ala Tyr
195 200 205

Asn Arg Lys Gln Arg Ser Ile Pro Leu Ser Pro Ile Val Pro Glu Ser
210 215 220

Ser Asp Pro Ala Ala Leu Lys Arg Ala Arg Asn Thr Glu Ala Ala Arg
225 230 235 240

Arg Ser Arg Ala Arg Lys Leu Gln Arg Met Lys Gln Leu Glu Asp Lys
245 250 255

Val Glu Glu Leu Leu Ser Lys Asn Tyr His Leu Glu Asn Glu Val Ala
260 265 270

Arg Leu Lys Lys Leu Val Gly Glu Arg
275 280

<210> SEQ ID NO 155
<211> LENGTH: 181
<212> TYPE: PRT
<213> ORGANISM: Escherichia coli

<400> SEQUENCE: 155

Met Lys Ile Lys Thr Leu Ala Ile Val Val Leu Ser Ala Leu Ser Leu
1 5 10 15

Ser Ser Thr Ala Ala Leu Ala Ala Ala Thr Thr Val Asn Gly Gly Thr
20 25 30

Val His Phe Lys Gly Glu Val Val Asn Ala Ala Cys Ala Val Asp Ala
35 40 45

Gly Ser Val Asp Gln Thr Val Gln Leu Gly Gln Val Arg Thr Ala Ser
50 55 60

Leu Ala Gln Glu Gly Ala Thr Ser Ser Ala Val Gly Phe Asn Ile Gln
65 70 75 80

Leu Asn Asp Cys Asp Thr Asn Val Ala Ser Lys Ala Ala Val Ala Phe
85 90 95

Leu Gly Thr Ala Ile Asp Ala Gly His Thr Asn Val Leu Ala Leu Gln
100 105 110

Ser Ser Ala Ala Gly Ser Ala Thr Asn Val Gly Val Gln Ile Leu Asp

-continued

```
        115                 120                 125

Arg Thr Gly Ala Ala Leu Thr Leu Asp Gly Ala Thr Phe Ser Ser Glu
    130                 135                 140

Thr Thr Leu Asn Asn Gly Thr Asn Thr Ile Pro Phe Gln Ala Arg Tyr
145                 150                 155                 160

Phe Ala Gly Ala Ala Thr Pro Gly Ala Ala Asn Ala Asp Ala Thr Phe
                165                 170                 175

Lys Val Gln Tyr Gln
            180


<210> SEQ ID NO 156
<211> LENGTH: 447
<212> TYPE: DNA
<213> ORGANISM: Hepatitis B
<220> FEATURE:
<221> NAME/KEY: CDS
<222> LOCATION: (1)..(447)

<400> SEQUENCE: 156

atg gac att gac cct tat aaa gaa ttt gga gct act gtg gag tta ctc       48
Met Asp Ile Asp Pro Tyr Lys Glu Phe Gly Ala Thr Val Glu Leu Leu
  1               5                  10                  15

tcg ttt ttg cct tct gac ttc ttt cct tcc gta cga gat ctt cta gat       96
Ser Phe Leu Pro Ser Asp Phe Phe Pro Ser Val Arg Asp Leu Leu Asp
             20                  25                  30

acc gcc gca gct ctg tat cgg gat gcc tta gag tct cct gag cat tgt      144
Thr Ala Ala Ala Leu Tyr Arg Asp Ala Leu Glu Ser Pro Glu His Cys
         35                  40                  45

tca cct cac cat act gca ctc agg caa gca att ctt tgc tgg gga gac      192
Ser Pro His His Thr Ala Leu Arg Gln Ala Ile Leu Cys Trp Gly Asp
     50                  55                  60

tta atg act cta gct acc tgg gtg ggt act aat tta gaa gat cca gca      240
Leu Met Thr Leu Ala Thr Trp Val Gly Thr Asn Leu Glu Asp Pro Ala
 65                  70                  75                  80

tct agg gac cta gta gtc agt tat gtc aac act aat gtg ggc cta aag      288
Ser Arg Asp Leu Val Val Ser Tyr Val Asn Thr Asn Val Gly Leu Lys
                 85                  90                  95

ttc aga caa tta ttg tgg ttt cac att tct tgt ctc act ttt gga aga      336
Phe Arg Gln Leu Leu Trp Phe His Ile Ser Cys Leu Thr Phe Gly Arg
            100                 105                 110

gaa acg gtt cta gag tat ttg gtc tct ttt gga gtg tgg att cgc act      384
Glu Thr Val Leu Glu Tyr Leu Val Ser Phe Gly Val Trp Ile Arg Thr
        115                 120                 125

cct cca gcc tat aga cca cca aat gcc cct atc cta tca acg ctt ccg      432
Pro Pro Ala Tyr Arg Pro Pro Asn Ala Pro Ile Leu Ser Thr Leu Pro
    130                 135                 140

gag act act gtt gtt                                                  447
Glu Thr Thr Val Val
145


<210> SEQ ID NO 157
<211> LENGTH: 149
<212> TYPE: PRT
<213> ORGANISM: Hepatitis B

<400> SEQUENCE: 157

Met Asp Ile Asp Pro Tyr Lys Glu Phe Gly Ala Thr Val Glu Leu Leu
  1               5                  10                  15

Ser Phe Leu Pro Ser Asp Phe Phe Pro Ser Val Arg Asp Leu Leu Asp
             20                  25                  30
```

-continued

```
Thr Ala Ala Ala Leu Tyr Arg Asp Ala Leu Glu Ser Pro Glu His Cys
            35                  40                  45

Ser Pro His His Thr Ala Leu Arg Gln Ala Ile Leu Cys Trp Gly Asp
 50                  55                  60

Leu Met Thr Leu Ala Thr Trp Val Gly Thr Asn Leu Glu Asp Pro Ala
 65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val
145

<210> SEQ ID NO 158
<211> LENGTH: 152
<212> TYPE: PRT
<213> ORGANISM: Hepatitis B

<400> SEQUENCE: 158

Met Asp Ile Asp Pro Tyr Lys Glu Phe Gly Ala Thr Val Glu Leu Leu
 1               5                  10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
 50                  55                  60

Leu Met Thr Leu Ala Thr Trp Val Gly Thr Asn Leu Glu Asp Gly Gly
 65                  70                  75                  80

Lys Gly Gly Ser Arg Asp Leu Val Val Ser Tyr Val Asn Thr Asn Val
                85                  90                  95

Gly Leu Lys Phe Arg Gln Leu Leu Trp Phe His Ile Ser Cys Leu Thr
            100                 105                 110

Phe Gly Arg Glu Thr Val Leu Glu Tyr Leu Val Ser Phe Gly Val Trp
        115                 120                 125

Ile Arg Thr Pro Pro Ala Tyr Arg Pro Pro Asn Ala Pro Ile Leu Ser
    130                 135                 140

Thr Leu Pro Glu Thr Thr Val Val
145                 150

<210> SEQ ID NO 159
<211> LENGTH: 56
<212> TYPE: DNA
<213> ORGANISM: Artificial Sequence
<220> FEATURE:
<223> OTHER INFORMATION: Oligonucleotide

<400> SEQUENCE: 159

tagatgatta cgccaagctt ataatagaaa tagttttttg aaaggaaagc agcatg      56

<210> SEQ ID NO 160
<211> LENGTH: 45
<212> TYPE: DNA
<213> ORGANISM: Artificial Sequence
```

-continued

<220> FEATURE:
<223> OTHER INFORMATION: Oligonucleotide

<400> SEQUENCE: 160
gtcaaaggcc ttgtcgacgt tattccatta cgcccgtcat tttgg 45

<210> SEQ ID NO 161
<211> LENGTH: 4623
<212> TYPE: DNA
<213> ORGANISM: Artificial Sequence
<220> FEATURE:
<223> OTHER INFORMATION: pFIMAIC

<400> SEQUENCE: 161
agacgaaagg gcctcgtgat acgcctattt ttataggtta atgtcatgat aataatggtt 60
tcttagacgt caggtggcac ttttcgggga aatgtgcgcg gaacccctat ttgtttattt 120
ttctaaatac attcaaatat gtatccgctc atgagacaat aaccctgata aatgcttcaa 180
taatattgaa aaaggaagag tatgagtatt caacatttcc gtgtcgccct tattcccttt 240
tttgcggcat tttgccttcc tgtttttgct cacccagaaa cgctggtgaa agtaaaagat 300
gctgaagatc agttgggtgc acgagtgggt tacatcgaac tggatctcaa cagcggtaag 360
atccttgaga gttttcgccc cgaagaacgt tttccaatga tgagcacttt taaagttctg 420
ctatgtggcg cggtattatc ccgtattgac gccgggcaag agcaactcgg tcgccgcata 480
cactattctc agaatgactt ggttgagtac tcaccagtca cagaaaagca tcttacggat 540
ggcatgacag taagagaatt atgcagtgct gccataacca tgagtgataa cactgcggcc 600
aacttacttc tgacaacgat cggaggaccg aaggagctaa ccgctttttt gcacaacatg 660
ggggatcatg taactcgcct tgatcgttgg gaaccggagc tgaatgaagc cataccaaac 720
gacgagcgtg acaccacgat gcctgtagca atggcaacaa cgttgcgcaa actattaact 780
ggcgaactac ttactctagc ttcccggcaa caattaatag actggatgga ggcggataaa 840
gttgcaggac cacttctgcg ctcggccctt ccggctggct ggtttattgc tgataaatct 900
ggagccggtg agcgtgggtc tcgcggtatc attgcagcac tggggccaga tggtaagccc 960
tcccgtatcg tagttatcta cacgacgggg agtcaggcaa ctatggatga acgaaataga 1020
cagatcgctg agataggtgc ctcactgatt aagcattggt aactgtcaga ccaagtttac 1080
tcatatatac tttagattga tttaaaactt catttttaat ttaaaaggat ctaggtgaag 1140
atcctttttg ataatctcat gaccaaaatc ccttaacgtg agttttcgtt ccactgagcg 1200
tcagaccccg tagaaaagat caaaggatct tcttgagatc cttttttct gcgcgtaatc 1260 tgctgcttgc aaacaaaaaa accaccgcta ccagcggtgg tttgtttgcc ggatcaagag 1320
ctaccaactc tttttccgaa ggtaactggc ttcagcagag cgcagatacc aaatactgtc 1380
cttctagtgt agccgtagtt aggccaccac ttcaagaact ctgtagcacc gcctacatac 1440
ctcgctctgc taatcctgtt accagtggct gctgccagtg gcgataagtc gtgtcttacc 1500
gggttggact caagacgata gttaccggat aaggcgcagc ggtcgggctg aacggggggt 1560
tcgtgcacac agcccagctt ggagcgaacg acctacaccg aactgagata cctacagcgt 1620
gagctatgag aaagcgccac gcttcccgaa gggagaaagg cggacaggta tccggtaagc 1680
ggcagggtcg gaacaggaga gcgcacgagg gagcttccag ggggaaacgc ctggtatctt 1740
tatagtcctg tcgggtttcg ccacctctga cttgagcgtc gatttttgtg atgctcgtca 1800 gggggcgga gcctatggaa aaacgccagc aacgcggcct ttttacggtt cctggccttt 1860

-continued

```
tgctggcctt ttgctcacat gttctttcct gcgttatccc ctgattctgt ggataaccgt   1920
attaccgcct ttgagtgagc tgataccgct cgccgcagcc gaacgaccga gcgcagcgag   1980
tcagtgagcg aggaagcgga agagcgccca atacgcaaac cgcctctccc cgcgcgttgg   2040
ccgattcatt aatgcagctg gcacgacagg tttcccgact ggaaagcggg cagtgagcgc   2100
aacgcaatta atgtgagtta gctcactcat taggcacccc aggctttaca ctttatgctt   2160
ccggctcgta tgttgtgtgg aattgtgagc ggataacaat ttcacacagg aaacagctat   2220
gaccatgatt acgccaagct tataatagaa atagtttttt gaaaggaaag cagcatgaaa   2280
attaaaactc tggcaatcgt tgttctgtcg gctctgtccc tcagttctac agcggctctg   2340
gccgctgcca cgacggttaa tggtgggacc gttcacttta aaggggaagt tgttaacgcc   2400
gcttgcgcag ttgatgcagg ctctgttgat caaaccgttc agttaggaca ggttcgtacc   2460
gcatcgctgg cacaggaagg agcaaccagt tctgctgtcg gttttaacat tcagctgaat   2520
gattgcgata ccaatgttgc atctaaagcc gctgttgcct tttaggtac ggcgattgat    2580
gcgggtcata ccaacgttct ggctctgcag agttcagctg cgggtagcgc aacaaacgtt   2640
ggtgtgcaga tcctggacag aacgggtgct gcgctgacgc tggatggtgc gacatttagt   2700
tcagaaacaa ccctgaataa cggaaccaat accattccgt tccaggcgcg ttattttgca   2760
accggggccg caaccccggg tgctgctaat gcggatgcga ccttcaaggt tcagtatcaa   2820
taacctaccc aggttcaggg acgtcattac gggcagggat gcccaccctt gtgcgataaa   2880
aataacgatg aaaaggaaga gattatttct attagcgtcg ttgctgccaa tgtttgctct   2940
ggccggaaat aaatggaata ccacgttgcc cggcggaaat atgcaatttc agggcgtcat   3000
tattgcggaa acttgccgga ttgaagccgg tgataaacaa atgacggtca atatggggca   3060
aatcagcagt aaccggtttc atgcggttgg ggaagatagc gcaccggtgc cttttgttat   3120
tcatttacgg gaatgtagca cggtggtgag tgaacgtgta ggtgtggcgt ttcacggtgt   3180
cgcggatggt aaaaatccgg atgtgctttc cgtgggagag ggccagggga tagccaccaa   3240
tattggcgta gcgttgtttg atgatgaagg aaacctcgta ccgattaatc gtcctccagc   3300
aaactggaaa cggctttatt caggctctac ttcgctacat ttcatcgcca aatatcgtgc   3360
taccgggcgt cgggttactg gcggcatcgc caatgcccag gcctggttct ctttaaccta   3420
tcagtaattg ttcagcagat aatgtgataa caggaacagg acagtgagta ataaaaacgt   3480
caatgtaagg aaatcgcagg aaataacatt ctgcttgctg gcaggtatcc tgatgttcat   3540
ggcaatgatg gttgccggac gcgctgaagc gggagtggcc ttaggtgcga ctcgcgtaat   3600
ttatccggca gggcaaaaac aagagcaact tgccgtgaca aataatgatg aaaatagtac   3660
ctatttaatt caatcatggg tggaaaatgc cgatggtgta aaggatggtc gttttatcgt   3720
gacgcctcct ctgtttgcga tgaagggaaa aaaagagaat accttacgta ttcttgatgc   3780
aacaaataac caattgccac aggaccggga aagtttattc tggatgaacg ttaaagcgat   3840
tccgtcaatg gataaatcaa aattgactga gaatacgcta cagctcgcaa ttatcagccg   3900
cattaaactg tactatcgcc cggctaaatt agcgttgcca cccgatcagg ccgcagaaaa   3960
attaagattt cgtcgtagcg cgaattctct gacgctgatt aacccgacac cctattacct   4020
gacggtaaca gagttgaatg ccggaacccg ggttcttgaa aatgcattgg tgcctccaat   4080
gggcgaaagc acggttaaat tgccttctga tgcaggaagc aatattactt accgaacaat   4140
aaatgattat ggcgcactta cccccaaaat gacgggcgta atggaataac gtcgactcta   4200
gaggatcccc gggtaccgag ctcgaattca ctggccgtcg ttttacaacg tcgtgactgg   4260
```

-continued gaaaaccctg gcgttaccca acttaatcgc cttgcagcac atccccctttt cgccagctgg 4320 cgtaatagcg aagaggcccg caccgatcgc ccttcccaac agttgcgcag cctgaatggc 4380
gaatggcgcc tgatgcggta ttttctcctt acgcatctgt gcggtatttc acaccgcata 4440
tggtgcactc tcagtacaat ctgctctgat gccgcatagt taagccagcc ccgacacccg 4500
ccaacacccg ctgacgcgcc ctgacgggct tgtctgctcc cggcatccgc ttacagacaa 4560
gctgtgaccg tctccgggag ctgcatgtgt cagaggtttt caccgtcatc accgaaacgc 4620
gcg 4623

<210> SEQ ID NO 162
<211> LENGTH: 42
<212> TYPE: DNA
<213> ORGANISM: Artificial Sequence
<220> FEATURE:
<223> OTHER INFORMATION: Oligonucleotide

<400> SEQUENCE: 162
aagatcttaa gctaagcttg aattctctga cgctgattaa cc 42

<210> SEQ ID NO 163
<211> LENGTH: 41
<212> TYPE: DNA
<213> ORGANISM: Artificial Sequence
<220> FEATURE:
<223> OTHER INFORMATION: Oligonucleotide

<400> SEQUENCE: 163
acgtaaagca tttctagacc gcggatagta atcgtgctat c 41

<210> SEQ ID NO 164
<211> LENGTH: 5681
<212> TYPE: DNA
<213> ORGANISM: Artificial Sequence
<220> FEATURE:
<223> OTHER INFORMATION: pFIMD

<400> SEQUENCE: 164
tcaccgtcat caccgaaacg cgcgagacga aagggcctcg tgatacgcct atttttatag 60
gttaatgtca tgataataat ggtttcttag acgtcaggtg gcacttttcg gggaaatgtg 120
cgcggaaccc ctatttgttt atttttctaa atacattcaa atatgtatcc gctcatgaga 180
caataaccct gataaatgct tcaataatat tgaaaaagga agagtatgag tattcaacat 240
ttccgtgtcg cccttattcc cttttttgcg gcattttgcc ttcctgtttt tgctcaccca 300
gaaacgctgg tgaaagtaaa agatgctgaa gatcagttgg gtgcacgagt gggttacatc 360
gaactggatc tcaacagcgg taagatcctt gagagttttc gccccgaaga acgttttcca 420
atgatgagca cttttaaagt tctgctatgt ggcgcggtat tatcccgtat tgacgccggg 480
caagagcaac tcggtcgccg catacactat tctcagaatg acttggttga gtactcacca 540
gtcacagaaa agcatcttac ggatggcatg acagtaagag aattatgcag tgctgccata 600
accatgagtg ataacactgc ggccaactta cttctgacaa cgatcggagg accgaaggag 660
ctaaccgctt ttttgcacaa catgggggat catgtaactc gccttgatcg ttgggaaccg 720
gagctgaatg aagccatacc aaacgacgag cgtgacacca cgatgcctgt agcaatggca 780
acaacgttgc gcaaactatt aactggcgaa ctacttactc tagcttcccg gcaacaatta 840
atagactgga tggaggcgga taaagttgca ggaccacttc tgcgctcggc ccttccggct 900

-continued

```
ggctggttta ttgctgataa atctggagcc ggtgagcgtg ggtctcgcgg tatcattgca    960
gcactggggc cagatggtaa gccctcccgt atcgtagtta tctacacgac ggggagtcag   1020
gcaactatgg atgaacgaaa tagacagatc gctgagatag gtgcctcact gattaagcat   1080
tggtaactgt cagaccaagt ttactcatat atactttaga ttgatttaaa acttcatttt   1140
taatttaaaa ggatctaggt gaagatcctt tttgataatc tcatgaccaa aatcccttaa   1200
cgtgagtttt cgttccactg agcgtcagac cccgtagaaa agatcaaagg atcttcttga   1260
gatccttttt ttctgcgcgt aatctgctgc ttgcaaacaa aaaaaccacc gctaccagcg   1320
gtggtttgtt tgccggatca agagctacca actctttttc cgaaggtaac tggcttcagc   1380
agagcgcaga taccaaatac tgtccttcta gtgtagccgt agttaggcca ccacttcaag   1440
aactctgtag caccgcctac atacctcgct ctgctaatcc tgttaccagt ggctgctgcc   1500
agtggcgata agtcgtgtct taccgggttg gactcaagac gatagttacc ggataaggcg   1560
cagcggtcgg gctgaacggg gggttcgtgc acacagccca gcttggagcg aacgacctac   1620
accgaactga gatacctaca gcgtgagcta tgagaaagcg ccacgcttcc cgaagggaga   1680
aaggcggaca ggtatccggt aagcggcagg gtcggaacag gagagcgcac gagggagctt   1740
ccagggggaa acgcctggta tctttatagt cctgtcgggt ttcgccacct ctgacttgag   1800
cgtcgatttt tgtgatgctc gtcagggggg cggagcctat ggaaaaacgc cagcaacgcg   1860
gcctttttac ggttcctggc cttttgctgg ccttttgctc acatgttctt tcctgcgtta   1920
tcccctgatt ctgtggataa ccgtattacc gcctttgagt gagctgatac cgctcgccgc   1980
agccgaacga ccgagcgcag cgagtcagtg agcgaggaag cggaagagcg cccaatacgc   2040
aaaccgcctc tccccgcgcg ttggccgatt cattaatgca gctggcacga caggtttccc   2100
gactggaaag cgggcagtga gcgcaacgca attaatgtga gttagctcac tcattaggca   2160
ccccaggctt tacactttat gcttccggct cgtatgttgt gtggaattgt gagcggataa   2220
caatttcaca caggaaacag ctatgaccat gattacgcca agcttgaatt ctctgacgct   2280
gattaacccg acaccctatt acctgacggt aacagagttg aatgccggaa cccgggttct   2340
tgaaaatgca ttggtgcctc caatgggcga aagcacggtt aaattgcctt ctgatgcagg   2400
aagcaatatt acttaccgaa caataaatga ttatggcgca cttaccccca aaatgacggg   2460
cgtaatggaa taacgcaggg ggaatttttc gcctgaataa aaagaattga ctgccggggt   2520
gattttaagc cggaggaata atgtcatatc tgaatttaag actttaccag cgaaacacac   2580
aatgcttgca tattcgtaag catcgtttgg ctggtttttt tgtccgactc gttgtcgcct   2640
gtgcttttgc cgcacaggca cctttgtcat ctgccgacct ctattttaat ccgcgctttt   2700
tagcggatga tccccaggct gtggccgatt tatcgcgttt tgaaaatggg caagaattac   2760
cgccagggac gtatcgcgtc gatatctatt tgaataatgg ttatatggca acgcgtgatg   2820
tcacatttaa tacgggcgac agtgaacaag ggattgttcc ctgcctgaca cgcgcgcaac   2880
tcgccagtat ggggctgaat acggcttctg tcgccggtat gaatctgctg gcggatgatg   2940
cctgtgtgcc attaaccaca atggtccagg acgctactgc gcatctggat gttggtcagc   3000
agcgactgaa cctgacgatc cctcaggcat ttatgagtaa tcgcgcgcgt ggttatattc   3060
ctcctgagtt atgggatccc ggtattaatg ccggattgct caattataat ttcagcggaa   3120
atagtgtaca gaatcggatt gggggtaaca gccattatgc atatttaaac ctacagagtg   3180
ggttaaatat tggtgcgtgg cgtttacgcg acaataccac ctggagttat aacagtagcg   3240
acagatcatc aggtagcaaa aataaatggc agcatatcaa tacctggctt gagcgagaca   3300
```

-continued

```
taataccgtt acgttcccgg ctgacgctgg gtgatggtta tactcagggc gatattttcg   3360
atggtattaa ctttcgcggc gcacaattgg cctcagatga caatatgtta cccgatagtc   3420
aaagaggatt tgccccggtg atccacggta ttgctcgtgg tactgcacag gtcactatta   3480
aacaaaatgg gtatgacatt tataatagta cggtgccacc ggggcctttt accatcaacg   3540
atatctatgc cgcaggtaat agtggtgact tgcaggtaac gatcaaagag gctgacggca   3600
gcacgcagat ttttaccgta ccctattcgt cagtcccgct tttgcaacgt gaagggcata   3660
ctcgttattc cattacggca ggagaatacc gtagtggaaa tgcgcagcag gaaaaaaccc   3720
gctttttcca gagtacatta ctccacggcc ttccggctgg ctggacaata tatggtggaa   3780
cgcaactggc ggatcgttat cgtgctttta atttcggtat cgggaaaaac atgggggcac   3840
tgggcgctct gtctgtggat atgacgcagg ctaattccac acttcccgat gacagtcagc   3900
atgacggaca atcggtgcgt tttctctata acaaatcgct caatgaatca ggcacgaata   3960
ttcagttagt gggttaccgt tattcgacca gcggatattt taatttcgct gatacaacat   4020
acagtcgaat gaatggctac aacattgaaa cacaggacgg agttattcag gttaagccga   4080
aattcaccga ctattacaac ctcgcttata acaaacgcgg gaaattacaa ctcaccgtta   4140
ctcagcaact cgggcgcaca tcaacactgt atttgagtgg tagccatcaa acttattggg   4200
gaacgagtaa tgtcgatgag caattccagg ctggattaaa tactgcgttc gaagatatca   4260
actggacgct cagctatagc ctgacgaaaa acgcctggca aaaaggacgg gatcagatgt   4320
tagcgcttaa cgtcaatatt cctttcagcc actggctgcg ttctgacagt aaatctcagt   4380
ggcgacatgc cagtgccagc tacagcatgt cacacgatct caacggtcgg atgaccaatc   4440
tggctggtgt atacggtacg ttgctggaag acaacaacct cagctatagc gtgcaaaccg   4500
gctatgccgg gggaggcgat ggaaatagcg gaagtacagg ctacgccacg ctgaattatc   4560
gcggtggtta cggcaatgcc aatatcggtt acagccatag cgatgatatt aagcagctct   4620
attacggagt cagcggtggg gtactggctc atgccaatgg cgtaacgctg ggcagccgt    4680
taaacgatac ggtggtgctt gttaaagcgc ctggcgcaaa agatgcaaaa gtcgaaaacc   4740
agacgggggt gcgtaccgac tggcgtggtt atgccgtgct gccttatgcc actgaatatc   4800
gggaaaatag agtggcgctg gataccaata ccctggctga taacgtcgat ttagataacg   4860
cggttgctaa cgttgttccc actcgtgggg cgatcgtgcg agcagagttt aaagcgcgcg   4920
ttgggataaa actgctcatg acgctgaccc acaataataa gccgctgccg tttggggcga   4980
tggtgacatc agagagtagc cagagtagcg gcattgttgc ggataatggt caggtttacc   5040
tcagcggaat gcctttagcg ggaaaagttc aggtgaaatg gggagaagag gaaaatgctc   5100
actgtgtcgc caattatcaa ctgccaccag agagtcagca gcagttatta acccagctat   5160
cagctgaatg tcgttaaggg ggcgtgatga gaaacaaacc tttttatctt ctgtgcgctt   5220
ttttgtggct ggcggtgagt cacgctttgg ctgcggatag cacgattact atccgcggtc   5280
tagaggatcc ccgggtaccg agctcgaatt cactggccgt cgttttacaa cgtcgtgact   5340
gggaaaaccc tggcgttacc caacttaatc gccttgcagc acatccccct ttcgccagct   5400
ggcgtaatag cgaagaggcc cgcaccgatc gcccttccca acagttgcgc agcctgaatg   5460
gcgaatggcg cctgatgcgg tattttctcc ttacgcatct gtgcggtatt tcacaccgca   5520
tatggtgcac tctcagtaca atctgctctg atgccgcata gttaagccag ccccgacacc   5580
cgccaacacc cgctgacgcg ccctgacggg cttgtctgct cccggcatcc gcttacagac   5640
```

-continued aagctgtgac cgtctccggg agctgcatgt gtcagaggtt t 5681

<210> SEQ ID NO 165
<211> LENGTH: 40
<212> TYPE: DNA
<213> ORGANISM: Artificial Sequence
<220> FEATURE:
<223> OTHER INFORMATION: Oligonucleotide

<400> SEQUENCE: 165
aattacgtga gcaagcttat gagaaacaaa cctttttatc 40

<210> SEQ ID NO 166
<211> LENGTH: 41
<212> TYPE: DNA
<213> ORGANISM: Artificial Sequence
<220> FEATURE:
<223> OTHER INFORMATION: Oligonucleotide

<400> SEQUENCE: 166
gactaaggcc tttctagatt attgataaac aaaagtcacg c 41

<210> SEQ ID NO 167
<211> LENGTH: 4637
<212> TYPE: DNA
<213> ORGANISM: Artificial Sequence
<220> FEATURE:
<223> OTHER INFORMATION: pFIMFGH

<400> SEQUENCE: 167
aaagggcctc gtgatacgcc tatttttata ggttaatgtc atgataataa tggtttctta 60
gacgtcaggt ggcacttttc ggggaaatgt gcgcggaacc cctatttgtt tatttttcta 120
aatacattca aatatgtatc cgctcatgag acaataaccc tgataaatgc ttcaataata 180
ttgaaaaagg aagagtatga gtattcaaca tttccgtgtc gcccttattc ccttttttgc 240
ggcattttgc cttcctgttt ttgctcaccc agaaacgctg gtgaaagtaa aagatgctga 300
agatcagttg ggtgcacgag tgggttacat cgaactggat ctcaacagcg gtaagatcct 360
tgagagtttt cgccccgaag aacgttttcc aatgatgagc acttttaaag ttctgctatg 420
tggcgcggta ttatcccgta ttgacgccgg gcaagagcaa ctcggtcgcc gcatacacta 480
ttctcagaat gacttggttg agtactcacc agtcacagaa aagcatctta cggatggcat 540
gacagtaaga gaattatgca gtgctgccat aaccatgagt gataacactg cggccaactt 600
acttctgaca acgatcggag gaccgaagga gctaaccgct tttttgcaca acatggggga 660
tcatgtaact cgccttgatc gttgggaacc ggagctgaat gaagccatac caaacgacga 720
gcgtgacacc acgatgcctg tagcaatggc aacaacgttg cgcaaactat taactggcga 780
actacttact ctagcttccc ggcaacaatt aatagactgg atggaggcgg ataaagttgc 840
aggaccactt ctgcgctcgg cccttccggc tggctggttt attgctgata aatctggagc 900
cggtgagcgt gggtctcgcg gtatcattgc agcactgggg ccagatggta agccctcccg 960
tatcgtagtt atctacacga cggggagtca ggcaactatg gatgaacgaa atagacagat 1020
cgctgagata ggtgcctcac tgattaagca ttggtaactg tcagaccaag tttactcata 1080
tatactttag attgatttaa aacttcattt ttaatttaaa aggatctagg tgaagatcct 1140
ttttgataat ctcatgacca aaatccctta acgtgagttt tcgttccact gagcgtcaga 1200
ccccgtagaa aagatcaaag gatcttcttg agatcctttt tttctgcgcg taatctgctg 1260
cttgcaaaca aaaaaaccac cgctaccagc ggtggtttgt ttgccggatc aagagctacc 1320

-continued

```
aactcttttt ccgaaggtaa ctggcttcag cagagcgcag ataccaaata ctgtccttct   1380
agtgtagccg tagttaggcc accacttcaa gaactctgta gcaccgccta catacctcgc   1440
tctgctaatc ctgttaccag tggctgctgc cagtggcgat aagtcgtgtc ttaccgggtt   1500
ggactcaaga cgatagttac cggataaggc gcagcggtcg ggctgaacgg ggggttcgtg   1560
cacacagccc agcttggagc gaacgaccta caccgaactg agatacctac agcgtgagct   1620
atgagaaagc gccacgcttc ccgaagggag aaaggcggac aggtatccgg taagcggcag   1680
ggtcggaaca ggagagcgca cgagggagct tccaggggga aacgcctggt atctttatag   1740
tcctgtcggg tttcgccacc tctgacttga gcgtcgattt ttgtgatgct cgtcaggggg   1800
gcggagccta tggaaaaacg ccagcaacgc ggccttttta cggttcctgg ccttttgctg   1860
gccttttgct cacatgttct ttcctgcgtt atcccctgat tctgtggata accgtattac   1920
cgcctttgag tgagctgata ccgctcgccg cagccgaacg accgagcgca gcgagtcagt   1980
gagcgaggaa gcggaagagc gcccaatacg caaaccgcct ctccccgcgc gttggccgat   2040
tcattaatgc agctggcacg acaggtttcc cgactggaaa gcgggcagtg agcgcaacgc   2100
aattaatgtg agttagctca ctcattaggc accccaggct ttacacttta tgcttccggc   2160
tcgtatgttg tgtggaattg tgagcggata acaatttcac acaggaaaca gctatgacca   2220
tgattacgcc aagcttatga gaaacaaacc tttttatctt ctgtgcgctt ttttgtggct   2280
ggcggtgagt cacgctttgg ctgcggatag cacgattact atccgcggct atgtcaggga   2340
taacggctgt agtgtggccg ctgaatcaac caattttact gttgatctga tggaaaacgc   2400
ggcgaagcaa tttaacaaca ttggcgcgac gactcctgtt gttccatttc gtattttgct   2460
gtcaccctgt ggtaatgccg tttctgccgt aaaggttggg tttactggcg ttgcagatag   2520
ccacaatgcc aacctgcttg cacttgaaaa tacggtgtca gcggcttcgg gactgggaat   2580
acagcttctg aatgagcagc aaaatcaaat accccttaat gctccatcgt ccgcgctttc   2640
gtggacgacc ctgacgccgg gtaaaccaaa tacgctgaat tttacgccc ggctaatggc   2700
gacacaggtg cctgtcactg cggggcatat caatgccacg gctaccttca ctcttgaata   2760
tcagtaactg gagatgctca tgaaatggtg caaacgtggg tatgtattgg cggcaatatt   2820
ggcgctcgca agtgcgacga tacaggcagc cgatgtcacc atcacggtga acggtaaggt   2880
cgtcgccaaa ccgtgtacgg tttccaccac caatgccacg gttgatctcg gcgatcttta   2940
ttctttcagt cttatgtctg ccggggcggc atcggcctgg catgatgttg cgcttgagtt   3000
gactaattgt ccggtgggaa cgtcgagggt cactgccagc ttcagcgggg cagccgacag   3060
taccggatat tataaaaacc aggggaccgc gcaaaacatc cagttagagc tacaggatga   3120
cagtggcaac acattgaata ctggcgcaac caaaacagtt caggtggatg attcctcaca   3180
atcagcgcac ttcccgttac aggtcagagc attgacagta aatggcggag ccactcaggg   3240
aaccattcag gcagtgatta gcatcaccta tacctacagc tgaacccgaa gagatgattg   3300
taatgaaacg agttattacc ctgtttgctg tactgctgat gggctggtcg gtaaatgcct   3360
ggtcattcgc ctgtaaaacc gccaatggta ccgctatccc tattggcggt ggcagcgcca   3420
atgtttatgt aaaccttgcg cccgtcgtga atgtggggca aaacctggtc gtggatcttt   3480
cgacgcaaat cttttgccat aacgattatc cggaaaccat tacagactat gtcacactgc   3540
aacgaggctc ggcttatggc ggcgtgttat ctaatttttc cgggaccgta aaatatagtg   3600
gcagtagcta tccatttcct accaccagcg aaacgccgcg cgttgtttat aattcgagaa   3660
```

-continued

```
cggataagcc gtggccggtg gcgctttatt tgacgcctgt gagcagtgcg ggcggggtgg   3720
cgattaaagc tggctcatta attgccgtgc ttattttgcg acagaccaac aactataaca   3780
gcgatgattt ccagtttgtg tggaatattt acgccaataa tgatgtggtg gtgcctactg   3840
gcggctgcga tgtttctgct cgtgatgtca ccgttactct gccggactac cctggttcag   3900
tgccaattcc tcttaccgtt tattgtgcga aaagccaaaa cctggggtat tacctctccg   3960
gcacaaccgc agatgcgggc aactcgattt tcaccaatac cgcgtcgttt tcacctgcac   4020
agggcgtcgg cgtacagttg acgcgcaacg gtacgattat tccagcgaat aacacggtat   4080
cgttaggagc agtagggact tcggcggtga gtctgggatt aacggcaaat tatgcacgta   4140
ccggagggca ggtgactgca gggaatgtgc aatcgattat tggcgtgact tttgtttatc   4200
aataatctag aggatccccg ggtaccgagc tcgaattcac tggccgtcgt tttacaacgt   4260
cgtgactggg aaaaccctgg cgttacccaa cttaatcgcc ttgcagcaca tccccctttc   4320
gccagctggc gtaatagcga agaggcccgc accgatcgcc cttcccaaca gttgcgcagc   4380
ctgaatggcg aatggcgcct gatgcggtat tttctcctta cgcatctgtg cggtatttca   4440
caccgcatat ggtgcactct cagtacaatc tgctctgatg ccgcatagtt aagccagccc   4500
cgacacccgc caacacccgc tgacgcgccc tgacgggctt gtctgctccc ggcatccgct   4560
tacagacaag ctgtgaccgt ctccgggagc tgcatgtgtc agaggttttc accgtcatca   4620
ccgaaacgcg cgagacg                                                  4637
```

<210> SEQ ID NO 168
<211> LENGTH: 9299
<212> TYPE: DNA
<213> ORGANISM: Artificial Sequence
<220> FEATURE:
<223> OTHER INFORMATION: pFIMAICDFGH

<400> SEQUENCE: 168

```
cgagacgaaa gggcctcgtg atacgcctat ttttataggt taatgtcatg ataataatgg     60
tttcttagac gtcaggtggc acttttcggg gaaatgtgcg cggaacccct atttgtttat    120
ttttctaaat acattcaaat atgtatccgc tcatgagaca ataaccctga taaatgcttc    180
aataatattg aaaaaggaag agtatgagta ttcaacattt ccgtgtcgcc cttattccct    240
tttttgcggc attttgcctt cctgtttttg ctcacccaga aacgctggtg aaagtaaaag    300
atgctgaaga tcagttgggt gcacgagtgg gttacatcga actggatctc aacagcggta    360
agatccttga gagttttcgc cccgaagaac gttttccaat gatgagcact tttaaagttc    420
tgctatgtgg cgcggtatta tcccgtattg acgccgggca agagcaactc ggtcgccgca    480
tacactattc tcagaatgac ttggttgagt actcaccagt cacagaaaag catcttacgg    540
atggcatgac agtaagagaa ttatgcagtg ctgccataac catgagtgat aacactgcgg    600
ccaacttact tctgacaacg atcggaggac cgaaggagct aaccgctttt ttgcacaaca    660
tgggggatca tgtaactcgc cttgatcgtt gggaaccgga gctgaatgaa gccataccaa    720
acgacgagcg tgacaccacg atgcctgtag caatggcaac aacgttgcgc aaactattaa    780
ctggcgaact acttactcta gcttcccggc aacaattaat agactggatg gaggcggata    840
aagttgcagg accacttctg cgctcggccc ttccggctgg ctggtttatt gctgataaat    900
ctggagccgg tgagcgtggg tctcgcggta tcattgcagc actggggcca gatggtaagc    960
cctcccgtat cgtagttatc tacacgacgg ggagtcaggc aactatggat gaacgaaata   1020
gacagatcgc tgagataggt gcctcactga ttaagcattg gtaactgtca gaccaagttt   1080
```

-continued

```
actcatatat actttagatt gatttaaaac ttcattttta atttaaaagg atctaggtga   1140
agatcctttt tgataatctc atgaccaaaa tcccttaacg tgagttttcg ttccactgag   1200
cgtcagaccc cgtagaaaag atcaaaggat cttcttgaga tccttttttt ctgcgcgtaa   1260
tctgctgctt gcaaacaaaa aaaccaccgc taccagcggt ggtttgtttg ccggatcaag   1320
agctaccaac tctttttccg aaggtaactg gcttcagcag agcgcagata ccaaatactg   1380
tccttctagt gtagccgtag ttaggccacc acttcaagaa ctctgtagca ccgcctacat   1440
acctcgctct gctaatcctg ttaccagtgg ctgctgccag tggcgataag tcgtgtctta   1500
ccgggttgga ctcaagacga tagttaccgg ataaggcgca gcggtcgggc tgaacggggg   1560
gttcgtgcac acagcccagc ttggagcgaa cgacctacac cgaactgaga tacctacagc   1620
gtgagctatg agaaagcgcc acgcttcccg aagggagaaa ggcggacagg tatccggtaa   1680
gcggcagggt cggaacagga gagcgcacga gggagcttcc agggggaaac gcctggtatc   1740
tttatagtcc tgtcgggttt cgccacctct gacttgagcg tcgatttttg tgatgctcgt   1800
caggggggcg gagcctatgg aaaaacgcca gcaacgcggc ctttttacgg ttcctggcct   1860
tttgctggcc ttttgctcac atgttctttc ctgcgttatc ccctgattct gtggataacc   1920
gtattaccgc ctttgagtga gctgataccg ctcgccgcag ccgaacgacc gagcgcagcg   1980
agtcagtgag cgaggaagcg gaagagcgcc caatacgcaa accgcctctc cccgcgcgtt   2040
ggccgattca ttaatgcagc tggcacgaca ggtttcccga ctggaaagcg ggcagtgagc   2100
gcaacgcaat taatgtgagt tagctcactc attaggcacc ccaggcttta cactttatgc   2160
ttccggctcg tatgttgtgt ggaattgtga gcggataaca atttcacaca ggaaacagct   2220
atgaccatga ttacgccaag cttataatag aaatagtttt ttgaaaggaa agcagcatga   2280
aaattaaaac tctggcaatc gttgttctgt cggctctgtc cctcagttct acagcggctc   2340
tggccgctgc cacgacggtt aatggtggga ccgttcactt taaaggggaa gttgttaacg   2400
ccgcttgcgc agttgatgca ggctctgttg atcaaaccgt tcagttagga caggttcgta   2460
ccgcatcgct ggcacaggaa ggagcaacca gttctgctgt cggttttaac attcagctga   2520
atgattgcga taccaatgtt gcatctaaag ccgctgttgc ctttttaggt acggcgattg   2580
atgcgggtca taccaacgtt ctggctctgc agagttcagc tgcgggtagc gcaacaaacg   2640
ttggtgtgca gatcctggac agaacgggtg ctgcgctgac gctggatggt gcgacattta   2700
gttcagaaac aaccctgaat aacggaacca ataccattcc gttccaggcg cgttattttg   2760
caaccggggc cgcaaccccg ggtgctgcta atgcggatgc gaccttcaag gttcagtatc   2820
aataacctac ccaggttcag ggacgtcatt acgggcaggg atgcccaccc ttgtgcgata   2880
aaaataacga tgaaaaggaa gagattattt ctattagcgt cgttgctgcc aatgtttgct   2940
ctggccggaa ataaatggaa taccacgttg cccggcggaa atatgcaatt tcagggcgtc   3000
attattgcgg aaacttgccg gattgaagcc ggtgataaac aaatgacggt caatatgggg   3060
caaatcagca gtaaccggtt tcatgcggtt ggggaagata gcgcaccggt gccttttgtt   3120
attcatttac gggaatgtag cacggtggtg agtgaacgtg taggtgtggc gtttcacggt   3180
gtcgcggatg gtaaaaatcc ggatgtgctt tccgtgggag aggggccagg gatagccacc   3240
aatattggcg tagcgttgtt tgatgatgaa ggaaacctcg taccgattaa tcgtcctcca   3300
gcaaactgga aacggcttta ttcaggctct acttcgctac atttcatcgc caaatatcgt   3360
gctaccgggc gtcgggttac tggcggcatc gccaatgccc aggcctggtt ctctttaacc   3420
```

-continued

```
tatcagtaat tgttcagcag ataatgtgat aacaggaaca ggacagtgag taataaaaac   3480
gtcaatgtaa ggaaatcgca ggaaataaca ttctgcttgc tggcaggtat cctgatgttc   3540
atggcaatga tggttgccgg acgcgctgaa gcgggagtgg ccttaggtgc gactcgcgta   3600
atttatccgg cagggcaaaa acaagagcaa cttgccgtga caaataatga tgaaaatagt   3660
acctatttaa ttcaatcatg ggtggaaaat gccgatggtg taaaggatgg tcgttttatc   3720
gtgacgcctc ctctgtttgc gatgaaggga aaaaaagaga ataccttacg tattcttgat   3780
gcaacaaata accaattgcc acaggaccgg gaaagtttat tctggatgaa cgttaaagcg   3840
attccgtcaa tggataaatc aaaattgact gagaatacgc tacagctcgc aattatcagc   3900
cgcattaaac tgtactatcg cccggctaaa ttagcgttgc cacccgatca ggccgcagaa   3960
aaattaagat ttcgtcgtag cgcgaattct ctgacgctga ttaacccgac accctattac   4020
ctgacggtaa cagagttgaa tgccggaacc cgggttcttg aaaatgcatt ggtgcctcca   4080
atgggcgaaa gcacggttaa attgccttct gatgcaggaa gcaatattac ttaccgaaca   4140
ataaatgatt atggcgcact tacccccaaa atgacgggcg taatggaata acgcaggggg   4200
aatttttcgc ctgaataaaa agaattgact gccggggtga ttttaagccg gaggaataat   4260
gtcatatctg aatttaagac tttaccagcg aaacacacaa tgcttgcata ttcgtaagca   4320
tcgtttggct ggtttttttg tccgactcgt tgtcgcctgt gcttttgccg cacaggcacc   4380
tttgtcatct gccgacctct attttaatcc gcgcttttta gcggatgatc cccaggctgt   4440
ggccgattta tcgcgttttg aaaatgggca agaattaccg ccagggacgt atcgcgtcga   4500
tatctatttg aataatggtt atatggcaac gcgtgatgtc acatttaata cgggcgacag   4560
tgaacaaggg attgttccct gcctgacacg cgcgcaactc gccagtatgg ggctgaatac   4620
ggcttctgtc gccggtatga atctgctggc ggatgatgcc tgtgtgccat taaccacaat   4680
ggtccaggac gctactgcgc atctggatgt tggtcagcag cgactgaacc tgacgatccc   4740
tcaggcattt atgagtaatc gcgcgcgtgg ttatattcct cctgagttat gggatcccgg   4800
tattaatgcc ggattgctca attataattt cagcggaaat agtgtacaga atcggattgg   4860
gggtaacagc cattatgcat atttaaacct acagagtggg ttaaatattg gtgcgtggcg   4920
tttacgcgac aataccacct ggagttataa cagtagcgac agatcatcag gtagcaaaaa   4980
taaatggcag catatcaata cctggcttga gcgagacata ataccgttac gttcccggct   5040
gacgctgggt gatggttata ctcagggcga tattttcgat ggtattaact ttcgcggcgc   5100
acaattggcc tcagatgaca atatgttacc cgatagtcaa agaggatttg ccccggtgat   5160
ccacggtatt gctcgtggta ctgcacaggt cactattaaa caaaatgggt atgacattta   5220
taatagtacg gtgccaccgg ggccttttac catcaacgat atctatgccg caggtaatag   5280
tggtgacttg caggtaacga tcaaagaggc tgacggcagc acgcagattt ttaccgtacc   5340
ctattcgtca gtcccgcttt tgcaacgtga agggcatact cgttattcca ttacggcagg   5400
agaataccgt agtggaaatg cgcagcagga aaaaacccgc tttttccaga gtacattact   5460
ccacggcctt ccggctggct ggacaatata tggtggaacg caactggcgg atcgttatcg   5520
tgcttttaat ttcggtatcg ggaaaaacat gggggcactg ggcgctctgt ctgtggatat   5580
gacgcaggct aattccacac ttcccgatga cagtcagcat gacggacaat cggtgcgttt   5640
tctctataac aaatcgctca atgaatcagg cacgaatatt cagttagtgg gttaccgtta   5700
ttcgaccagc ggatatttta atttcgctga tacaacatac agtcgaatga atggctacaa   5760
cattgaaaca caggacggag ttattcaggt taagccgaaa ttcaccgact attacaacct   5820
```

-continued

```
cgcttataac aaacgcggga aattacaact caccgttact cagcaactcg ggcgcacatc   5880
aacactgtat ttgagtggta gccatcaaac ttattgggga acgagtaatg tcgatgagca   5940
attccaggct ggattaaata ctgcgttcga agatatcaac tggacgctca gctatagcct   6000
gacgaaaaac gcctggcaaa aaggacggga tcagatgtta gcgcttaacg tcaatattcc   6060
tttcagccac tggctgcgtt ctgacagtaa atctcagtgg cgacatgcca gtgccagcta   6120
cagcatgtca cacgatctca acggtcggat gaccaatctg gctggtgtat acggtacgtt   6180
gctggaagac aacaacctca gctatagcgt gcaaaccggc tatgccgggg gaggcgatgg   6240
aaatagcgga agtacaggct acgccacgct gaattatcgc ggtggttacg gcaatgccaa   6300
tatcggttac agccatagcg atgatattaa gcagctctat tacggagtca gcggtggggt   6360
actggctcat gccaatggcg taacgctggg gcagccgtta aacgatacgg tggtgcttgt   6420
taaagcgcct ggcgcaaaag atgcaaaagt cgaaaaccag acgggggtgc gtaccgactg   6480
gcgtggttat gccgtgctgc cttatgccac tgaatatcgg gaaaatagag tggcgctgga   6540
taccaatacc ctggctgata acgtcgattt agataacgcg gttgctaacg ttgttcccac   6600
tcgtggggcg atcgtgcgag cagagtttaa agcgcgcgtt gggataaaac tgctcatgac   6660
gctgacccac aataataagc cgctgccgtt tggggcgatg gtgacatcag agagtagcca   6720
gagtagcggc attgttgcgg ataatggtca ggtttacctc agcggaatgc ctttagcggg   6780
aaaagttcag gtgaaatggg gagaagagga aaatgctcac tgtgtcgcca attatcaact   6840
gccaccagag agtcagcagc agttattaac ccagctatca gctgaatgtc gttaaggggg   6900
cgtgatgaga aacaaacctt tttatcttct gtgcgctttt ttgtggctgg cggtgagtca   6960
cgctttggct gcggatagca cgattactat ccgcggctat gtcagggata acggctgtag   7020
tgtggccgct gaatcaacca attttactgt tgatctgatg gaaaacgcgg cgaagcaatt   7080
taacaacatt ggcgcgacga ctcctgttgt tccatttcgt attttgctgt caccctgtgg   7140
taatgccgtt tctgccgtaa aggttgggtt tactggcgtt gcagatagcc acaatgccaa   7200
cctgcttgca cttgaaaata cggtgtcagc ggcttcggga ctgggaatac agcttctgaa   7260
tgagcagcaa aatcaaatac cccttaatgc tccatcgtcc gcgctttcgt ggacgaccct   7320
gacgccgggt aaaccaaata cgctgaattt ttacgcccgg ctaatggcga cacaggtgcc   7380
tgtcactgcg gggcatatca atgccacggc taccttcact cttgaatatc agtaactgga   7440
gatgctcatg aaatggtgca aacgtgggta tgtattggcg gcaatattgg cgctcgcaag   7500
tgcgacgata caggcagccg atgtcaccat cacggtgaac ggtaaggtcg tcgccaaacc   7560
gtgtacggtt tccaccacca atgccacggt tgatctcggc gatctttatt ctttcagtct   7620
tatgtctgcc ggggcggcat cggcctggca tgatgttgcg cttgagttga ctaattgtcc   7680
ggtgggaacg tcgagggtca ctgccagctt cagcggggca gccgacagta ccggatatta   7740
taaaaaccag gggaccgcgc aaaacatcca gttagagcta caggatgaca gtggcaacac   7800
attgaatact ggcgcaacca aaacagttca ggtggatgat tcctcacaat cagcgcactt   7860
cccgttacag gtcagagcat tgacagtaaa tggcggagcc actcagggaa ccattcaggc   7920
agtgattagc atcacctata cctacagctg aacccgaaga gatgattgta atgaaacgag   7980
ttattaccct gtttgctgta ctgctgatgg gctggtcggt aaatgcctgg tcattcgcct   8040
gtaaaaccgc caatggtacc gctatcccta ttggcggtgg cagcgccaat gtttatgtaa   8100
accttgcgcc cgtcgtgaat gtggggcaaa acctggtcgt ggatctttcg acgcaaatct   8160
```

-continued

```
tttgccataa cgattatccg gaaaccatta cagactatgt cacactgcaa cgaggctcgg   8220

cttatggcgg cgtgttatct aatttttccg ggaccgtaaa atatagtggc agtagctatc   8280

catttcctac caccagcgaa acgccgcgcg ttgtttataa ttcgagaacg gataagccgt   8340

ggccggtggc gctttatttg acgcctgtga gcagtgcggg cggggtggcg attaaagctg   8400

gctcattaat tgccgtgctt attttgcgac agaccaacaa ctataacagc gatgatttcc   8460

agtttgtgtg gaatatttac gccaataatg atgtggtggt gcctactggc ggctgcgatg   8520

tttctgctcg tgatgtcacc gttactctgc cggactaccc tggttcagtg ccaattcctc   8580

ttaccgttta ttgtgcgaaa agccaaaacc tggggtatta cctctccggc acaaccgcag   8640

atgcgggcaa ctcgattttc accaataccg cgtcgttttc acctgcacag ggcgtcggcg   8700

tacagttgac gcgcaacggt acgattattc cagcgaataa cacggtatcg ttaggagcag   8760

tagggacttc ggcggtgagt ctgggattaa cggcaaatta tgcacgtacc ggagggcagg   8820

tgactgcagg gaatgtgcaa tcgattattg gcgtgacttt tgtttatcaa taatctagaa   8880

ggatccccgg gtaccgagct cgaattcact ggccgtcgtt ttacaacgtc gtgactggga   8940

aaaccctggc gttacccaac ttaatcgcct tgcagcacat ccccctttcg ccagctggcg   9000

taatagcgaa gaggcccgca ccgatcgccc ttcccaacag ttgcgcagcc tgaatggcga   9060

atggcgcctg atgcggtatt ttctccttac gcatctgtgc ggtatttcac accgcatatg   9120

gtgcactctc agtacaatct gctctgatgc cgcatagtta agccagcccc gacacccgcc   9180

aacacccgct gacgcgccct gacgggcttg tctgctcccg gcatccgctt acagacaagc   9240

tgtgaccgtc tccgggagct gcatgtgtca gaggttttca ccgtcatcac cgaaacgcg    9299
```

```
<210> SEQ ID NO 169
<211> LENGTH: 8464
<212> TYPE: DNA
<213> ORGANISM: Artificial Sequence
<220> FEATURE:
<223> OTHER INFORMATION: pFIMAICDFG

<400> SEQUENCE: 169
```

```
cgagacgaaa gggcctcgtg atacgcctat ttttataggt taatgtcatg ataataatgg     60

tttcttagac gtcaggtggc acttttcggg gaaatgtgcg cggaacccct atttgtttat    120

ttttctaaat acattcaaat atgtatccgc tcatgagaca ataaccctga taaatgcttc    180

aataatattg aaaaaggaag agtatgagta ttcaacattt ccgtgtcgcc cttattccct    240

tttttgcggc attttgcctt cctgtttttg ctcacccaga aacgctggtg aaagtaaaag    300

atgctgaaga tcagttgggt gcacgagtgg gttacatcga actggatctc aacagcggta    360

agatccttga gagttttcgc cccgaagaac gttttccaat gatgagcact tttaaagttc    420

tgctatgtgg cgcggtatta tcccgtattg acgccgggca agagcaactc ggtcgccgca    480

tacactattc tcagaatgac ttggttgagt actcaccagt cacagaaaag catcttacgg    540

atggcatgac agtaagagaa ttatgcagtg ctgccataac catgagtgat aacactgcgg    600

ccaacttact tctgacaacg atcggaggac cgaaggagct aaccgctttt ttgcacaaca    660

tgggggatca tgtaactcgc cttgatcgtt gggaaccgga gctgaatgaa gccataccaa    720

acgacgagcg tgacaccacg atgcctgtag caatggcaac aacgttgcgc aaactattaa    780

ctggcgaact acttactcta gcttcccggc aacaattaat agactggatg gaggcggata    840

aagttgcagg accacttctg cgctcggccc ttccggctgg ctggtttatt gctgataaat    900

ctggagccgg tgagcgtggg tctcgcggta tcattgcagc actggggcca gatggtaagc    960
```

-continued

```
cctcccgtat cgtagttatc tacacgacgg ggagtcaggc aactatggat gaacgaaata   1020
gacagatcgc tgagataggt gcctcactga ttaagcattg gtaactgtca gaccaagttt   1080
actcatatat actttagatt gatttaaaac ttcattttta atttaaaagg atctaggtga   1140
agatcctttt tgataatctc atgaccaaaa tcccttaacg tgagttttcg ttccactgag   1200
cgtcagaccc cgtagaaaag atcaaaggat cttcttgaga tccttttttt ctgcgcgtaa   1260
tctgctgctt gcaaacaaaa aaaccaccgc taccagcggt ggtttgtttg ccggatcaag   1320
agctaccaac tctttttccg aaggtaactg gcttcagcag agcgcagata ccaaatactg   1380
tccttctagt gtagccgtag ttaggccacc acttcaagaa ctctgtagca ccgcctacat   1440
acctcgctct gctaatcctg ttaccagtgg ctgctgccag tggcgataag tcgtgtctta   1500
ccgggttgga ctcaagacga tagttaccgg ataaggcgca gcggtcgggc tgaacggggg   1560
gttcgtgcac acagcccagc ttggagcgaa cgacctacac cgaactgaga tacctacagc   1620
gtgagctatg agaaagcgcc acgcttcccg aagggagaaa ggcggacagg tatccggtaa   1680
gcggcagggt cggaacagga gagcgcacga gggagcttcc agggggaaac gcctggtatc   1740
tttatagtcc tgtcgggttt cgccacctct gacttgagcg tcgatttttg tgatgctcgt   1800
caggggggcg gagcctatgg aaaaacgcca gcaacgcggc ctttttacgg ttcctggcct   1860
tttgctggcc ttttgctcac atgttctttc ctgcgttatc ccctgattct gtggataacc   1920
gtattaccgc ctttgagtga gctgataccg ctcgccgcag ccgaacgacc gagcgcagcg   1980
agtcagtgag cgaggaagcg gaagagcgcc caatacgcaa accgcctctc cccgcgcgtt   2040
ggccgattca ttaatgcagc tggcacgaca ggtttcccga ctggaaagcg ggcagtgagc   2100
gcaacgcaat taatgtgagt tagctcactc attaggcacc ccaggcttta cactttatgc   2160
ttccggctcg tatgttgtgt ggaattgtga gcggataaca atttcacaca ggaaacagct   2220
atgaccatga ttacgccaag cttataatag aaatagtttt ttgaaaggaa agcagcatga   2280
aaattaaaac tctggcaatc gttgttctgt cggctctgtc cctcagttct acagcggctc   2340
tggccgctgc cacgacggtt aatggtggga ccgttcactt taaaggggaa gttgttaacg   2400
ccgcttgcgc agttgatgca ggctctgttg atcaaaccgt tcagttagga caggttcgta   2460
ccgcatcgct ggcacaggaa ggagcaacca gttctgctgt cggttttaac attcagctga   2520
atgattgcga taccaatgtt gcatctaaag ccgctgttgc ctttttaggt acggcgattg   2580
atgcgggtca taccaacgtt ctggctctgc agagttcagc tgcgggtagc gcaacaaacg   2640
ttggtgtgca gatcctggac agaacgggtg ctgcgctgac gctggatggt gcgacattta   2700
gttcagaaac aaccctgaat aacggaacca ataccattcc gttccaggcg cgttattttg   2760
caaccggggc cgcaaccccg ggtgctgcta atgcggatgc gaccttcaag gttcagtatc   2820
aataacctac ccaggttcag ggacgtcatt acgggcaggg atgcccaccc ttgtgcgata   2880
aaaataacga tgaaaaggaa gagattattt ctattagcgt cgttgctgcc aatgtttgct   2940
ctggccggaa ataaatggaa taccacgttg cccggcggaa atatgcaatt tcagggcgtc   3000
attattgcgg aaacttgccg gattgaagcc ggtgataaac aaatgacggt caatatgggg   3060
caaatcagca gtaaccggtt tcatgcggtt ggggaagata gcgcaccggt gccttttgtt   3120
attcatttac gggaatgtag cacggtggtg agtgaacgtg taggtgtggc gtttcacggt   3180
gtcgcggatg gtaaaaatcc ggatgtgctt tccgtgggag aggggccagg gatagccacc   3240
aatattggcg tagcgttgtt tgatgatgaa ggaaacctcg taccgattaa tcgtcctcca   3300
```

-continued gcaaactgga aacggcttta ttcaggctct acttcgctac atttcatcgc caaatatcgt 3360
gctaccgggc gtcgggttac tggcggcatc gccaatgccc aggcctggtt ctctttaacc 3420
tatcagtaat tgttcagcag ataatgtgat aacaggaaca ggacagtgag taataaaaac 3480
gtcaatgtaa ggaaatcgca ggaaataaca ttctgcttgc tggcaggtat cctgatgttc 3540
atggcaatga tggttgccgg acgcgctgaa gcgggagtgg ccttaggtgc gactcgcgta 3600
atttatccgg cagggcaaaa acaagagcaa cttgccgtga caaataatga tgaaaatagt 3660
acctatttaa ttcaatcatg ggtggaaaat gccgatggtg taaaggatgg tcgttttatc 3720
gtgacgcctc ctctgtttgc gatgaaggga aaaaaagaga ataccttacg tattcttgat 3780
gcaacaaata accaattgcc acaggaccgg gaaagtttat tctggatgaa cgttaaagcg 3840
attccgtcaa tggataaatc aaaattgact gagaatacgc tacagctcgc aattatcagc 3900
cgcattaaac tgtactatcg cccggctaaa ttagcgttgc cacccgatca ggccgcagaa 3960
aaattaagat ttcgtcgtag cgcgaattct ctgacgctga ttaacccgac accctattac 4020
ctgacggtaa cagagttgaa tgccggaacc cgggttcttg aaaatgcatt ggtgcctcca 4080
atgggcgaaa gcacggttaa attgccttct gatgcaggaa gcaatattac ttaccgaaca 4140
ataaatgatt atggcgcact tacccccaaa atgacgggcg taatggaata acgcaggggg 4200
aatttttcgc ctgaataaaa agaattgact gccggggtga ttttaagccg gaggaataat 4260
gtcatatctg aatttaagac tttaccagcg aaacacacaa tgcttgcata ttcgtaagca 4320
tcgtttggct ggtttttttg tccgactcgt tgtcgcctgt gcttttgccg cacaggcacc 4380
tttgtcatct gccgacctct attttaatcc gcgcttttta gcggatgatc cccaggctgt 4440
ggccgattta tcgcgttttg aaaatgggca agaattaccg ccagggacgt atcgcgtcga 4500
tatctatttg aataatggtt atatggcaac gcgtgatgtc acatttaata cgggcgacag 4560
tgaacaaggg attgttccct gcctgacacg cgcgcaactc gccagtatgg ggctgaatac 4620
ggcttctgtc gccggtatga atctgctggc ggatgatgcc tgtgtgccat taaccacaat 4680
ggtccaggac gctactgcgc atctggatgt tggtcagcag cgactgaacc tgacgatccc 4740
tcaggcattt atgagtaatc gcgcgcgtgg ttatattcct cctgagttat gggatcccgg 4800
tattaatgcc ggattgctca attataattt cagcggaaat agtgtacaga atcggattgg 4860
gggtaacagc cattatgcat atttaaacct acagagtggg ttaaatattg gtgcgtggcg 4920
tttacgcgac aataccacct ggagttataa cagtagcgac agatcatcag gtagcaaaaa 4980
taaatggcag catatcaata cctggcttga gcgagacata ataccgttac gttcccggct 5040
gacgctgggt gatggttata ctcagggcga tattttcgat ggtattaact ttcgcggcgc 5100
acaattggcc tcagatgaca atatgttacc cgatagtcaa agaggatttg ccccggtgat 5160
ccacggtatt gctcgtggta ctgcacaggt cactattaaa caaaatgggt atgacattta 5220
taatagtacg gtgccaccgg ggccttttac catcaacgat atctatgccg caggtaatag 5280
tggtgacttg caggtaacga tcaaagaggc tgacggcagc acgcagattt ttaccgtacc 5340
ctattcgtca gtcccgcttt tgcaacgtga agggcatact cgttattcca ttacggcagg 5400
agaataccgt agtggaaatg cgcagcagga aaaaacccgc tttttccaga gtacattact 5460
ccacggcctt ccggctggct ggacaatata tggtggaacg caactggcgg atcgttatcg 5520
tgcttttaat ttcggtatcg ggaaaaacat gggggcactg ggcgctctgt ctgtggatat 5580
gacgcaggct aattccacac ttcccgatga cagtcagcat gacggacaat cggtgcgttt 5640
tctctataac aaatcgctca atgaatcagg cacgaatatt cagttagtgg gttaccgtta 5700

-continued

```
ttcgaccagc ggatatttta atttcgctga tacaacatac agtcgaatga atggctacaa   5760
cattgaaaca caggacggag ttattcaggt taagccgaaa ttcaccgact attacaacct   5820
cgcttataac aaacgcggga aattacaact caccgttact cagcaactcg ggcgcacatc   5880
aacactgtat ttgagtggta gccatcaaac ttattgggga acgagtaatg tcgatgagca   5940
attccaggct ggattaaata ctgcgttcga agatatcaac tggacgctca gctatagcct   6000
gacgaaaaac gcctggcaaa aaggacggga tcagatgtta gcgcttaacg tcaatattcc   6060
tttcagccac tggctgcgtt ctgacagtaa atctcagtgg cgacatgcca gtgccagcta   6120
cagcatgtca cacgatctca acggtcggat gaccaatctg gctggtgtat acggtacgtt   6180
gctggaagac aacaacctca gctatagcgt gcaaaccggc tatgccgggg gaggcgatgg   6240
aaatagcgga agtacaggct acgccacgct gaattatcgc ggtggttacg gcaatgccaa   6300
tatcggttac agccatagcg atgatattaa gcagctctat tacggagtca gcggtggggt   6360
actggctcat gccaatggcg taacgctggg gcagccgtta aacgatacgg tggtgcttgt   6420
taaagcgcct ggcgcaaaag atgcaaaagt cgaaaaccag acgggggtgc gtaccgactg   6480
gcgtggttat gccgtgctgc cttatgccac tgaatatcgg gaaaatagag tggcgctgga   6540
taccaatacc ctggctgata acgtcgattt agataacgcg gttgctaacg ttgttcccac   6600
tcgtggggcg atcgtgcgag cagagtttaa agcgcgcgtt gggataaaac tgctcatgac   6660
gctgacccac aataataagc cgctgccgtt tggggcgatg gtgacatcag agagtagcca   6720
gagtagcggc attgttgcgg ataatggtca ggtttacctc agcggaatgc ctttagcggg   6780
aaaagttcag gtgaaatggg gagaagagga aaatgctcac tgtgtcgcca attatcaact   6840
gccaccagag agtcagcagc agttattaac ccagctatca gctgaatgtc gttaaggggg   6900
cgtgatgaga aacaaacctt tttatcttct gtgcgctttt ttgtggctgg cggtgagtca   6960
cgctttggct gcggatagca cgattactat ccgcggctat gtcagggata acggctgtag   7020
tgtggccgct gaatcaacca attttactgt tgatctgatg gaaaacgcgg cgaagcaatt   7080
taacaacatt ggcgcgacga ctcctgttgt tccatttcgt attttgctgt caccctgtgg   7140
taatgccgtt tctgccgtaa aggttgggtt tactggcgtt gcagatagcc acaatgccaa   7200
cctgcttgca cttgaaaata cggtgtcagc ggcttcggga ctgggaatac agcttctgaa   7260
tgagcagcaa aatcaaatac cccttaatgc tccatcgtcc gcgctttcgt ggacgaccct   7320
gacgccgggt aaaccaaata cgctgaattt ttacgcccgg ctaatggcga cacaggtgcc   7380
tgtcactgcg gggcatatca atgccacggc taccttcact cttgaatatc agtaactgga   7440
gatgctcatg aaatggtgca aacgtgggta tgtattggcg gcaatattgg cgctcgcaag   7500
tgcgacgata caggcagccg atgtcaccat cacggtgaac ggtaaggtcg tcgccaaacc   7560
gtgtacggtt tccaccacca atgccacggt tgatctcggc gatctttatt ctttcagtct   7620
tatgtctgcc ggggcggcat cggcctggca tgatgttgcg cttgagttga ctaattgtcc   7680
ggtgggaacg tcgagggtca ctgccagctt cagcggggca gccgacagta ccggatatta   7740
taaaaaccag gggaccgcgc aaaacatcca gttagagcta caggatgaca gtggcaacac   7800
attgaatact ggcgcaacca aaacagttca ggtggatgat tcctcacaat cagcgcactt   7860
cccgttacag gtcagagcat tgacagtaaa tggcggagcc actcagggaa ccattcaggc   7920
agtgattagc atcacctata cctacagctg aacccgaaga gatgattgta atgaaacgag   7980
ttattaccct gtttgctgta ctgctgatgg gctggtcggt aaatgcctgg tcattcgcct   8040
```

-continued

```
gtaaaaccgc caatggtacc gagctcgaat tcactggccg tcgttttaca acgtcgtgac   8100

tgggaaaacc ctggcgttac ccaacttaat cgccttgcag cacatccccc tttcgccagc   8160

tggcgtaata gcgaagaggc ccgcaccgat cgcccttccc aacagttgcg cagcctgaat   8220

ggcgaatggc gcctgatgcg gtattttctc cttacgcatc tgtgcggtat ttcacaccgc   8280

atatggtgca ctctcagtac aatctgctct gatgccgcat agttaagcca gccccgacac   8340

ccgccaacac ccgctgacgc gccctgacgg gcttgtctgc tcccggcatc cgcttacaga   8400

caagctgtga ccgtctccgg gagctgcatg tgtcagaggt tttcaccgtc atcaccgaaa   8460

cgcg                                                                8464
```

<210> SEQ ID NO 170
<211> LENGTH: 27
<212> TYPE: PRT
<213> ORGANISM: Artificial Sequence
<220> FEATURE:
<223> OTHER INFORMATION: Synthetic M2 Peptide

<400> SEQUENCE: 170

```
Ser Leu Leu Thr Glu Val Glu Thr Pro Ile Arg Asn Glu Trp Gly Cys
1               5                   10                  15

Arg Cys Asn Gly Ser Ser Asp Gly Gly Gly Cys
            20                  25
```

<210> SEQ ID NO 171
<211> LENGTH: 97
<212> TYPE: PRT
<213> ORGANISM: Artificial Sequence
<220> FEATURE:
<223> OTHER INFORMATION: Matrix protein M2

<400> SEQUENCE: 171

```
Met Ser Leu Leu Thr Glu Val Glu Thr Pro Ile Arg Asn Glu Trp Gly
1               5                   10                  15

Cys Arg Cys Asn Gly Ser Ser Asp Pro Leu Ala Ile Ala Ala Asn Ile
            20                  25                  30

Ile Gly Ile Leu His Leu Ile Leu Trp Ile Leu Asp Arg Leu Phe Phe
        35                  40                  45

Lys Cys Ile Tyr Arg Arg Phe Lys Tyr Gly Leu Lys Gly Gly Pro Ser
    50                  55                  60

Thr Glu Gly Val Pro Lys Ser Met Arg Glu Glu Tyr Arg Lys Glu Gln
65                  70                  75                  80

Gln Ser Ala Val Asp Ala Asp Asp Gly His Phe Val Ser Ile Glu Leu
                85                  90                  95

Glu
```

<210> SEQ ID NO 172
<211> LENGTH: 770
<212> TYPE: PRT
<213> ORGANISM: Homo Sapiens

<400> SEQUENCE: 172

```
Met Leu Pro Gly Leu Ala Leu Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45
```

-continued

```
Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
        275                 280                 285

Glu Val Cys Ser Glu Gln Ala Glu Thr Gly Pro Cys Arg Ala Met Ile
    290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
                325                 330                 335

Cys Met Ala Val Cys Gly Ser Ala Met Ser Gln Ser Leu Leu Lys Thr
            340                 345                 350

Thr Gln Glu Pro Leu Ala Arg Asp Pro Val Lys Leu Pro Thr Thr Ala
        355                 360                 365

Ala Ser Thr Pro Asp Ala Val Asp Lys Tyr Leu Glu Thr Pro Gly Asp
    370                 375                 380

Glu Asn Glu His Ala His Phe Gln Lys Ala Lys Glu Arg Leu Glu Ala
385                 390                 395                 400

Lys His Arg Glu Arg Met Ser Gln Val Met Arg Glu Trp Glu Glu Ala
                405                 410                 415

Glu Arg Gln Ala Lys Asn Leu Pro Lys Ala Asp Lys Lys Ala Val Ile
            420                 425                 430

Gln His Phe Gln Glu Lys Val Glu Ser Leu Glu Gln Glu Ala Ala Asn
        435                 440                 445

Glu Arg Gln Gln Leu Val Glu Thr His Met Ala Arg Val Glu Ala Met
    450                 455                 460

Leu Asn Asp Arg Arg Arg Leu Ala Leu Glu Asn Tyr Ile Thr Ala Leu
```

-continued

```
465                 470                 475                 480

Gln Ala Val Pro Pro Arg Pro Arg His Val Phe Asn Met Leu Lys Lys
                485                 490                 495

Tyr Val Arg Ala Glu Gln Lys Asp Arg Gln His Thr Leu Lys His Phe
            500                 505                 510

Glu His Val Arg Met Val Asp Pro Lys Lys Ala Ala Gln Ile Arg Ser
        515                 520                 525

Gln Val Met Thr His Leu Arg Val Ile Tyr Glu Arg Met Asn Gln Ser
    530                 535                 540

Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Asp Val
                565                 570                 575

Leu Ala Asn Met Ile Ser Glu Pro Arg Ile Ser Tyr Gly Asn Asp Ala
            580                 585                 590

Leu Met Pro Ser Leu Thr Glu Thr Lys Thr Thr Val Glu Leu Leu Pro
        595                 600                 605

Val Asn Gly Glu Phe Ser Leu Asp Asp Leu Gln Pro Trp His Ser Phe
    610                 615                 620

Gly Ala Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Lys Met Asp
            660                 665                 670

Ala Glu Phe Arg His Asp Ser Gly Tyr Glu Val His His Gln Lys Leu
        675                 680                 685

Val Phe Phe Ala Glu Asp Val Gly Ser Asn Lys Gly Ala Ile Ile Gly
    690                 695                 700

Leu Met Val Gly Gly Val Val Ile Ala Thr Val Ile Val Ile Thr Leu
705                 710                 715                 720

Val Met Leu Lys Lys Lys Gln Tyr Thr Ser Ile His His Gly Val Val
                725                 730                 735

Glu Val Asp Ala Ala Val Thr Pro Glu Glu Arg His Leu Ser Lys Met
            740                 745                 750

Gln Gln Asn Gly Tyr Glu Asn Pro Thr Tyr Lys Phe Phe Glu Gln Met
        755                 760                 765

Gln Asn
    770


<210> SEQ ID NO 173
<211> LENGTH: 82
<212> TYPE: PRT
<213> ORGANISM: Homo Sapiens

<400> SEQUENCE: 173

Gly Ser Gly Leu Thr Asn Ile Lys Thr Glu Glu Ile Ser Glu Val Lys
1               5                   10                  15

Met Asp Ala Glu Phe Arg His Asp Ser Gly Tyr Glu Val His His Gln
            20                  25                  30

Lys Leu Val Phe Phe Ala Glu Asp Val Gly Ser Asn Lys Gly Ala Ile
        35                  40                  45

Ile Gly Leu Met Val Gly Gly Val Val Ile Ala Thr Val Ile Ile Ile
    50                  55                  60
```

-continued

```
Thr Leu Val Met Leu Lys Lys Gln Tyr Thr Ser Asn His His Gly Val
65                  70                  75                  80

Val Glu


<210> SEQ ID NO 174
<211> LENGTH: 42
<212> TYPE: PRT
<213> ORGANISM: Unknown
<220> FEATURE:
<223> OTHER INFORMATION: Amyloid Beta Peptide

<400> SEQUENCE: 174

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40


<210> SEQ ID NO 175
<211> LENGTH: 12
<212> TYPE: PRT
<213> ORGANISM: Artificial Sequence
<220> FEATURE:
<223> OTHER INFORMATION: p33 peptide

<400> SEQUENCE: 175

Cys Gly Gly Lys Ala Val Tyr Asn Phe Ala Thr Met
1               5                   10


<210> SEQ ID NO 176
<211> LENGTH: 37
<212> TYPE: PRT
<213> ORGANISM: Artificial Sequence
<220> FEATURE:
<223> OTHER INFORMATION: DP178c peptide

<400> SEQUENCE: 176

Cys Tyr Thr Ser Leu Ile His Ser Leu Ile Glu Glu Ser Gln Asn Gln
1               5                   10                  15

Gln Glu Lys Asn Glu Gln Glu Leu Leu Glu Leu Asp Lys Trp Ala Ser
            20                  25                  30

Leu Trp Asn Trp Phe
        35


<210> SEQ ID NO 177
<211> LENGTH: 6
<212> TYPE: PRT
<213> ORGANISM: Artificial Sequence
<220> FEATURE:
<223> OTHER INFORMATION: c-terminal linker

<400> SEQUENCE: 177

Gly Ser Gly Gly Cys Gly
1               5


<210> SEQ ID NO 178
<211> LENGTH: 65
<212> TYPE: PRT
<213> ORGANISM: Artificial Sequence
<220> FEATURE:
<223> OTHER INFORMATION: GRA2

<400> SEQUENCE: 178
```

-continued

```
Lys Glu Ala Ala Gly Arg Gly Met Val Thr Val Gly Lys Lys Leu Ala
1               5                   10                  15

Asn Val Glu Ser Asp Arg Ser Thr Thr Thr Thr Gln Ala Pro Asp Ser
            20                  25                  30

Pro Asn Gly Leu Ala Glu Thr Glu Val Pro Val Glu Pro Gln Gln Arg
        35                  40                  45

Ala Ala His Val Pro Val Pro Asp Phe Ser Gln Gly Ser Gly Gly Cys
    50                  55                  60

Gly
65


<210> SEQ ID NO 179
<211> LENGTH: 18
<212> TYPE: PRT
<213> ORGANISM: Artificial Sequence
<220> FEATURE:
<223> OTHER INFORMATION: D2 peptide

<400> SEQUENCE: 179

Cys Gly Gly Thr Ser Asn Gly Ser Asn Pro Ser Thr Ser Tyr Gly Phe
1               5                   10                  15

Ala Asn


<210> SEQ ID NO 180
<211> LENGTH: 18
<212> TYPE: PRT
<213> ORGANISM: Artificial Sequence
<220> FEATURE:
<223> OTHER INFORMATION: B2 peptide

<400> SEQUENCE: 180

Cys Gly Gly Asp Ile Ser Asn Gly Tyr Gly Ala Ser Tyr Gly Asp Asn
1               5                   10                  15

Asp Ile


<210> SEQ ID NO 181
<211> LENGTH: 14
<212> TYPE: PRT
<213> ORGANISM: Artificial Sequence
<220> FEATURE:
<223> OTHER INFORMATION: muTNFa peptide

<400> SEQUENCE: 181

Cys Gly Gly Val Glu Glu Gln Leu Glu Trp Leu Ser Gln Arg
1               5                   10


<210> SEQ ID NO 182
<211> LENGTH: 22
<212> TYPE: PRT
<213> ORGANISM: Artificial Sequence
<220> FEATURE:
<223> OTHER INFORMATION: TNFa II (3'-TNFa II)

<400> SEQUENCE: 182

Ser Ser Gln Asn Ser Ser Asp Lys Pro Val Ala His Val Val Ala Asn
1               5                   10                  15

His Gly Val Gly Gly Cys
            20


<210> SEQ ID NO 183
<211> LENGTH: 20
<212> TYPE: PRT
<213> ORGANISM: Artificial Sequence
```

-continued

<220> FEATURE:
<223> OTHER INFORMATION: TNFa II (5' TNFa II)

<400> SEQUENCE: 183

Cys Ser Ser Gln Asn Ser Ser Asp Lys Pro Val Ala His Val Val Ala
1               5                   10                  15

Asn His Gly Val
            20

<210> SEQ ID NO 184
<211> LENGTH: 182
<212> TYPE: PRT
<213> ORGANISM: Escherichia coli

<400> SEQUENCE: 184

Met Lys Ile Lys Thr Leu Ala Ile Val Val Leu Ser Ala Leu Ser Leu
1               5                   10                  15

Ser Ser Thr Ala Ala Leu Ala Ala Ala Thr Thr Val Asn Gly Gly Thr
            20                  25                  30

Val His Phe Lys Gly Glu Val Val Asn Ala Ala Cys Ala Val Asp Ala
        35                  40                  45

Gly Ser Val Asp Gln Thr Val Gln Leu Gly Gln Val Arg Thr Ala Ser
    50                  55                  60

Leu Ala Gln Glu Gly Ala Thr Ser Ser Ala Val Gly Phe Asn Ile Gln
65                  70                  75                  80

Leu Asn Asp Cys Asp Thr Asn Val Ala Ser Lys Ala Ala Val Ala Phe
                85                  90                  95

Leu Gly Thr Ala Ile Asp Ala Gly His Thr Asn Val Leu Ala Leu Gln
            100                 105                 110

Ser Ser Ala Ala Gly Ser Ala Thr Asn Val Gly Val Gln Ile Leu Asp
        115                 120                 125

Arg Thr Gly Ala Ala Leu Thr Leu Asp Gly Ala Thr Phe Ser Ser Glu
    130                 135                 140

Thr Thr Leu Asn Asn Gly Thr Asn Thr Ile Pro Phe Gln Ala Arg Tyr
145                 150                 155                 160

Phe Ala Thr Gly Ala Ala Thr Pro Gly Ala Ala Asn Ala Asp Ala Thr
                165                 170                 175

Phe Lys Val Gln Tyr Gln
            180

<210> SEQ ID NO 185
<211> LENGTH: 152
<212> TYPE: PRT
<213> ORGANISM: Hepatitis B virus

<400> SEQUENCE: 185

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Ile Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Thr Asn Leu Glu Asp Gly Gly
65                  70                  75                  80

-continued

```
Lys Gly Gly Ser Arg Asp Leu Val Val Ser Tyr Val Asn Thr Asn Met
                85                  90                  95

Gly Leu Lys Ile Arg Gln Leu Leu Trp Phe His Ile Ser Cys Leu Thr
            100                 105                 110

Phe Gly Arg Glu Thr Val Leu Glu Tyr Leu Val Ser Phe Gly Val Trp
        115                 120                 125

Ile Arg Thr Pro Pro Ala Tyr Arg Pro Pro Asn Ala Pro Ile Leu Ser
    130                 135                 140

Thr Leu Pro Glu Thr Thr Val Val
145                 150


<210> SEQ ID NO 186
<211> LENGTH: 152
<212> TYPE: PRT
<213> ORGANISM: Hepatitis B virus

<400> SEQUENCE: 186

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Ser
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Thr Asn Leu Glu Asp Gly Gly
65                  70                  75                  80

Lys Gly Gly Ser Arg Asp Leu Val Val Ser Tyr Val Asn Thr Asn Met
                85                  90                  95

Gly Leu Lys Ile Arg Gln Leu Leu Trp Phe His Ile Ser Ser Leu Thr
            100                 105                 110

Phe Gly Arg Glu Thr Val Leu Glu Tyr Leu Val Ser Phe Gly Val Trp
        115                 120                 125

Ile Arg Thr Pro Pro Ala Tyr Arg Pro Pro Asn Ala Pro Ile Leu Ser
    130                 135                 140

Thr Leu Pro Glu Thr Thr Val Val
145                 150
```